United States Patent
Ma et al.

(10) Patent No.: US 12,010,910 B2
(45) Date of Patent: Jun. 11, 2024

(54) NITROGEN-CONTAINING COMPOUND, AND ELECTRONIC ELEMENT AND ELECTRONIC DEVICE COMPRISING SAME

(71) Applicant: SHAANXI LIGHTE OPTOELECTRONICS MATERIAL CO., LTD., Shaanxi (CN)

(72) Inventors: Tiantian Ma, Shaanxi (CN); Lei Yang, Shaanxi (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 18/550,745

(22) PCT Filed: Apr. 1, 2022

(86) PCT No.: PCT/CN2022/084845
§ 371 (c)(1),
(2) Date: Sep. 15, 2023

(87) PCT Pub. No.: WO2022/222737
PCT Pub. Date: Oct. 27, 2022

(65) Prior Publication Data
US 2024/0114775 A1    Apr. 4, 2024

(30) Foreign Application Priority Data
Apr. 21, 2021    (CN) .......................... 202110430770.X

(51) Int. Cl.
*H10K 85/60*    (2023.01)
*C07C 211/61*    (2006.01)
(Continued)

(52) U.S. Cl.
CPC .......... *H10K 85/633* (2023.02); *C07C 211/61* (2013.01); *C07C 255/58* (2013.01);
(Continued)

(58) Field of Classification Search
CPC ............................ C07C 211/61; H10K 85/633
See application file for complete search history.

(56) References Cited

FOREIGN PATENT DOCUMENTS

| CN | 107915648 A | 4/2018 |
|----|-------------|--------|
| CN | 110229071 A | 9/2019 |

(Continued)

OTHER PUBLICATIONS

Machine-generated English-language translation of WO2023/113381A1.*

(Continued)

*Primary Examiner* — Vu A Nguyen
(74) *Attorney, Agent, or Firm* — Nixon & Vanderhye P.C.

(57) ABSTRACT

The present disclosure belongs to the technical field of organic materials, and provides a nitrogen-containing compound, and an electronic element and an electronic device comprising same. The nitrogen-containing compound has a structure as presented by chemical formula 1.

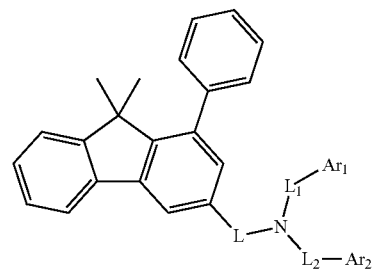

8 Claims, 2 Drawing Sheets

(51) Int. Cl.
  *C07C 255/58* (2006.01)
  *C07D 209/86* (2006.01)
  *C07D 307/91* (2006.01)
  *C07D 333/76* (2006.01)
  *C07D 405/12* (2006.01)
  *C07D 409/12* (2006.01)
  *C07F 7/08* (2006.01)
  *H10K 30/00* (2023.01)
  *H10K 50/18* (2023.01)

(52) U.S. Cl.
  CPC ......... *C07D 209/86* (2013.01); *C07D 307/91* (2013.01); *C07D 333/76* (2013.01); *C07D 405/12* (2013.01); *C07D 409/12* (2013.01); *C07F 7/081* (2013.01); *H10K 85/636* (2023.02); *C07B 2200/05* (2013.01); *C07C 2603/18* (2017.05); *C07C 2603/97* (2017.05); *H10K 30/00* (2023.02); *H10K 50/181* (2023.02); *H10K 85/624* (2023.02); *H10K 85/626* (2023.02); *H10K 85/6572* (2023.02); *H10K 85/6574* (2023.02); *H10K 85/6576* (2023.02)

(56) References Cited

FOREIGN PATENT DOCUMENTS

| | | | |
|---|---|---|---|
| CN | 111278803 | A | 6/2020 |
| CN | 111344379 | A | 6/2020 |
| CN | 113223987 | A | 8/2021 |
| CN | 113861040 | A * | 12/2021 |
| KR | 20160127429 | A | 11/2016 |
| KR | 20180112962 | A | 10/2018 |
| KR | 2377494 | B1 * | 3/2022 |
| WO | 2020225071 | A1 | 11/2020 |
| WO | 2020226298 | A1 | 11/2020 |
| WO | 2021060723 | A1 | 4/2021 |

OTHER PUBLICATIONS

First Office Action of China National Intellectual Property Administration for CN Application No. 202110430770.X issued Dec. 14, 2021, 19 pages.
International Search Report for PCT/CN2022/084845 dated May 26, 2022, 5 pages.
Written Opinion of the ISA for PCT/CN2022/084845 dated May 26, 2022, 5 pages.
Notification to Grant Patent Right dated Apr. 1, 2022 issued in Chinese Application No. 202110430770.X with English translation (7 pages).

* cited by examiner

NITROGEN-CONTAINING COMPOUND, AND ELECTRONIC ELEMENT AND ELECTRONIC DEVICE COMPRISING SAME

CROSS-REFERENCE OF RELATED APPLICATIONS

This application is the U.S. national phase of International Application No. PCT/CN2022/084845 filed Apr. 1, 2022 which designated the U.S. and claims priority to Chinese Patent Application No. 202110430770.X filed Apr. 21, 2021, the entire contents of each of which are hereby incorporated by reference.

FIELD OF THE INVENTION

The present disclosure relates to the technical field of organic materials, and in particular to a nitrogen-containing compound, an electronic element using the nitrogen-containing compound, and an electronic device using the electronic element.

BACKGROUND OF THE INVENTION

Organic electroluminescent components, also known as organic light-emitting diodes, relates to the phenomenon that an organic luminescent material emits light in response to excitation by an electric current under the influence of an electric field, which is a process of converting electric energy into light energy. Compared with inorganic luminescent materials, organic electroluminescent components have advantages of being emissive, and of large optical path ranges, low driving voltages, high brightness, high efficiency, low energy consumption, and simple fabrication processes. It is because of these advantages that organic luminescent materials and components have become one of the most popular scientific research topics in the scientific and industrial circles.

An organic electroluminescent component typically includes an anode, a hole transport layer, an electroluminescent layer as an energy conversion layer, an electron transport layer, and a cathode. When a voltage is applied to the cathode and the anode, an electric field is formed between the two electrodes. Under the influence of the electric field, electrons on the cathode side migrate to the electroluminescent layer, and holes on the anode side also migrate to the electroluminescent layer. The electrons and the holes recombine in the electroluminescent layer, forming excitons. The excitons in excited states release energy, causing the electroluminescent layer to emit light to the outside.

In existing technologies, KR1020160127429A, CN111.278803A, CN110229071A, etc. have disclosed materials that can be used to form a hole transport layer in an organic electroluminescent component. However, it is still necessary to continue to develop new materials to further improve the performance of electronic components.

SUMMARY OF THE INVENTION

An objective of the present disclosure is to provide a nitrogen-containing compound, and an electronic element and an electronic device comprising the nitrogen-containing compound so as to improve the performance of electronic elements and electronic devices.

To achieve the above objective, the present disclosure adopts the following technical solutions.

According to a first aspect of the present disclosure, there is provided a nitrogen-containing compound having a structure shown in Chemical Formula 1:

Chmeical Formula 1

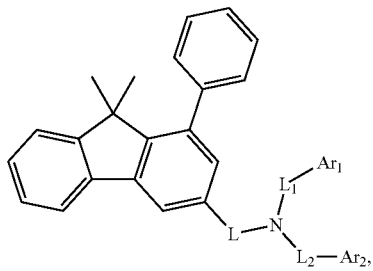

wherein:
L, $L_1$, and $L_2$ are each independently selected from the group consisting of single bond, substituted or unsubstituted arylene having 6 to 30 carbon atoms, and substituted or unsubstituted heteroarylene having 3 to 30 carbon atoms;

$Ar_1$ and $Ar_2$ are each independently selected from substituted or unsubstituted aryl having 6 to 30 carbon atoms, and substituted or unsubstituted heteroaryl having 3 to 30 carbon atoms;

substituents in L, $L_1$, $L_2$, $Ar_1$, and $Ar_2$ are identical to or different from one another, and are each independently selected from the group consisting of deuterium, halogen, cyano, heteroaryl having 3 to 20 carbon atoms, aryl having 6 to 20 carbon atoms, trialkylsilyl having 3 to 12 carbon atoms, triarylsilyl having 18 to 24 carbon atoms, alkyl having 1 to 10 carbon atoms, halogenated alkyl having 1 to 10 carbon atoms, cycloalkyl having 3 to 10 carbon atoms, heterocycloalkyl having 2 to 10 carbon atoms, alkoxy having 1 to 10 carbon atoms, alkylthio having 1 to 10 carbon atoms, aryloxy having 6 to 18 carbon atoms, arylthio having 6 to 18 carbon atoms, and phosphonooxy having 6 to 18 carbon atoms; and optionally, in L, $L_1$, $L_2$, $Ar_1$, and $Ar_2$, any two adjacent substituents form a ring.

The nitrogen-containing compound provided in the present disclosure is a triarylamine-type molecular structure with 1-phenyl-3-amino-9,9-dimethyfflluorene as the core group. This type of molecular structure exhibits a deep HOMO energy level and high hole mobility, and therefore has excellent hole injection and hole transport properties when used as an electron blocking layer of an organic electroluminescent device, thereby giving the device good voltage and efficiency characteristics. Further, there is a large dihedral angle between the phenyl group linked at the 1-position and the dimethylfluorenyl group, which can effectively improve steric hindrance in the compound and reduce intermolecular forces, providing the material with excellent amorphous morphology and good film-forming properties, thereby prolonging service life of the component. The nitrogen-containing compound, when used in an electron blocking layer of an organic electroluminescent device, can effectively reduce the operating voltage of the device, enhance the efficiency thereof, and prolong service life thereof.

According to a second aspect of the present disclosure, an electronic element is provided. The electronic element includes an anode and a cathode disposed opposite to each other, and a functional layer disposed between the anode and the cathode. The functional layer comprises the nitrogen-containing compound described in the first aspect.

According to a third aspect of the present disclosure, an electronic device is provided. The electronic device includes the electronic element described in the second aspect.

BRIEF DESCRIPTION OF THE DRAWINGS

The accompanying drawings incorporated into this specification and forming a part of the specification show embodiments of the present disclosure, and are used to explain principles of the present disclosure together with the description. In these drawings, similar reference signs are used to designate similar elements. The drawings described below show only some embodiments of the present disclosure, but not all embodiments. For those of ordinary skill in the art, other drawings can be obtained based on these drawings without any creative work. The above and other features and advantages of the present disclosure will become more apparent by elaborating exemplary embodiments thereof with reference to the accompanying drawings.

LIST OF REFERENCE SIGNS

Figure 1:
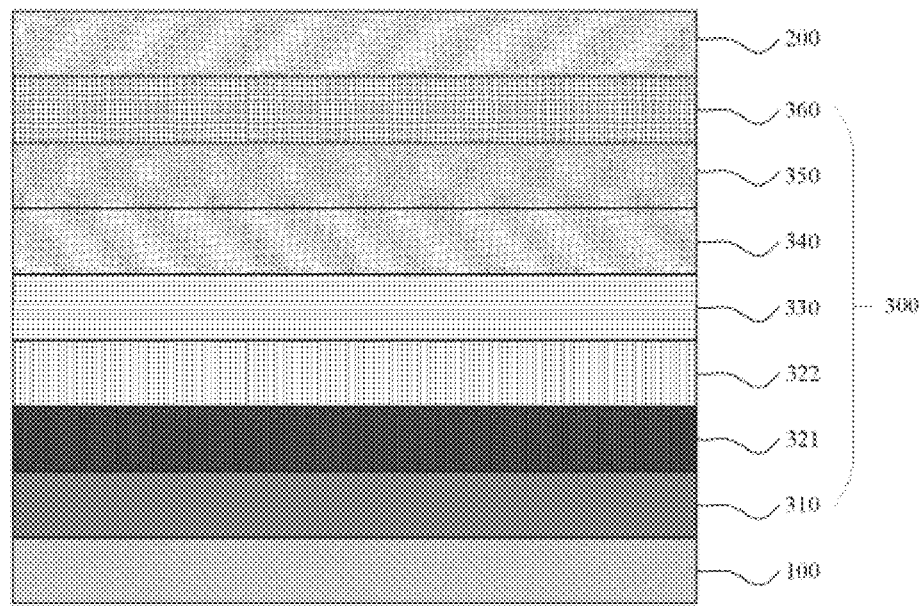
FIG. 1 is a schematic structural diagram of an organic electroluminescent device according to an embodiment of the present disclosure.

100: anode; 200: cathode; 300: functional layer; 310: hole injection layer;
321: hole transport layer; 322: electron blocking layer;
330: organic light-emitting layer; 340: hole blocking layer;
350: electron transport layer; 360: electron injection layer;
370: photoelectric conversion layer; 400: first electronic device;
500: second electronic device.

DETAILED DESCRIPTION OF THE EMBODIMENTS

Exemplary embodiments will now be described more comprehensively with reference to the accompanying drawings. The exemplary embodiments, however, can be implemented in a to variety of forms and should not be interpreted as being limited to the examples set forth herein. On the contrary, these embodiments are provided to make the present disclosure more comprehensive and complete, and to communicate the concepts of these exemplary embodiments fully to those of ordinary skill in the art. Features, structures, or characteristics described herein can be combined in one or more embodiments in any suitable manner. In the following description, many specific details are provided to give a full understanding of the embodiments of the present disclosure.

In the drawings, thicknesses of regions and layers may be exaggerated for clarity. Similar reference signs in the drawings designate same or similar structures, and therefore a detailed description thereof will be omitted.

The present disclosure provides a nitrogen-containing compound having a structure shown in Chemical Formula 1:

Chemical Formula 1

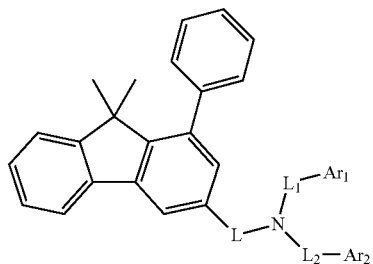

wherein:
L, $L_1$, and $L_2$ are each independently selected from single bond, substituted or unsubstituted arylene having 6 to 30 carbon atoms, and substituted or unsubstituted heteroarylene having 3 to 30 carbon atoms;

$Ar_1$ and $Ar_2$ are each independently selected from substituted or unsubstituted aryl having 6 to 30 carbon atoms, and substituted or unsubstituted heteroaryl having 3 to 30 carbon atoms;

substituents in L, $L_1$, $L_2$, $Ar_1$ and $Ar_2$ are identical to or different from one another, and are each independently selected from the group consisting of deuterium, halogen, cyano, heteroaryl having 3 to 20 carbon atoms, aryl having 6 to 20 carbon atoms, trialkylsilyl having 3 to 12 carbon atoms, triarylsilyl having 18 to 24 carbon atoms, alkyl having 1 to 10 carbon atoms, halogenated alkyl having 1 to 10 carbon atoms, cycloalkyl having 3 to 10 carbon atoms, heterocycloalkyl having 2 to 10 carbon atoms, alkoxy having 1 to 10 carbon atoms, alkylthio having 1 to 10 carbon atoms, aryloxy having 6 to 18 carbon atoms, arylthio having 6 to 18 carbon atoms, and phosphonooxy having 6 to 18 carbon atoms; and optionally, in L, $L_1$, $L_2$, $Ar_1$, and $Ar_2$, any two adjacent substituents form a ring.

In the present disclosure, the term "optional" or "optionally" means that the subsequently to described event or circumstance may or may not occur, i.e., including instances where an event or circumstance occurs and instances where the event or circumstance does not occur. For example, "optionally, any two adjacent substituents form a ring" means that the two substituents may or may not form a ring, i.e., including instances where the two adjacent substituents form a ring and instances where the two adjacent substituents do not form a ring.

In the present disclosure, the expression "any adjacent" in "any two adjacent substituents form a ring" may involve instances where there are two substituents on a same atom and also instances where there is one substituent on each of two adjacent atoms. When there are two substituents on a same atom, the two substituents, together with the atom to which they are attached, may form a saturated or unsaturated ring; and when there is one substituent on each of two adjacent atoms, the two substituents may be fused into a ring. For example, when $Ar_1$ has two or more than two substituents and any adjacent substituents form a ring, the ring formed is a saturated or unsaturated 5-13-membered ring such as a benzene ring, a naphthalene ring, a phenanthrene ring, an anthracene ring, a fluorene ring, a cyclopentane ring, cyclohexane, adamantine, etc.

In the present disclosure, the expression "each . . . independently" may be used interchangeably with the expressions " . . . each independently" and " . . . independently", and all these expressions should be interpreted in a broad sense. They can not only mean that, for same symbols in a same group, the selection of a specific option for one of the symbols and the selection of a specific option for another one of the symbols do not affect each other, but also mean that for same symbols in different groups, the selection of a specific option for one of the symbols and the selection of a specific option for another one of the symbols do not affect each other. Taking

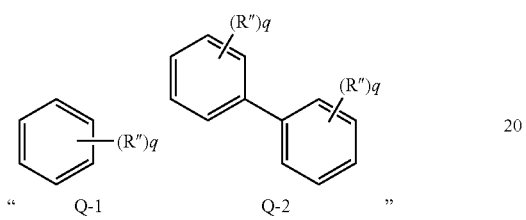

" Q-1      Q-2 "

as an example, each q is independently selected from 0, 1, 2, and 3, and each R" is independently selected from hydrogen, deuterium, fluorine, and chlorine, which means: in Formula Q-1, there are q substituents R" on the benzene ring, wherein each of the substituents R" may be identical or different, with the selection of an option for one of the substituents R" and the selection of an option for another one of the substituents R" not affecting each other; and in Formula Q-2, there are q substituents R" on each of the two benzene rings of biphenyl, wherein the number q of the substituent R" on one benzene ring and the number q of the substituent R" on the other benzene ring may be the same or different, and each substituent R" may be identical or different, with the selection of an option for one of the substituents R" and the selection of an option for another one of the substituents R" not affecting each other.

In the present disclosure, a non-positional bond is single bond "  " extending from a ring system, and it indicates that the linkage bond can be linked at one end thereof to any position in the ring system through which the bond passes, and linked at the other end thereof to the rest of the compound molecule.

For example, as shown in Formula (f) below, the naphthalyl group represented by Formula (f) is linked to other positions of the molecule via two non-positional bonds passing through the two rings, which indicates any of possible linkages shown in Formulae (f-1) to (f-10):

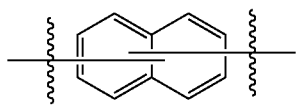

(f)

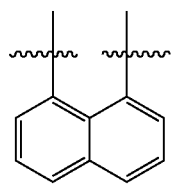

(f-1)

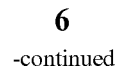

(f-2)

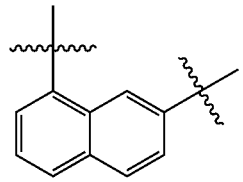

(f-3)

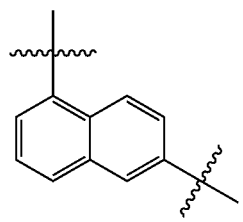

(f-4)

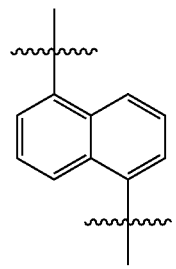

(f-5)

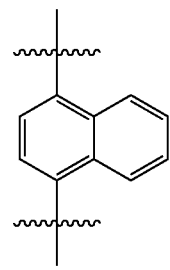

(f-6)

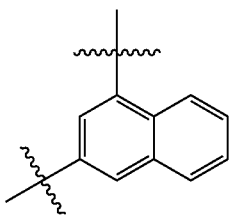

(f-7)

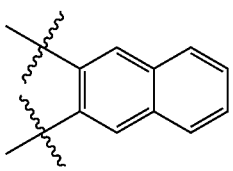

(f-8)

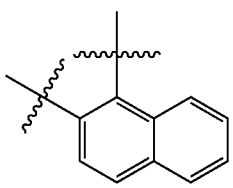

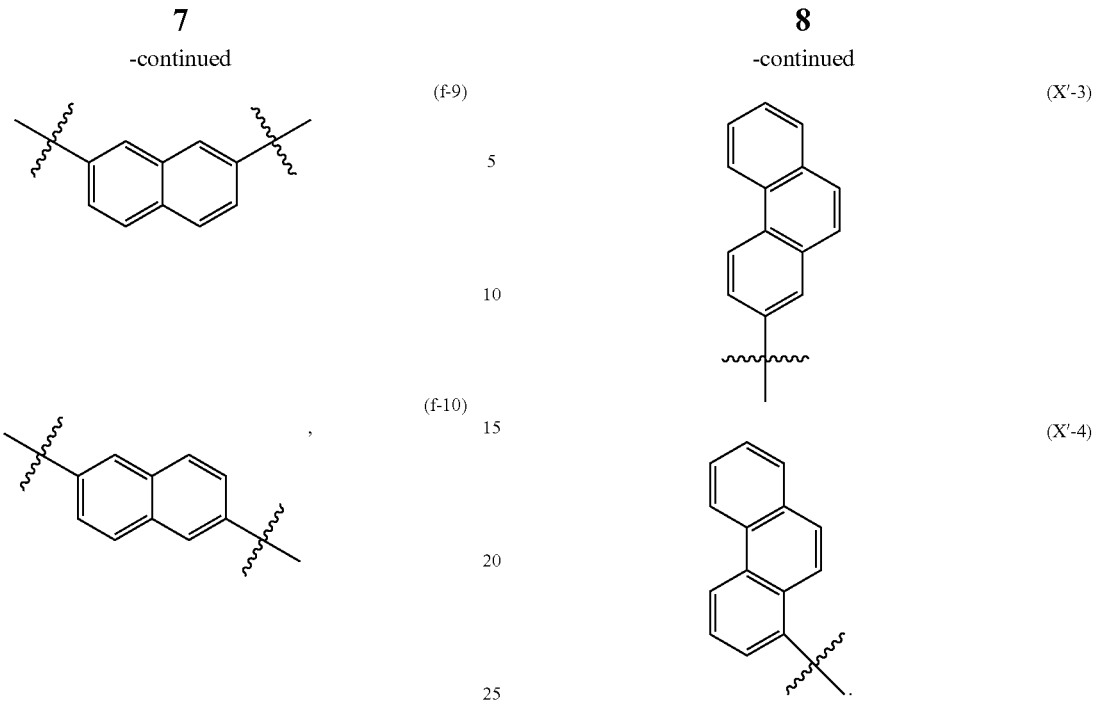

As another example, as shown in Formula (X') below, the phenanthryl group represented by Formula (X') is linked to other positions of the molecule via a non-positional bond extending from the middle of a side benzene ring, which indicates any of possible linkages shown in Formulae (X'-1) to (X'-4):

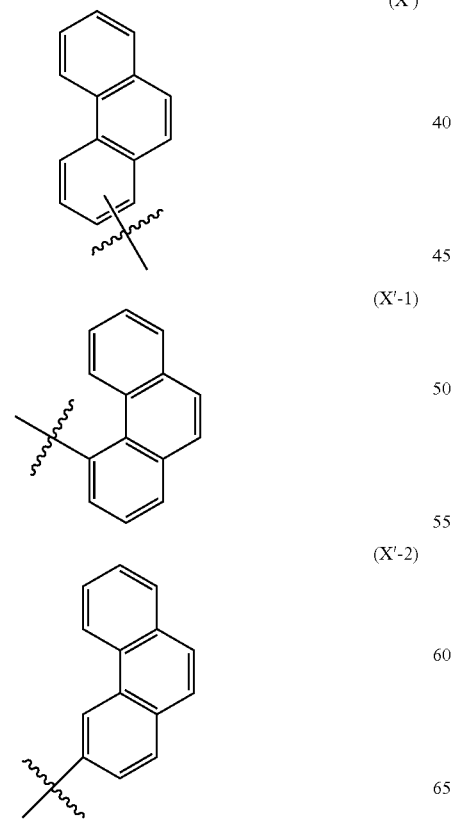

A non-orientating substituent in the present disclosure refers to a substituent linked via single bond extending from the center of a ring system, and it means that the substituent may be linked to any possible position in the ring system. For example, as shown in Formula (Y) below, the substituent R' represented by Formula (Y) is linked to a quinoline ring via a non-positional bond, which indicates any of possible linkages shown in Formulae (Y-1) to (Y-7):

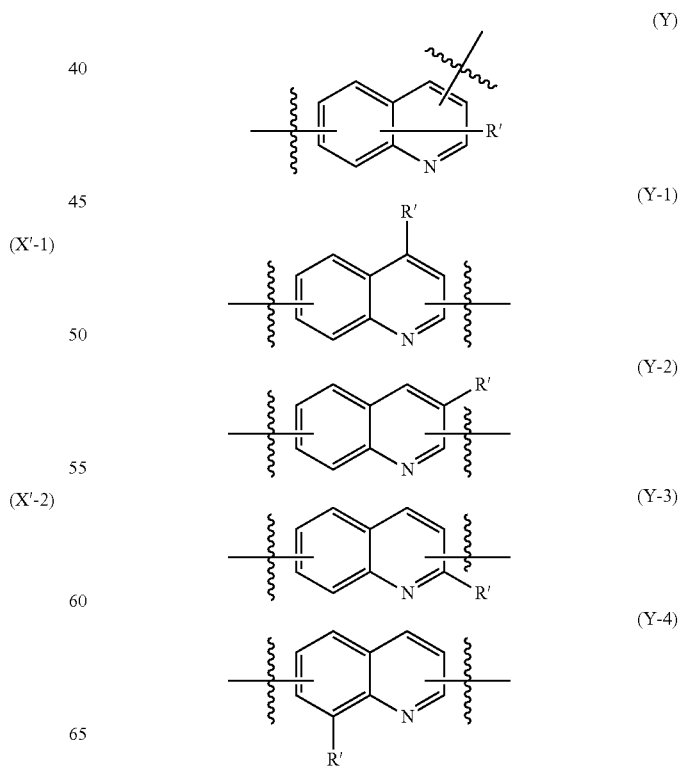

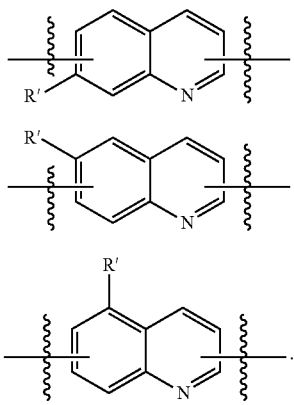

In the present disclosure, a number of carbon atoms of L, $L_1$, $L_2$, $Ar_1$, and $Ar_2$ refers to the number of all carbon atoms. For example, if L is selected from substituted arylene having 12 carbon atoms, then the number of all carbon atoms of the arylene group and the substituents thereon is 12. For example, if $Ar_1$ is

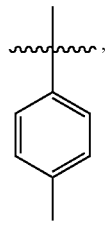 [SMILES: *c1ccc(C)cc1]

then the number of s carbon atoms is 7; if L is

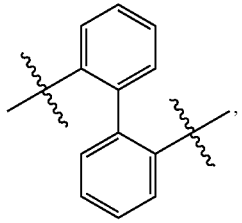 [SMILES: *c1ccccc1-c1ccccc1*]

then the number of its carbon atoms is 12.

In the present disclosure, when no specific definition is provided, "hetero" means that a functional group includes at least one heteroatom such as B, N, O, S, Se, Si, or R with remaining atoms being carbon and hydrogen. An unsubstituted alkyl group may be a "saturated alkyl group" without any double bonds or triple bonds.

In the present disclosure, "alkyl" may include linear alkyl orbranched alkyl. The alkyl group may have 1 to 10 carbon atoms, and in the present disclosure, a numerical range such as "1 to 10" is intended to include each integer in the given range. For example, "alkyl having 1 to 10 carbon atoms" refers to an alkyl group that may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

Optionally, alkyl is selected from alkyl having 1 to 5 carbon atoms, specific examples thereof including, but not limited to, a methyl, an ethyl, an n-propyl, an isopropyl, a n-butyl, an isobutyl, a sec-butyl, a tert-butyl, and a hexyl.

In the present disclosure, "cycloalkyl" refers to a group derived from a saturated cyclic carbon chain structure. The cycloalkyl group may have 3 to 10 carbon atoms, and in the present disclosure, a numerical range such as "3 to 10" is intended to include each integer in the given range. For example, "cycloalkyl having 3 to 10 carbon atoms" refers to a cycloalkyl group that may contain 3 carbon atoms, 4 carbon atoms, 5 carbon atoms, 6 carbon atoms, 7 carbon atoms, 8 carbon atoms, 9 carbon atoms, or 10 carbon atoms. Optionally, specific examples of cycloalkyl groups include, but are not limited to, cyclopentyl, cyciohexyl, etc.

In the present disclosure, "aryl" refers to any functional group or substituent group derived from an aromatic carbon ring. The aryl group may be a monocyclic aryl group (e.g., phenyl) or a polycyclic aryl group. In other words, the aryl group may be a monocyclic aryl group, a fused cycloaryl group, two or more monocyclic aryl groups linked by carbon-carbon bond conjugation, a monocyclic aryl group and a fused cycloaryl group linked by carbon-carbon bond conjugation, two or more fused cycloaryl groups linked by carbon-carbon bond conjugation. That is, unless otherwise specified, two or more aromatic groups linked by carbon-carbon bond conjugation may also be regarded as an aryl group in the present disclosure. Among them, fused cycloaryl groups may include, for example, bicyclic fused cycloaryl groups (e.g., naphthyl), tricyclic fused aryl groups (e.g., phenanthryl, fluorenyl, anthryl), etc. The aryl group does not contain a heteroatom such as B, N, O, S, P, Se, and Si. For example, in the present disclosure, biphenyl and triphenyl are aryl groups. Examples of aryl groups may include, but are not limited to, phenyl, naphthyl, fluorenyl, anthryl, phenanthryl, biphenyl, triphenyl, tetraphenyl, pentaphenyl, benzo[9,10] phenanthryl, pyrenyl, benzofluoranthryl, chrysenyl, etc.

In the present disclosure, "substituted or unsubstituted aryl" may contain 6 to 30 carbon atoms. In some embodiments, the number of carbon atoms in a substituted or unsubstituted aryl group is 6 to 25. In other embodiments, the number of carbon atoms in a substituted or unsubstituted aryl group is 6 to 18. In other embodiments, the number of carbon atoms in a substituted or unsubstituted aryl group may be 6 to 13. For example, in the present disclosure, the number of carbon atoms of a substituted or unsubstituted aryl group may be 6, 10, 12, 13, 14, 15, 18, 20, 24, 25, or 30. The number of carbon atoms may be of course in other quantities, which are not listed herein. In the present disclosure, a biphenyl group may also be interpreted as phenyl-substituted phenyl.

In the present disclosure, "arylene" refers to a divalent or polyvalent group formed by further removing one or more hydrogen atoms from an aryl group.

In the present disclosure, substituted aryl may mean that one or more hydrogen atoms in the aryl group are substituted by a group such as a deuterium atom, halogen, cyano, aryl, heteroaryl, trialkylsilyl, alkyl, cycloalkyl, alkoxy, alkylthio, etc. It should be appreciated that the number of carbon atoms of a substituted aryl group refers to the number of all carbon atoms of the aryl group and the substituents on the aryl group. For example, substituted aryl having 18 carbon atoms means that the number of all carbon atoms of the aryl group and substituents thereof is 18.

In the present disclosure, specific examples of aryl as substituents include, but are not limited to phenyl, naphthyl, anthryl, phenanthryl, ditnethylfluorenyl, biphenyl, diphenylfluorenyl, spirobilluorenyl, etc.

In the present disclosure, fluorenyl may be substituted, and two substituents thereof may combine with each other to form a Spiro structure, specific examples thereof including, but not limited to, the following structures:

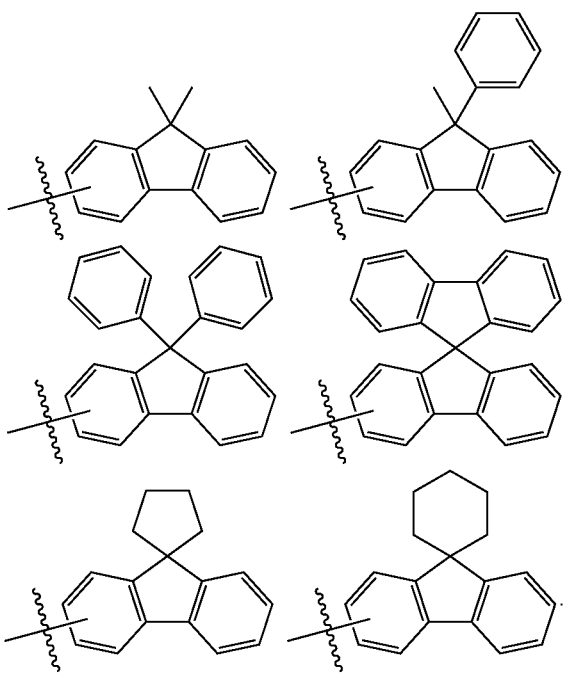

In the present disclosure, "heteroaryl" refers to a monovalent aromatic ring containing at least one heteroatom or a derivative thereof. The heteroatom may be at least one of B, O, N, P, Si, Se, and S. A heteroaryl group may be a monocyclic heteroaryl group or a polycyclic heteroaryl group. In other words, a heteroaryl group may be a single aromatic ring system, or a plurality of aromatic ring systems linked by carbon-carbon bond conjugation, with any of the aromatic ring systems being an aromatic monocyclic ring or a fused aromatic ring. For example, heteroaryl groups may include, but are not limited to, thiophenyl, furyl, pyrrolyl, imidazolyl, thiazolyl, oxazolyl, oxadiazolyl, triazolyl, pyridyl, bipyridyl, pyrimidyl, triazinyl, acridinyl, pyridazinyl, pyrazinyl, quinolinyl, quinazolinyl, quinoxalinyl, phenoxazinyl, phthalazinyl, pyndopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothiophenyl, dibenzothiophenyl, thienothiophenyl, benzofuranyl, phenanthrolinyl, isoxazolyl, thiadiazolyl, benzothiazolyl, phenothiazinyl, silylfiuorenyl, dibenzofuranyl, N-arylcarbazolyl (such as N-phenylcarbazolyl), N-heteroarylcarbazolyl (such as N-pyridylcarbazolyl), N-alkylcarbazolyl (such as N-methylcarbazolyl), etc. Among these, thiophenyl, furyl, and phenanthrolinyl are each a heteroaryl of a single aromatic ring system; and N-arylcarbazolyl and N-heteroarylcarbazolyl are each a heteroaryl of polycyclic systems linked by carbon-carbon bond conjugation. "substituted or unsubstituted heteroaryl" in the present disclosure may contain 3 to 30 carbon atoms. In some embodiments, the number of carbon atoms in a substituted or unsubstituted heteroaryl may be 3 to 25. In other embodiments, the number of carbon atoms in a substituted or unsubstituted heteroaryl may be 5 to 20. In other embodiments, the number of carbon atoms in a substituted or unsubstituted heteroaryl may be 12 to 20. For example, the number of carbon atoms in a substituted or unsubstituted heteroaryl may be 3, 4, 5, 7, 12, 13, 18, 20, 24, 25 or 30. The number of carbon atoms may be of course in other quantities, which will not be listed herein.

In the present disclosure, "heteroarylene" is a divalent group formed by further removing one hydrogen atom from a heteroaryl group.

In the present disclosure, "substituted heteroaryl" may mean that one or more than two hydrogen atoms in the heteroaryl group are substituted by a group such as a deuterium atom, halogen, cyano, aryl, heteroaryl, trialkylsilyl, alkyl, cycloalkyl, alkoxy, alkylthio, etc. It should be appreciated that the number of carbon atoms of a substituted heteroaryl group is the number of all carbon atoms of the heteroaryl group and substituents on the heteroaryl group.

In the present disclosure, specific examples of heteroaryl as substituents include, but are not limited to, dibenzofuranyl, dibenzothiophenyl, carbazolyl, N-phenylcarbazolyl, phenanthrolinyl, etc.

In the present disclosure, the halogen group may include fluorine, iodine, bromine, chlorine, etc.

In the present disclosure, specific examples of trialkyisilyl having 3 to 12 carbon atoms include, but are not limited to, trimethylsilyl and triethylsilyl.

In the present disclosure, specific examples of triarylsilyl having 18 to 24 carbon atomsinclude, but are not limited to, triphenylsilyl, etc.

In the present disclosure, specific examples of halogenated alkyl having 1 to 10 carbon atoms include, but are not limited to, trifluoromethyl, trifluoroethyl, etc.

According to an embodiment of the present disclosure, L, $L_1$, and $L_2$ are each independently selected from single bond, substituted or unsubstituted arylene having 6 to carbon atoms, and substituted or unsubstituted heteroarylene having 5 to 20 carbon atoms.

Optionally, substituents in L, $L_1$, and $L_2$ are identical or different, and are each independently selected from deuterium, halogen, cyano, alkyl having 1 to 5 carbon atoms, halogenated alkyl having 1 to 5 carbon atoms, and aryl having 6 to 12 carbon atoms.

Specifically, specific examples of the substituents in L, $L_1$, and $L_2$ include, but are not limited to, deuterium, fluorine, cyano, methyl, ethyl, n-propyl, isopropyl, tert-butyl, trifluoromethyl, phenyl, naphthyl, and biphenyl.

According to an embodiment of the present disclosure, L is selected from single bond, an unsubstituted phenylene, an unsubstituted naphthylene, an unsubstituted biphenylene, and an unsubstituted dibenzofuranylene.

Specifically, L is selected from single bond or a group consisting of the following groups:

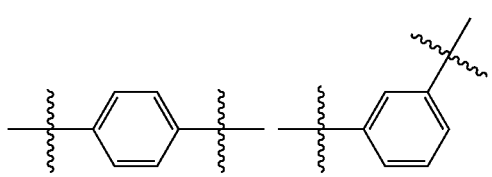

-continued

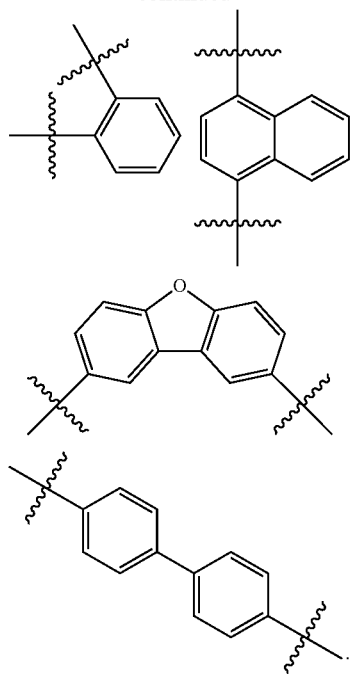

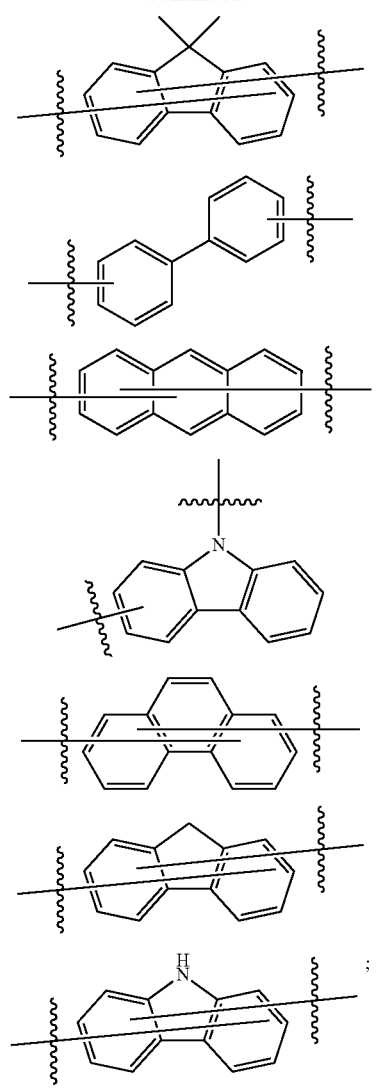

According to an embodiment of the present disclosure, $L_1$ and $L_2$ are each independently selected from the group consisting of single bond, substituted or unsubstituted phenylene, substituted or unsubstituted naphthylene, substituted or unsubstituted anthrylene, substituted or unsubstituted phenanthrylene, substituted or unsubstituted biphenylene, substituted or unsubstituted fluorenylidene, substituted or unsubstituted dibenzofuranylene, substituted or unsubstituted dibenzothienylene, and substituted or unsubstituted carbazolylene.

Optionally, substituents in $L_1$ and $L_2$ are identical or different, and are each independently selected from the group consisting of deuterium, fluorine, cyano, methyl, ethyl, n-propyl, isopropyl, tert-butyl, phenyl, naphthyl, and biphenyl.

According to another embodiment of the present disclosure, $L_1$ and $L_2$ are each independently selected from the group consisting of single bond, and substituted or unsubstituted groups V, the unsubstituted groups V being selected from the group consisting of the following groups:

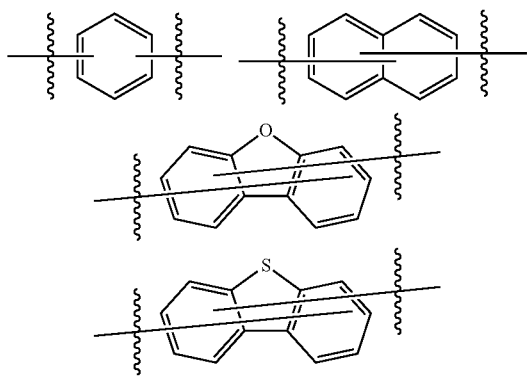

wherein, the substituted groups V each have one or more substituents each independently selected from the group consisting of deuterium, fluorine, cyano, methyl, ethyl, n-propyl, isopropyl, tert-butyl, phenyl, naphthyl, and biphenyl; and when the number of the substituents in the group V is greater than 1, the substituents are the same or different.

Optionally, $L_1$ and $L_2$ are each independently selected from single bond or the group consisting of the following groups:

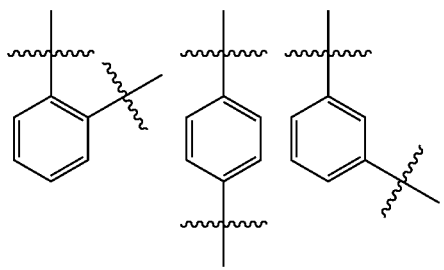

-continued

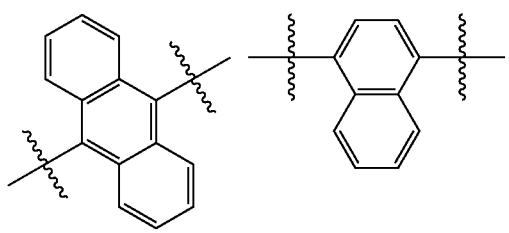
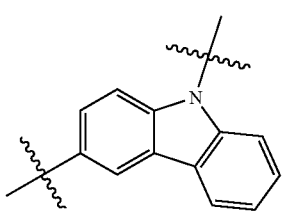
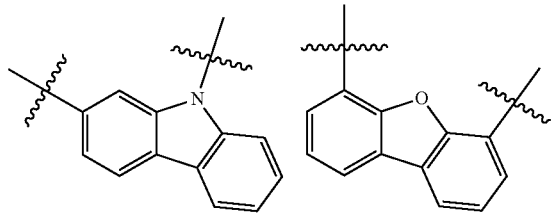
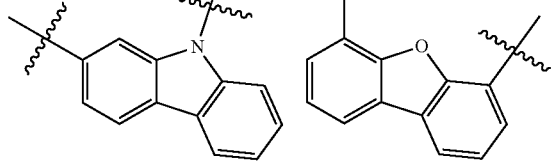
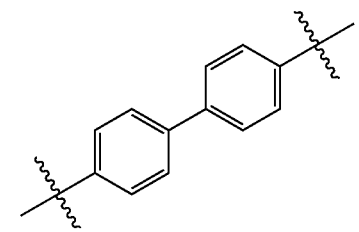
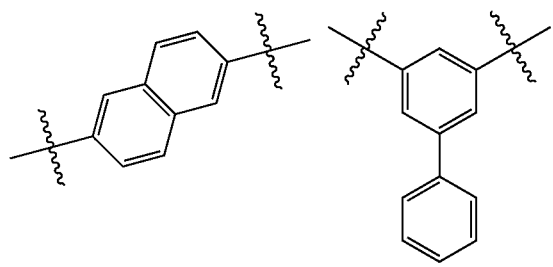
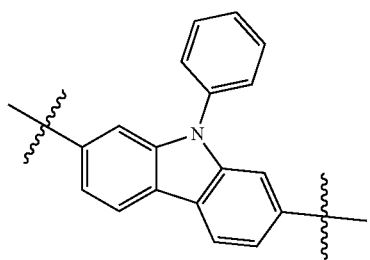

-continued

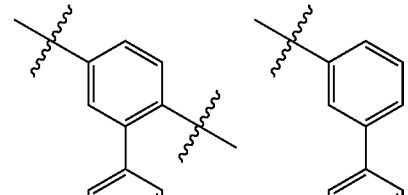
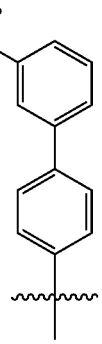
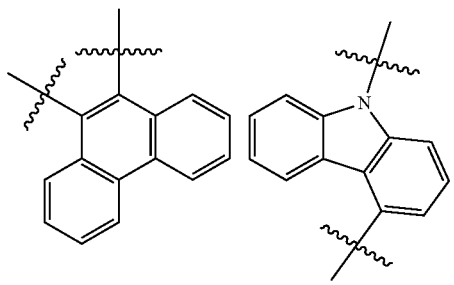
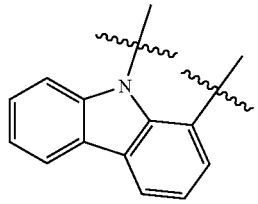
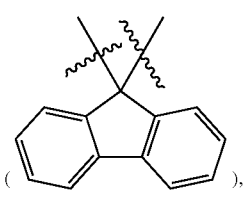 [SMILES: *C1(*)c2ccccc2-c2ccccc21]

According to an embodiment of the present disclosure, $Ar_1$ and $Ar_2$ are identical or different, and are each independently selected from substituted or unsubstituted aryl having 6 to 25 carbon atoms, and substituted or unsubstituted heteroaryl having 5 to 20 carbon atoms.

Optionally, substituents in $Ar_1$ and $Ar_2$ are identical or different, and are each independently selected from deuterium, halogen, cyano, alkyl having 1 to 5 carbon atoms, aryl having 6 to 20 carbon atoms, heteroaryl having 12 to 18 carbon atoms, cycloalkyl having 5 to 10 carbon atoms, trialkylsilyl having 3 to 12 carbon atoms, and triphenylsilyl.

Optionally, among the substituents of $Ar_1$ and $Ar_2$ any two adjacent substituents form a saturated or unsaturated ring having 5 to 13 carbon atoms. For example, in the substituents of $Ar_1$ and $Ar_2$, any two adjacent substituents form a fluorene ring cyclopentane,

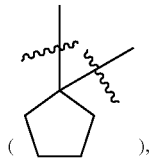

or cyclohexane

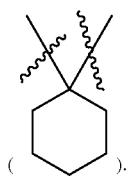

Specifically, the substituents of Ar₁ and Ar₂ include, but are not limited to, deuterium, fluorine, cyano, methyl, ethyl, n-propyl, isopropyl, Cert-butyl, phenyl, naphthyl, biphenyl, cyclopentyl, cyclohexyl, adamantyl, trimethylsilyl, and triphenylsilyl.

According to an embodiment of the present disclosure, $Ar_1$ and $Ar_2$ are identical or different, and are each independently selected from the group consisting of substituted or unsubstituted phenyl, substituted or unsubstituted naphthyl, substituted or unsubstituted biphenyl, substituted or unsubstituted fluorenyl, substituted or unsubstituted phenanthryl, substituted or unsubstituted triphenyl, substituted or unsubstituted dibenzofuranyl, substituted or unsubstituted dibenzothiophenyl, substituted or unsubstituted carbazolyi, and substituted or unsubstituted triphenylene.

According to an embodiment of the present disclosure, $Ar_1$ and $Ar_2$ are selected from substituted or unsubstituted groups W, the unsubstituted groups W being selected from the group consisting of the following groups:

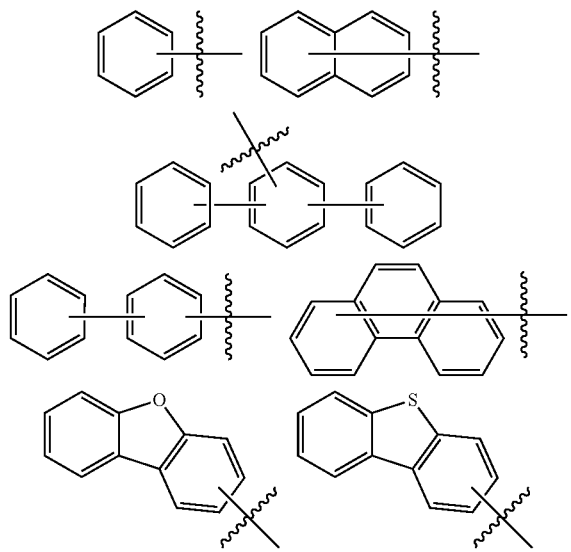

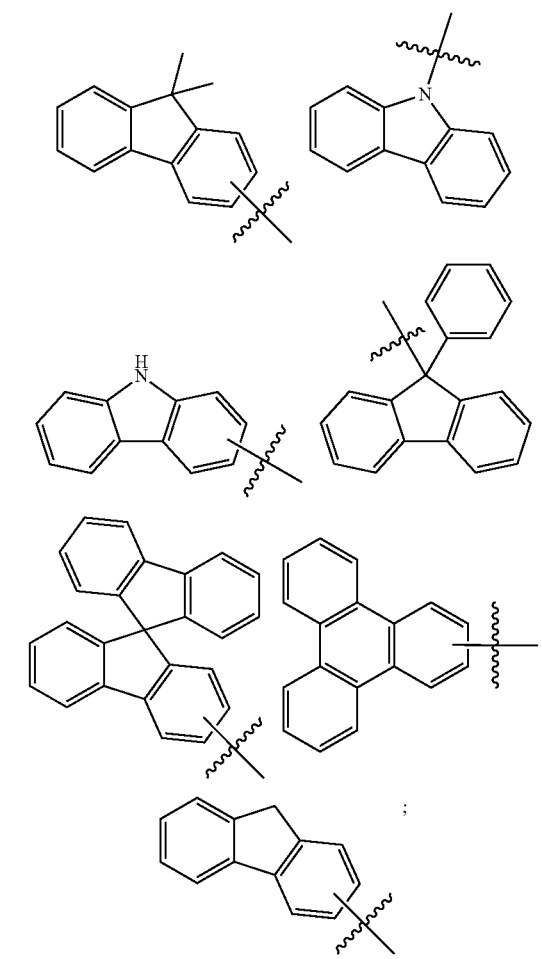

wherein, the substituted groups W each have one or more substituents, each independently selected from the group consisting of deuterium, fluorine, cyano, methyl, ethyl, n-propyl, isopropyl, tert-butyl, phenyl, naphthyl, biphenyl, cyclopentyl, cyclohexyl, adamantyl, trimethylsilyl, and triphenylsilyl and when the number of the substituents in the group W is greater than 1, the substituents are the same or different.

Specifically, $Ar_1$ and $Ar_2$ are selected from the group consisting of the following groups, but are not limited thereto:

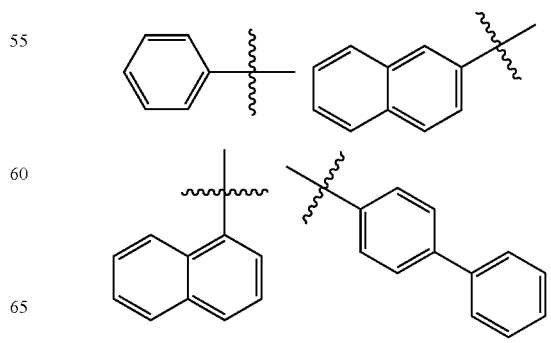

-continued
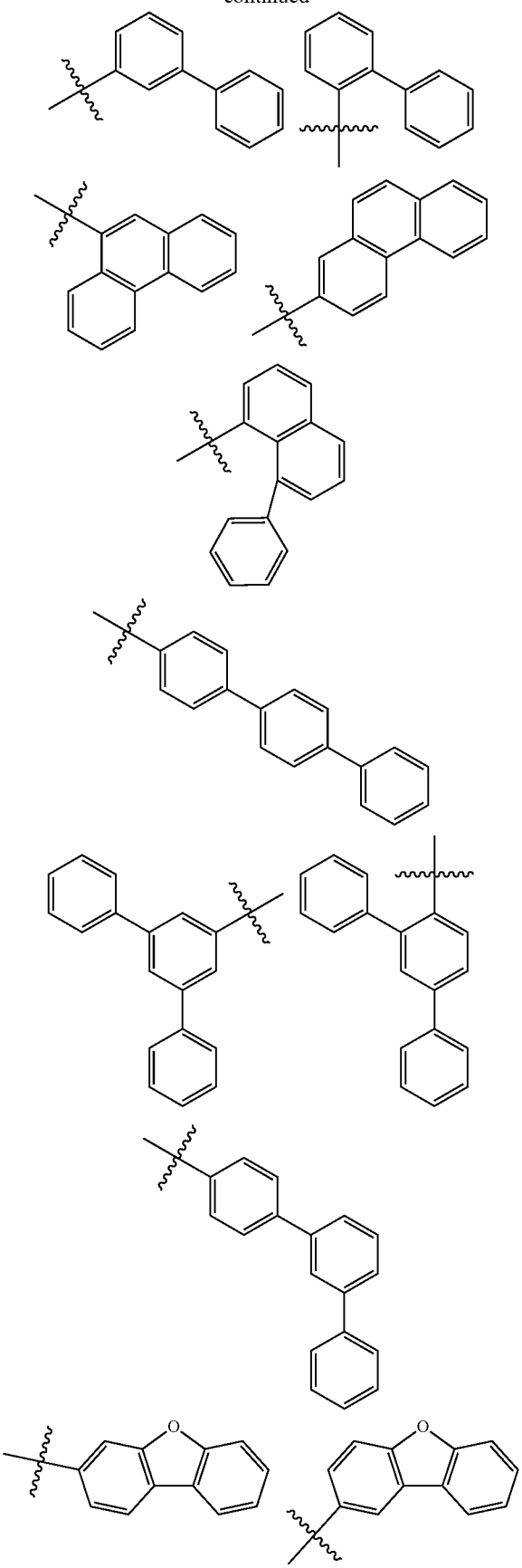
-continued
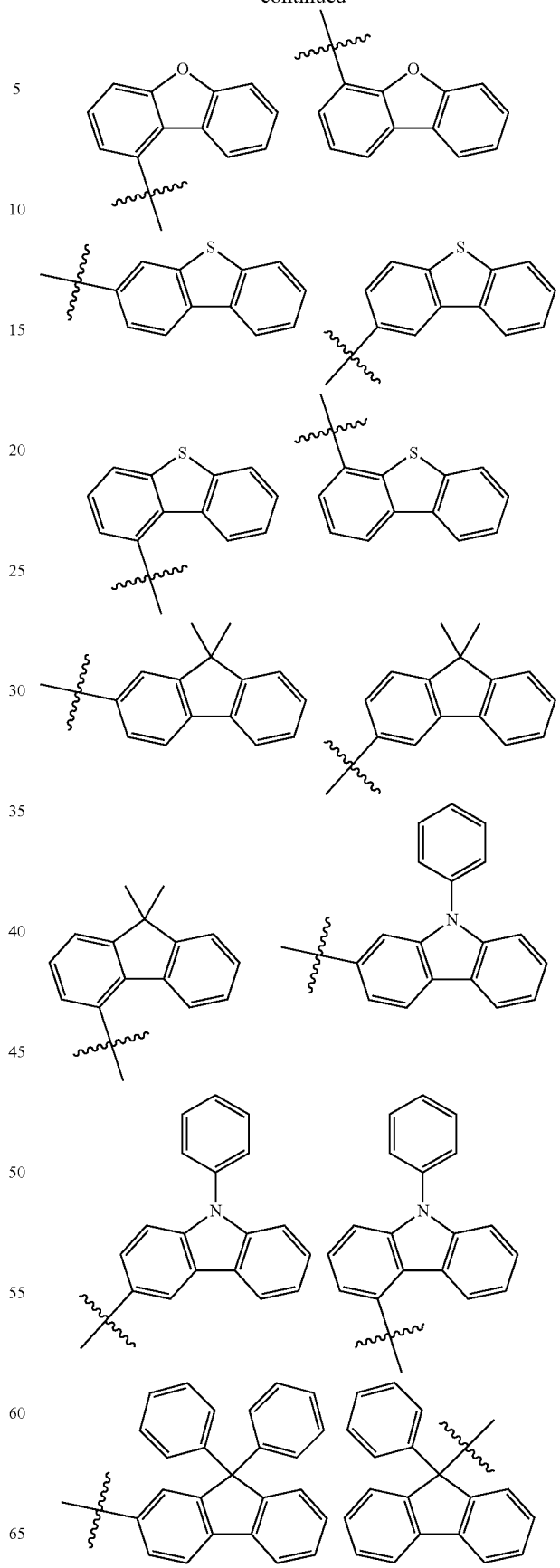

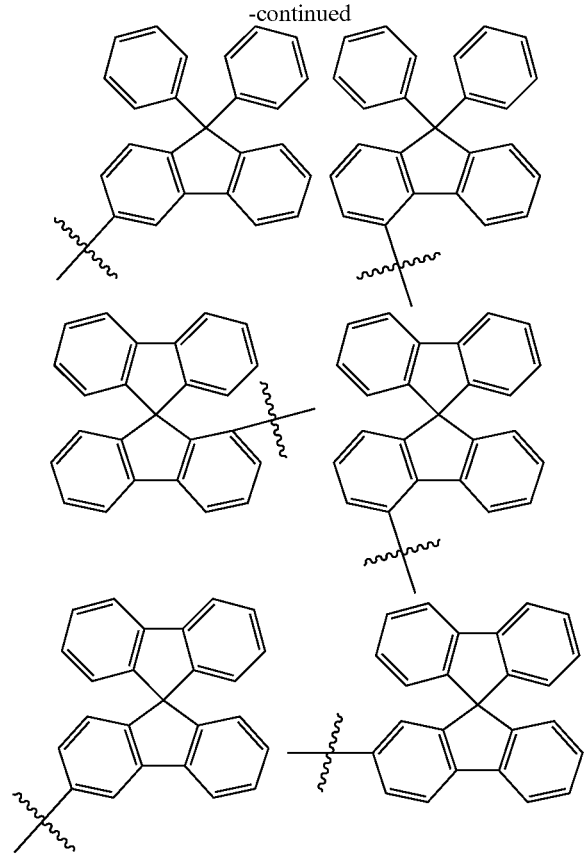
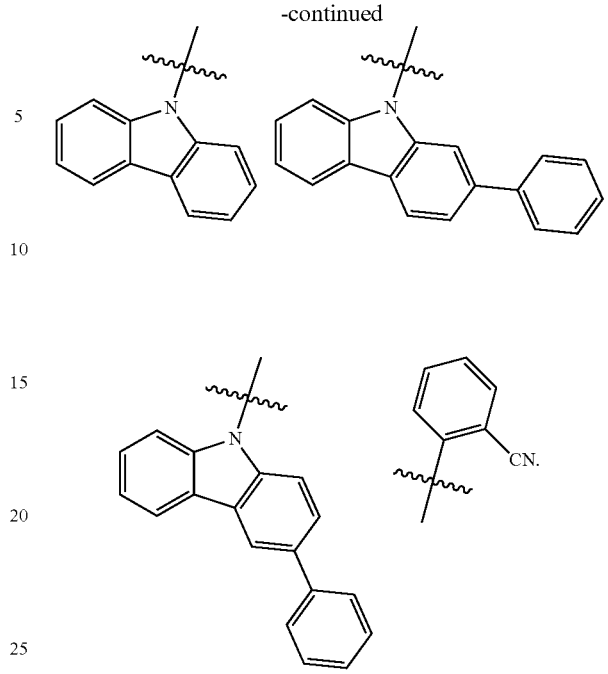
Optionally, the nitrogen-containing compound is selected from the group consisting of the following compounds, but is not limited thereto:
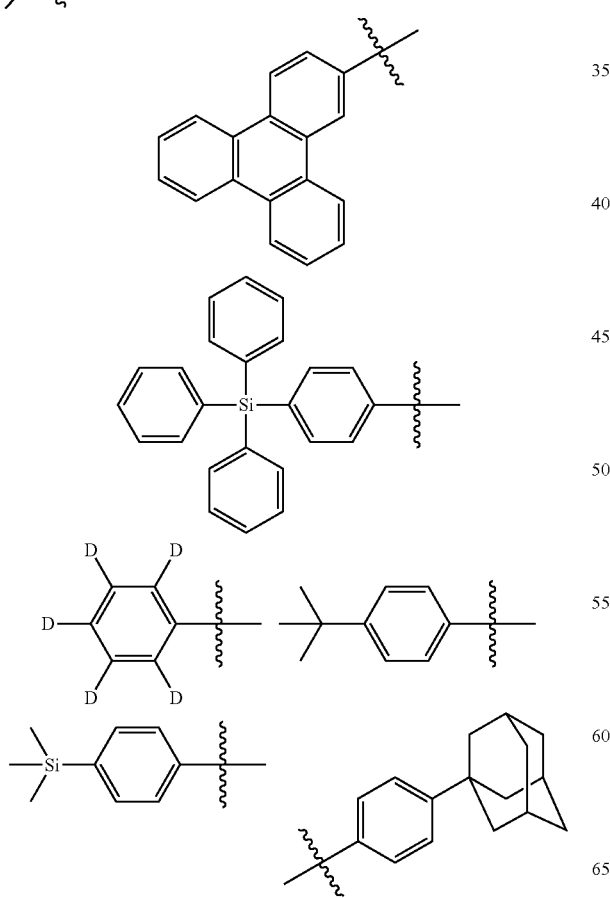
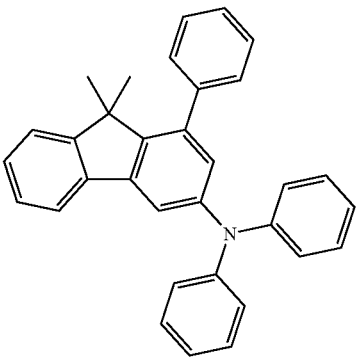
1
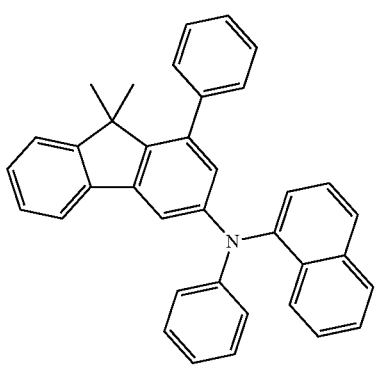
2

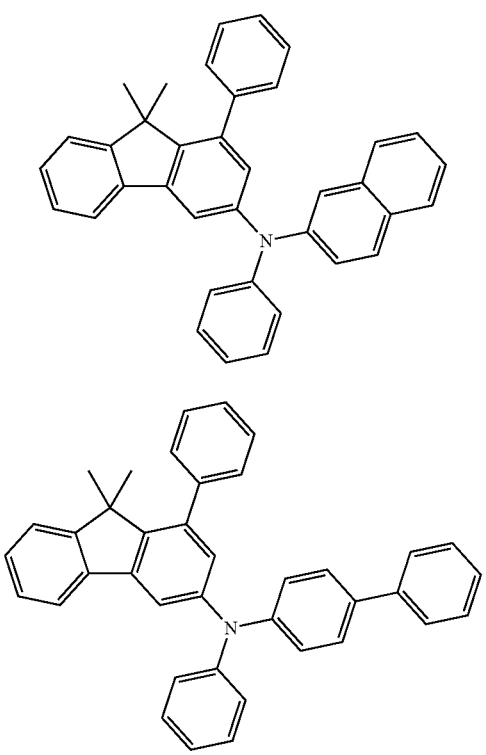
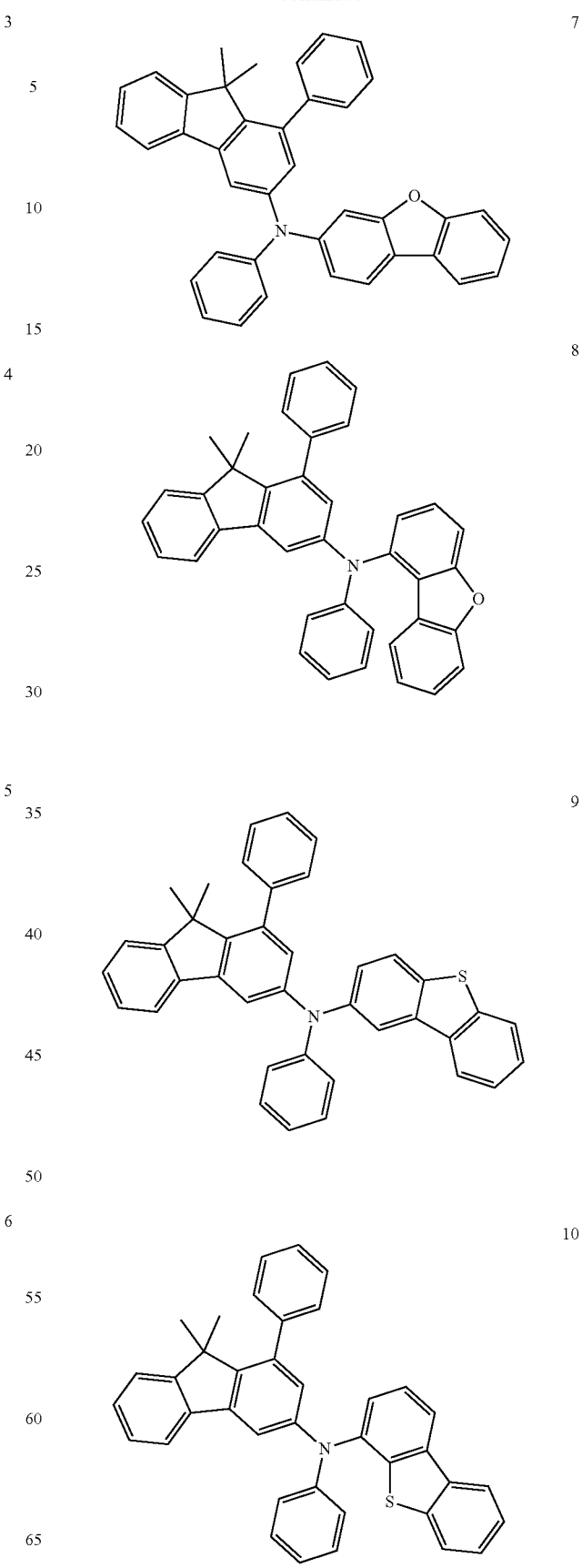

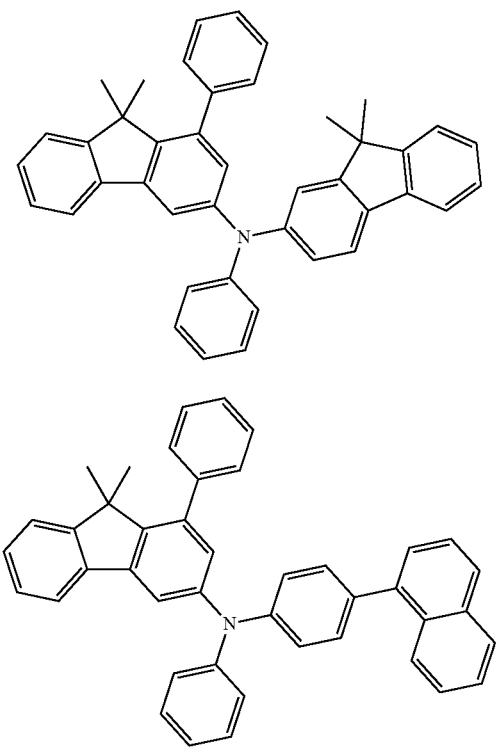
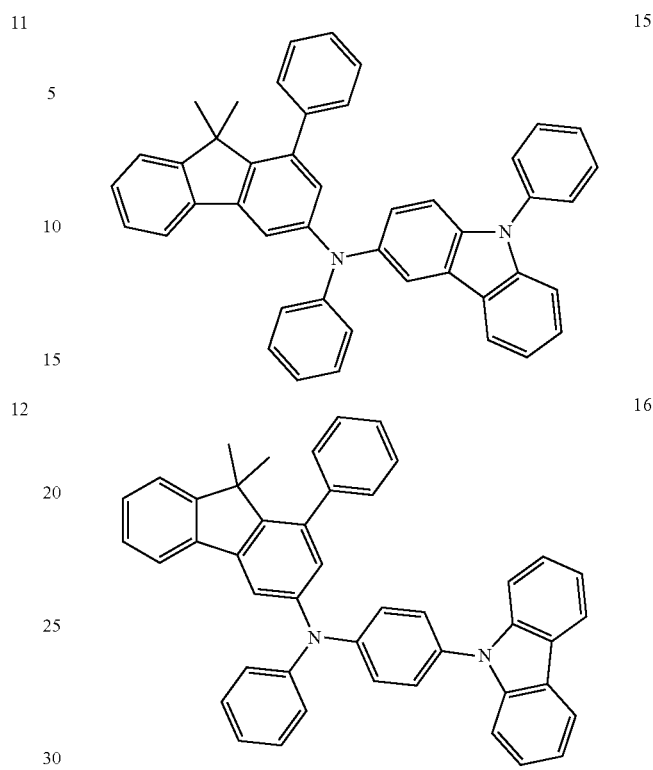
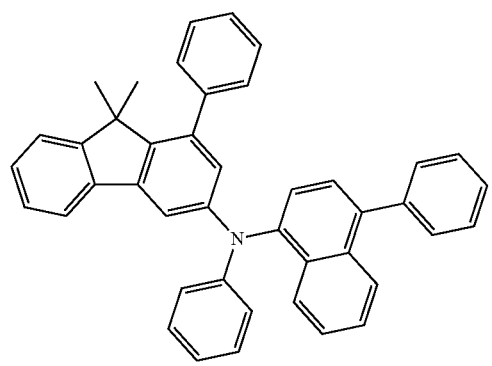
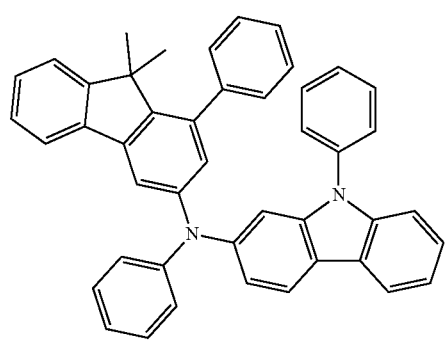

19
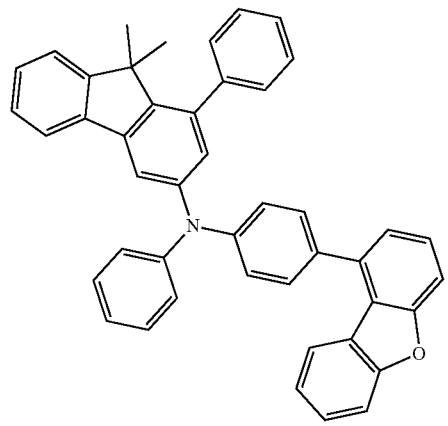
20
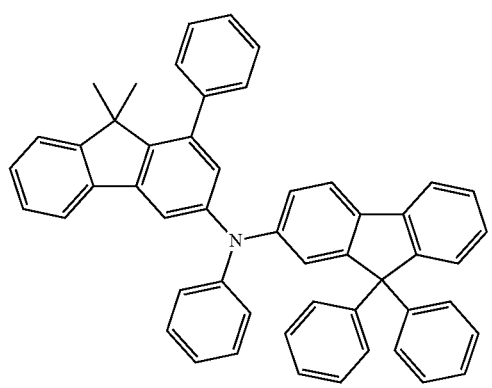
21
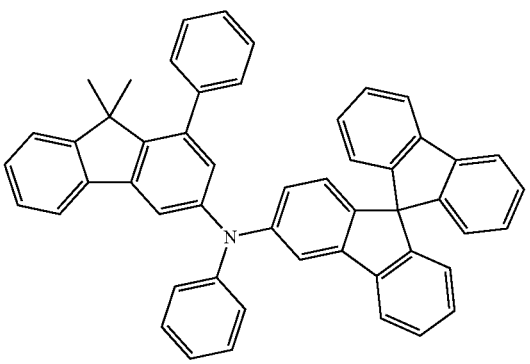
22
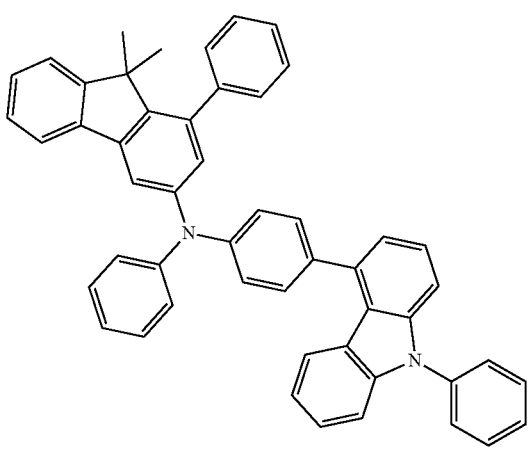
23
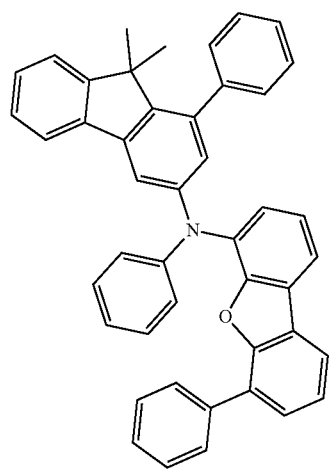
24
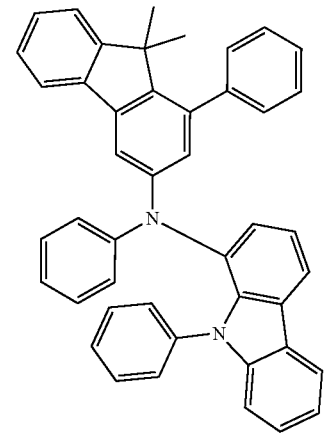
25
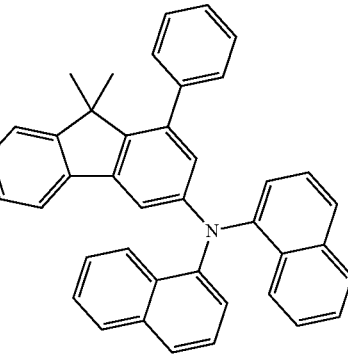
26
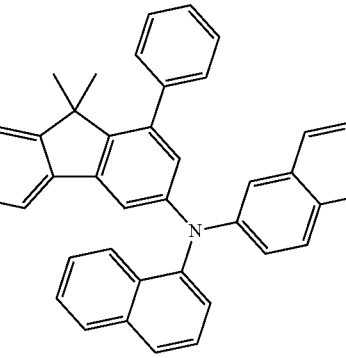

27
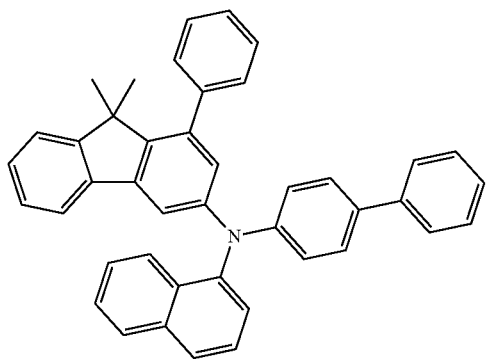
28
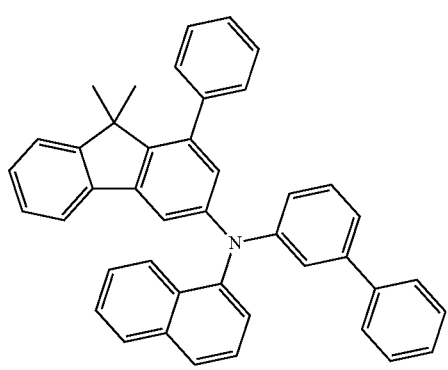
29
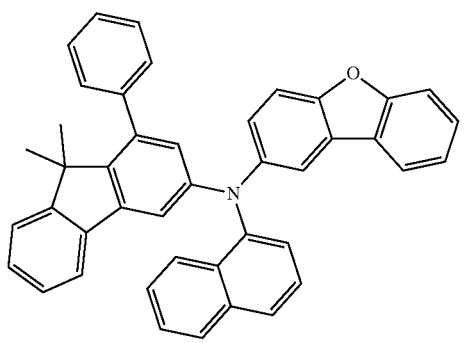
30
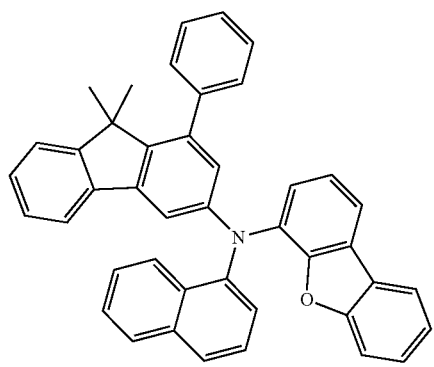
31
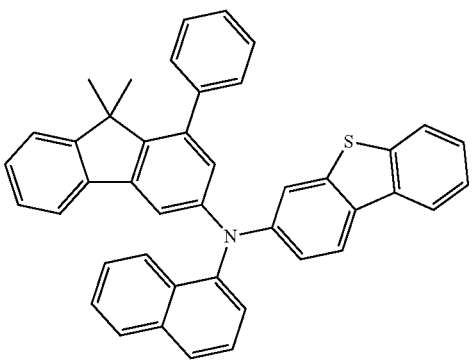
32
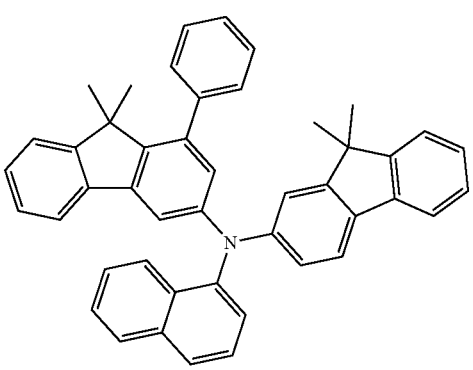
33
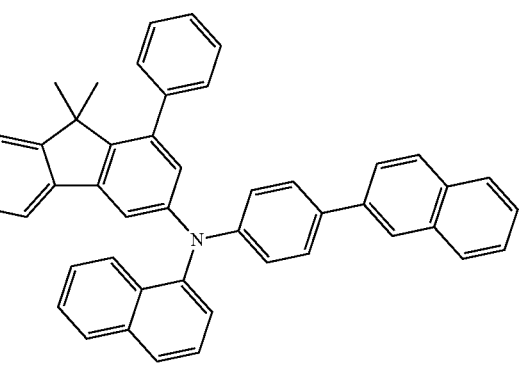
34
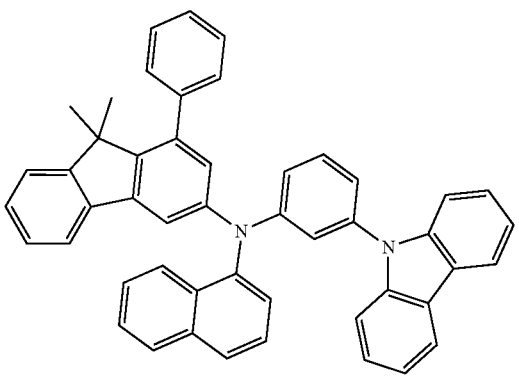

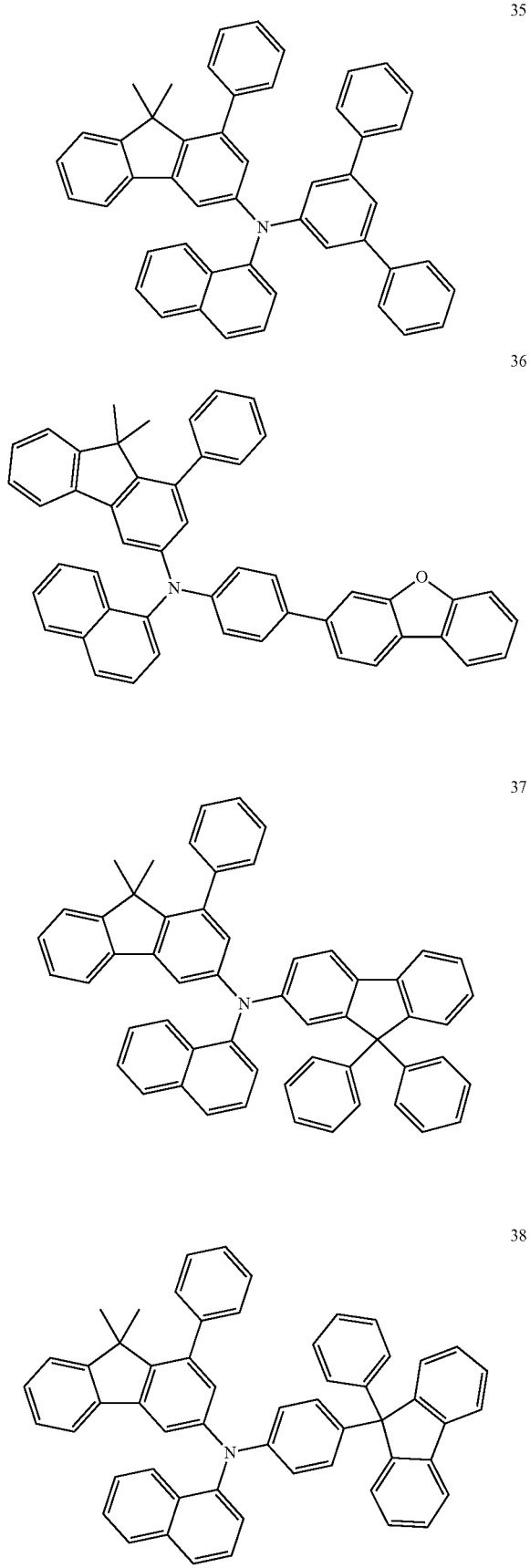
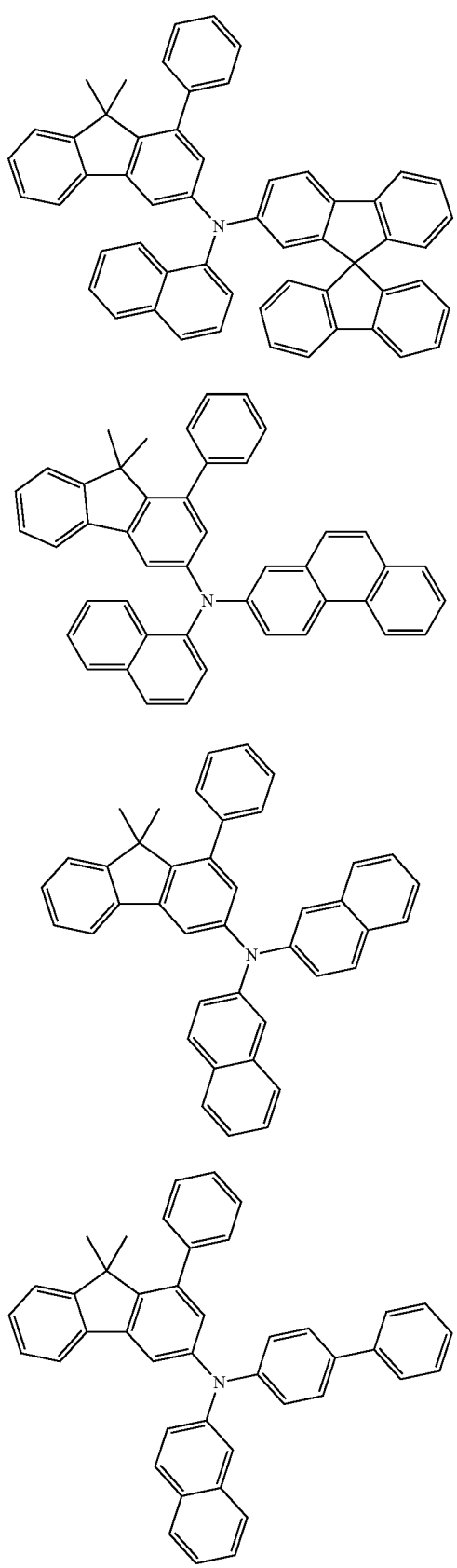

43
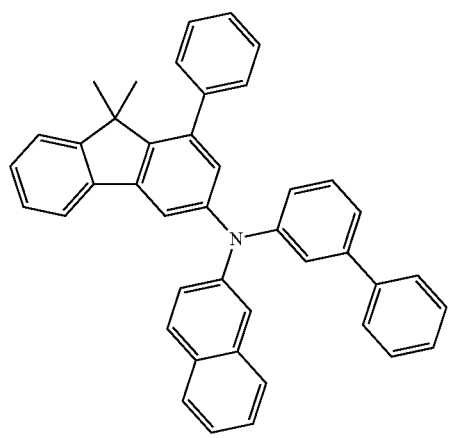
44
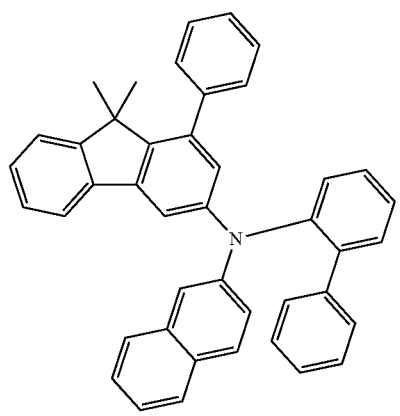
45
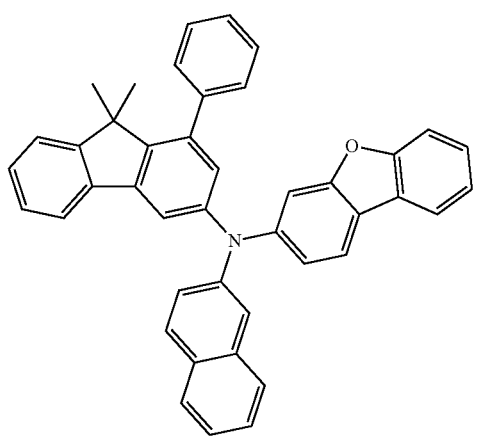
46
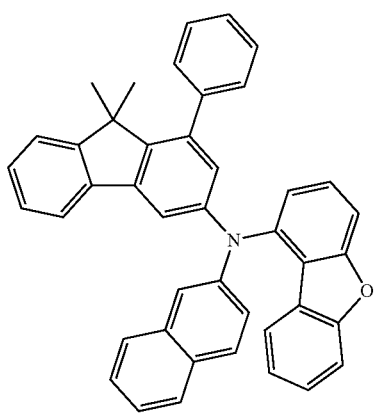
47
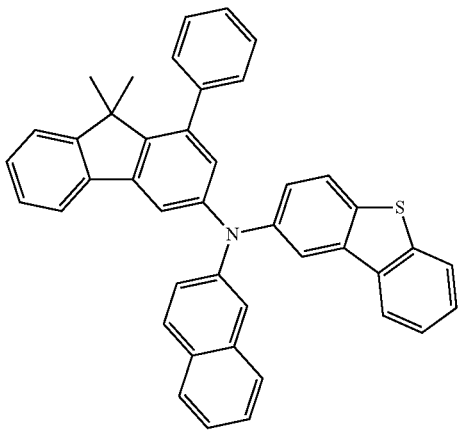
48
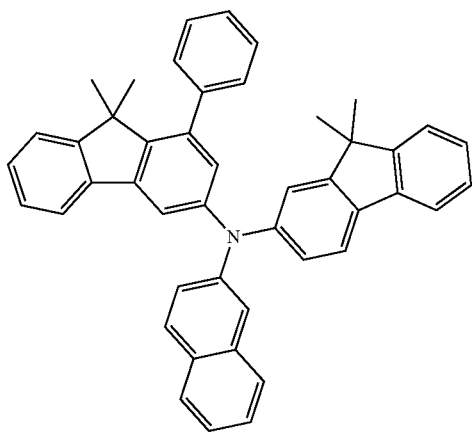

49
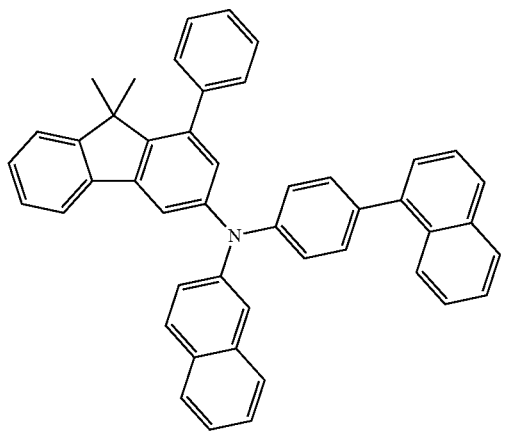
50
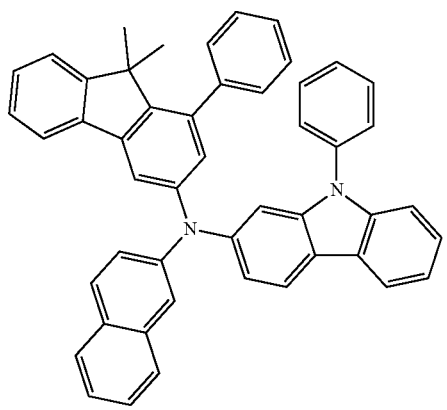
51
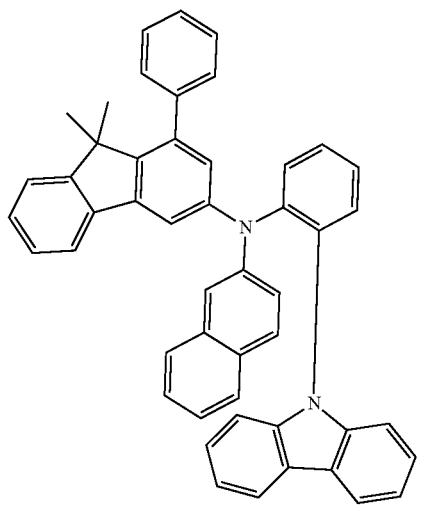
52
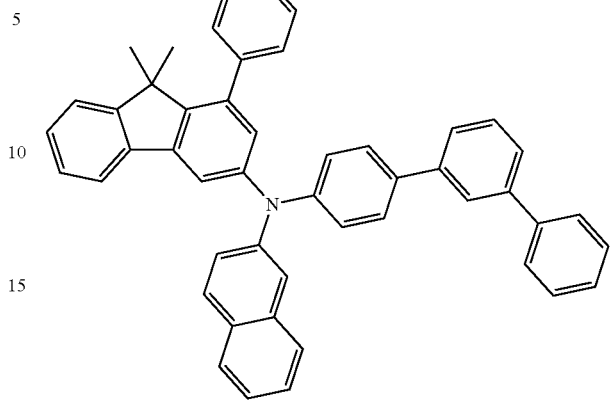
53
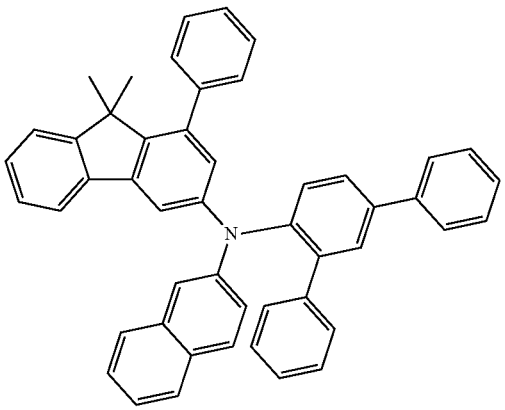
54
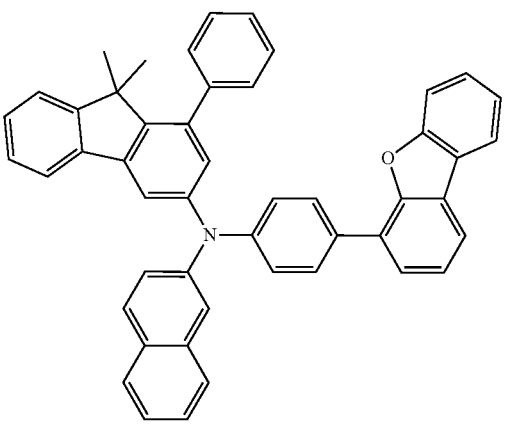

55
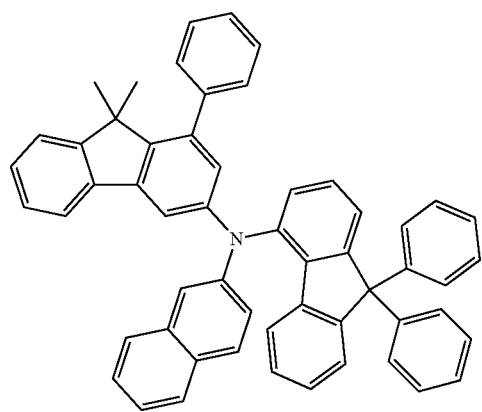
56
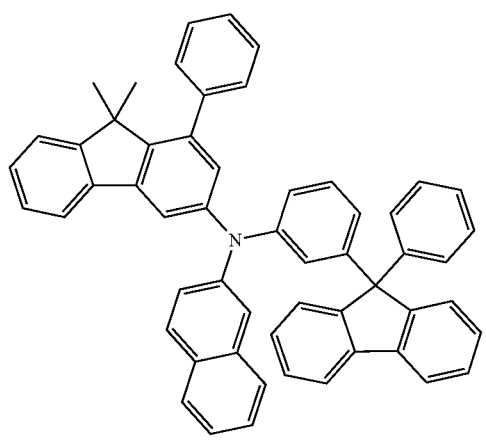
57
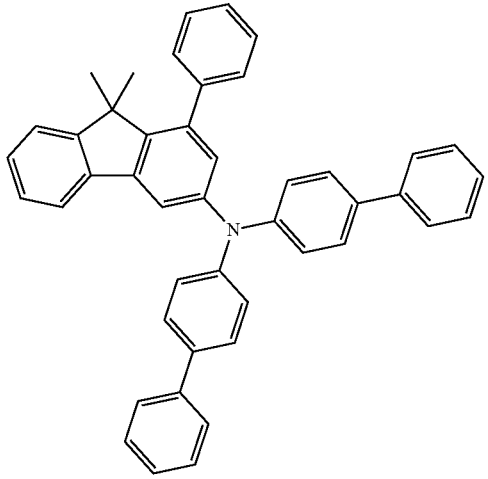
58
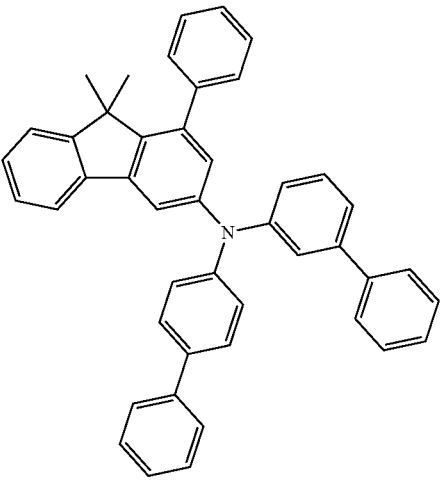
59
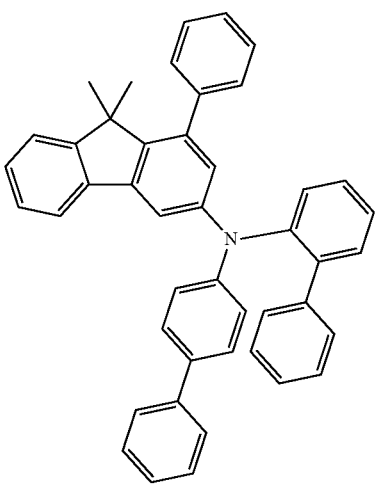
60
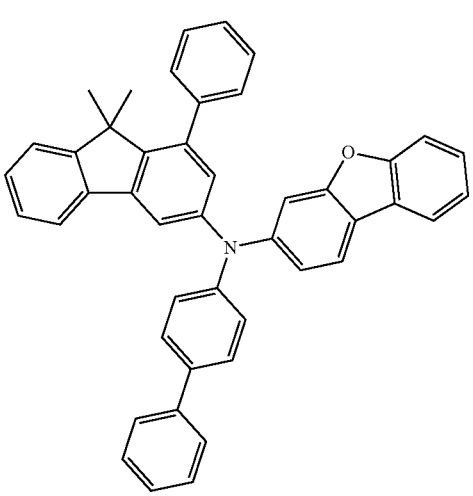

61
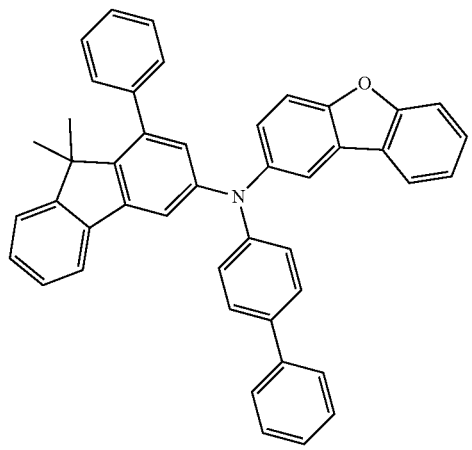
62
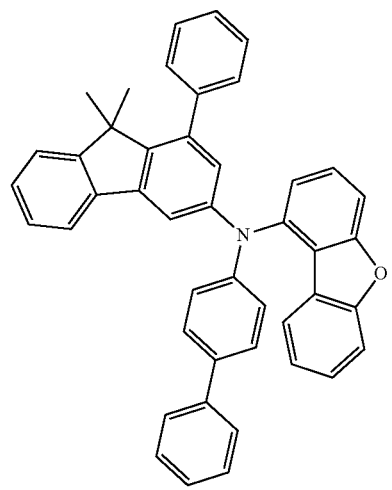
63
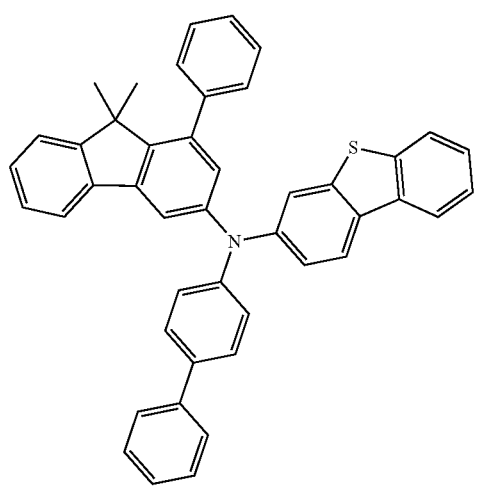
64
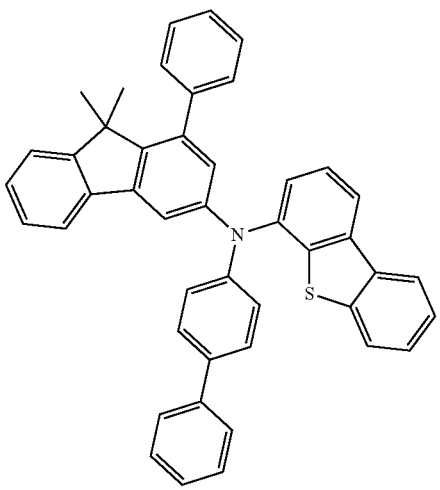
65
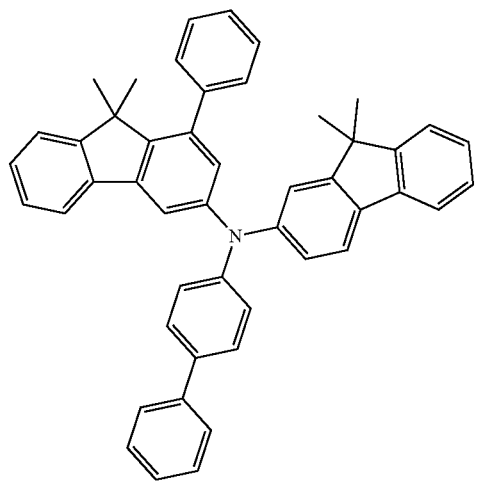
66
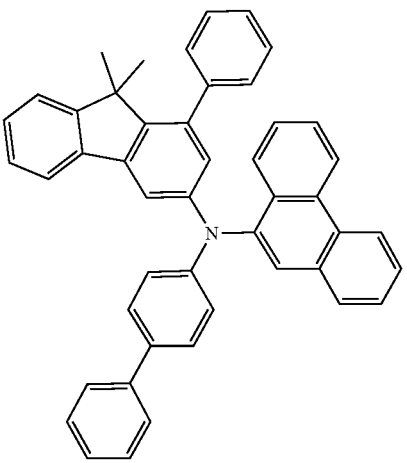

67
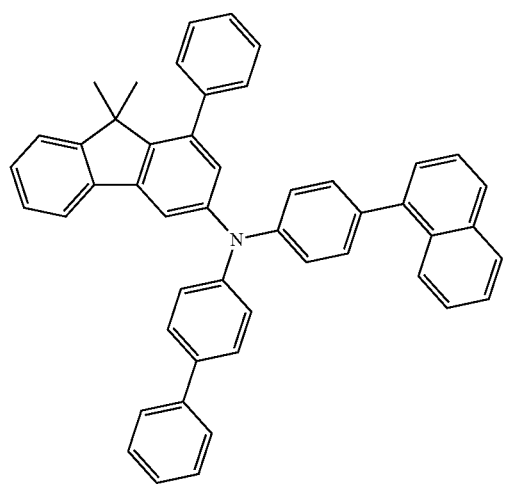
68
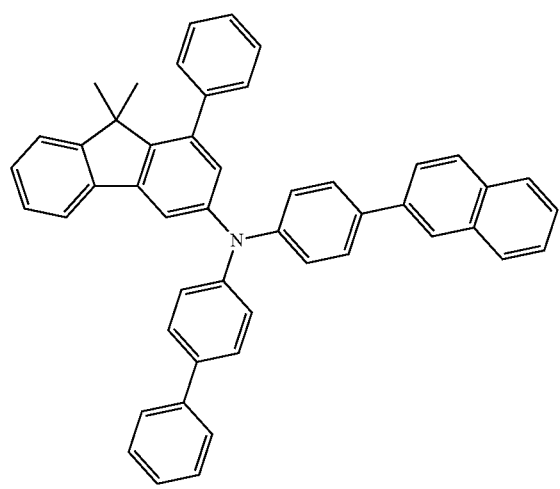
69
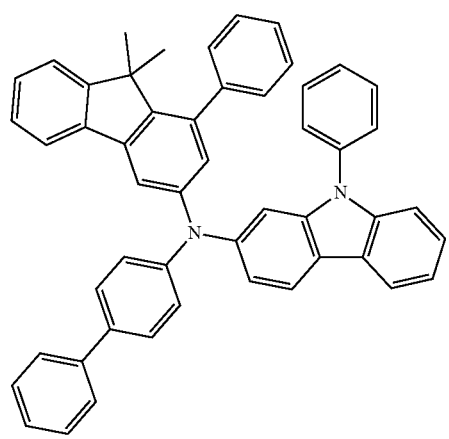
70
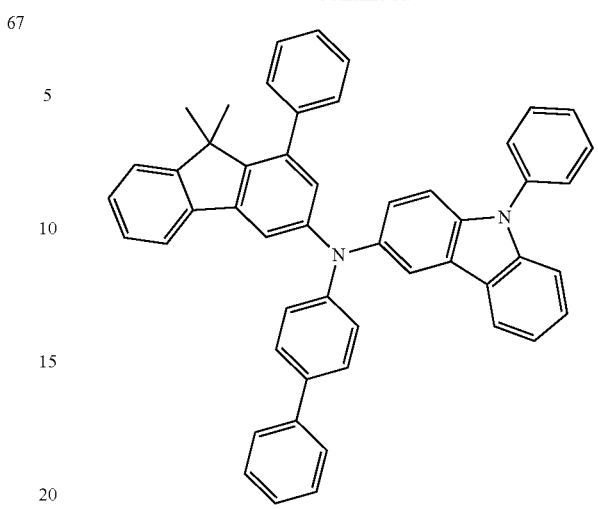
71
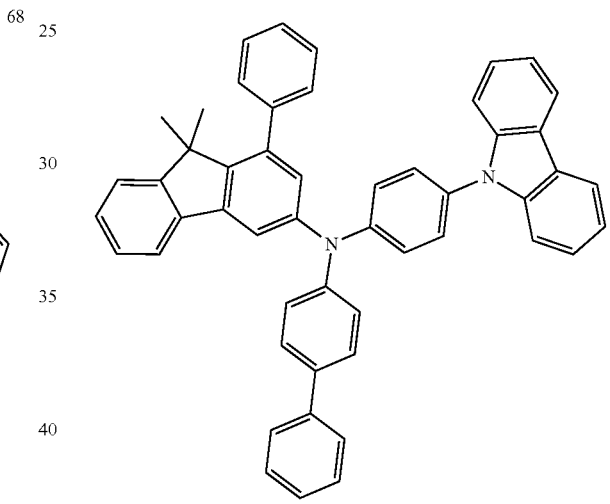
72
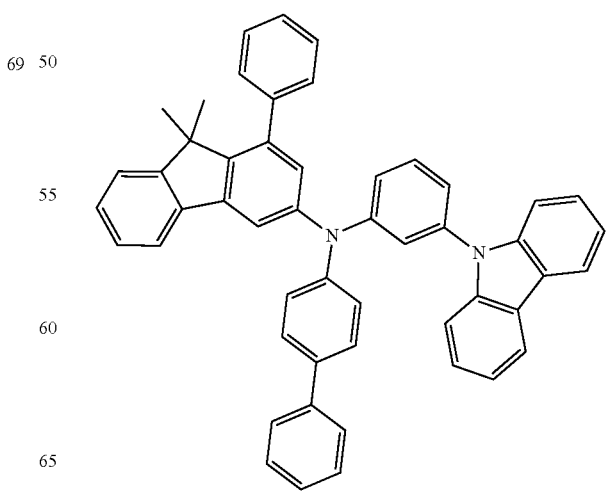

73
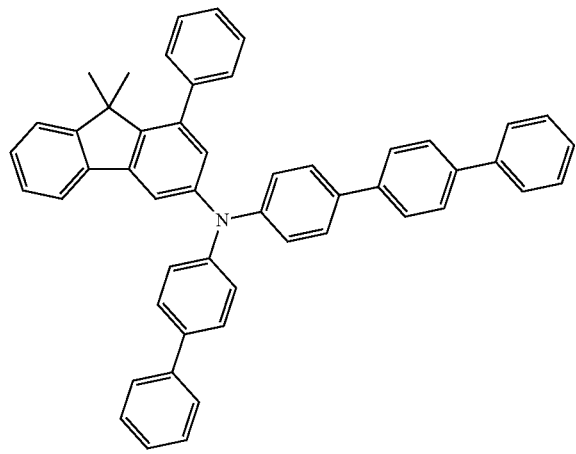
76
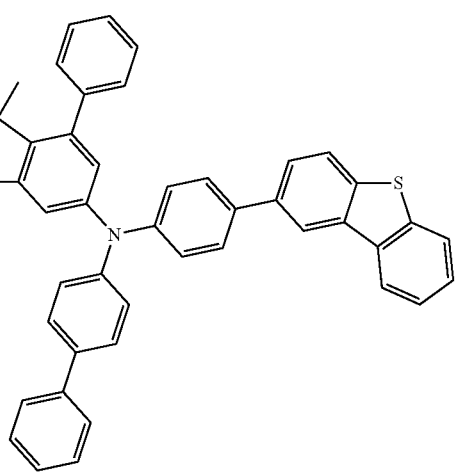
74
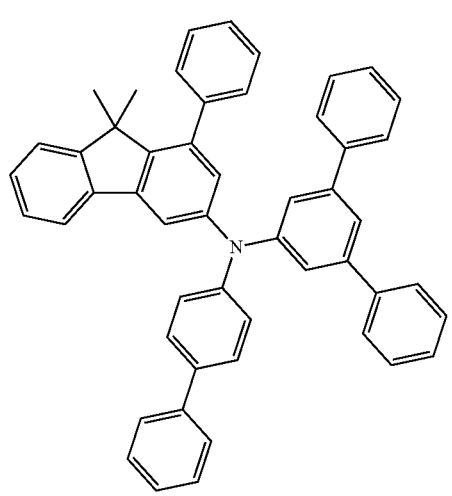
77
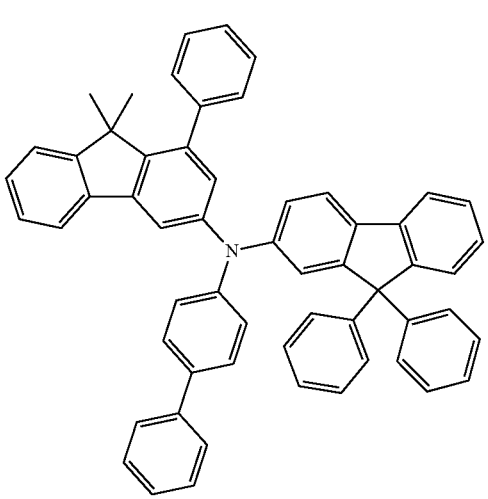
75
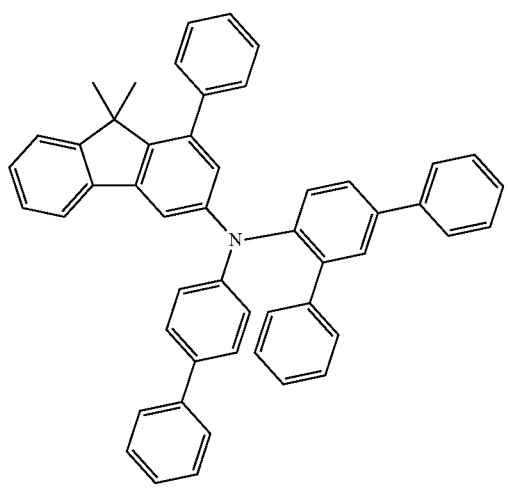
78
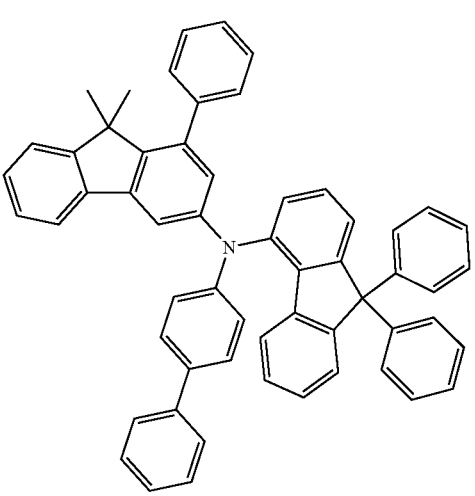

79
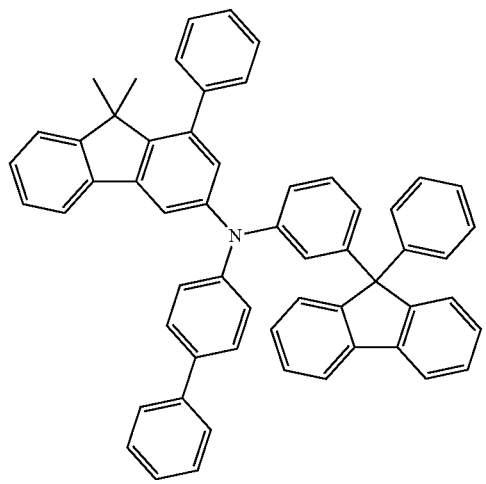
80
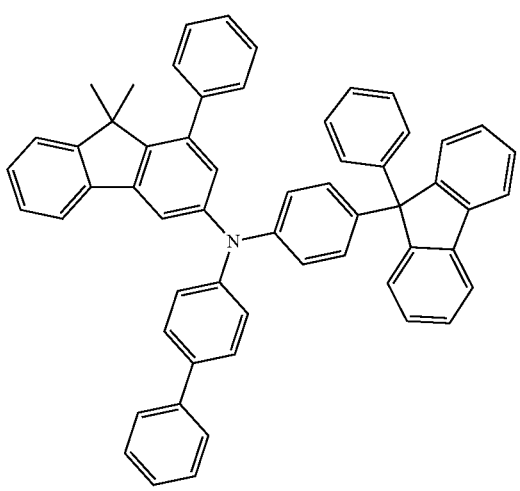
81
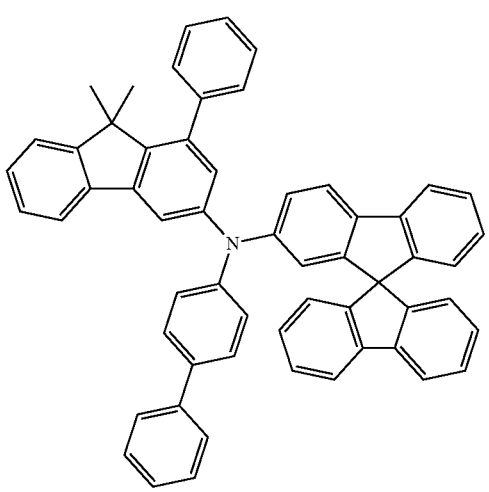
82
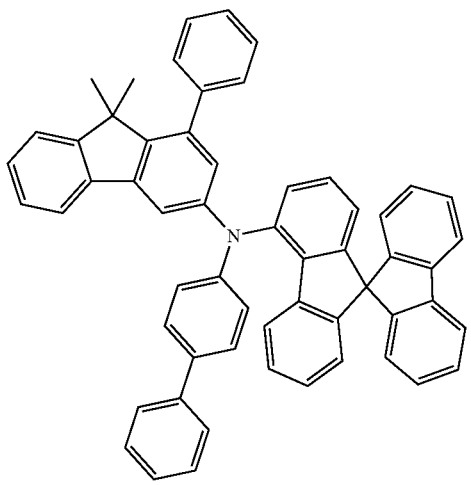
83
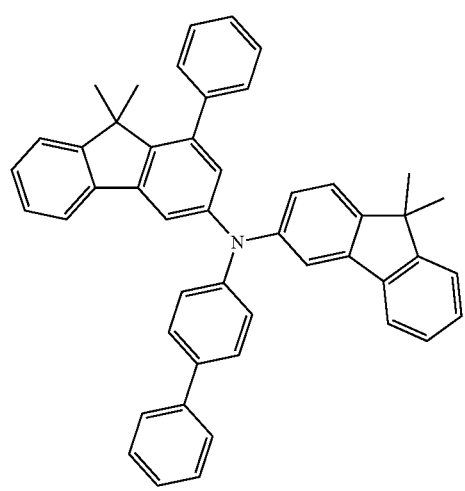
84
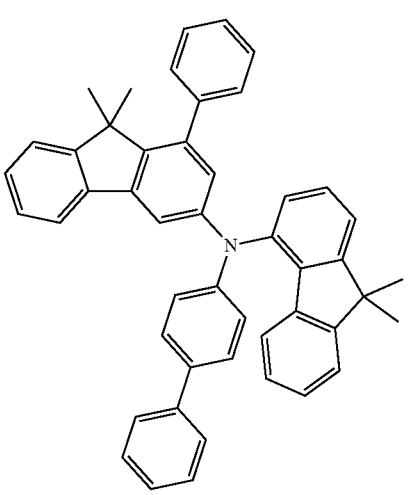

85
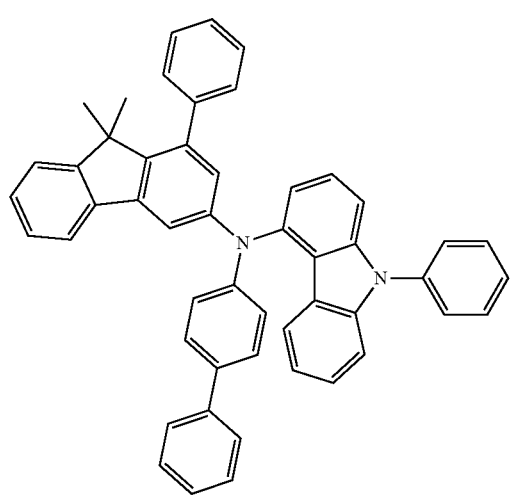
86
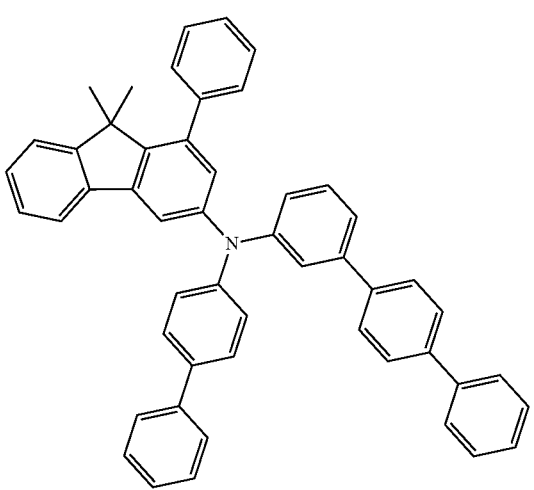
87
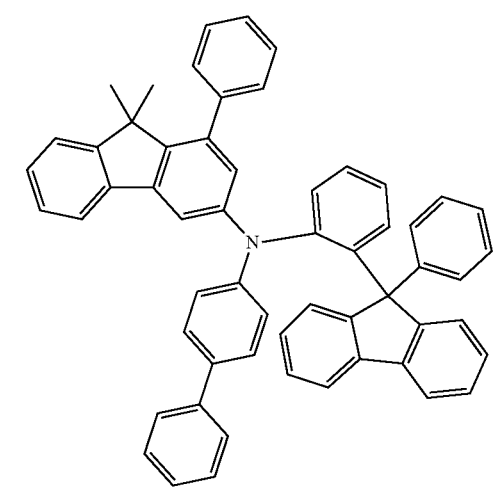
88
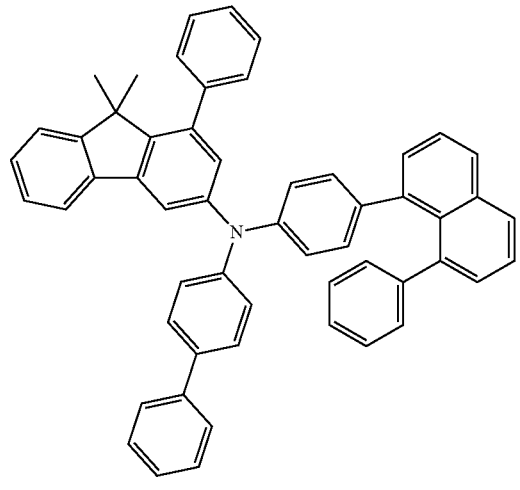
89
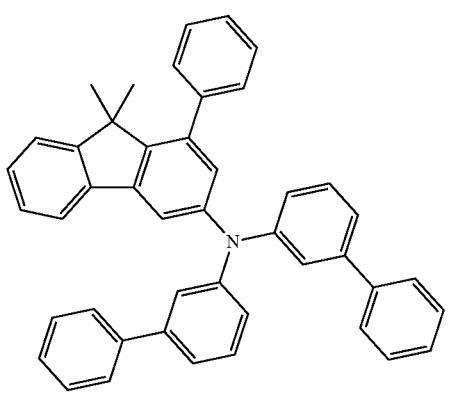
90
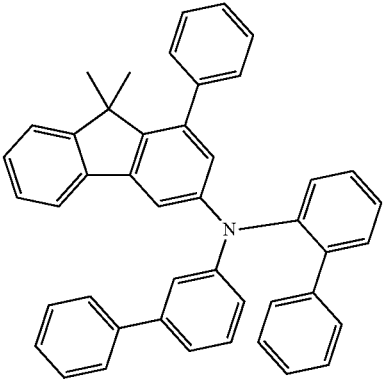
91
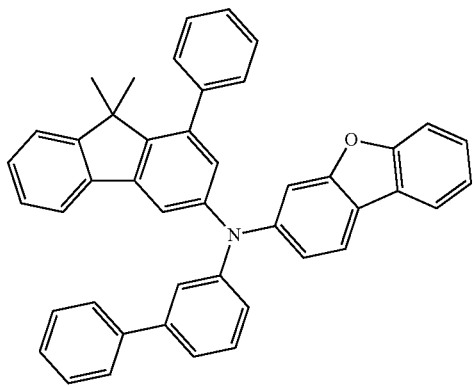

92
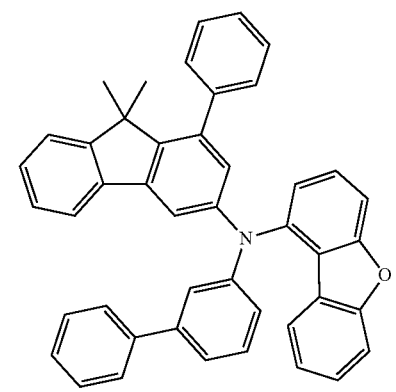
96
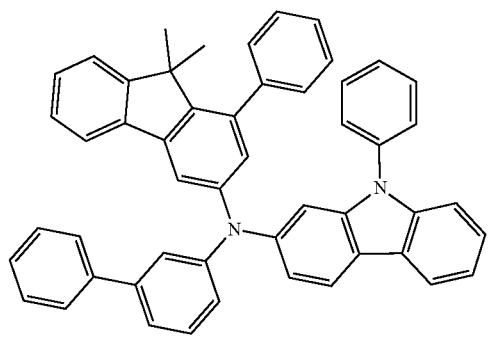
93
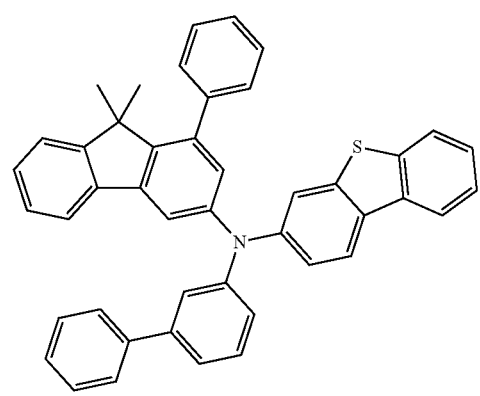
97
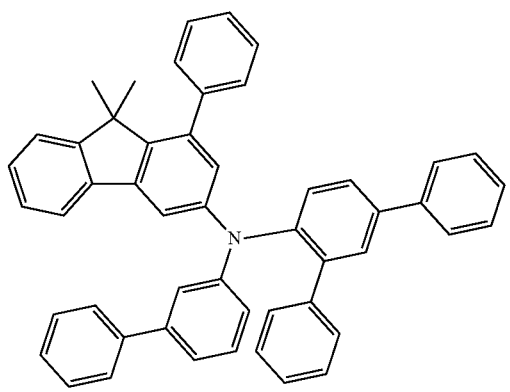
94
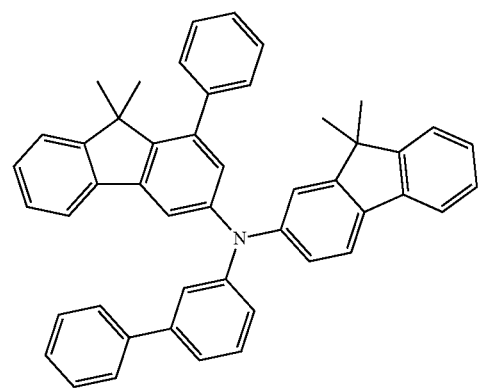
98
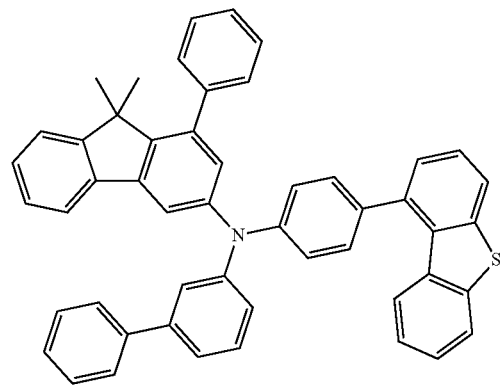
95
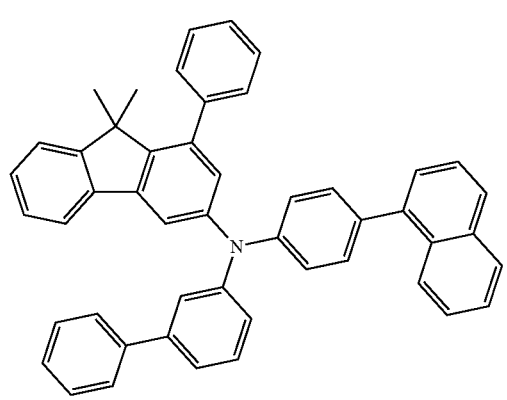
99
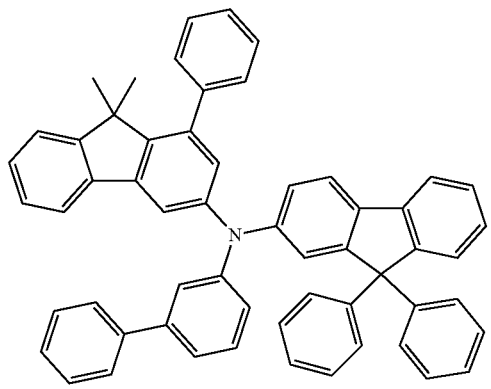

-continued
100
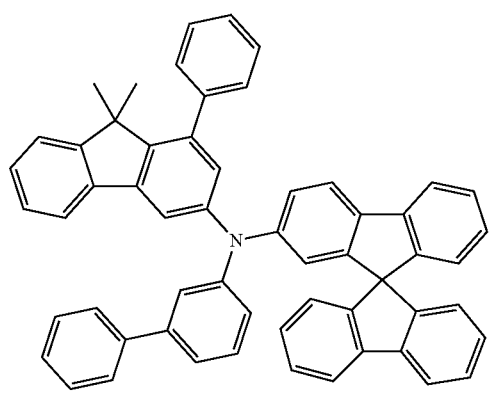
101
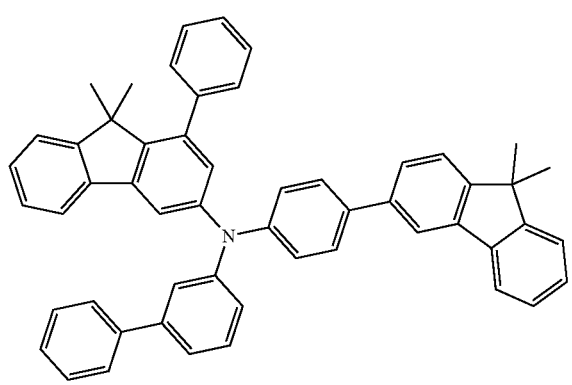
102
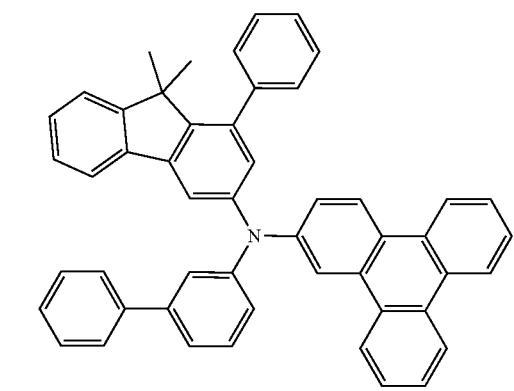
103
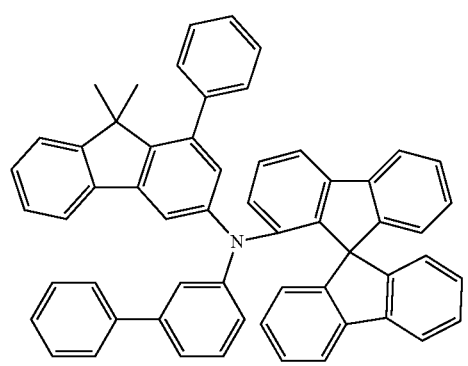
-continued
104
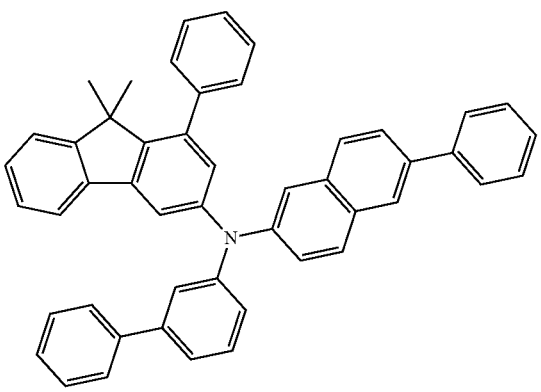
105
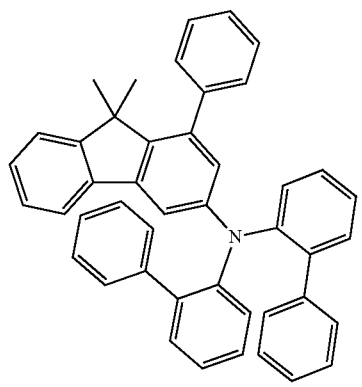
106
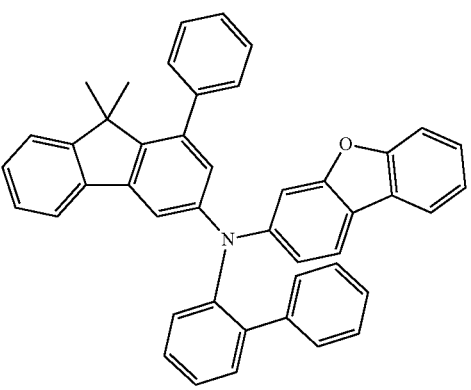
107
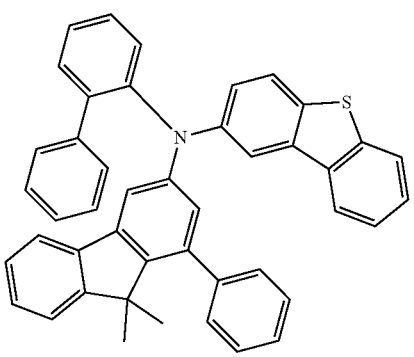

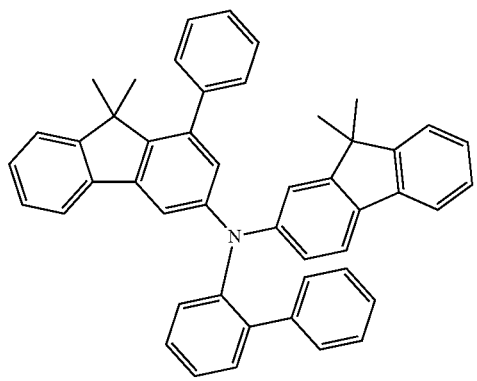
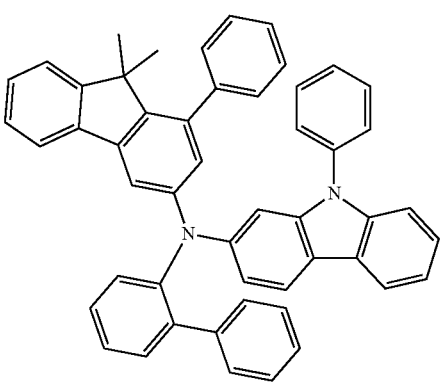

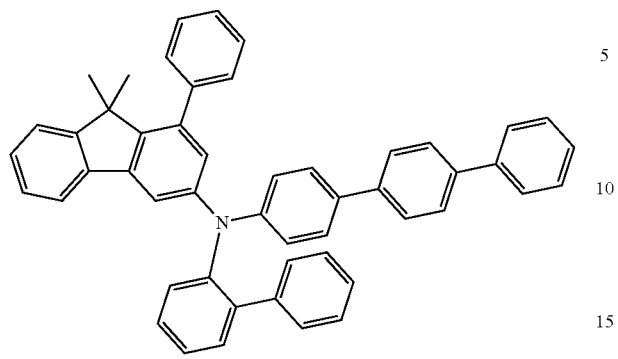
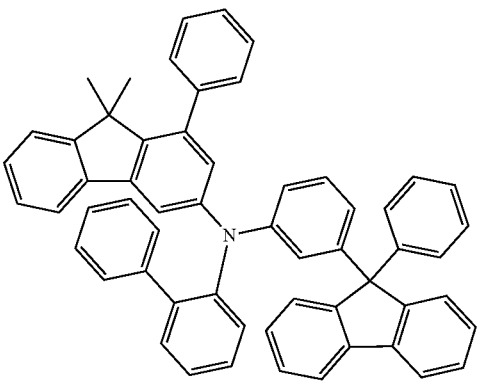
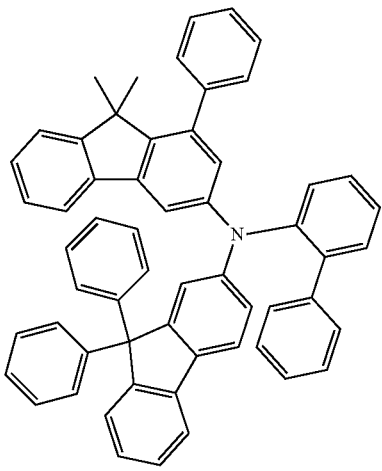
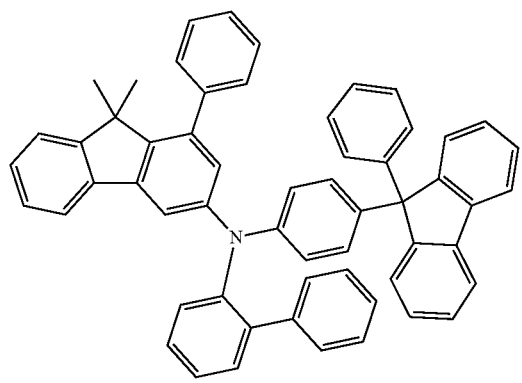

124
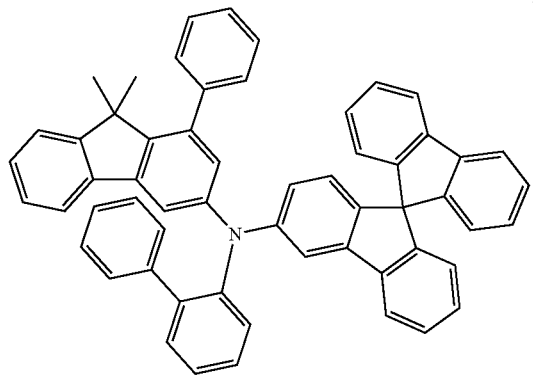
125
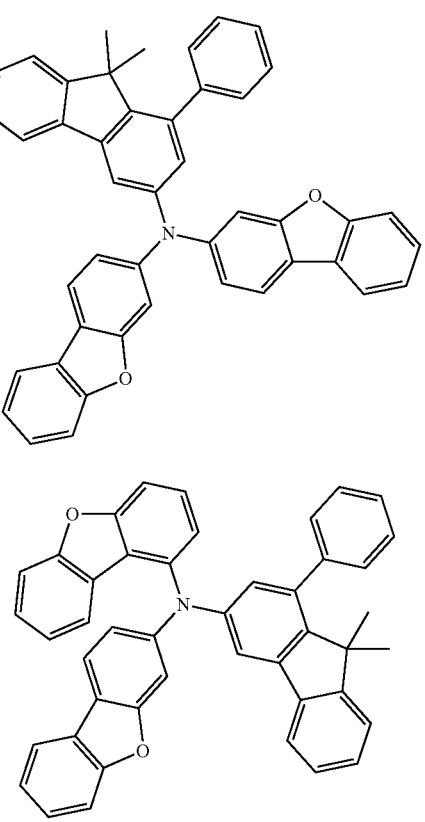
126
127
128
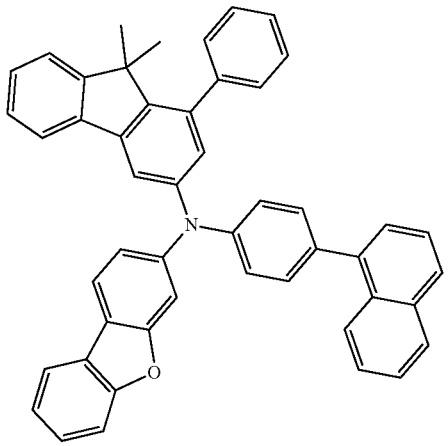
129
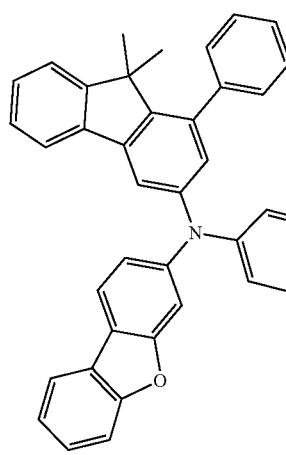
130
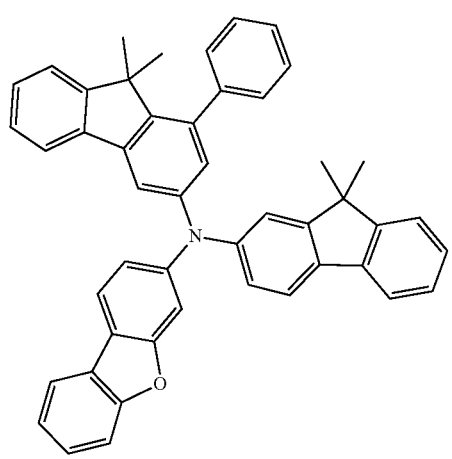

131
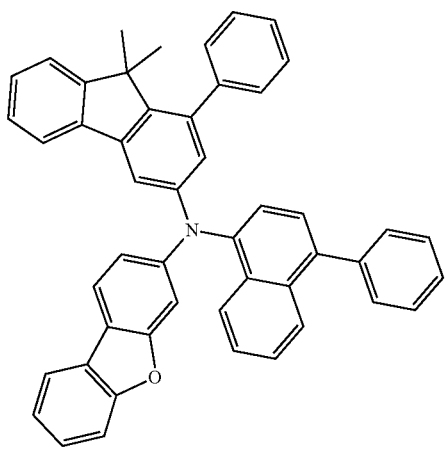
132
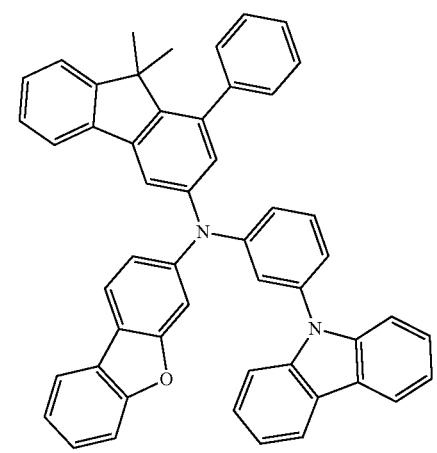
133
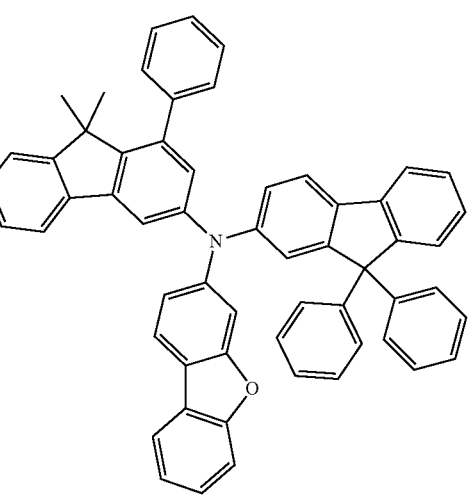
134
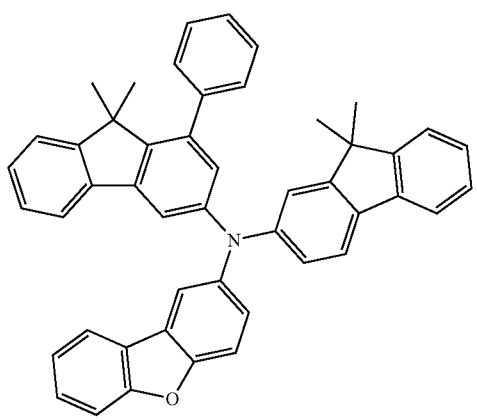
135
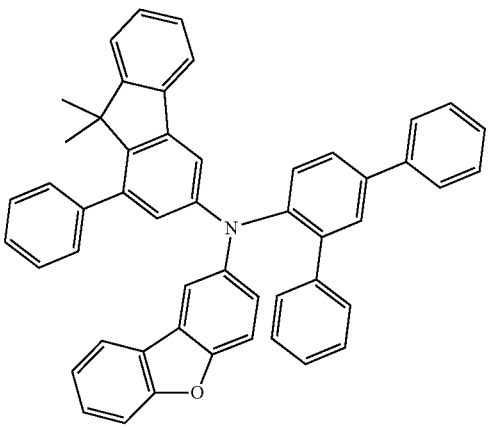
136
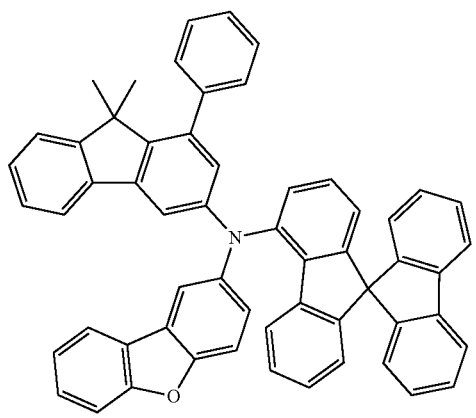
137
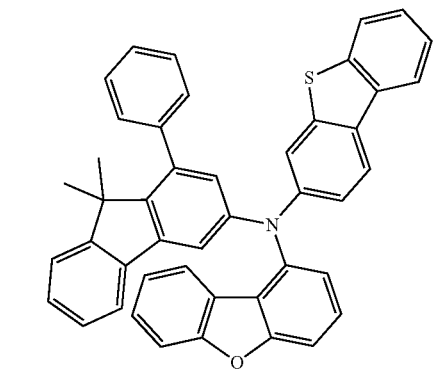

-continued
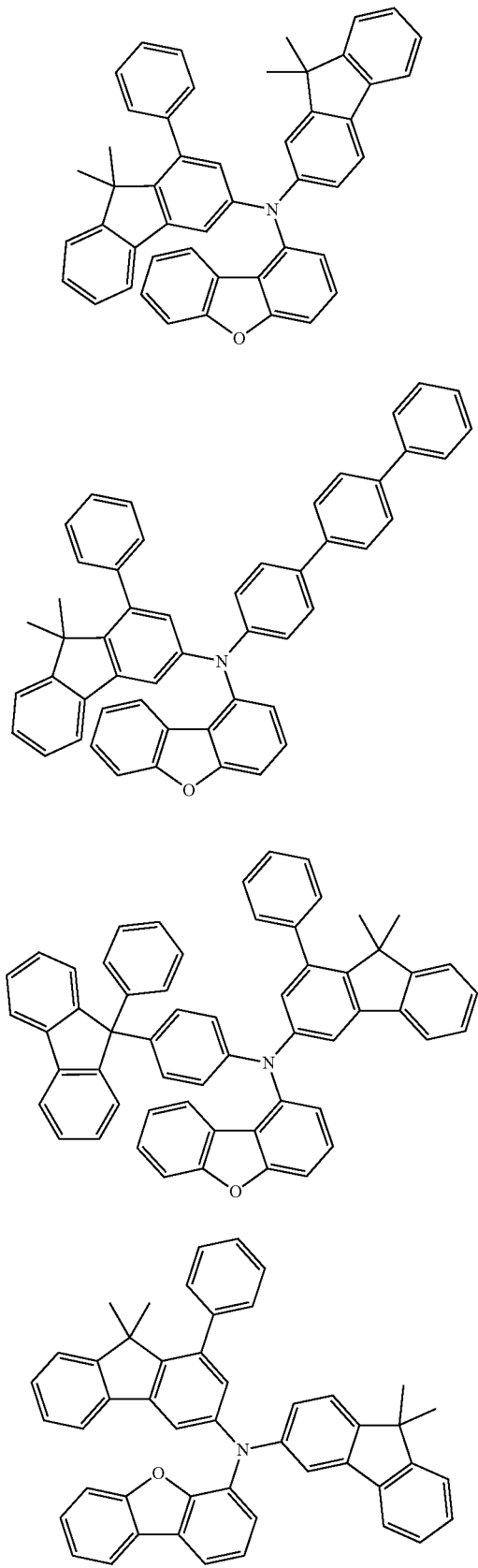
-continued
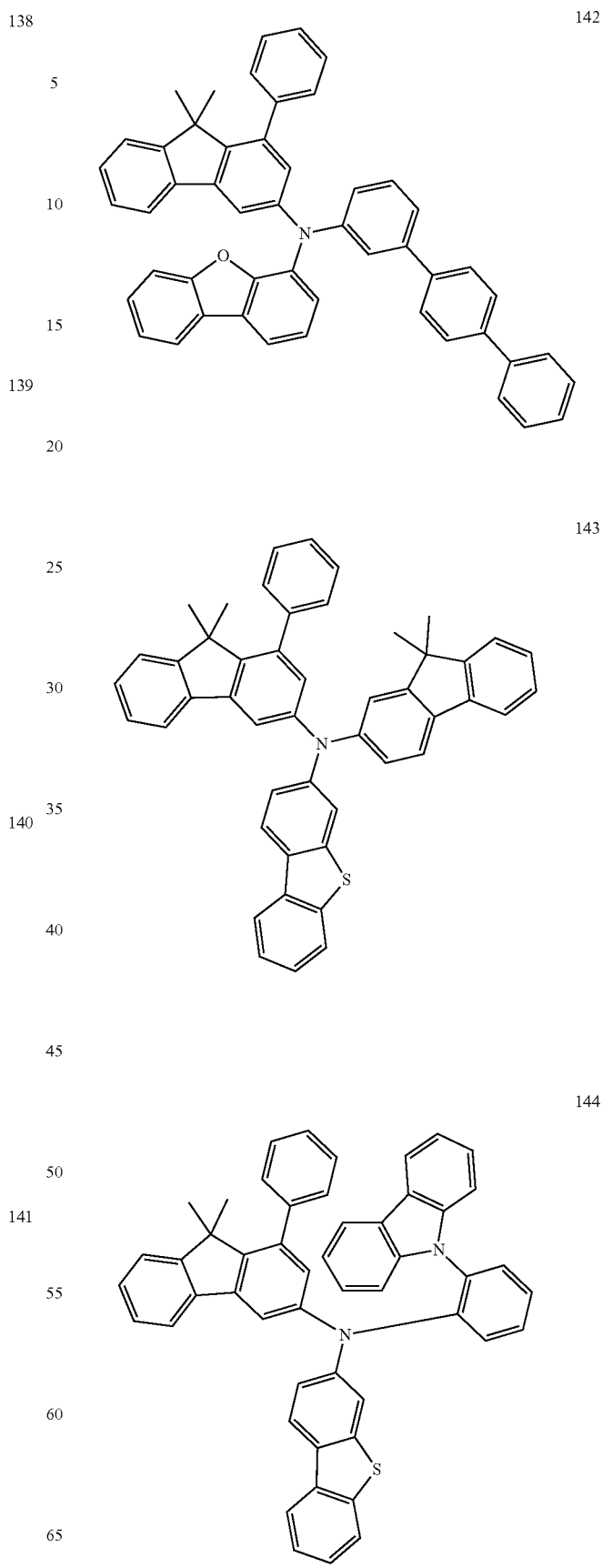

145
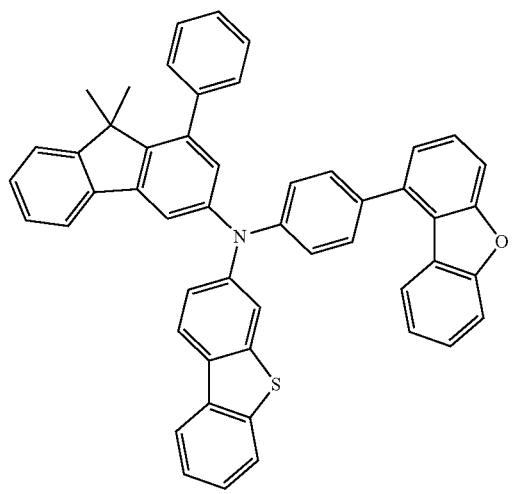
146
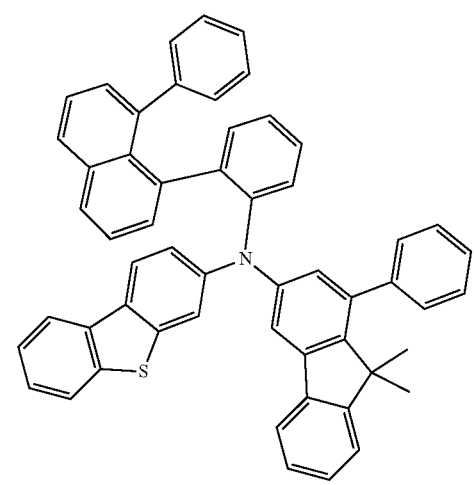
147
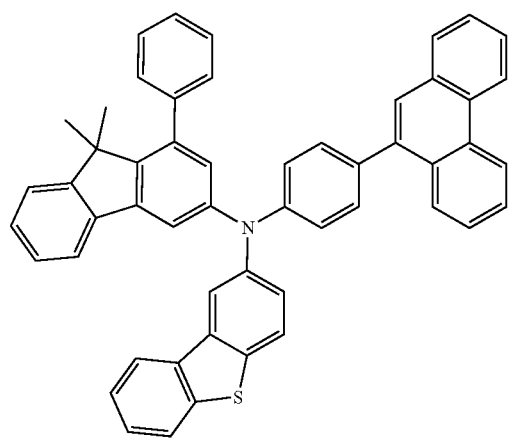
148
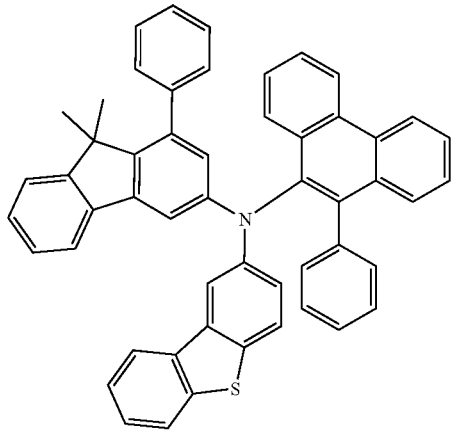
149
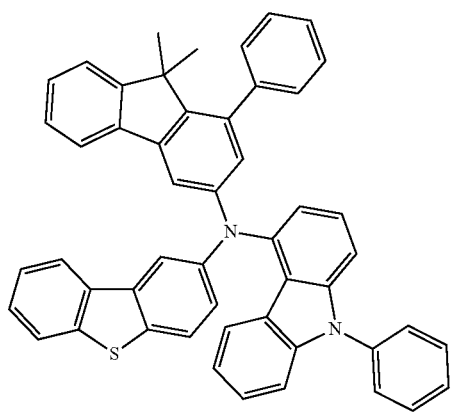
150
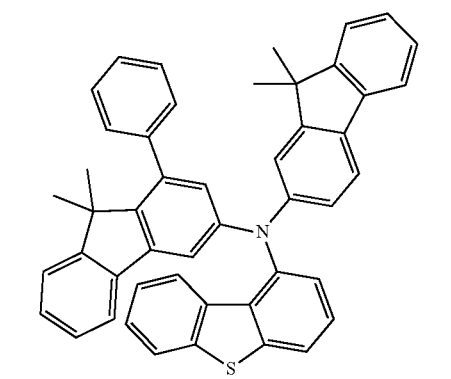
151
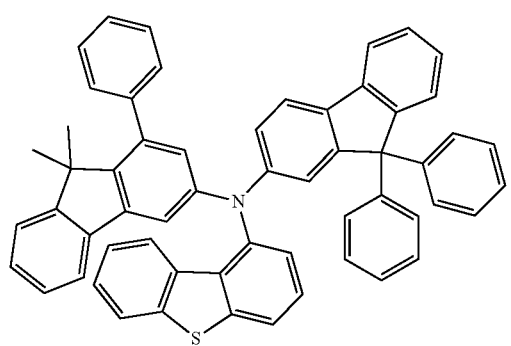

152
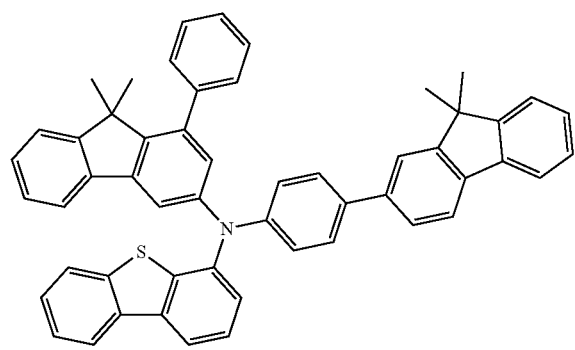
155
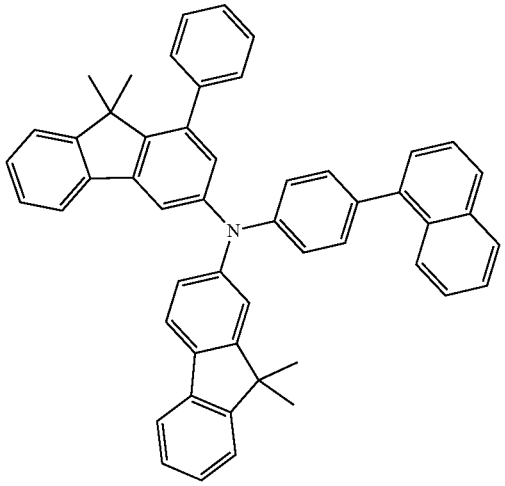
153
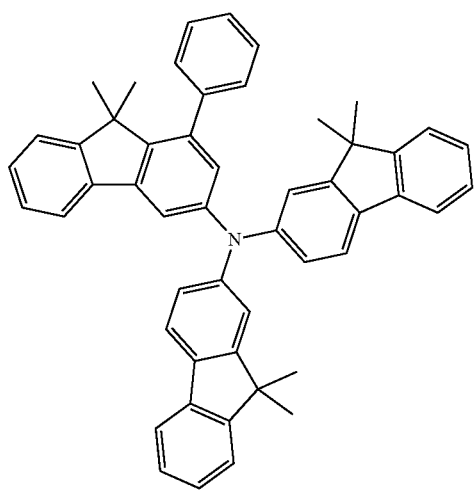
156
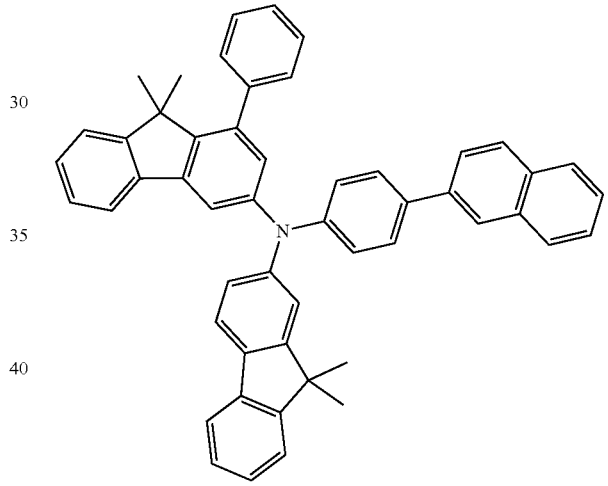
154
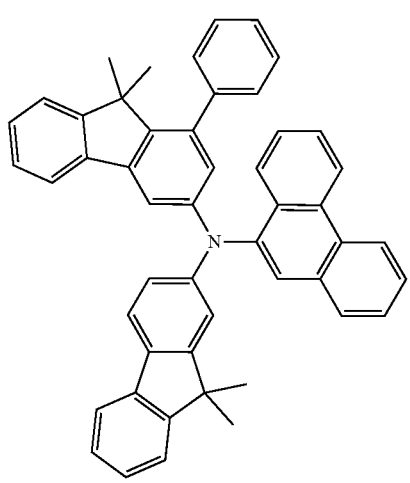
157
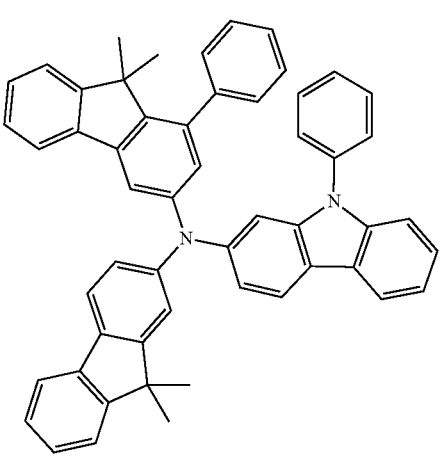

158
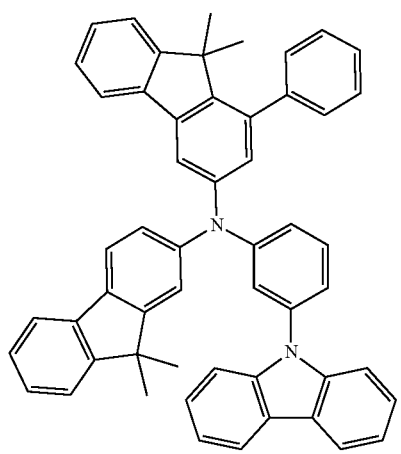
159
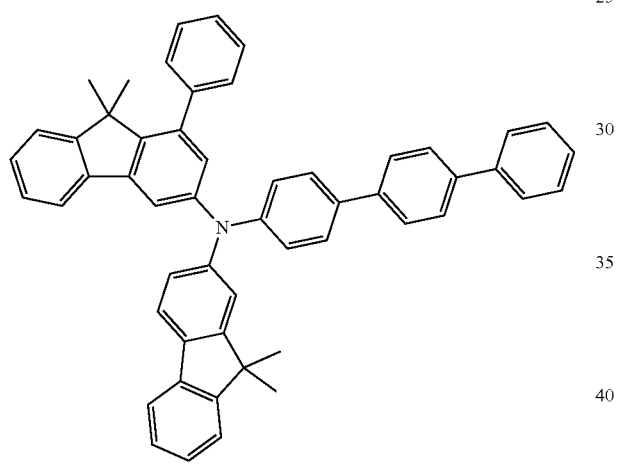
160
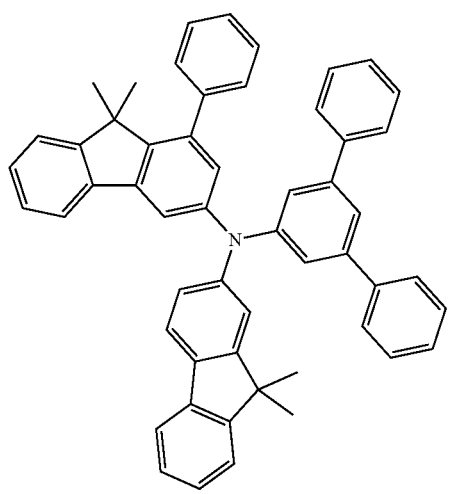
161
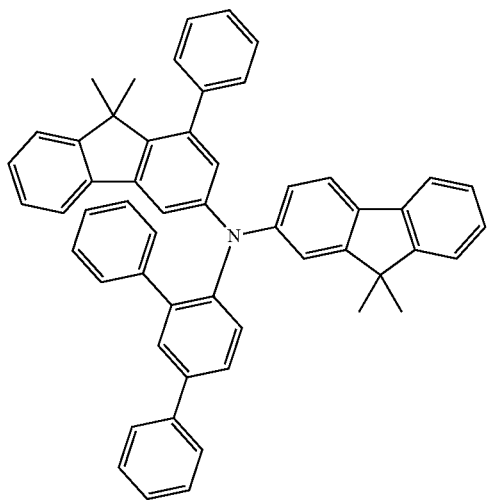
162
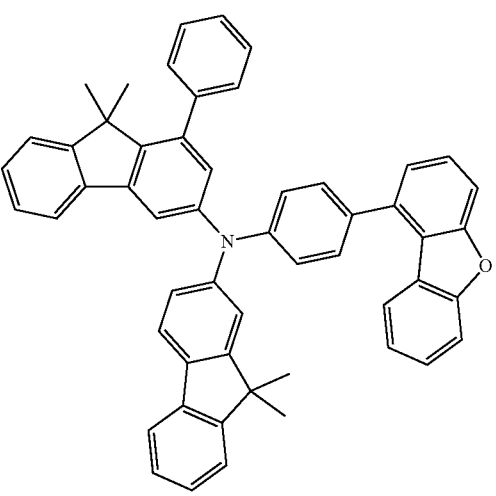
163
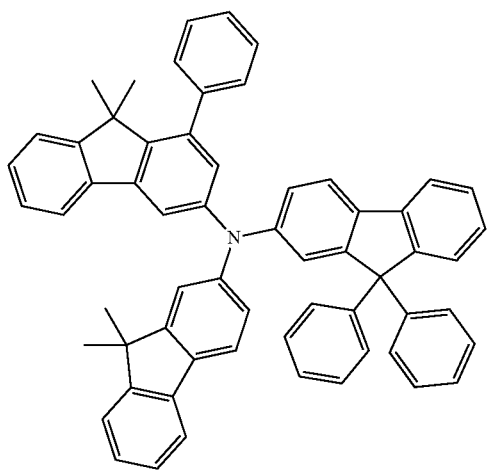

164
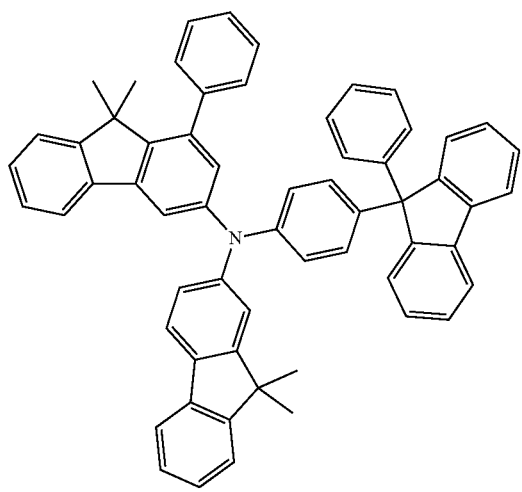
165
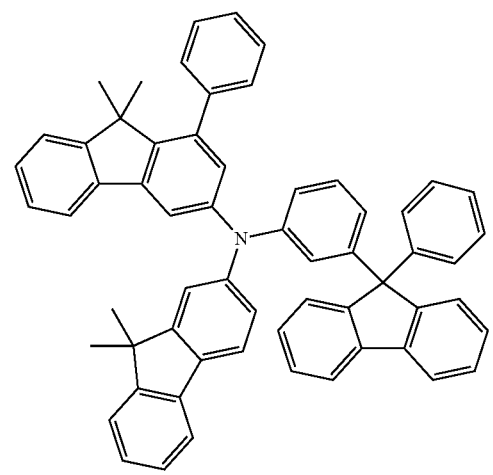
166
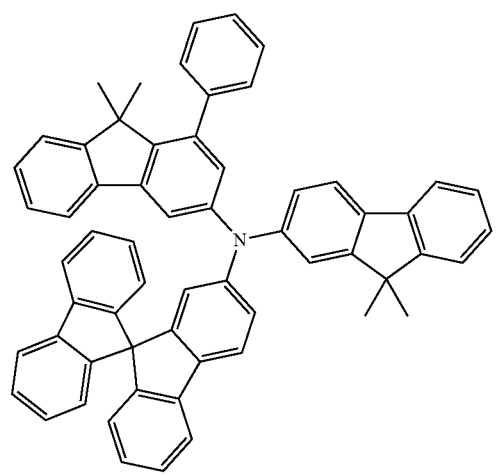
167
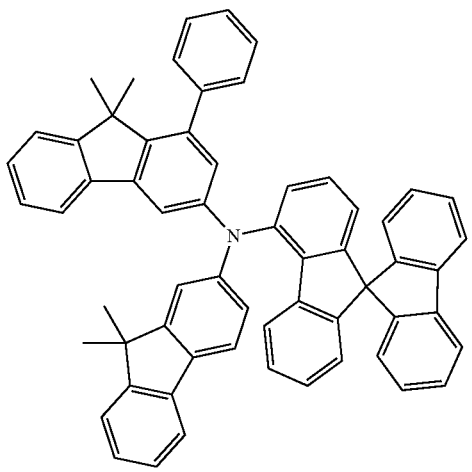
168
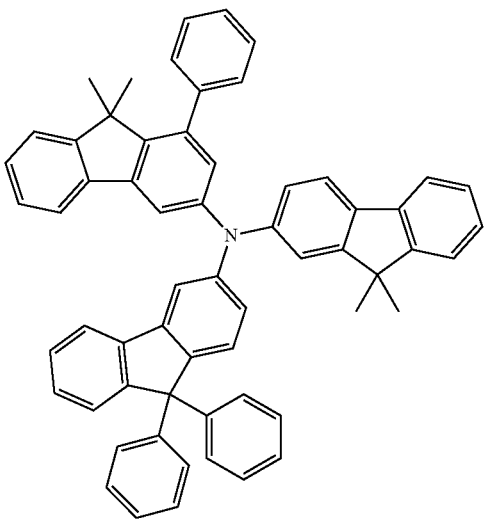
169
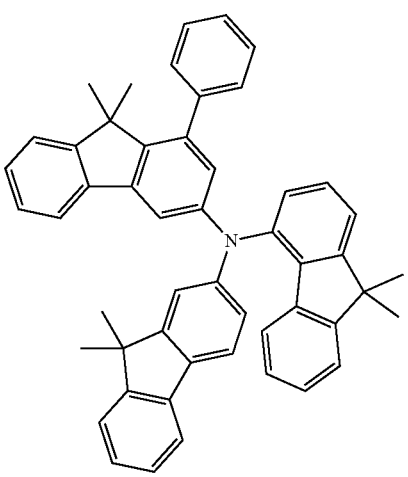

170
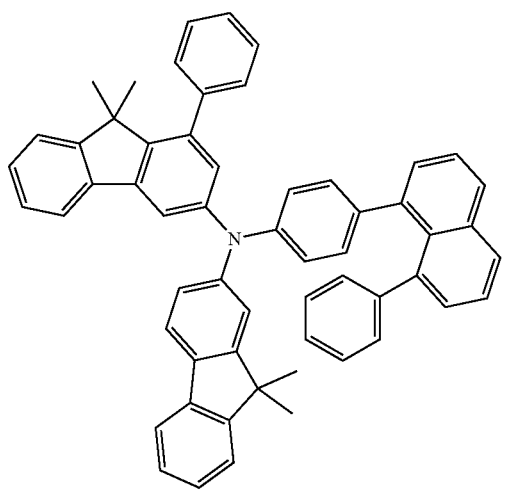
171
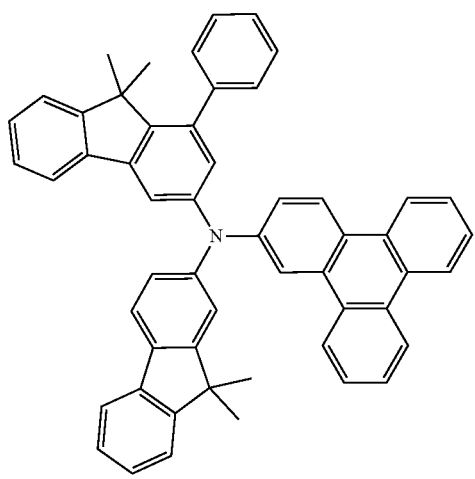
172
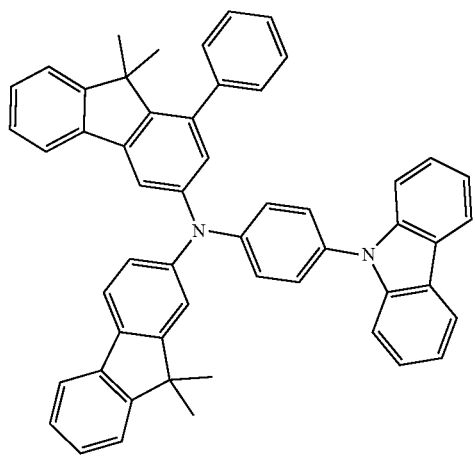
173
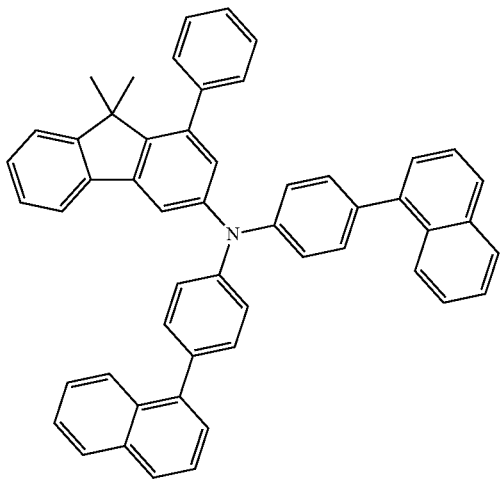
174
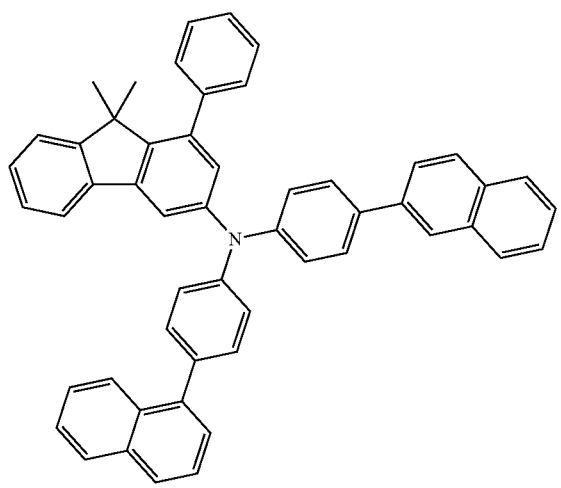
175
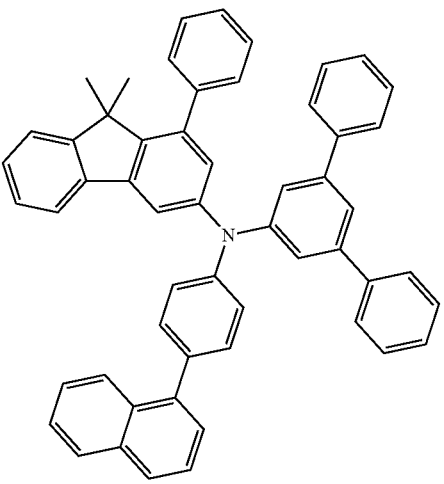

-continued
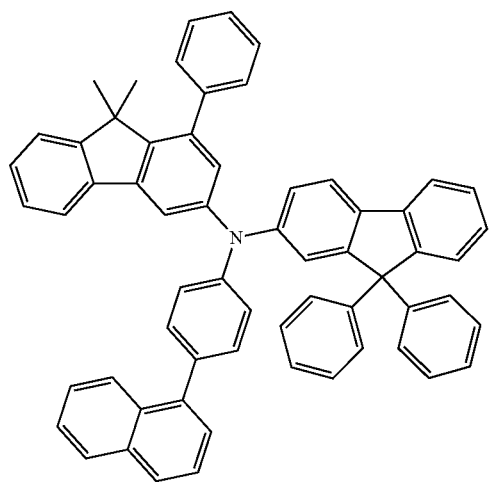
176
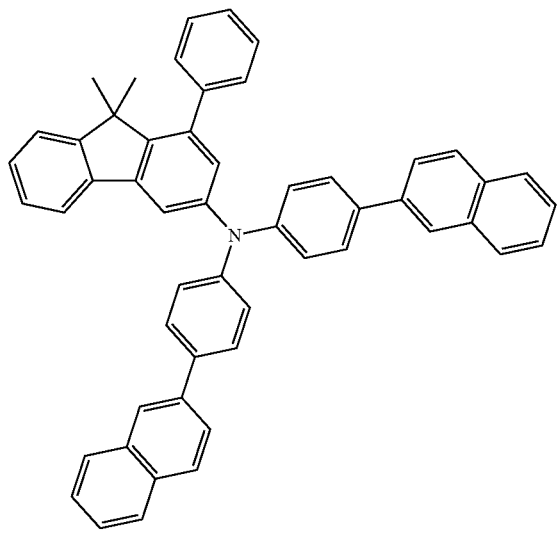
177
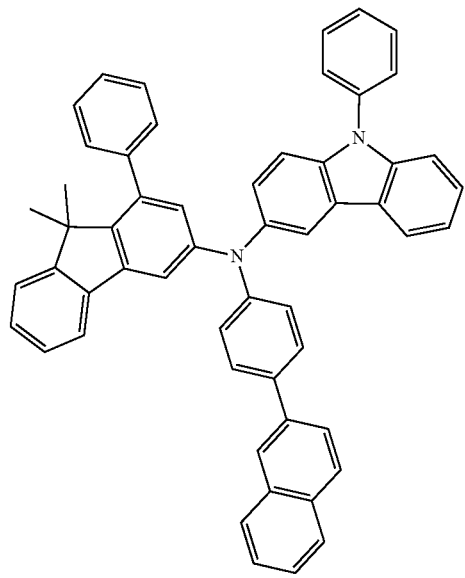
178
-continued
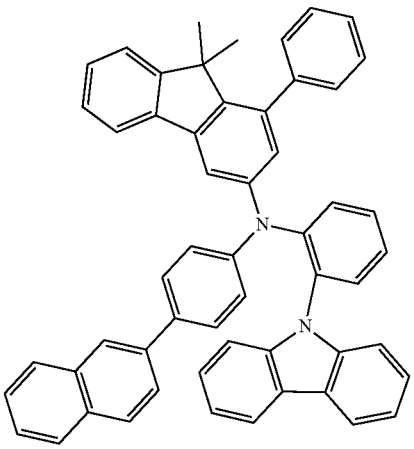
179
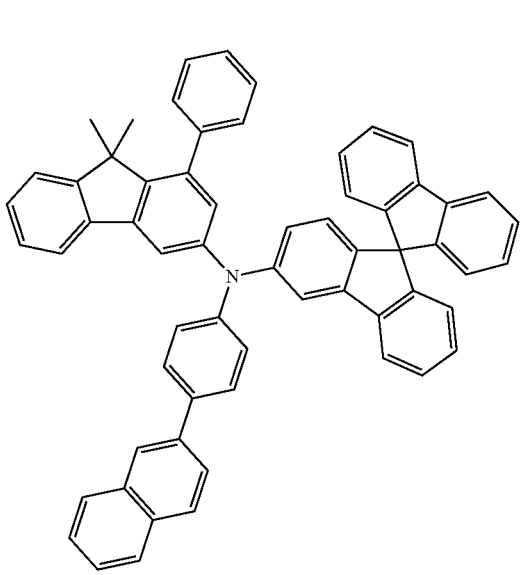
180
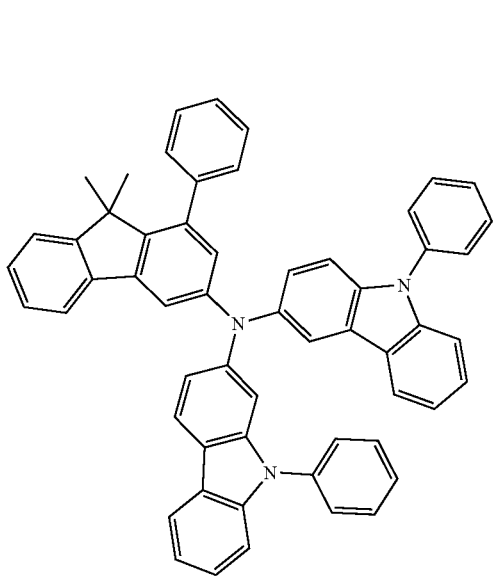
181

75
-continued
182
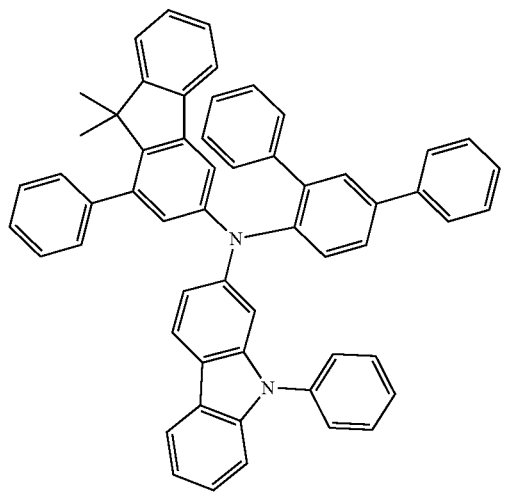
183
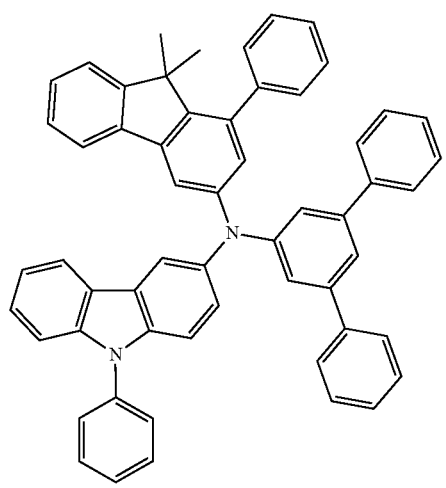
184
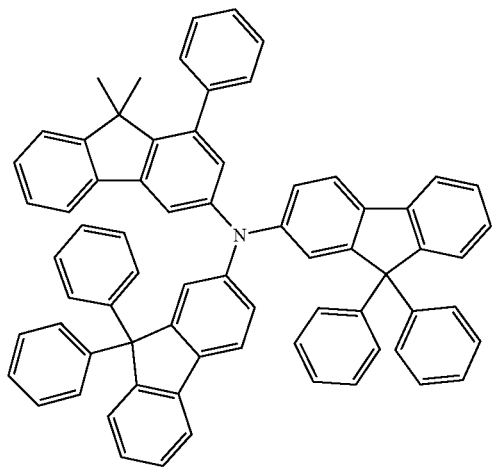
76
-continued
185
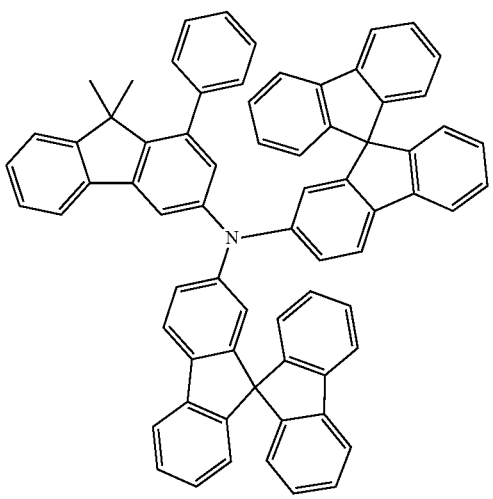
186
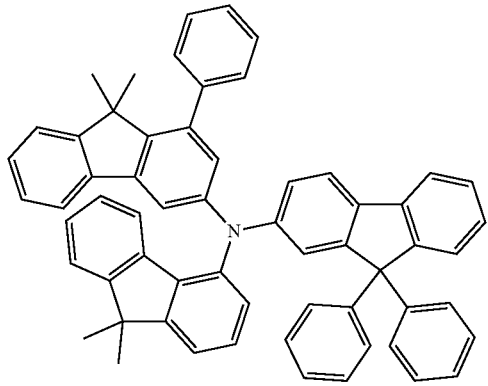
187
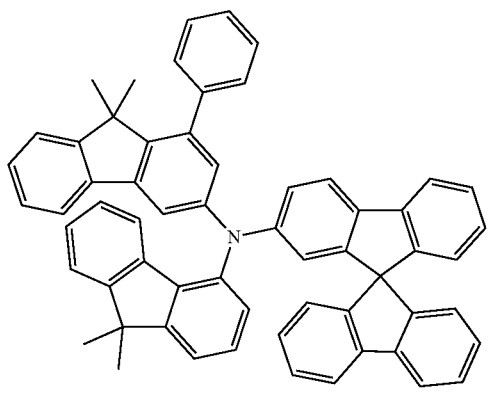

188
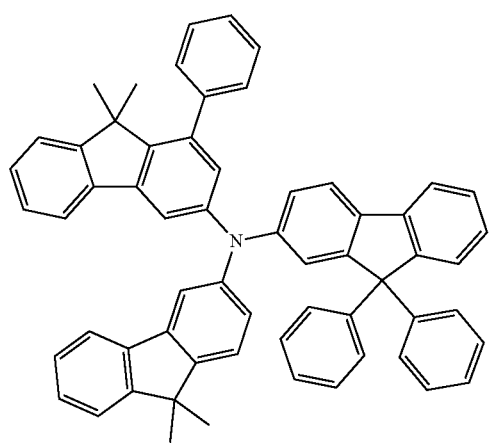
189
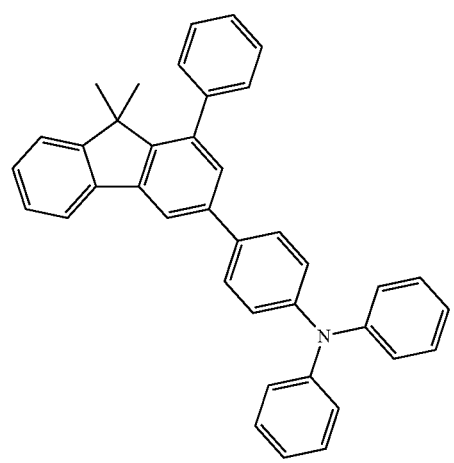
190
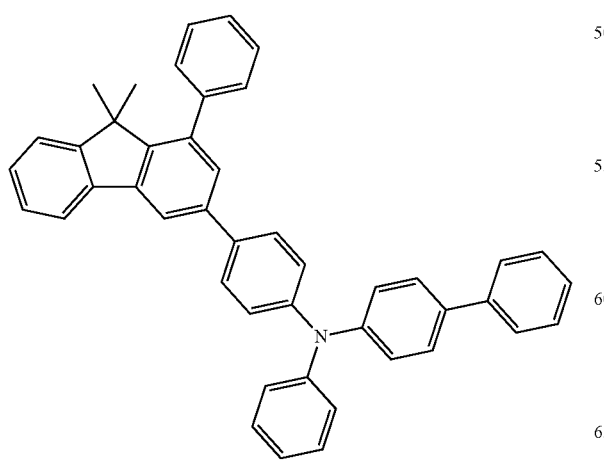
191
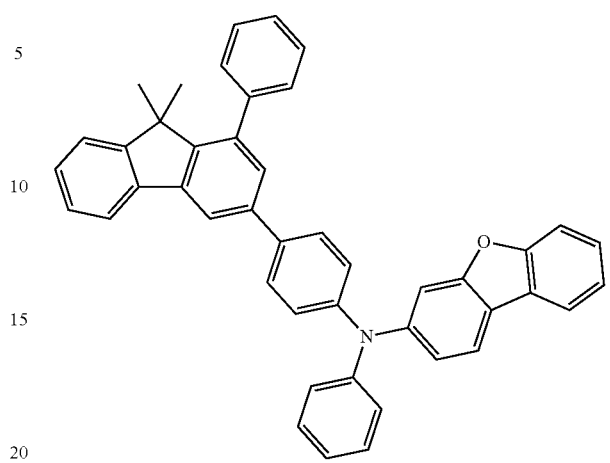
192
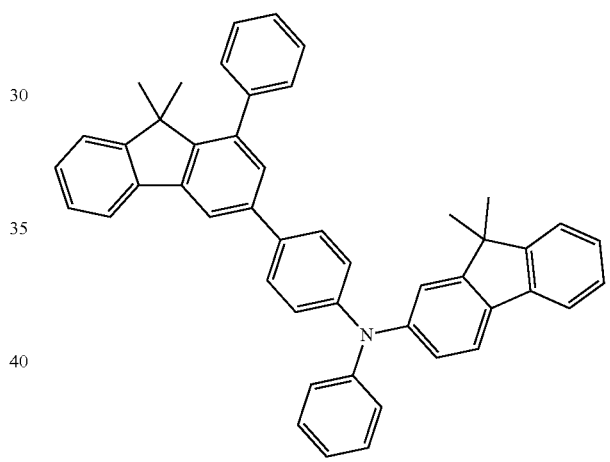
193
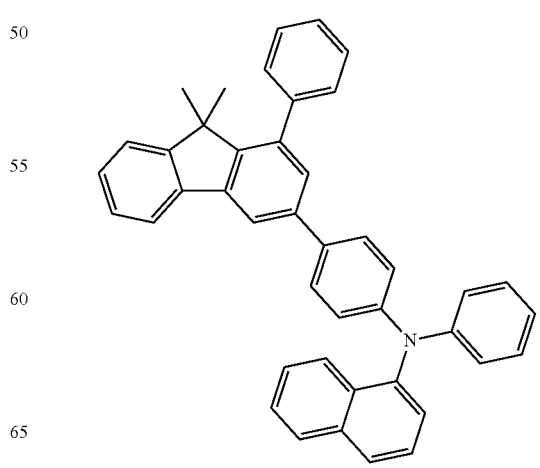

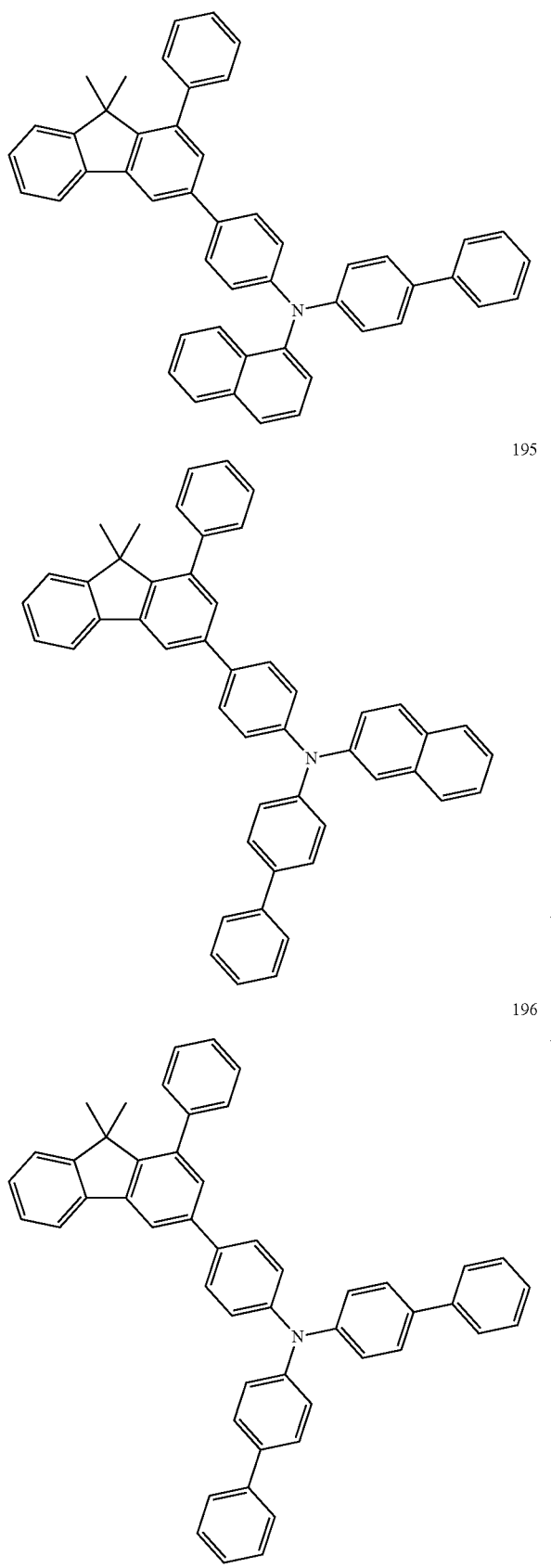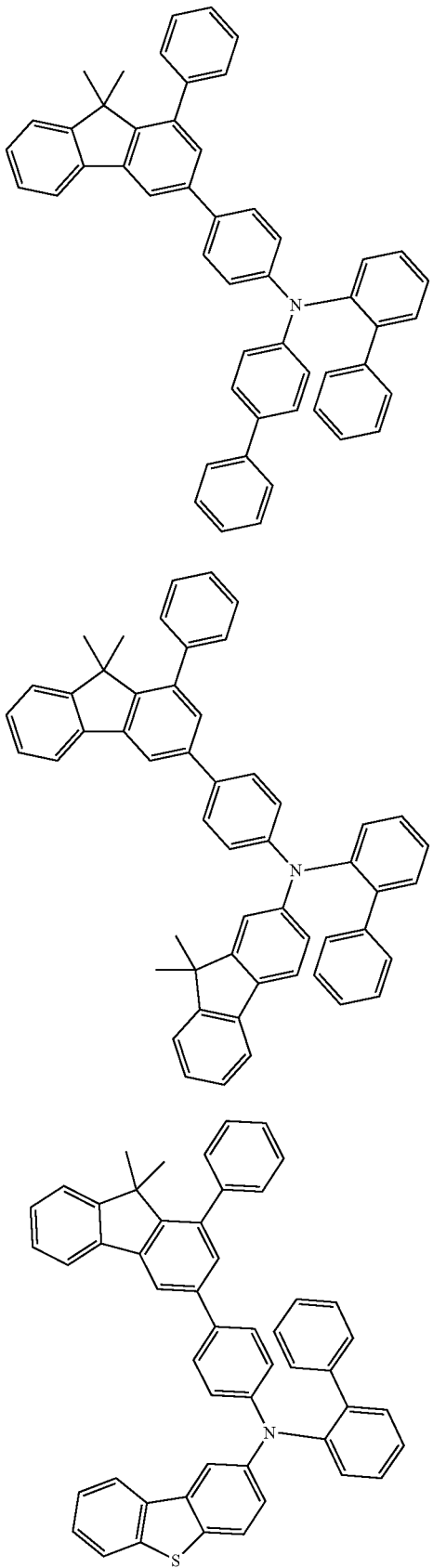

200
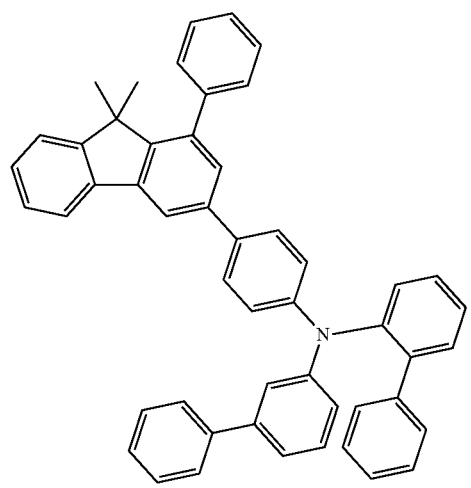
201
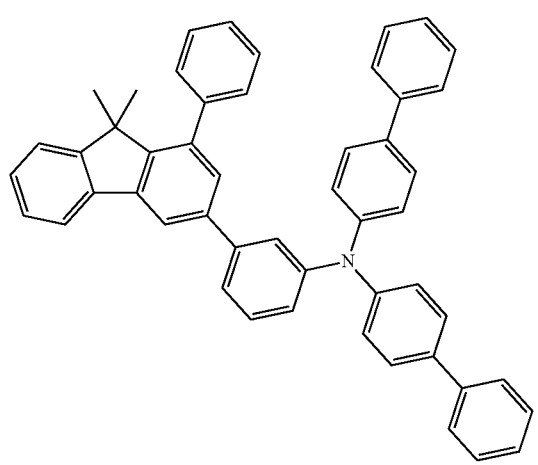
202
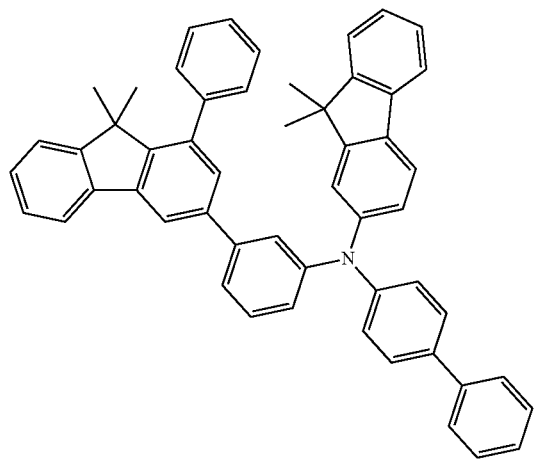
203
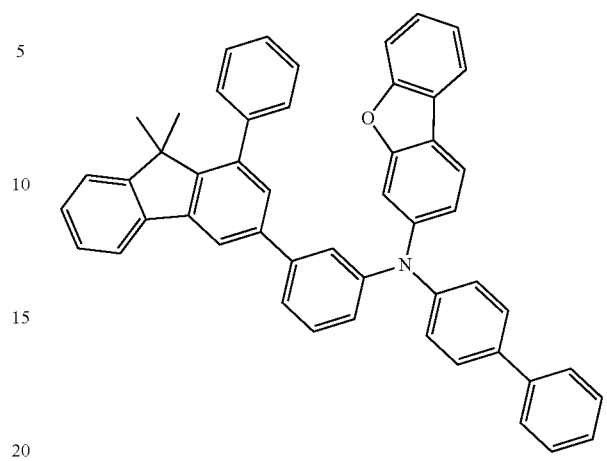
204
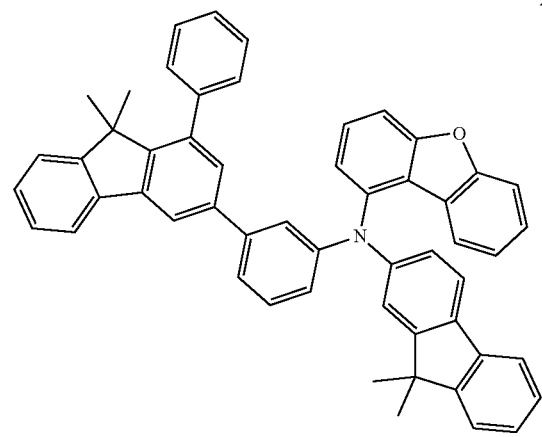
205
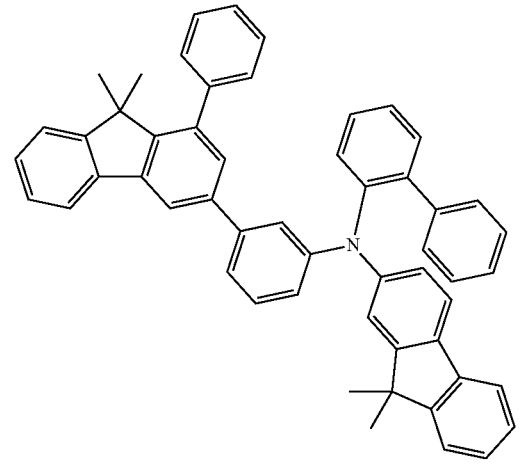

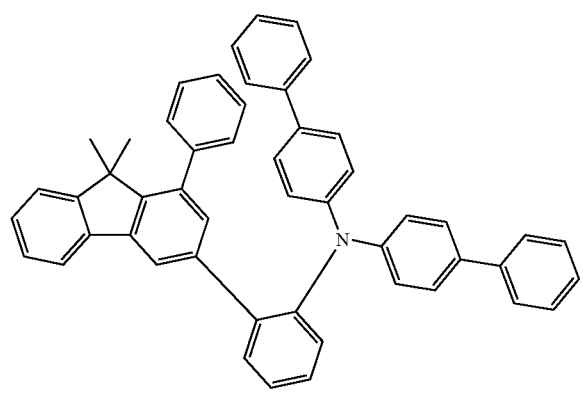
206
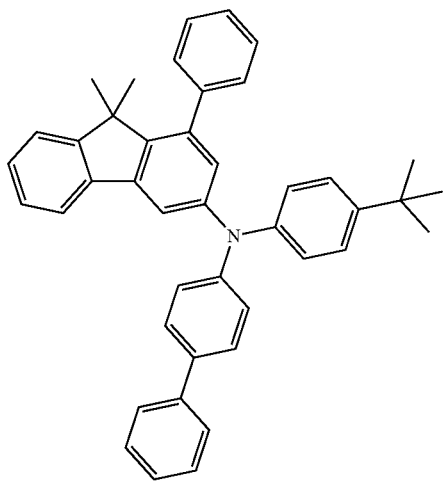
209
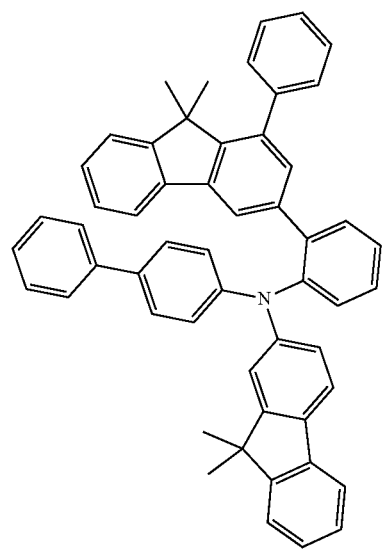
207
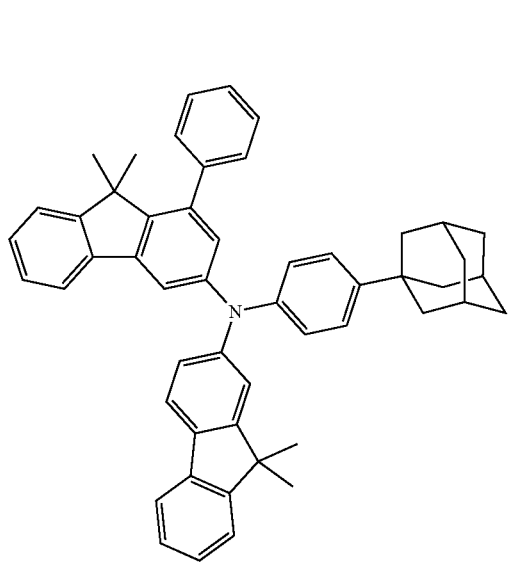
210
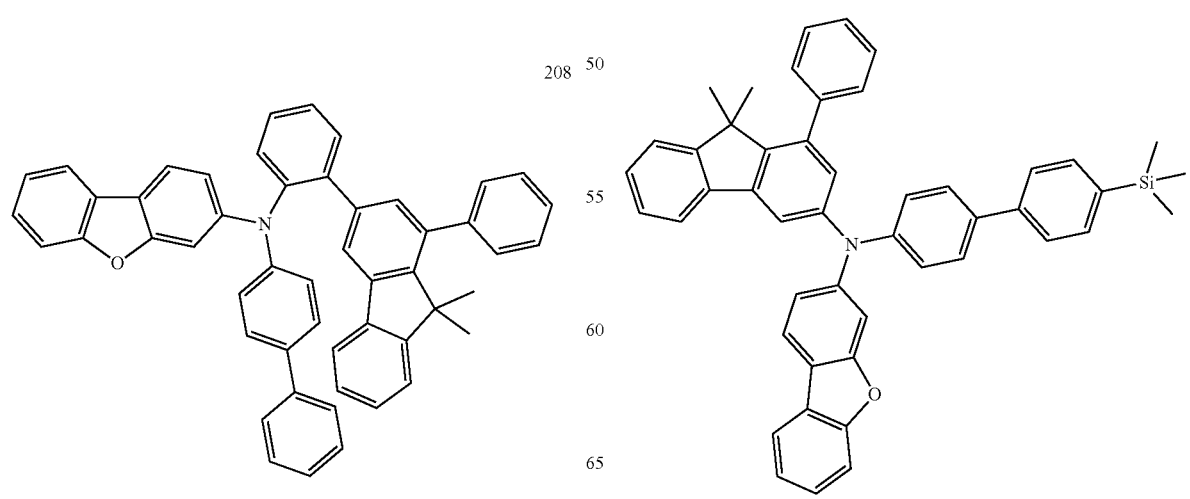

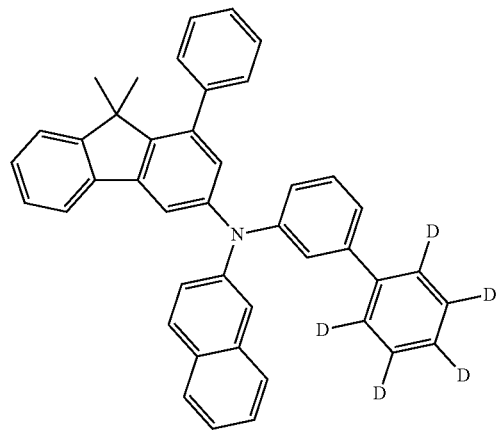
212
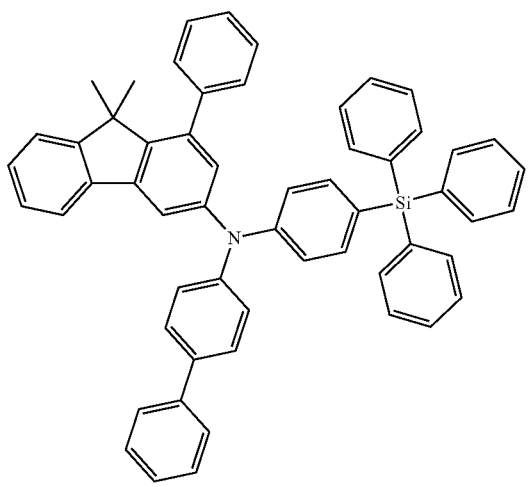
213
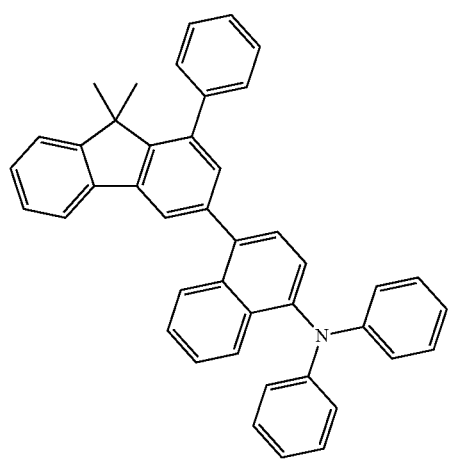
214
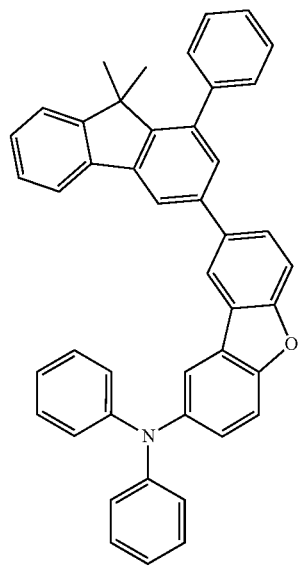
215
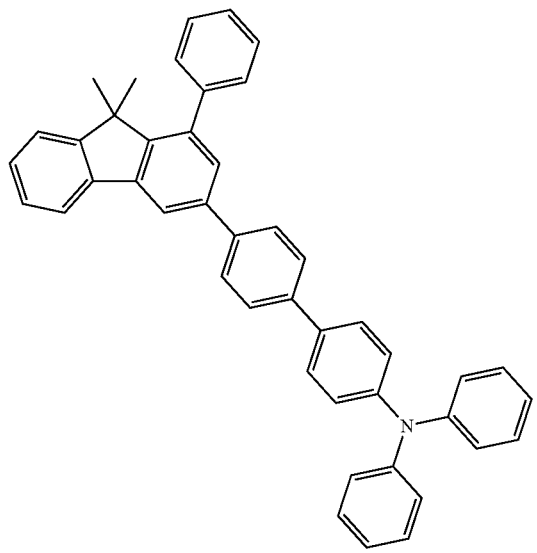
216

-continued

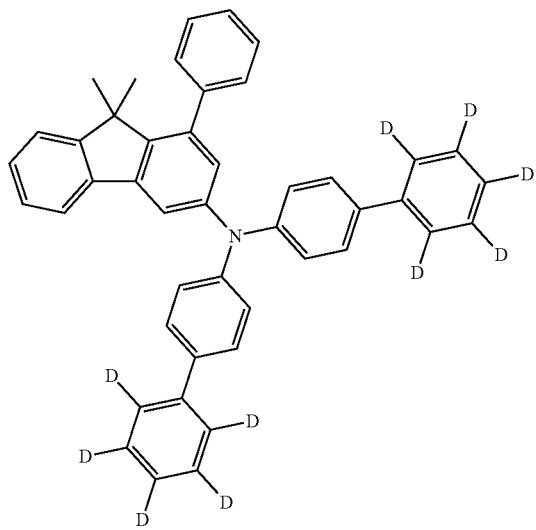
217

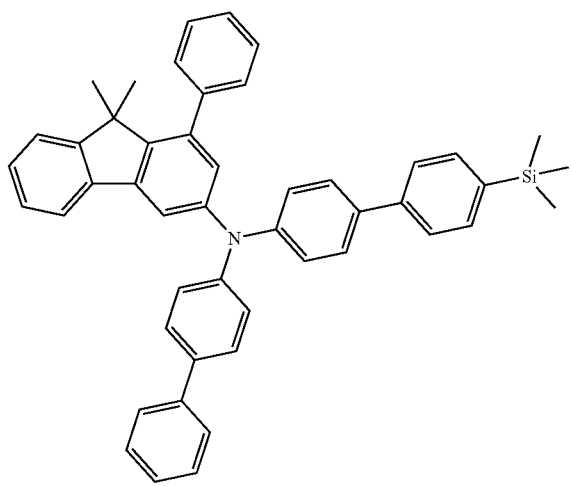
218

219

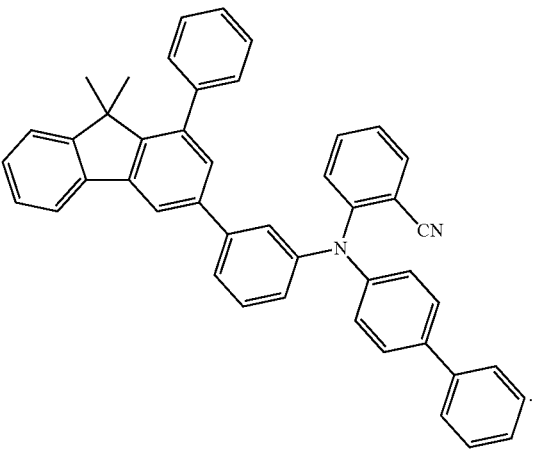
220

The present disclosure also provides an electronic element including an anode and a cathode disposed opposite to each other, and a functional layer disposed between the anode and the cathode. The functional layer comprises the nitrogen-containing compound of the present disclosure.

According to an embodiment, the electronic element is an organic electroluminescent device. As shown in FIG. 1, the organic electroluminescent device includes an anode 100 and a cathode 200 disposed opposite to each other, and a functional layer 300 disposed between the anode 100 and the cathode 200. The functional layer 300 comprises the nitrogen-containing compound provided in the present disclosure.

Optionally, the functional layer 300 includes an electron blocking layer 322. The electron blocking layer 322 comprises the nitrogen-containing compound provided in the present disclosure. The electron blocking layer 322 may be composed of the nitrogen-containing compound provided in the present disclosure, or may be composed of the nitrogen-containing compound provided in the present disclosure together with other materials.

Optionally, the functional layer 300 includes a hole transport layer 321 or a hole injection layer 310. The hole transport layer 321 or the hole injection layer 310 may comprise the nitrogen-containing compound provided in the present disclosure so as to enhance the ability to transport holes in the electronic element.

In a specific embodiment of the present disclosure, the organic electroluminescent device may include an anode 100, a hole transport layer 321, an electron blocking layer 322, an organic emissive layer 330 as an energy conversion layer, an electron transport layer 350, and a cathode 200 that are stacked in sequence. The nitrogen-containing compound of the present disclosure may be used in the electron blocking layer 322 of the organic electroluminescent device to effectively improve the luminescence efficiency, prolong service life, and reduce a driving voltage of the organic electroluminescent device.

Optionally, the anode 100 comprises the following anode material, which is preferably a high-work function material contributing to injection of holes into the functional layer. Specific examples of the anode material include, but are not limited to: metals such as nickel, platinum, vanadium, chromium, copper, zinc, gold, and alloys thereof; metal oxides such as zinc oxide, indium oxide, indium tin oxide (ITO), and indium zinc oxide (IZO); combinations of metals and oxides, such as ZnO:Al or $SnO_2$:Sb, and conductive polymers such as poly(3-methylthiophene), poly[3,4-(ethylene-1,2-dioxy)thiophene] (PERT), polypyrrole, and polyaniline, Preferably, a transparent electrode comprising indium tin oxide (ITO) is included as the anode.

Optionally, the hole transport layer 321 may include one or more hole transport materials. The hole transport materials may be selected from carbazole polymers, carbazole-linked triarylamine compounds, and other types of compounds, and the present disclosure is not particularly restricted in this respect. For example, the hole transport layer 321 is composed of compound HT-01.

Optionally, the organic light-emitting layer 330 may be composed of a single luminescent material, or may comprise a host material and a guest material. Optionally, the organic light-emitting layer 330 is composed of a host material and a guest material. Holes injected into the organic light-emitting layer 330 and electrons injected into the organic light-emitting layer 330 can recombine in the organic light-emitting layer 330 to form excitons. The excitons transmit energy to the host material, and the host material transmits the energy to the guest material, thereby enabling the guest material to emit light.

The host material of the organic light-emitting layer 330 may be a metal chelating compound, a bisstyryl derivative, an aromatic amine derivative, a dibenzofuran derivative, or other types of materials, and the present disclosure is not particularly restricted in this respect. For example, the host material of the organic light-emitting layer 330 is RH-01.

The guest material of the organic light-emitting layer 330 may be a compound having a condensed aryl ring or a derivative thereof, a compound having a heteroaryl ring or a derivative thereof, an aromatic amine derivative, or other materials, and the present disclosure is not particularly restricted in this respect. For example, the guest material of the organic emissive layer 330 is $Ir(Piq)_2(acac)$.

The electron transport layer 350 may be a single-layer structure or a multi-layer structure, and may comprise one or more electron transport materials. The electron transport materials may be selected from benzimidazole derivatives, oxadiazole derivatives, quinoxaline derivatives, and other electron transport materials, and the present disclosure is not particularly restricted in this respect. For example, the electron transport layer 350 is composed of ET-01 and LiQ.

Optionally, the cathode 200 comprises a cathode material, which is a low-work function material contributing to injection of electrons into the functional layer. Specific examples of the cathode material include, but are not limited to, metals such as magnesium, calcium, sodium, potassium, titanium, indium, yttrium, lithium, gadolinium, aluminum, silver, tin, lead, and alloys thereof; or multilayer materials such as LiF/Al, Liq/Al, $LiO_2$/Al, LiF/Ca, LiF/Al, and $BaF_2$/Ca. Preferably, a metal electrode comprising silver and magnesium is included as the cathode.

Optionally, as shown in FIG. 1, a hole injection layer 310 may be further provided between the anode 100 and the hole transport layer 321 to enhance the ability to inject holes into the hole transport layer 321. The hole injection layer 310 may be composed of an inorganic material selected from benzidine derivatives, starburst arylamine compounds, phthalocyanine derivatives, and other materials, and the present disclosure is not particularly restricted in this respect. For example, the hole injection layer 310 is composed of HAT-CN.

Optionally, as shown in FIG. 1, an electron injection layer 360 may be further provided between the cathode 200 and the electron transport layer 350 to enhance the ability to inject to electrons into the electron transport layer 350. The electron injection layer 360 may comprise an inorganic material such as an alkali metal sulfide, an alkali metal halide, or may comprise a complex of an alkali metal and an organic compound. For example, the electron injection layer 360 is composed of LiQ.

Optionally, a hole blocking layer 340 may also be provided between the organic emissive layer 330 and the electron transport layer 350.

Optionally, the organic electroluminescent component is a red electroluminescence device.

Figure 2:
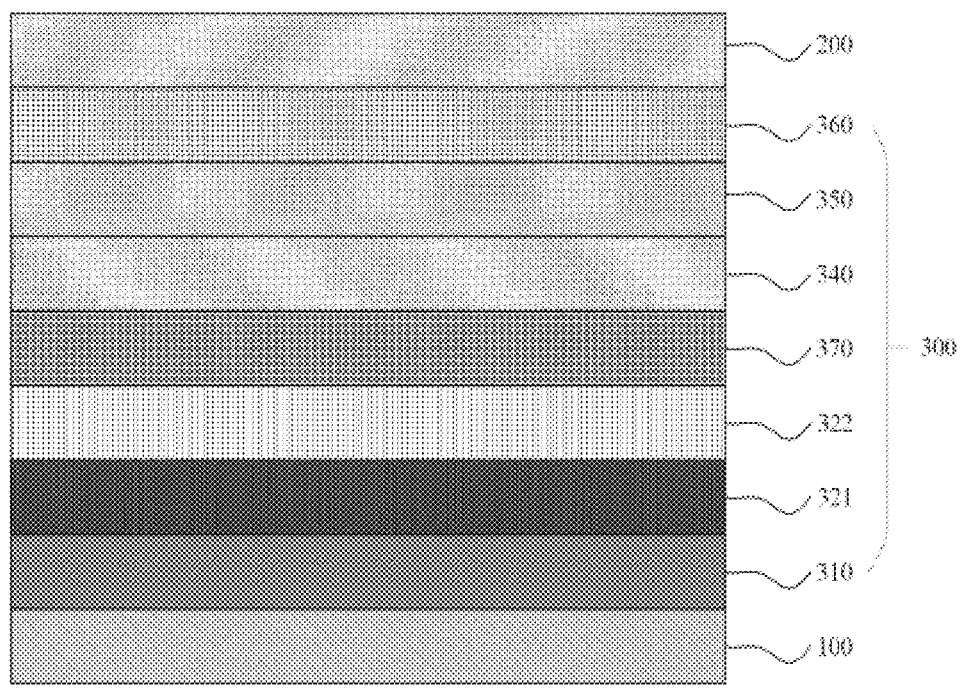
FIG. 2 is a schematic structural diagram of a photoelectric conversion device according to an embodiment of the present disclosure.

According to another embodiment, the electronic element is a photoelectric conversion device. As shown in FIG. 2, the photoelectric conversion device may include an anode 100 and a cathode 200 disposed opposite to each other, and a functional layer 300 disposed between the anode 100 and the cathode 200. The functional layer 300 comprises the nitrogen-containing compound provided in the present disclosure.

Optionally, the functional layer 300 includes an electron blocking layer 322. The electron blocking layer 322 comprises the nitrogen-containing compound provided in the present disclosure. The electron blocking layer 322 may be composed of the nitrogen-containing compound provided in the present disclosure, or may be composed of the nitrogen-containing compound provided in the present disclosure together with other materials.

Optionally, as shown in FIG. 2, the photoelectric conversion device may include an anode 100, a hole transport layer 321, an electron blocking layer 322, a photoelectric conversion layer 370 as an energy conversion layer, an electron transport layer 350, and a cathode 200 that are stacked in sequence. The nitrogen-containing compound of the present disclosure can be used in the electron blocking layer 322 of the photoelectric conversion device to effectively improve the luminescence efficiency, prolong service life, and increase the open-circuit voltage of the photoelectric conversion device.

Optionally, a hole injection layer 310 may be further provided between the anode 100 and the hole transport layer 321.

Optionally, an electron injection layer 360 may be further provided between the cathode 200 and the electron transport layer 350.

Optionally, a hole blocking layer 340 may be further provided between the photoelectric conversion layer 370 and the electron transport layer 350.

Optionally, the photoelectric conversion device may be a solar cell, especially an organic thin-film solar cell, According to a specific embodiment, as shown in FIG. 2, the solar cell includes an anode 100, a hole injection layer 310, a hole transport layer 321, an electron blocking layer 322, a photoelectric conversion layer 370, a hole blocking layer 340, an electron transport to layer 350, an electron injection layer 360, and a cathode 200 that are stacked in sequence. The electron blocking layer 322 comprises the nitrogen-containing compound of the present disclosure.

The present disclosure also provides an electronic device including the electronic element described in the second aspect of the present disclosure.

Figure 3:
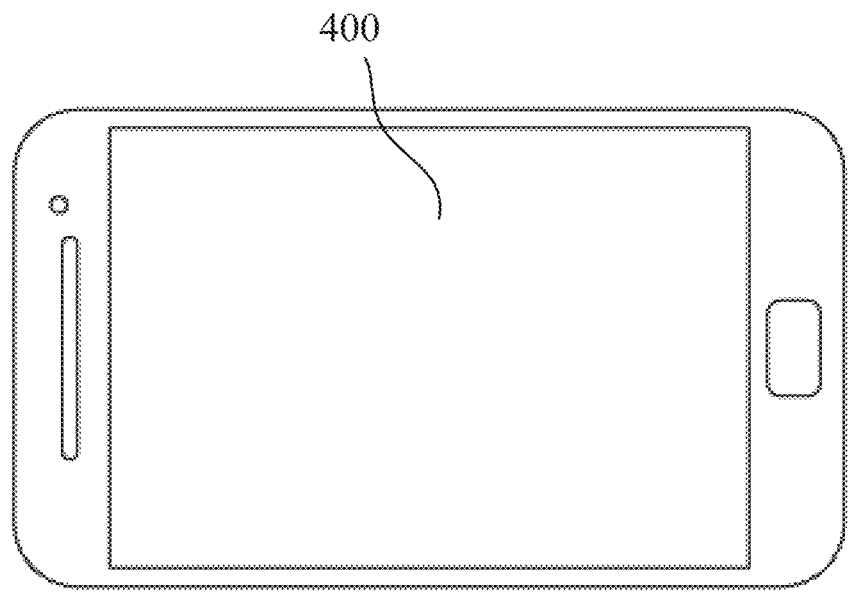
FIG. 3 is a schematic structural diagram of an electronic device according to an embodiment of the present disclosure.

According to an embodiment, as shown in FIG. 3, the electronic device is a first electronic device 400 including the above described organic electroluminescent component. The first electronic device 400 may be a display device, a lighting device, an optical communication device, or other type of electronic devices, which, for example, may include, but are not limited to, computer screens, mobile phone screens, televisions, electronic paper, emergency lamps, optical modules, etc.

Figure 4:
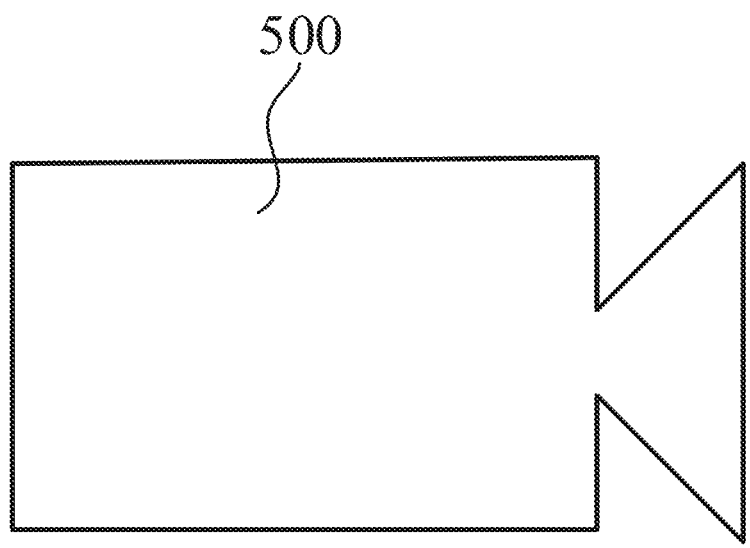
FIG. 4 is a schematic structural diagram of an electronic device according to another embodiment of the present disclosure.

According to another embodiment, as shown in FIG. 4, the electronic device is a second electronic device 500 including the above described photoelectric conversion component. The second electronic device 500 may be a solar power generation device, a light detector, a fingerprint recognition device, an optical module, a CCD camera, or other types of electronic devices.

The nitrogen-containing compound of the present disclosure and use thereof are described below in conjunction with synthesis embodiments and embodiments. Unless otherwise indicated, raw materials and materials used may be obtained commercially or by known methods in the art.

Synthesis Embodiments: Compound Synthesis

Synthesis of Intermediates:

Intermediates of secondary amine compounds needed in experimental embodiments were synthesized using the following generic method 1 or method 2.

Method 1:

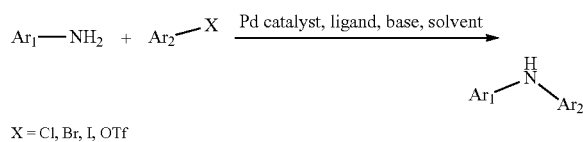

X = Cl, Br, I, OTf

Method 2:

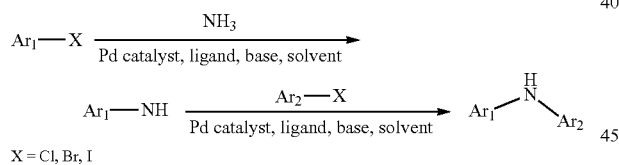

X = Cl, Br, I

Reference can be made to the prior art CN107004770A for the above methods.

Synthesis of Intermediate i:

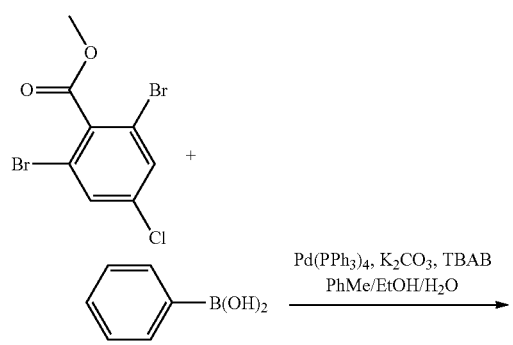

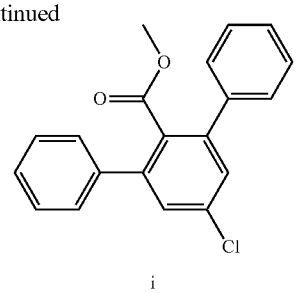

2,6-dibromo-4-chlorobenzoate (70.0 g; 213.2 mmol), phenylboronic acid (65.0 g; 532.9 mmol), tetrakis(triphenylphosphine)palladium (9.9 g; 8.5 mmol); potassium carbonate (117.8 g; 852.7 mmol), tetrabutylammonium bromide (27.5 g; 85.3 mmol), toluene (600 mL), ethanol (150 mL), and deionized water (150 mL) were added to a round-bottom flask, and under nitrogen protection, a resulting mixture was stirred and heated to 75° C.-80° C. for a reaction for 48 hours. The reaction mixture was cooled to room temperature, washed with water, and separated for an organic phase. The organic phase was dried over anhydrous magnesium sulfate, followed by removal of the solvent under reduced pressure, obtaining a crude product. The crude product was purified by silica gel column chromatography with ethyl acetate/n-heptane as an eluent, yielding light gray solid Intermediate i (46.5 g; yield 68%).

Synthesis of Intermediate ii:

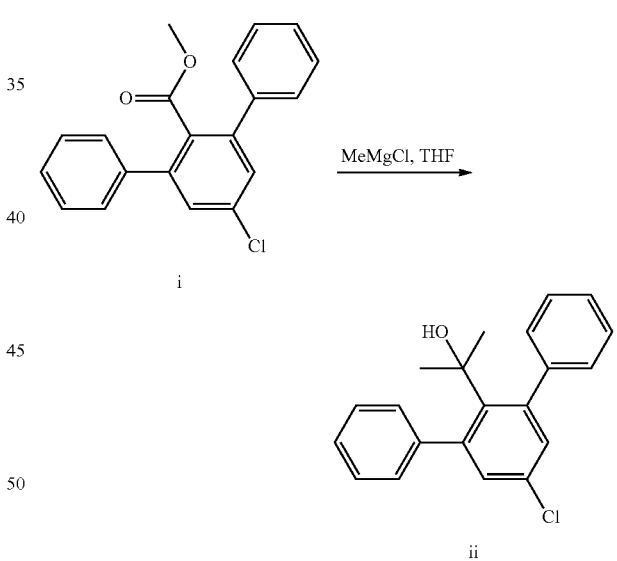

Intermediate i (46.0 g; 142.5 mmol) and dried tetrahydrofuran (500 mL) were added to a round-bottom flask, and under nitrogen protection, a resulting mixture was stirred and cooled to −15° C. to −10° C.; a solution of methylmagnesium chloride (85.3 g; 1140.1 mmol) in tetrahydrofuran was slowly added dropwise. After the dropwise addition, the resulting mixture was stirred at −15° C. to −10° C. for 1 hour, heated to 20-25° C. for a reaction for 16 hours under stirring. A saturated aqueous solution of ammonium chloride was added to the reaction solution. The reaction solution was extracted with dichloromethane and separated for an organic phase. The organic phase was dried over anhydrous magnesium sulfate, followed by removal of the solvent under reduced pressure, obtaining a crude product. The crude product was purified by silica gel column chromatography with ethyl acetate/n-heptane as an eluent, yielding white solid Intermediate ii (26.0 g; yield 57%).

Synthesis of Intermediate a:

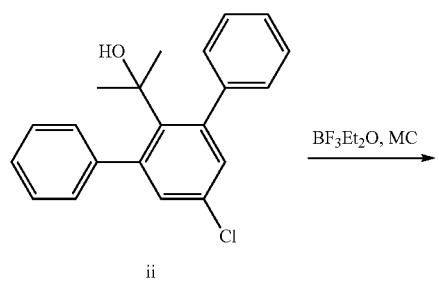

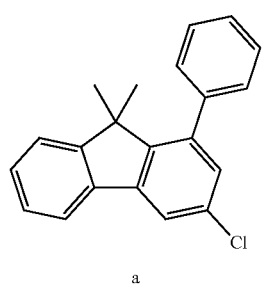

Intermediate ii (25.2 g, 78.1 mmol) and dichloromethane (400 mL) were added to a round-bottom flask, and under nitrogen protection, a resulting mixture was stirred and cooled to −5° C. to 0° C., boron trifluoride etherate (16.6 g; 117.1 mmol) was slowly added dropwise. After the dropwise addition, the resulting mixture was stirred at −5° C. to 0° C. for 1 hour, heated to 20-25° C. for a reaction for 1 hour under stirring. A sodium bicarbonate aqueous solution and dichloromethane were added to the reaction solution. The reaction solution was separated for an organic phase. The organic phase was dried over anhydrous magnesium sulfate, followed by removal of the solvent under reduced pressure, obtaining a crude product. The crude product was purified by silica gel column chromatography with a dichloromethane/n-heptane system, yielding white powdered Intermediate a (15.5 g; yield 65%), m/z=305.1[M+H]$^+$.

Synthesis of Intermediate a0:

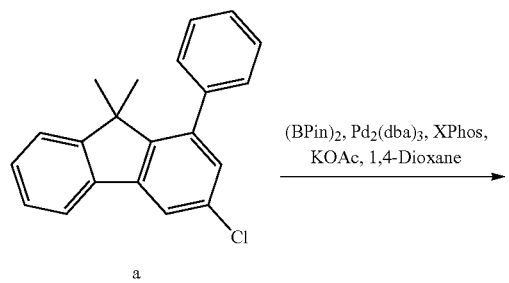

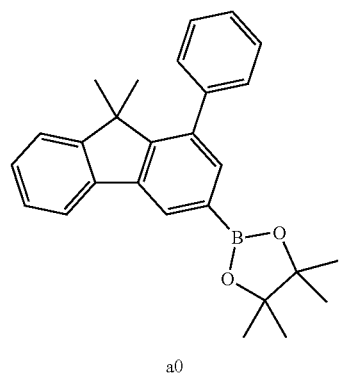

Intermediate a (12.0 g; 39.4 mmol), bis(pinacolato)diboron (12.5 g; 49.2 mmol), tris(dibenzylideneacetone)dipalladium (0.4 g; 0.4 mmol), 2-dicyclohexylphosphino-2',4',6-triisopropylbiphenyl (0.4 g; 0.8 mmol), potassium acetate (7.7 g; 78.7 mmol), and 1,4-dioxane (100 mL) were added to a flask, and under nitrogen protection, a reaction mixture was heated to 100° C.-105° C., and stirred to allow a reaction under reflux for 12 hours. The reaction solution was cooled to room temperature, followed by adding dichloromethane and water, and then separation, obtaining an organic phase. The organic phase was washed with water and then dried over anhydrous magnesium sulfate, followed by removal of the solvent under reduced pressure, obtaining a crude product. The crude product was purified by silica gel column chromatography with a dichloromethane/n-heptane system, yielding light yellow solid Intermediate a0 (113 g; yield 72%).

Synthesis of Intermediate a1

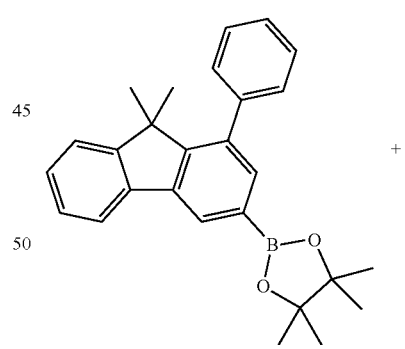

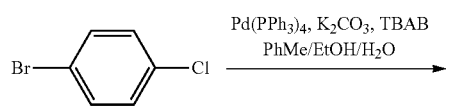

-continued

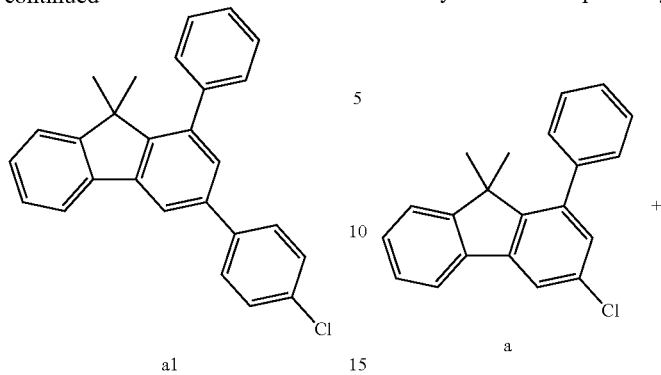

a1

Synthesis Example 1: Synthesis of Compound 68

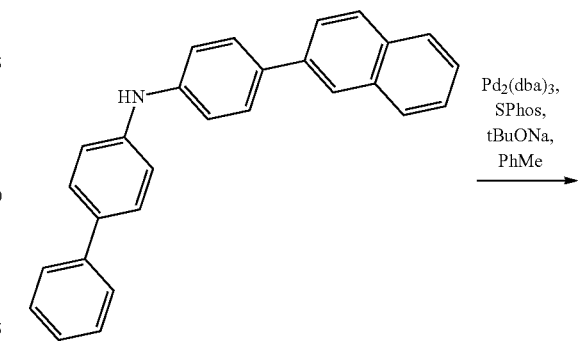

a

Intermediate a0 (11.0 g; 27.8 mmol), 4-bromochlorobenzene (5.6 g; 29.1 mmol), tetrakis(triphenylphosphine)palladium (0.6 g; 0.6 mmol), potassium carbonate (7.7 g; 55.5 mmol), tetrabutylammonium bromide (1.8 g; 5.6 mmol), toluene (80 mL), ethanol (20 mL), and deionized water (20 mL) were added to a round-bottom flask, under nitrogen protection, resulting mixture was heated to 75-80° C. and stirred to allow a reaction for 10 hours. The reaction mixture was cooled to room temperature, washed with water, and separated for an organic phase. The organic phase was dried over anhydrous magnesium sulfate, followed by removal of the solvent under reduced pressure, obtaining a crude product. The crude product was purified with dichloromethane/n-heptane by silica gel column chromatography as an eluent, yielding white solid Intermediate a1 (8.8 g; yield 83%).

Intermediates shown in Table 1 were synthesized using the same method for synthesizing Intermediate a1, with 4-bromochlorobenzene being replaced with reactant A in Table 1.

TABLE 1

| Intermediate | Reactant A | Structure | Yield (%) |
|---|---|---|---|
| a2 | ![Br-C6H4-Cl structure] | ![fluorene structure with phenyl and chlorophenyl] | 69% |
| a3 | ![Br-dibenzofuran-Cl structure] | ![dibenzofuran-fluorene structure] | 72% |

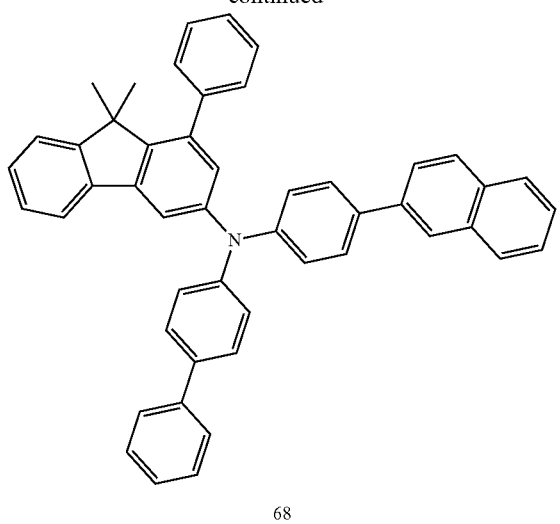

68

Intermediate a (4.4 g; 14.4 mmol), N-(4-(2-naphthyl)phenyl)-[1,1'-biphenyl]-4-amine (5.4 g; 14.4 mmol), tris(dibenzylideneacetone)dipalladium (0.1 g; 0.1 mmol), 2-dicyclohexylphosphino-2,6-dimethoxybiphenyl (0.1 g; 0.3 mmol), sodium tert-butoxide (2.1 g; 21.7 mmol), and toluene (50 mL) were added to a nitrogen-protected round-bottom flask, and heated to 105° C.-110° C. under stirring for a reaction for 8 hours. The reaction solution was cooled to room temperature, washed with water, and a resulting organic phase was separated. The organic phase was dried over anhydrous magnesium sulfate, followed by removal of the solvent under reduced pressure, obtaining a crude product. The crude product was purified with dichloromethane/n-heptane by silica gel column chromatography, and then recrystallized and purified with dichloroethane/n-heptane, yielding white solid Compound 68 (4.9 g; yield 53%).

Synthesis Examples 2 to 38

Compounds shown in Table 2 were synthesized using the method for synthesizing Compound 68, with N-(4-(2-naphthyl)phenyl)-[1,1'-biphenyl]-4-amine being replaced with reactant B in Table 2.

TABLE 2

| Compound | Reactant B | Structure | Yield (%) |
|---|---|---|---|
| 2 | | 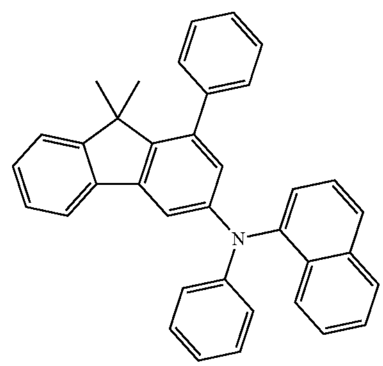 [SMILES: CC1(C)c2ccccc2-c2cc(N(c3ccccc3)c3cccc4ccccc34)cc(-c3ccccc3)c21] | 40 |
| 7 | | 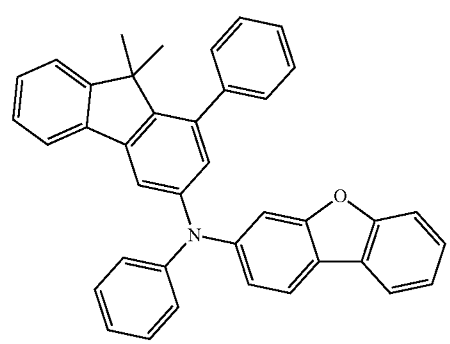 [SMILES: CC1(C)c2ccccc2-c2cc(N(c3ccccc3)c3ccc4c(c3)oc3ccccc34)cc(-c3ccccc3)c21] | 50 |

TABLE 2-continued

| Compound | Reactant B | Structure | Yield (%) |
|---|---|---|---|
| 21 | | 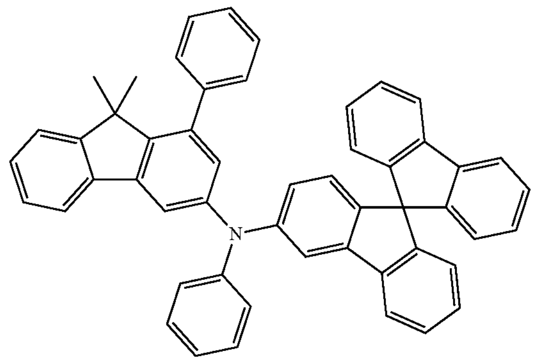 [SMILES: CC1(C)c2ccccc2-c2cc(N(c3ccccc3)c3ccc4c(c3)-c3ccccc3C43c4ccccc4-c4ccccc43)cc(-c3ccccc3)c21] | 57 |
| 27 | | 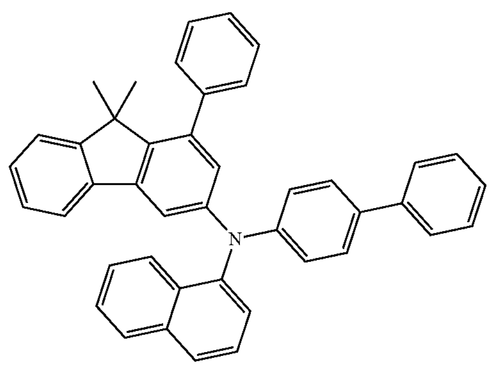 [SMILES: CC1(C)c2ccccc2-c2cc(N(c3ccc(-c4ccccc4)cc3)c3cccc4ccccc34)cc(-c3ccccc3)c21] | 48 |
| 47 | | 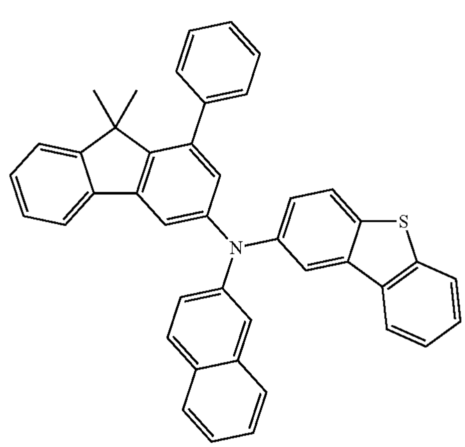 [SMILES: CC1(C)c2ccccc2-c2cc(N(c3ccc4ccccc4c3)c3ccc4sc5ccccc5c4c3)cc(-c3ccccc3)c21] | 61 |

TABLE 2-continued

| Compound | Reactant B | Structure | Yield (%) |
|---|---|---|---|
| 57 | | 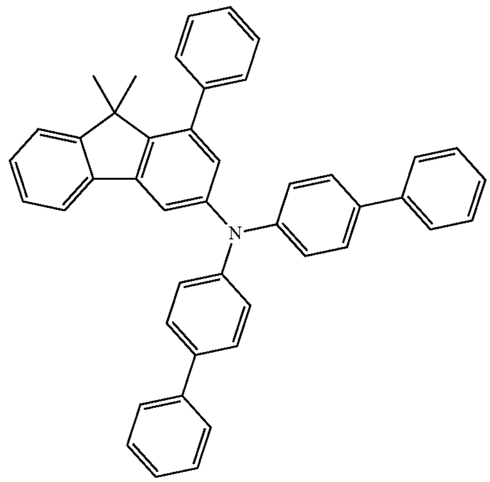 [SMILES: CC1(C)c2ccccc2-c2cc(N(c3ccc(-c4ccccc4)cc3)c3ccc(-c4ccccc4)cc3)cc(-c3ccccc3)c21] | 48 |
| 65 | | 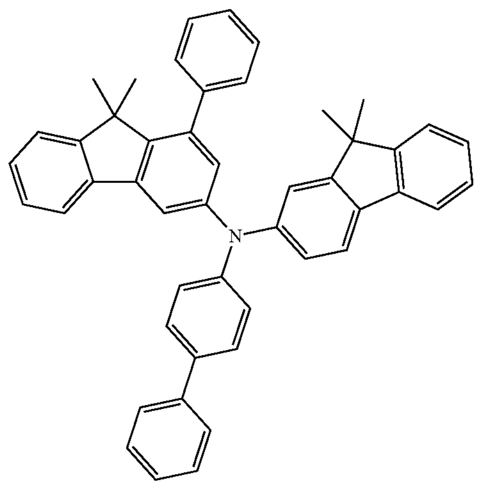 [SMILES: CC1(C)c2ccccc2-c2ccc(N(c3ccc(-c4ccccc4)cc3)c3cc(-c4ccccc4)c4c(c3)-c3ccccc3C4(C)C)cc21] | 57 |
| 75 | | 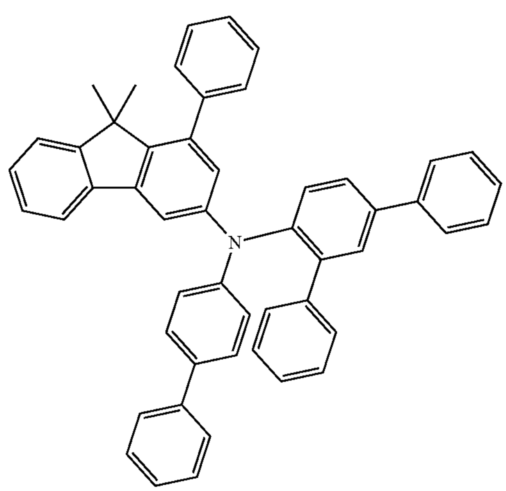 [SMILES: CC1(C)c2ccccc2-c2cc(N(c3ccc(-c4ccccc4)cc3)c3ccc(-c4ccccc4)cc3-c3ccccc3)cc(-c3ccccc3)c21] | 44 |

TABLE 2-continued

| Compound | Reactant B | Structure | Yield (%) |
|---|---|---|---|
| 79 | | 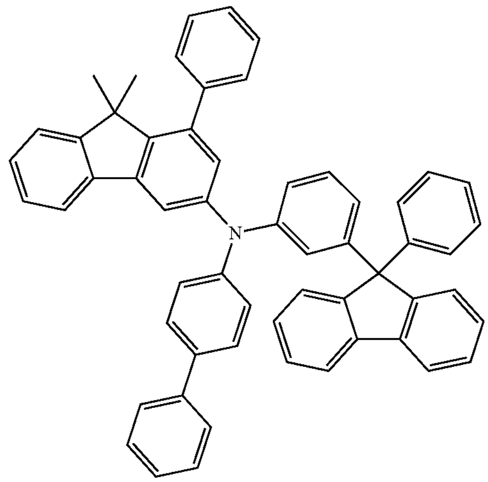 [SMILES: CC1(C)c2ccccc2-c2cc(N(c3ccc(-c4ccccc4)cc3)c3cccc(C4(c5ccccc5)c5ccccc5-c5ccccc54)c3)cc(-c3ccccc3)c21] | 37 |
| 92 | | 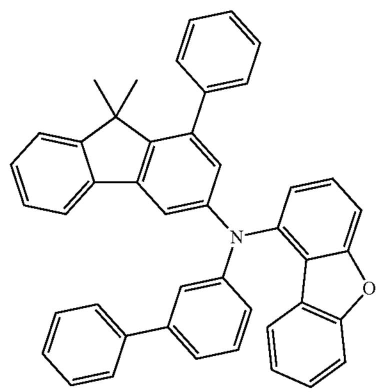 [SMILES: CC1(C)c2ccccc2-c2cc(N(c3cccc(-c4ccccc4)c3)c3cccc4oc5ccccc5c34)cc(-c3ccccc3)c21] | 40 |
| 96 | | 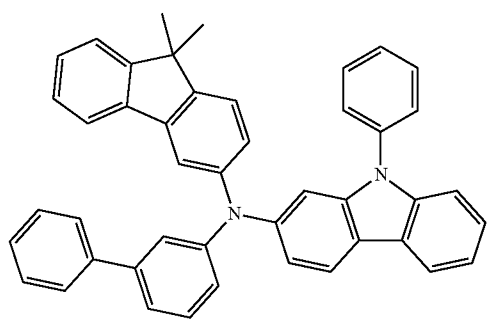 [SMILES: CC1(C)c2ccccc2-c2cc(N(c3cccc(-c4ccccc4)c3)c3ccc4c5ccccc5n(-c5ccccc5)c4c3)ccc21] | 56 |
| 108 | | 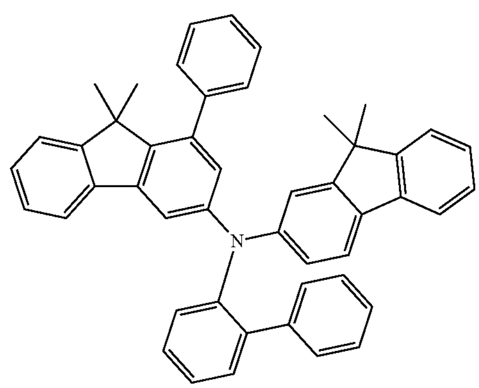 [SMILES: CC1(C)c2ccccc2-c2ccc(N(c3cc(-c4ccccc4)c4c(c3)-c3ccccc3C4(C)C)c3ccccc3-c3ccccc3)cc21] | 61 |

TABLE 2-continued

| Compound | Reactant B | Structure | Yield (%) |
|---|---|---|---|
| 115 | | 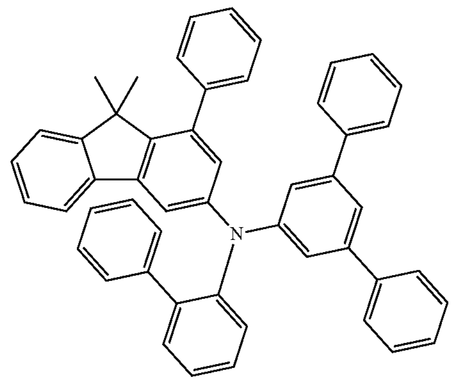 [SMILES: CC1(C)c2ccccc2-c2cc(N(c3cc(-c4ccccc4)cc(-c4ccccc4)c3)c3ccccc3-c3ccccc3)cc(-c3ccccc3)c21] | 45 |
| 121 | | 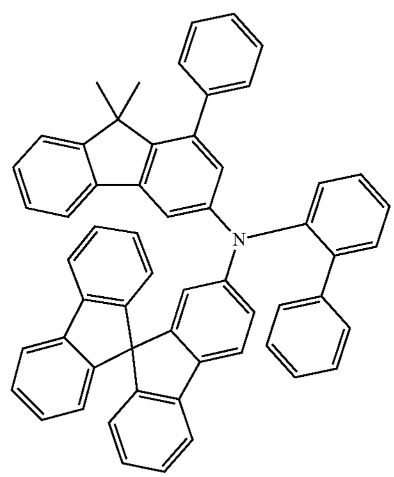 [SMILES: CC1(C)c2ccccc2-c2cc(N(c3ccc4c(c3)C3(c5ccccc5-c5ccccc53)c3ccccc3-4)c3ccccc3-c3ccccc3)cc(-c3ccccc3)c21] | 42 |
| 128 | | 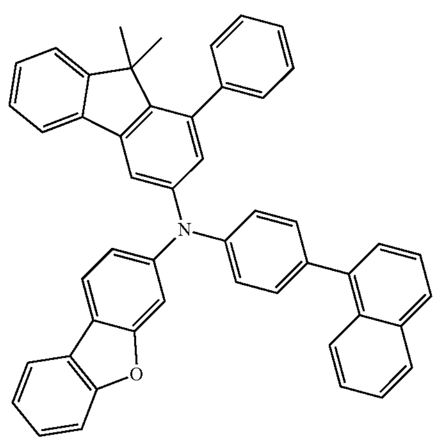 [SMILES: CC1(C)c2ccccc2-c2cc(N(c3ccc(-c4cccc5ccccc45)cc3)c3ccc4c(c3)oc3ccccc34)cc(-c3ccccc3)c21] | 62 |

TABLE 2-continued

| Compound | Reactant B | Structure | Yield (%) |
|---|---|---|---|
| 135 | | 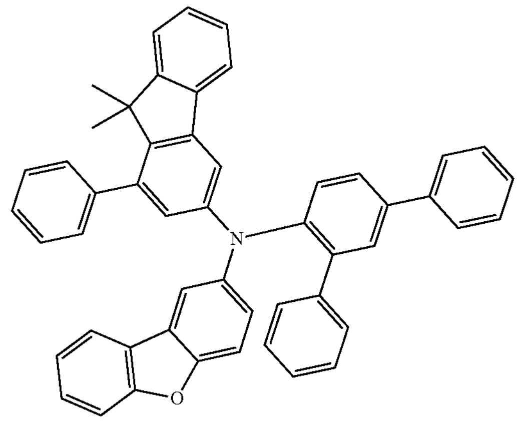 [SMILES: CC1(C)c2ccccc2-c2cc(N(c3ccc4oc5ccccc5c4c3)c3ccc(-c4ccccc4)cc3-c3ccccc3)cc(-c3ccccc3)c21] | 47 |
| 141 | | 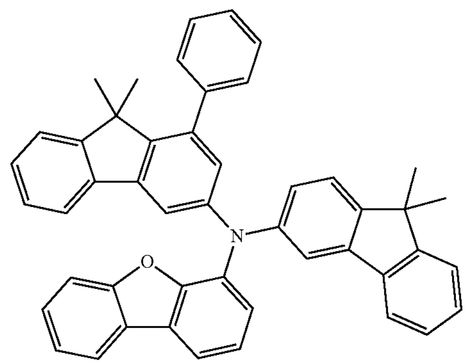 [SMILES: CC1(C)c2ccccc2-c2cc(N(c3cc(-c4ccccc4)c4c(c3)-c3ccccc3C4(C)C)c3cccc4c3oc3ccccc34)ccc21] | 53 |
| 144 | | 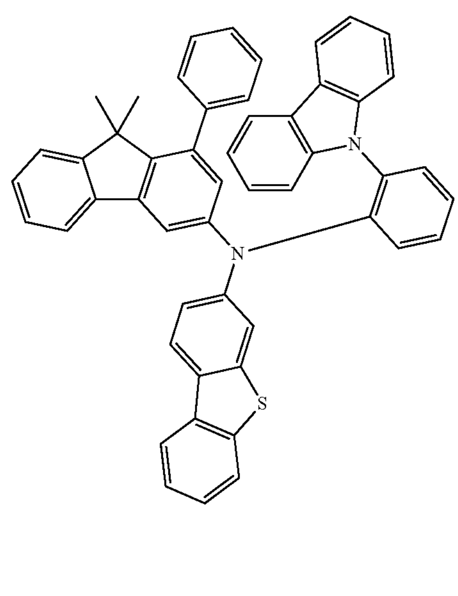 [SMILES: CC1(C)c2ccccc2-c2cc(N(c3ccc4c(c3)sc3ccccc34)c3ccccc3-n3c4ccccc4c4ccccc43)cc(-c3ccccc3)c21] | 33 |

TABLE 2-continued

| Compound | Reactant B | Structure | Yield (%) |
|---|---|---|---|
| 153 | | 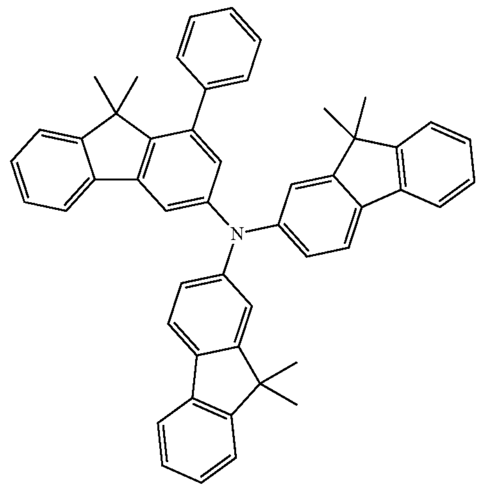 [SMILES: CC1(C)c2ccccc2-c2ccc(N(c3cc(-c4ccccc4)c4c(c3)-c3ccccc3C4(C)C)c3ccc4c(c3)C(C)(C)c3ccccc3-4)cc21] | 57 |
| 158 | | 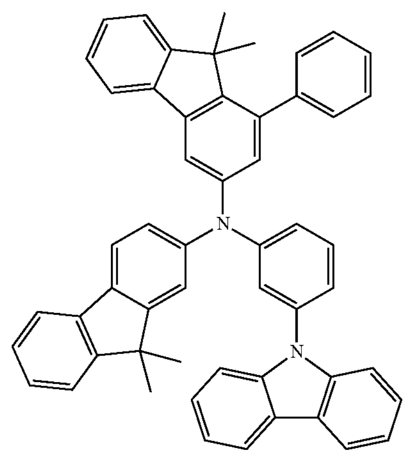 [SMILES: CC1(C)c2ccccc2-c2ccc(N(c3cccc(-n4c5ccccc5c5ccccc54)c3)c3cc(-c4ccccc4)c4c(c3)-c3ccccc3C4(C)C)cc21] | 41 |
| 161 | | 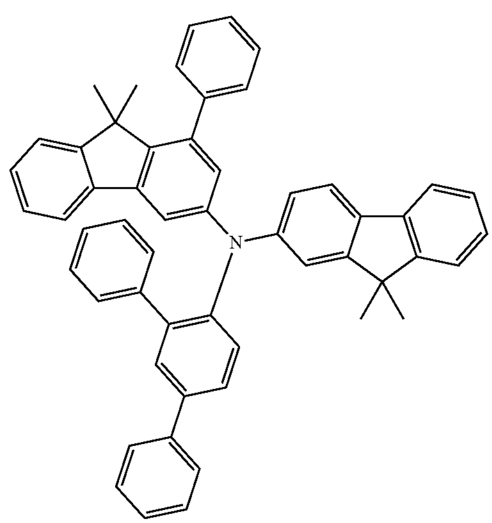 [SMILES: CC1(C)c2ccccc2-c2ccc(N(c3cc(-c4ccccc4)c4c(c3)-c3ccccc3C4(C)C)c3ccc(-c4ccccc4)cc3-c3ccccc3)cc21] | 40 |

TABLE 2-continued

| Compound | Reactant B | Structure | Yield (%) |
|---|---|---|---|
| 170 | | 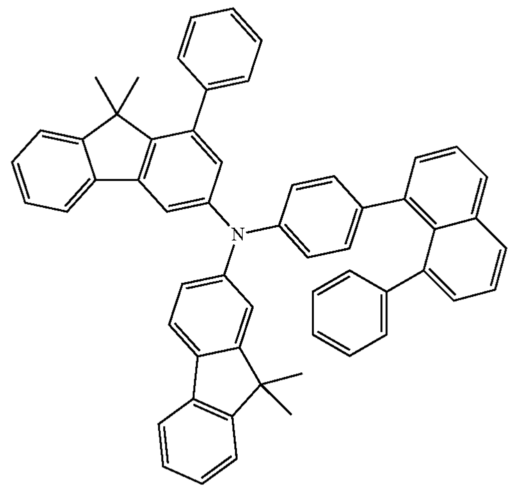 [SMILES: CC1(C)c2ccccc2-c2ccc(N(c3ccc(-c4cccc5cccc(-c6ccccc6)c45)cc3)c3cc(-c4ccccc4)c4c(c3)-c3ccccc3C4(C)C)cc21] | 56 |
| 173 | | 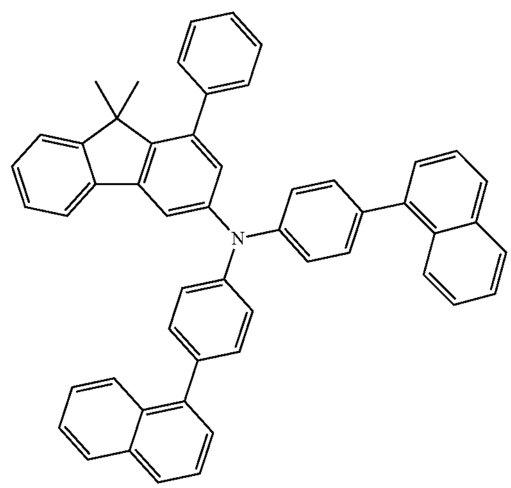 [SMILES: CC1(C)c2ccccc2-c2cc(N(c3ccc(-c4cccc5ccccc45)cc3)c3ccc(-c4cccc5ccccc45)cc3)cc(-c3ccccc3)c21] | 41 |
| 177 | | 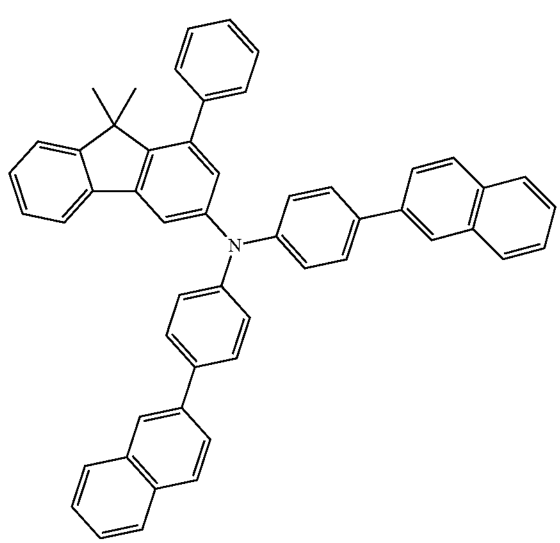 [SMILES: CC1(C)c2ccccc2-c2cc(N(c3ccc(-c4ccc5ccccc5c4)cc3)c3ccc(-c4ccc5ccccc5c4)cc3)cc(-c3ccccc3)c21] | 55 |

TABLE 2-continued

| Compound | Reactant B | Structure | Yield (%) |
|---|---|---|---|
| 184 | | 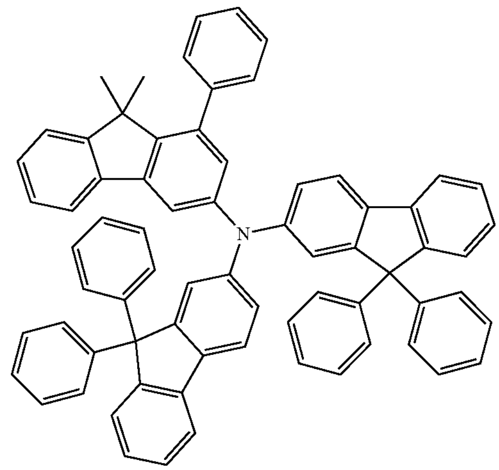 [SMILES: CC1(C)c2ccccc2-c2cc(N(c3ccc4c(c3)C(c3ccccc3)(c3ccccc3)c3ccccc3-4)c3ccc4c(c3)C(c3ccccc3)(c3ccccc3)c3ccccc3-4)cc(-c3ccccc3)c21] | 44 |
| 188 | | 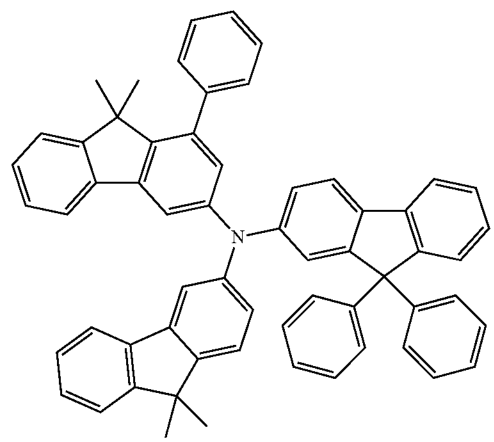 [SMILES: CC1(C)c2ccccc2-c2cc(N(c3cc(-c4ccccc4)c4c(c3)-c3ccccc3C4(C)C)c3ccc4c(c3)C(c3ccccc3)(c3ccccc3)c3ccccc3-4)ccc21] | 64 |
| 209 | | 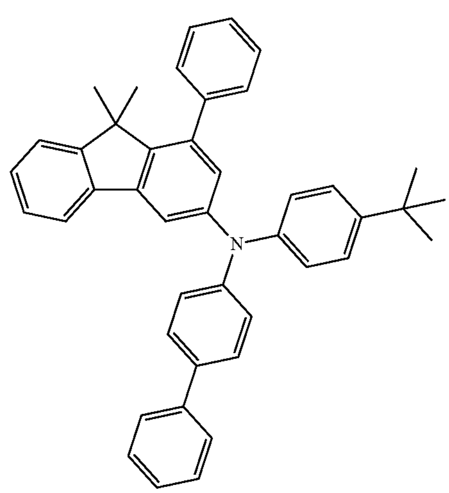 [SMILES: CC(C)(C)c1ccc(N(c2ccc(-c3ccccc3)cc2)c2cc(-c3ccccc3)c3c(c2)-c2ccccc2C3(C)C)cc1] | 53 |

TABLE 2-continued

| Compound | Reactant B | Structure | Yield (%) |
|---|---|---|---|
| 213 | | 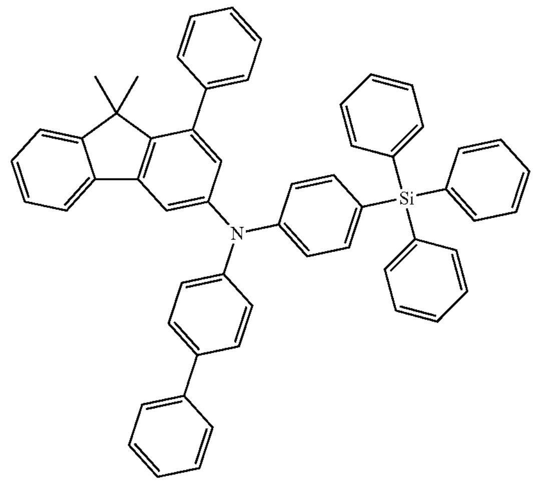 [SMILES: CC1(C)c2ccccc2-c2cc(N(c3ccc(-c4ccccc4)cc3)c3ccc([Si](c4ccccc4)(c4ccccc4)c4ccccc4)cc3)cc(-c3ccccc3)c21] | 46 |
| 217 | | 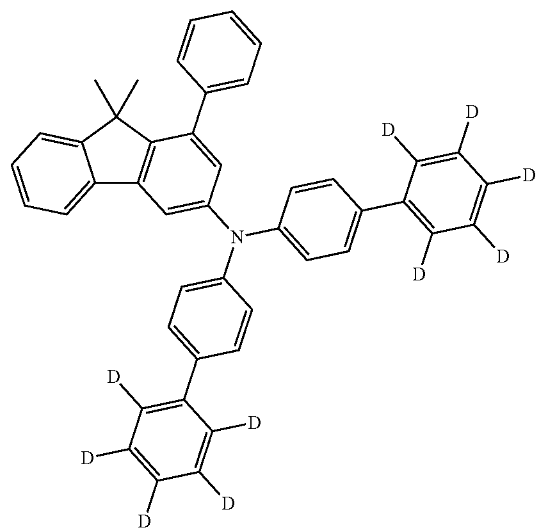 [SMILES: [2H]c1c([2H])c([2H])c(-c2ccc(N(c3ccc(-c4c([2H])c([2H])c([2H])c([2H])c4[2H])cc3)c3cc(-c4ccccc4)c4c(c3)-c3ccccc3C4(C)C)cc2)c([2H])c1[2H]] | 66 |
| 218 | | 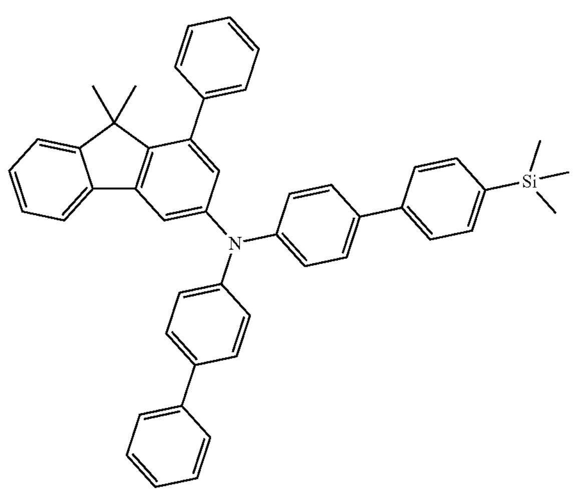 [SMILES: CC1(C)c2ccccc2-c2cc(N(c3ccc(-c4ccccc4)cc3)c3ccc(-c4ccc([Si](C)(C)C)cc4)cc3)cc(-c3ccccc3)c21] | 55 |

Compounds shown in Table 3 were synthesized using the method for synthesizing Compound 68, with Intermediate a being replaced with reactant C in Table 3 and with N-(4-(2-naphthyl)phenyl)-[1,1'-biphenyl]-4-amine being replaced with reactant D in Table 3.

TABLE 3

| Compound | Reactant C | Reactant D |
|---|---|---|
| 190 | | |
| 196 | | |
| 203 | | |
| 205 | | |

TABLE 3-continued
| | | |
|---|---|---|
| 215 | 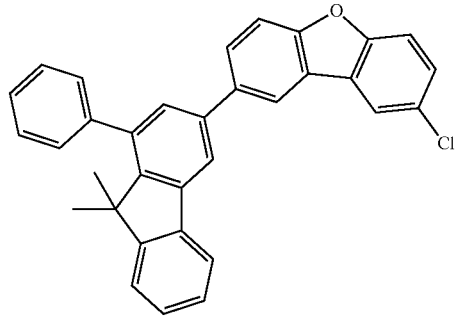 [SMILES: CC1(C)c2ccccc2-c2cc(-c3ccc4oc5ccc(Cl)cc5c4c3)cc(-c3ccccc3)c21] | 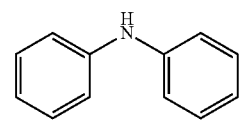 [SMILES: c1ccc(Nc2ccccc2)cc1] |
| 219 | 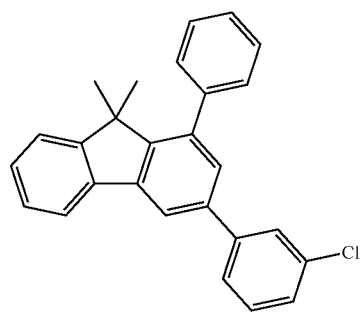 [SMILES: CC1(C)c2ccccc2-c2cc(-c3cccc(Cl)c3)cc(-c3ccccc3)c21] | 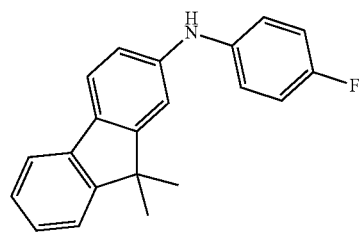 [SMILES: CC1(C)c2ccccc2-c2ccc(Nc3ccc(F)cc3)cc21] |
| 220 | 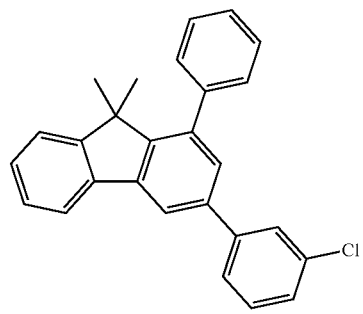 [SMILES: CC1(C)c2ccccc2-c2cc(-c3cccc(Cl)c3)cc(-c3ccccc3)c21] | 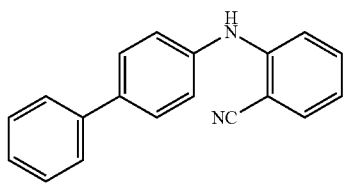 [SMILES: N#Cc1ccccc1Nc1ccc(-c2ccccc2)cc1] |
| Compound | Structure | Yield (%) |
|---|---|---|
| 190 | 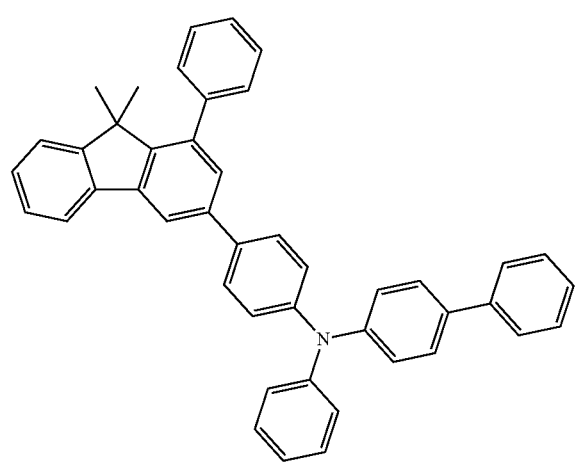 [SMILES: CC1(C)c2ccccc2-c2cc(-c3ccc(N(c4ccccc4)c4ccc(-c5ccccc5)cc4)cc3)cc(-c3ccccc3)c21] | 56 |

TABLE 3-continued
| 196 | 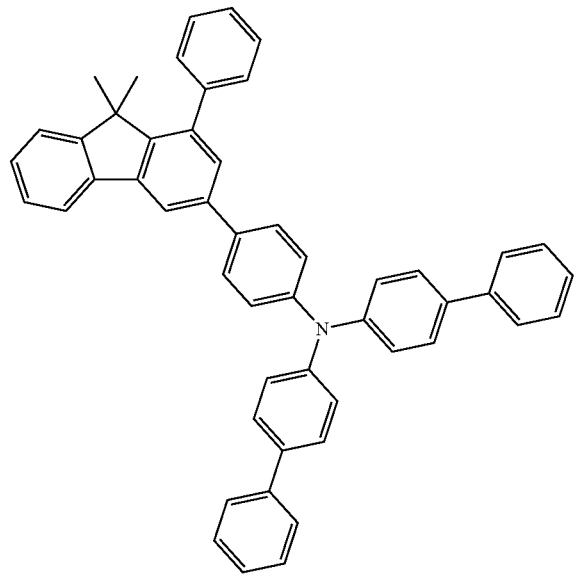 [SMILES: CC1(C)c2ccccc2-c2cc(-c3ccc(N(c4ccc(-c5ccccc5)cc4)c4ccc(-c5ccccc5)cc4)cc3)cc(-c3ccccc3)c21] | 48 |
| 203 | 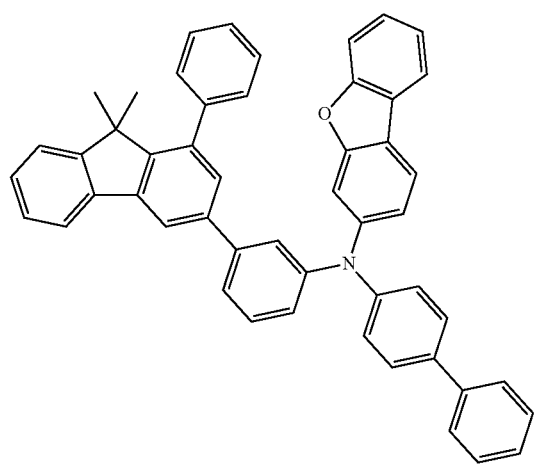 [SMILES: CC1(C)c2ccccc2-c2cc(-c3cccc(N(c4ccc(-c5ccccc5)cc4)c4ccc5c(c4)oc4ccccc45)c3)cc(-c3ccccc3)c21] | 65 |
| 205 | 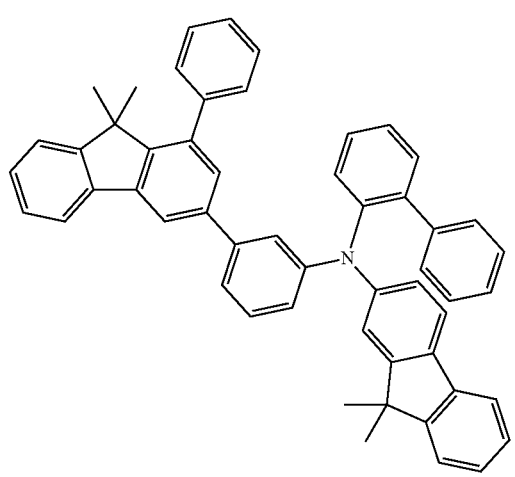 [SMILES: CC1(C)c2ccccc2-c2ccc(N(c3cccc(-c4cc(-c5ccccc5)c5c(c4)-c4ccccc4C5(C)C)c3)c3ccccc3-c3ccccc3)cc21] | 60 |

TABLE 3-continued
215 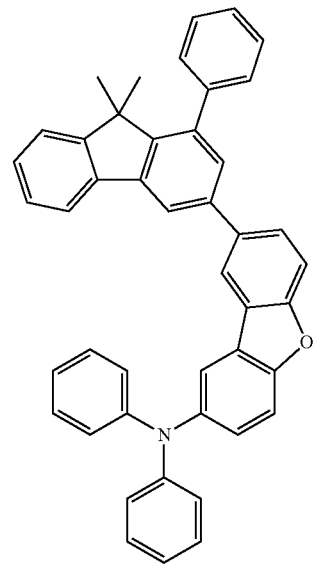 [SMILES: CC1(C)c2ccccc2-c2cc(-c3ccc4oc5ccc(N(c6ccccc6)c6ccccc6)cc5c4c3)cc(-c3ccccc3)c21] 63
219 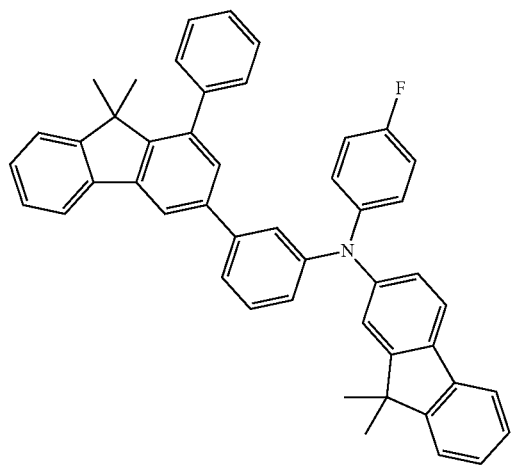 [SMILES: CC1(C)c2ccccc2-c2ccc(N(c3ccc(F)cc3)c3cccc(-c4cc(-c5ccccc5)c5c(c4)-c4ccccc4C5(C)C)c3)cc21] 54
220 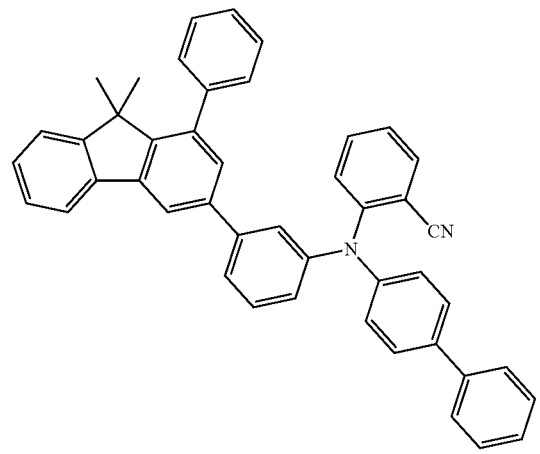 [SMILES: CC1(C)c2ccccc2-c2cc(-c3cccc(N(c4ccc(-c5ccccc5)cc4)c4ccccc4C#N)c3)cc(-c3ccccc3)c21] 47

Mass spectrometry data for the compounds in the synthesis examples are shown in Table 4.

TABLE 4

| Compound | m/z | Compound | m/z |
|---|---|---|---|
| Compound 2 | m/z = 488.2[M + H]+ | Compound 135 | m/z = 680.3[M + H]+ |
| Compound 7 | m/z = 528.2[M + H]+ | Compound 141 | m/z = 644.3[M + H]+ |
| Compound 21 | m/z = 676.3[M + H]+ | Compound 144 | m/z = 709.3[M + H]+ |
| Compound 27 | m/z = 564.3[M + H]+ | Compound 153 | m/z = 670.3[M + H]+ |
| Compound 47 | m/z = 594.2[M + H]+ | Compound 158 | m/z = 719.3[M + H]+ |
| Compound 57 | m/z = 590.3[M + H]+ | Compound 161 | m/z = 706.3[M + H]+ |
| Compound 65 | m/z = 630.3[M + H]+ | Compound 170 | m/z = 756.4[M + H]+ |
| Compound 68 | m/z = 640.3[M + H]+ | Compound 173 | m/z = 690.3[M + H]+ |
| Compound 75 | m/z = 666.3[M + H]+ | Compound 177 | m/z = 690.3[M + H]+ |
| Compound 79 | m/z = 754.3[M + H]+ | Compound 184 | m/z = 918.4[M + H]+ |
| Compound 92 | m/z = 604.3[M + H]+ | Compound 188 | m/z = 794.4[M + H]+ |
| Compound 96 | m/z = 679.3[M + H]+ | Compound 190 | m/z = 590.3[M + H]+ |
| Compound 108 | m/z = 630.3[M + H]+ | Compound 196 | m/z = 666.3[M + H]+ |
| Compound 115 | m/z = 666.3[M + H]+ | Compound 203 | m/z = 680.3[M + H]+ |
| Compound 121 | m/z = 752.3[M + H]+ | Compound 205 | m/z = 706.3[M + H]+ |
| Compound 128 | m/z = 654.3[M + H]+ | Compound 209 | m/z = 570.3[M + H]+ |
| Compound 213 | m/z = 772.3[M + H]+ | Compound 217 | m/z = 600.4[M + H]+ |
| Compound 218 | m/z = 662.3[M + H]+ | Compound 215 | m/z = 604.3[M + H]+ |
| Compound 219 | m/z = 648.3[M + H]+ | Compound 220 | m/z = 615.3[M + H]+ |

NMR data for some of the intermediates and the compounds are shown in Table 5 below.

TABLE 5

| Compound | NMR data |
|---|---|
| Intermediate a | $^1$H NMR (CD$_2$Cl$_2$, 400 MHz): 7.76 (s, 1H), 7.71 (d, 1H), 7.40 (d, 1H), 7.36-7.28 (m, 8H), 1.20 (s, 6H). |
| Compound 68 | $^1$H NMR (CD$_2$Cl$_2$, 400 MHz): 8.10 (s, 1H), 7.91 (d, 1H), 7.88 (d, 1H), 7.83 (d, 1H), 7.75 (d, 2H), 7.70 (d, 1H), 7.67-7.64 (m, 3H), 7.59 (d, 2H), 7.48-7.43 (m, 6H), 7.40 (t, 1H), 7.38-7.31 (m, 7H), 7.29 (d, 2H), 7.24 (d, 2H), 7.19 (s, 1H), 1.22 (s, 6H). |

Fabrication and Evaluation of Organic Electroluminescent Devices

EXAMPLE 1

An anode was prepared by the following processes. An ITO substrate (manufactured by Corning) with a thickness of 1500 Å was cut to have dimensions of 40 mm×40 mm×0.7 mm, and then fabricated, by a photoetching process, into an experimental substrate with patterns of a cathode, of an anode, and of an insulation layer, followed by surface treatment using ultraviolet ozone and O$_2$:N$_2$ plasma to increase the work function of the anode (experimental substrate) and to descum.

HAT-CN was deposited by vacuum evaporation on the experimental substrate (anode) to form a hole injection layer (HIL) with a thickness of 100 Å, and HT-01 was deposited by evaporation on the hole injection layer to form a hole transport layer with a thickness of 800 Å.

Compound 2 was deposited by vacuum evaporation on the hole transport layer to form an electron blocking layer with a thickness of 950 Å.

RH-01 and Ir(Piq)$_2$(acac) were co-deposited by evaporation on the electron blocking layer in a ratio of 95%:5% to form an organic light-emitting layer (red light-emitting layer, R-EML) with a thickness of 350 Å.

ET-01 and LiQ were mixed in a weight ratio of 1:1 and deposited by evaporation on the organic light-emitting layer to form an electron transport layer (ETL) with a thickness of 300 Å; LiQ was deposited by evaporation on the electron transport layer to form an electron injection layer (EIL) with a thickness of 10 Å; and then magnesium (Mg) and silver (Ag) were mixed in a ratio of 1:9 and deposited by vacuum evaporation on the electron injection layer to form a cathode with a thickness of 105 Å.

Furthermore, CP-1 was deposited by evaporation on the above cathode to form an organic capping layer (CPL) with a thickness of 650 Å, thereby completing the fabrication of an organic electroluminescent device.

EXAMPLES 2 TO 38

Organic electroluminescent devices were fabricated by the same method as used in Example 1, except that Compound 2 was replaced with a compound shown in Table 6 below when an electron blocking layer was formed.

COMPARATIVE EXAMPLE 1

An organic electroluminescent device was fabricated by the same method as used in Example 1, except that Compound 2 was replaced with Compound NPB when an electron blocking layer was formed.

COMPARATIVE EXAMPLE 2

An organic electroluminescent device was fabricated by the same method as used in Example 1, except that Compound 2 was replaced with Compound A when an electron blocking layer was formed.

COMPARATIVE EXAMPLE 3

An organic electroluminescent device was fabricated by the same method as used in Example 1, except that Compound 2 was replaced with Compound B when an electron blocking layer was formed.

COMPARATIVE EXAMPLE 4

An organic electroluminescent devices was fabricated by the same method as used in Example 1, except that Compound 2 was replaced with Compound C when an electron blocking layer was formed.

COMPARATIVE EXAMPLE 5
An organic electroluminescent device was fabricated by the same method as used in Example 1, except that Compound 2 was replaced with Compound D when an electron blocking layer was formed.
Structures of the materials used in the above examples and comparative examples are shown in Table 6 below.
TABLE 6
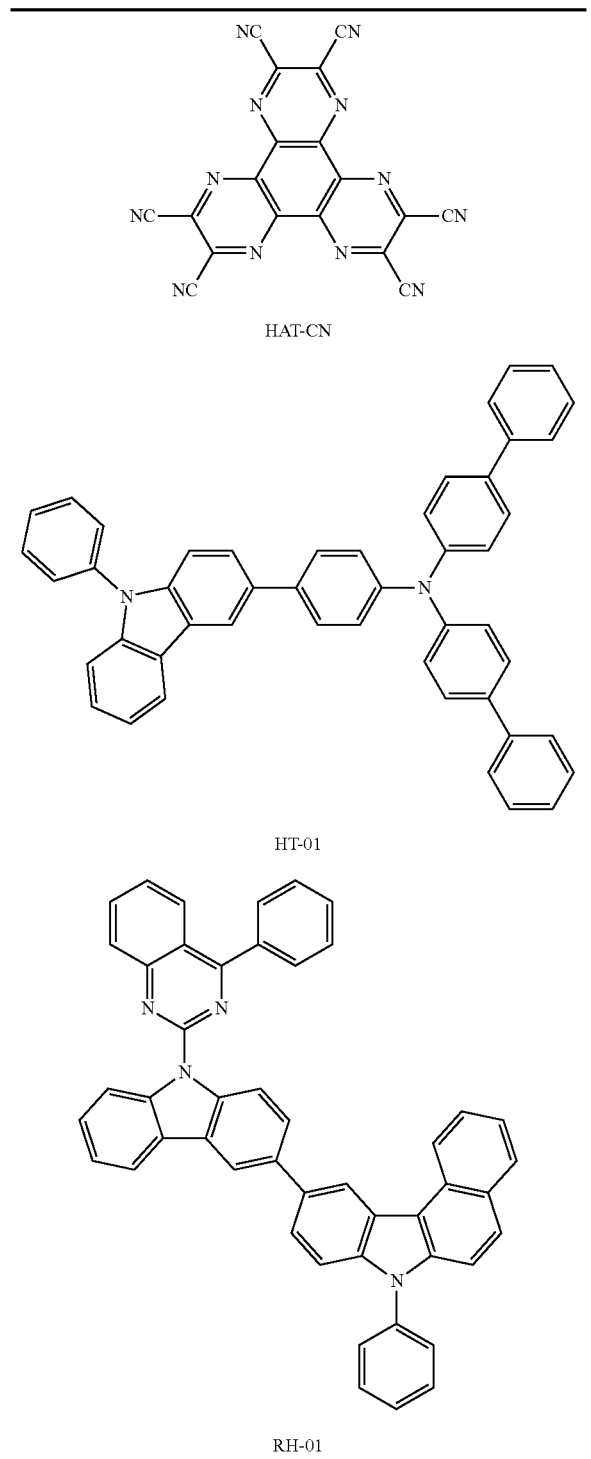
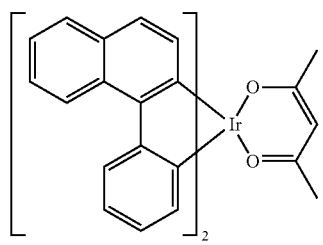
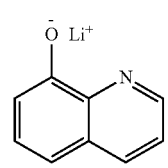

TABLE 6-continued

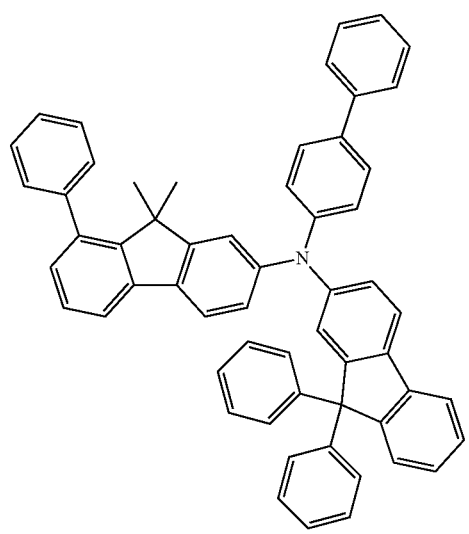 [SMILES: CC1(C)c2cc(N(c3ccc(-c4ccccc4)cc3)c3ccc4c(c3)C(c3ccccc3)(c3ccccc3)c3ccccc3-4)ccc2-c2cccc(-c3ccccc3)c21]

Compound A

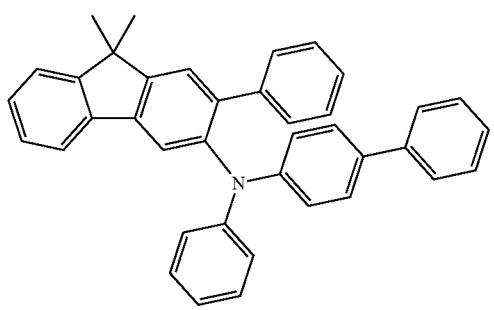 [SMILES: CC1(C)c2ccccc2-c2cc(N(c3ccccc3)c3ccc(-c4ccccc4)cc3)c(-c3ccccc3)cc21]

Compound B

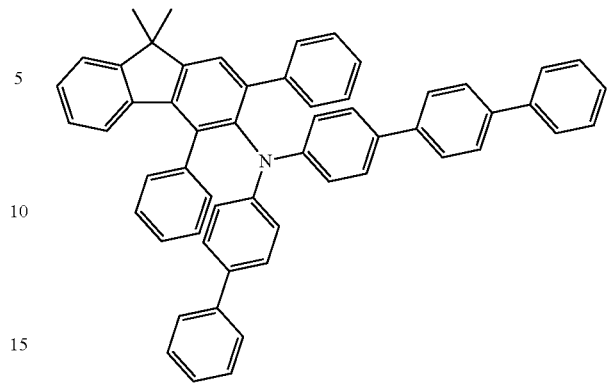

Compound C

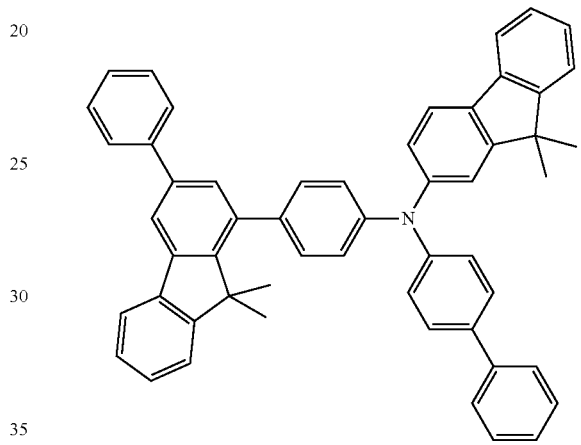

Compound D

The organic electroluminescent devices fabricated above were tested for their performance under the condition of 20 mA/cm². Results are shown in Table 7 below.

TABLE 7

| Examples | Electron blocking layer | Volt (V) | Cd/A | lm/W | CIE-x | CIE-y | EQE % | T95(hrs) @20 mA/cm² |
|---|---|---|---|---|---|---|---|---|
| Example 1 | Compound 2 | 3.81 | 34.6 | 28.5 | 0.68 | 0.32 | 23.5 | 243 |
| Example 2 | Compound 7 | 3.84 | 35.4 | 28.9 | 0.68 | 0.32 | 24.0 | 235 |
| Example 3 | Compound 21 | 3.90 | 34.2 | 27.5 | 0.68 | 0.32 | 23.2 | 242 |
| Example 4 | Compound 27 | 3.86 | 35.4 | 28.8 | 0.68 | 0.32 | 24.1 | 242 |
| Example 5 | Compound 47 | 3.90 | 34.1 | 27.5 | 0.68 | 0.32 | 23.2 | 230 |
| Example 6 | Compound 57 | 3.87 | 35.3 | 28.6 | 0.68 | 0.32 | 24.0 | 231 |
| Example 7 | Compound 65 | 3.88 | 35.0 | 28.4 | 0.68 | 0.32 | 23.8 | 236 |
| Example 8 | Compound 68 | 3.83 | 35.2 | 28.9 | 0.68 | 0.32 | 23.9 | 230 |
| Example 9 | Compound 75 | 3.80 | 34.3 | 28.3 | 0.68 | 0.32 | 23.3 | 230 |
| Example 10 | Compound 79 | 3.83 | 33.9 | 27.8 | 0.68 | 0.32 | 23.0 | 227 |
| Example 11 | Compound 92 | 3.82 | 33.4 | 27.4 | 0.68 | 0.32 | 22.7 | 231 |
| Example 12 | Compound 96 | 3.82 | 34.1 | 28.1 | 0.68 | 0.32 | 23.2 | 243 |
| Example 13 | Compound 108 | 3.91 | 33.1 | 26.6 | 0.68 | 0.32 | 22.5 | 235 |
| Example 14 | Compound 115 | 3.83 | 33.6 | 27.6 | 0.68 | 0.32 | 22.8 | 232 |
| Example 15 | Compound 121 | 3.81 | 33.4 | 27.5 | 0.68 | 0.32 | 22.7 | 237 |
| Example 16 | Compound 128 | 3.91 | 35.2 | 28.3 | 0.68 | 0.32 | 23.9 | 238 |
| Example 17 | Compound 135 | 3.87 | 34.6 | 28.1 | 0.68 | 0.32 | 23.5 | 234 |
| Example 18 | Compound 141 | 3.85 | 35.1 | 28.6 | 0.68 | 0.32 | 23.8 | 228 |
| Example 19 | Compound 144 | 3.91 | 34.6 | 27.8 | 0.68 | 0.32 | 23.5 | 240 |
| Example 20 | Compound 153 | 3.83 | 34.5 | 28.3 | 0.68 | 0.32 | 23.5 | 237 |
| Example 21 | Compound 158 | 3.88 | 33.4 | 27.0 | 0.68 | 0.32 | 22.7 | 230 |
| Example 22 | Compound 161 | 3.83 | 33.6 | 27.6 | 0.68 | 0.32 | 22.9 | 228 |
| Example 23 | Compound 170 | 3.86 | 34.5 | 28.1 | 0.68 | 0.32 | 23.5 | 241 |
| Example 24 | Compound 173 | 3.84 | 33.0 | 27.0 | 0.68 | 0.32 | 22.5 | 236 |
| Example 25 | Compound 177 | 3.91 | 33.9 | 27.2 | 0.68 | 0.32 | 23.1 | 236 |

TABLE 7-continued

| Examples | Electron blocking layer | Volt (V) | Cd/A | lm/W | CIE-x | CIE-y | EQE % | T95(hrs) @20 mA/cm$^2$ |
|---|---|---|---|---|---|---|---|---|
| Example 26 | Compound 184 | 3.84 | 34.9 | 28.6 | 0.68 | 0.32 | 23.8 | 227 |
| Example 27 | Compound 188 | 3.90 | 35.4 | 28.5 | 0.68 | 0.32 | 24.1 | 242 |
| Example 28 | Compound 190 | 3.90 | 35.2 | 28.3 | 0.68 | 0.32 | 23.9 | 234 |
| Example 29 | Compound 196 | 3.89 | 34.1 | 27.5 | 0.68 | 0.32 | 23.2 | 231 |
| Example 30 | Compound 203 | 3.82 | 35.2 | 29.0 | 0.68 | 0.32 | 23.9 | 229 |
| Example 31 | Compound 205 | 3.85 | 34.1 | 27.8 | 0.68 | 0.32 | 23.2 | 238 |
| Example 32 | Compound 209 | 3.83 | 33.8 | 27.7 | 0.68 | 0.32 | 23.0 | 231 |
| Example 33 | Compound 213 | 3.81 | 34.1 | 28.1 | 0.680 | 0.320 | 23.2 | 236 |
| Example 34 | Compound 215 | 3.86 | 27.3 | 22.2 | 0.680 | 0.320 | 18.6 | 232 |
| Example 35 | Compound 217 | 3.91 | 34.6 | 27.8 | 0.680 | 0.320 | 23.5 | 238 |
| Example 36 | Compound 218 | 3.89 | 34.8 | 28.1 | 0.680 | 0.320 | 23.7 | 236 |
| Example 37 | Compound 219 | 3.84 | 34.0 | 27.8 | 0.680 | 0.320 | 23.1 | 237 |
| Example 38 | Compound 220 | 3.89 | 34.0 | 27.5 | 0.680 | 0.320 | 23.1 | 228 |
| Comparative Example 1 | NPB | 4.40 | 17.2 | 13.4 | 0.68 | 0.32 | 11.5 | 102 |
| Comparative Example 2 | Compound A | 3.93 | 22.3 | 17.8 | 0.68 | 0.32 | 14.9 | 200 |
| Comparative Example 3 | Compound B | 3.92 | 24.5 | 19.6 | 0.68 | 0.32 | 16.4 | 185 |
| Comparative Example 4 | Compound C | 3.91 | 23.1 | 18.4 | 0.68 | 0.32 | 15.5 | 178 |
| Comparative Example 5 | Compound D | 3.88 | 20.3 | 16.2 | 0.68 | 0.32 | 13.6 | 160 |

As can be seen from the above table, compared with Comparative Examples 1 to 5, Examples 1 to 38, in which the nitrogen-containing compounds of the present disclosure are used as the material of the electron blocking layers of the red light-emitting electroluminescent devices, the luminous efficiency Cd/A is increased by by at least 11.4%, the external quantum efficiency EQE is increased by at least 13.4%, and the service life is increased by at least 13.5%.

Compared with Comparative Example 1

The Examples of the present disclosure significantly decrease the driving voltage of the devices, and also greatly improve the efficiency and service life thereof. Compared with Comparative Example 2, the Examples of the present disclosure prolong the service life and improve the luminescence efficiency in the case that the driving voltages of the devices are very close to one another. The reason may be that, the amino group in each of the nitrogen-containing compounds of the present disclosure is linked to the 3-position of the fluorenyl group, which, compared with the linkage of the 2-position of compound A, can enable the material to have a deeper HOMO energy level, thereby making it easier to inject holes into the emissive layer. Compared with the devices fabricated in Comparative Examples 3 to 4, the devices fabricated by using the nitrogen-containing compounds of the present disclosure have improved efficiency and prolonged service life in the case that the driving voltages are very close to one another. The reason may be that, compared with that in compounds B and C, the substitution of the phenyl group of the nitrogen-containing compounds of the present disclosure at the 1-position of the dimethylfluorenyl group enables the material to have better spatial morphology and molecular stacking, while maintaining the deep HOMO energy level and high hole mobility of the material.

The nitrogen-containing compounds of the present disclosure, when used in the fabrication of a red organic electroluminescent device, can thus improve the efficiency of the organic electroluminescent device and prolong service life thereof.

Those of ordinary skill in the art will appreciate that the above embodiments are specific embodiments of the present disclosure, and in practical application, various changes can be made to forms and details thereof without deviating from the spirit and scope of the present disclosure.

The invention claimed is:

1. A nitrogen-containing compound, having a structure shown in Chemical Formula 1:

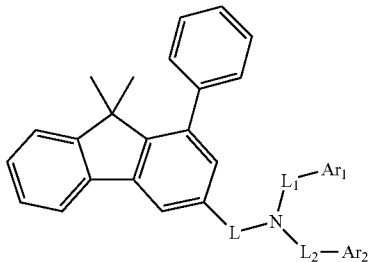

Chemical Formula 1 wherein:
L is selected from the group consisting of single bond, unsubstituted phenylene, and unsubstituted dibenzofuranylene;
$L_1$, and $L_2$ are each independently selected from the group consisting of single bond, substituted or unsubstituted phenylene, and substituted or unsubstituted biphenylene;
substituents in $L_1$ and $L_2$ are identical or different, and are each independently selected from the group consisting of deuterium, fluorine, cyano, methyl, ethyl, n-propyl, isopropyl, tert-butyl, and phenyl;
$Ar_1$ and $Ar_2$ are identical or different, and are each independently selected from the group consisting of substituted or unsubstituted phenyl, substituted or unsubstituted naphthyl, substituted or unsubstituted biphenyl, substituted or unsubstituted fluorenyl, substituted or unsubstituted triphenyl, substituted or unsubstituted dibenzofuranyl, substituted or unsubstituted dibenzothiophenyl, substituted or unsubstituted carbazolyl, and substituted or unsubstituted

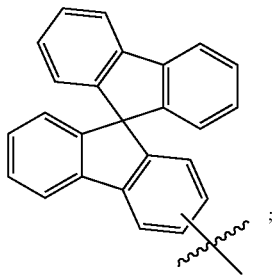

substituents in Ar$_1$ and Ar$_2$ are identical or different, and are each independently selected from the group consisting of deuterium, fluorine, cyano, methyl, ethyl, n-propyl, isopropyl, tert-butyl, phenyl, trimethylsilyl, and triphenylsilyl.

2. The nitrogen-containing compound according to claim 1, wherein L$_1$ and L$_2$ are each independently selected from the group consisting of single bond, and substituted or unsubstituted groups V, the unsubstituted groups V being selected from the group consisting of the following groups:

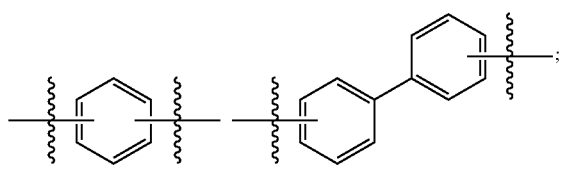

wherein the substituted groups V each have one or more substituents, the substituents being each independently selected from the group consisting of deuterium, fluorine, cyano, methyl, n-propyl, isopropyl, tert-butyl, and phenyl; and when the number of the substituents in the group V is greater than 1, the substituents are the same or different.

3. The nitrogen-containing compound according to claim 1, wherein Ar$_1$ and Ar$_2$ are selected from substituted or unsubstituted groups W, the unsubstituted groups W being selected from the group consisting of the following groups:

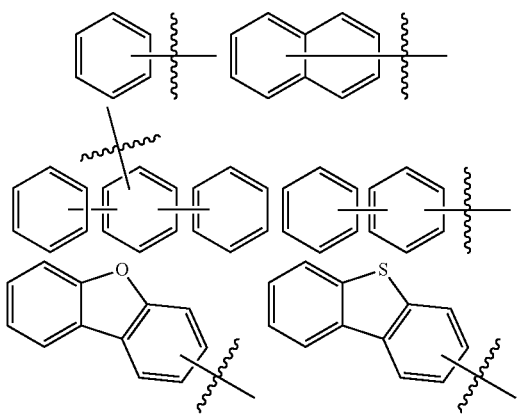

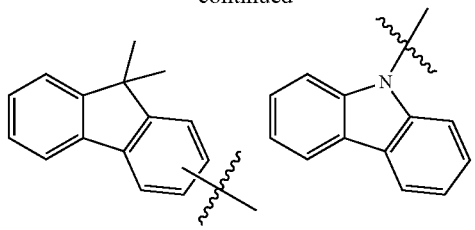

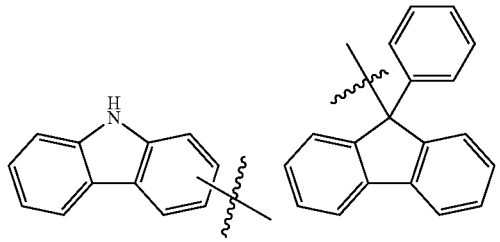

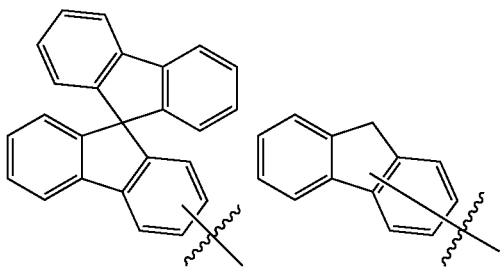

wherein the substituted groups W each have one or more substituents, the substituents being each independently selected from the group consisting of deuterium, fluorine, cyano, methyl, ethyl, n-propyl, isopropyl, tert-butyl, phenyl, trimethylsilyl, and triphenylsilyl; and when the number of the substituents in the group W is greater than 1, the substituents are the same or different.

4. The nitrogen-containing compound according to claim 1, wherein the nitrogen-containing compound is selected from the group consisting of the following compounds:

1

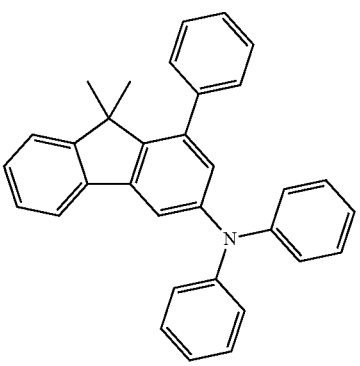

-continued
2
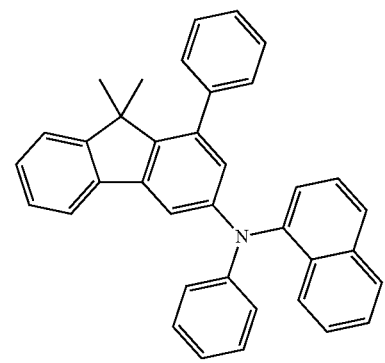
3
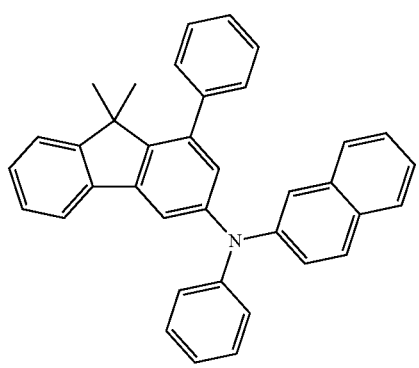
4
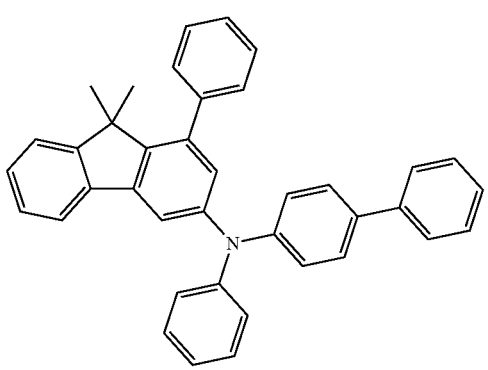
5
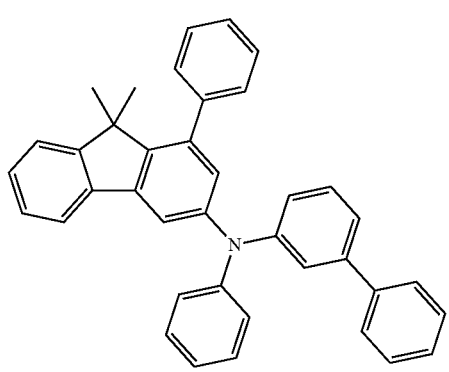
-continued
6
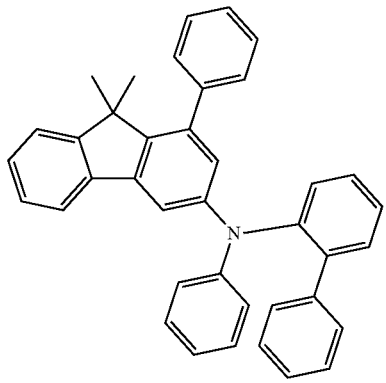
7
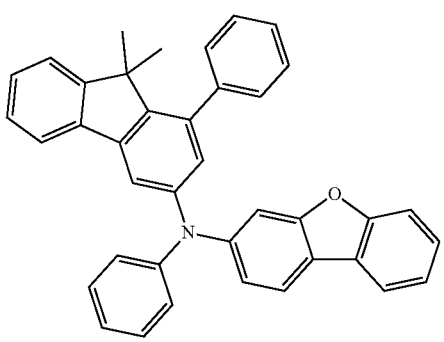
8
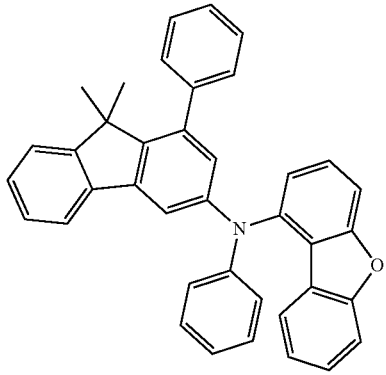
9
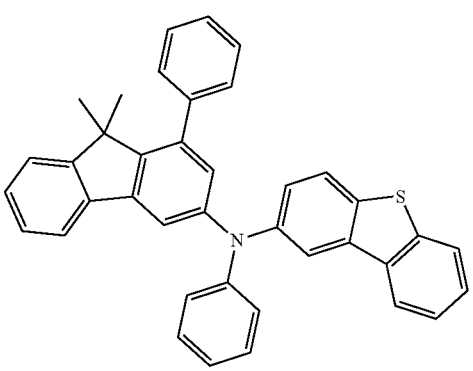

137
-continued
10
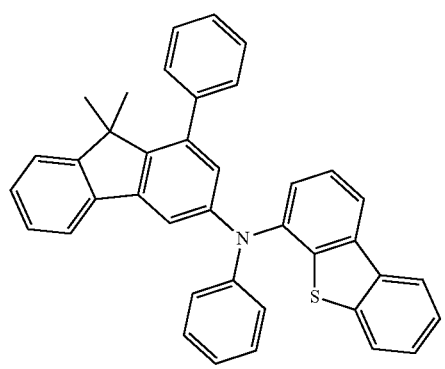
11
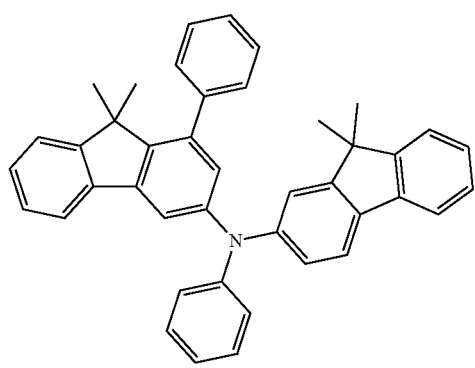
12
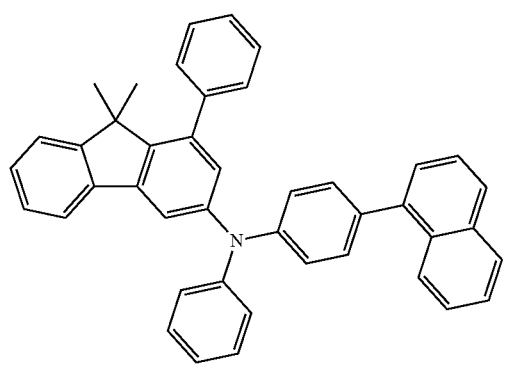
14
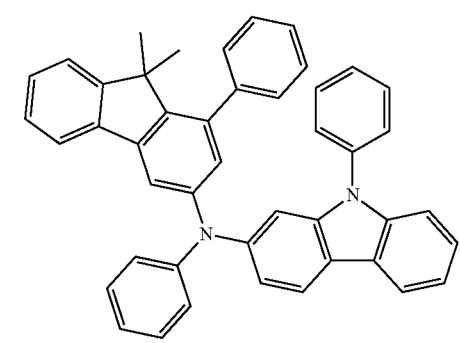
138
-continued
15
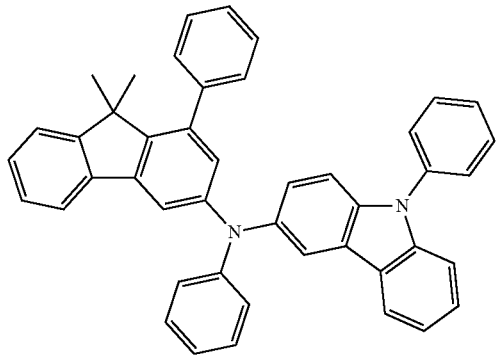
16
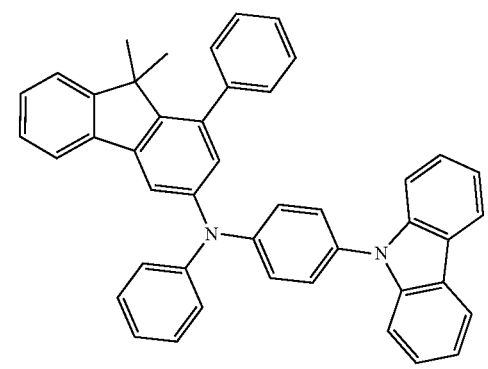
17
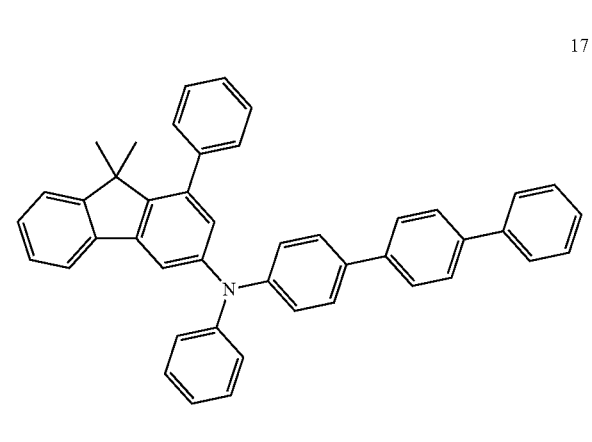
18
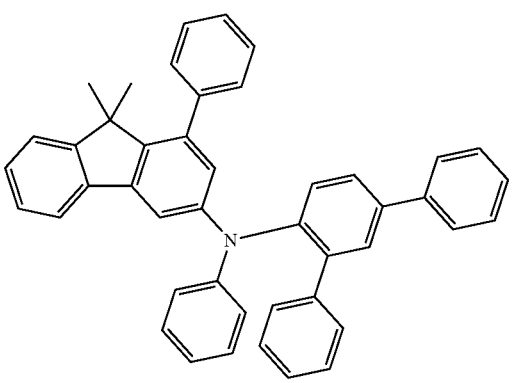

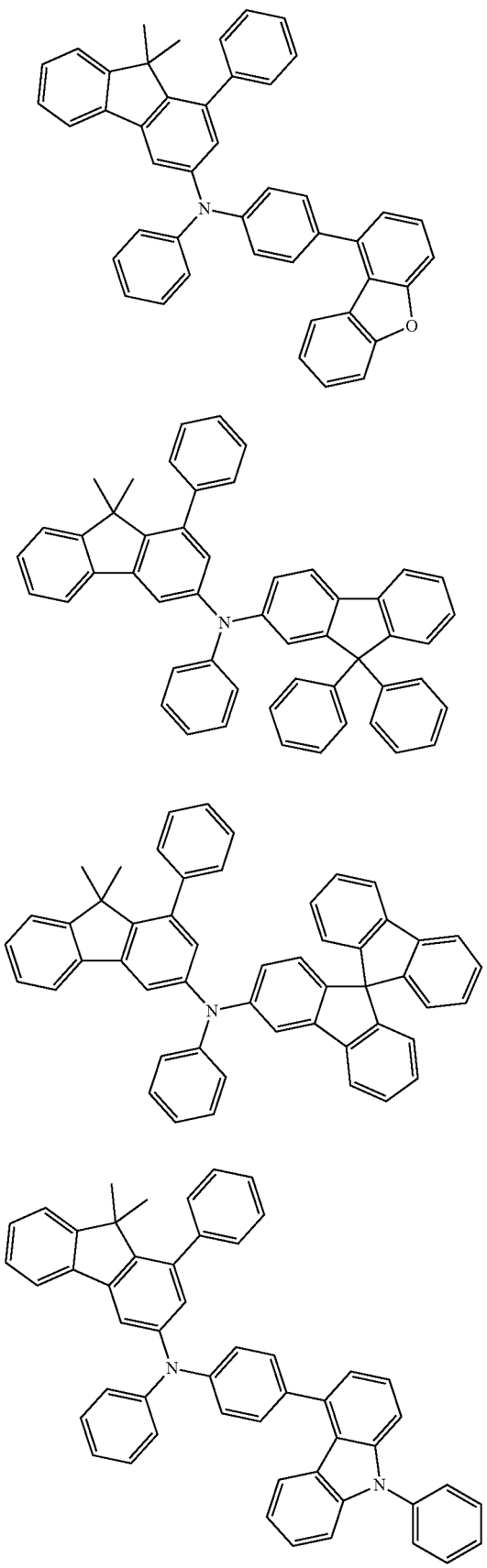
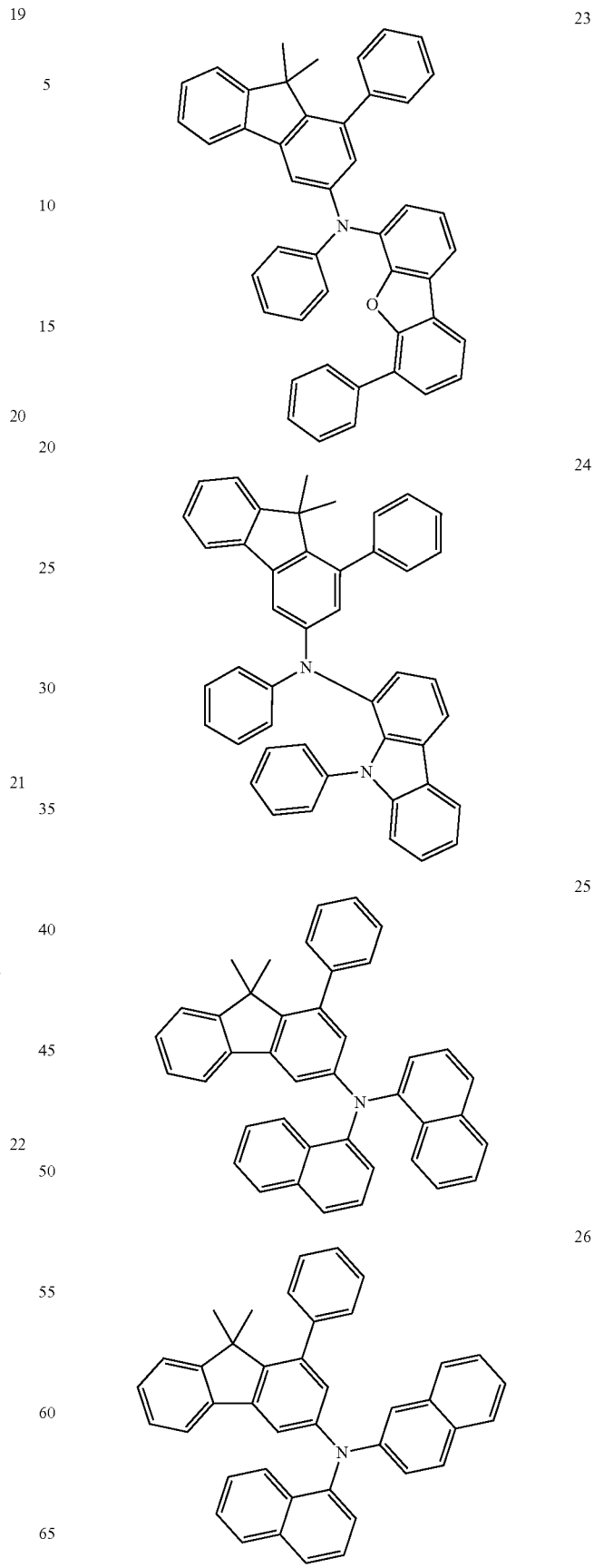

27
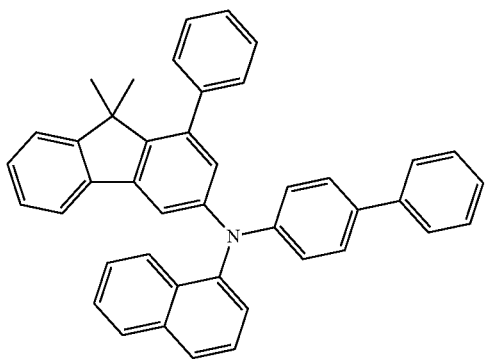
28
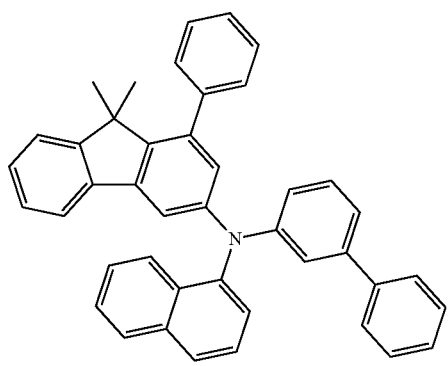
29
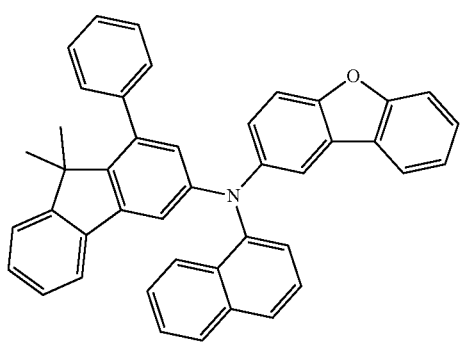
30
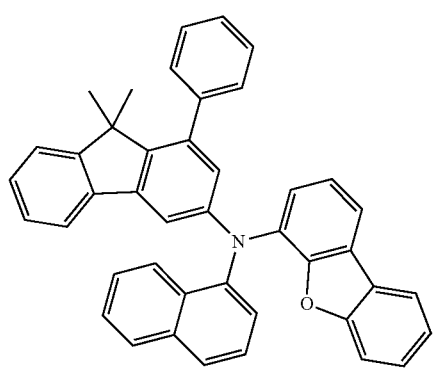
31
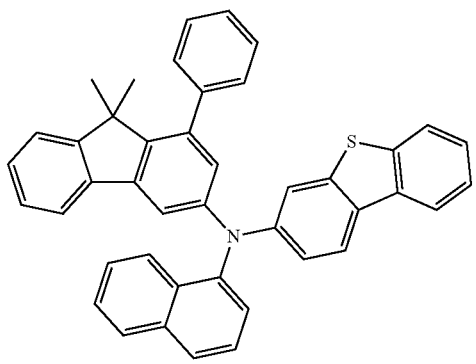
32
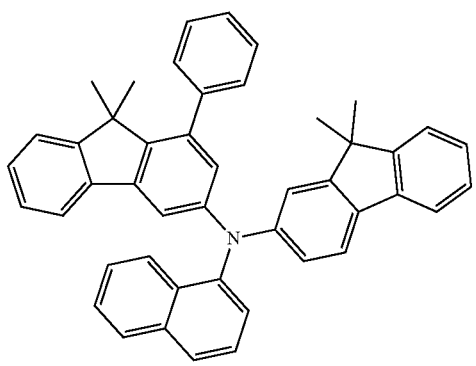
33
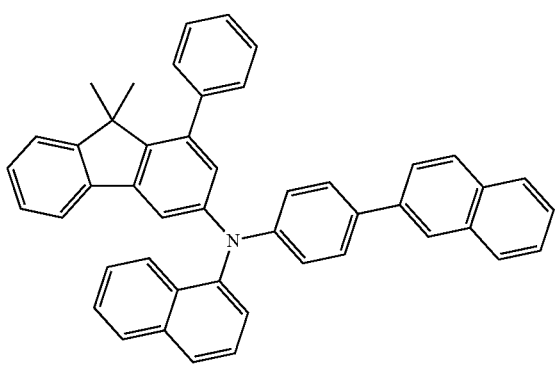
34
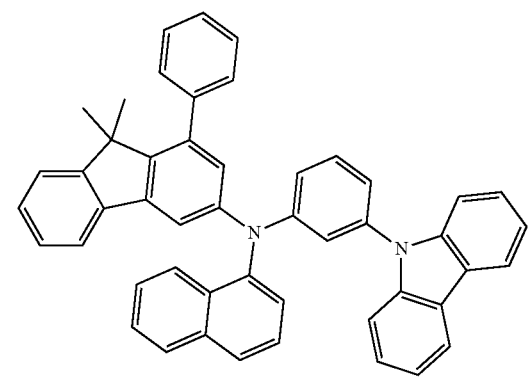

35
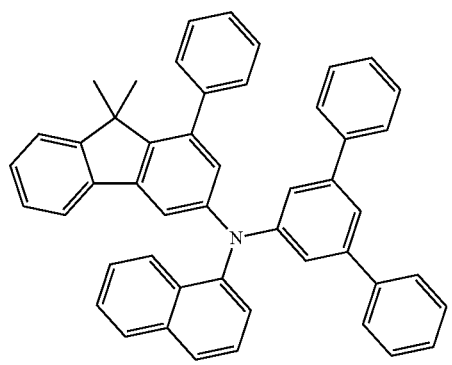
36
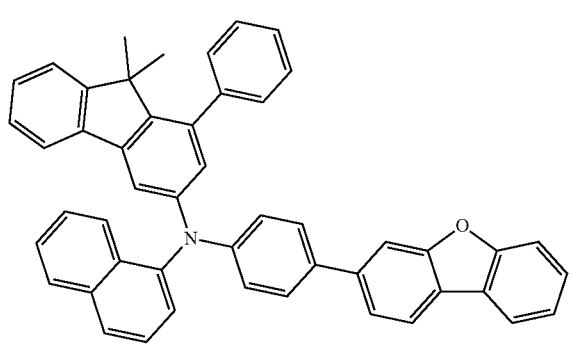
37
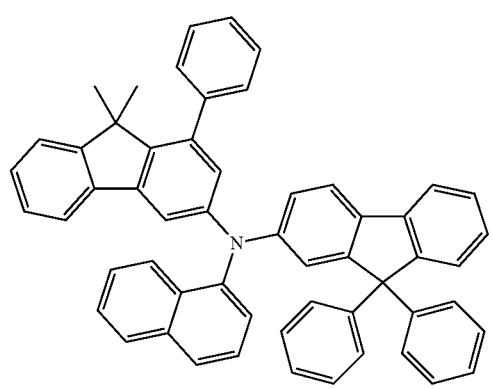
38
39
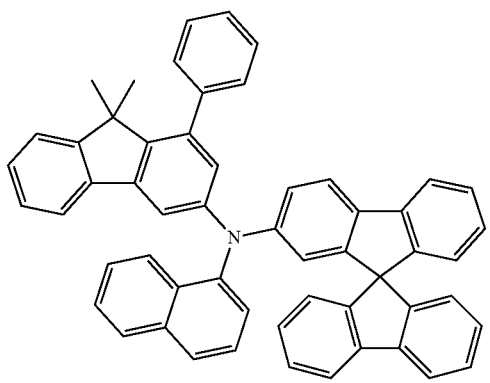
41
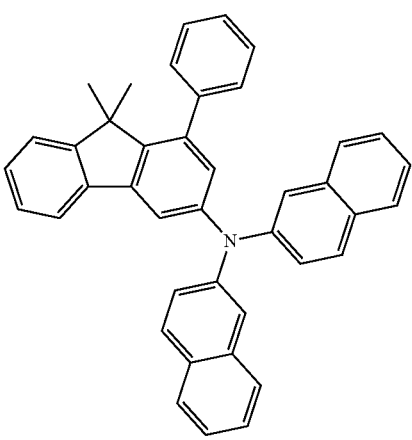
42
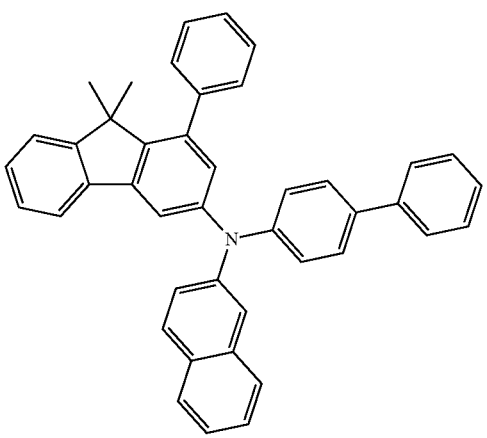

43
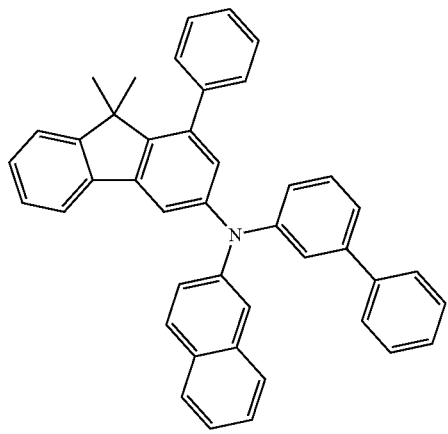
44
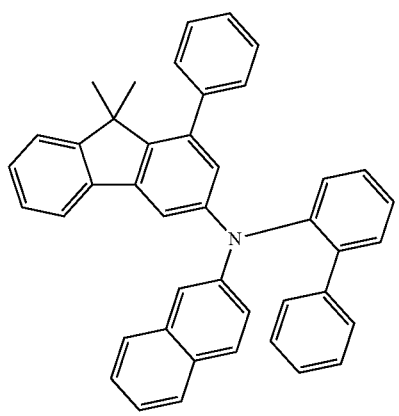
45
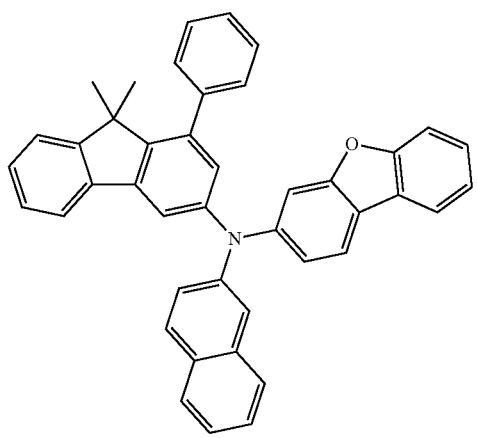
46
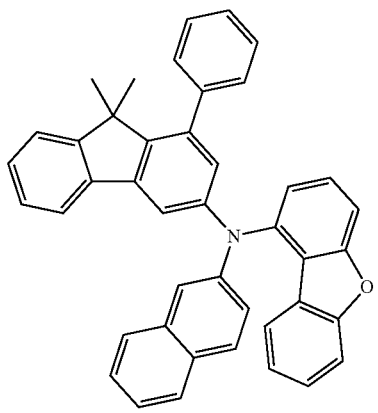
47
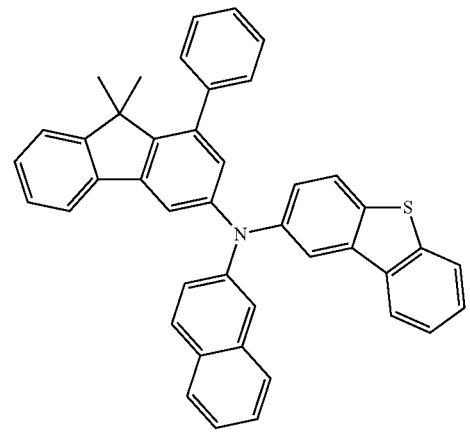
48
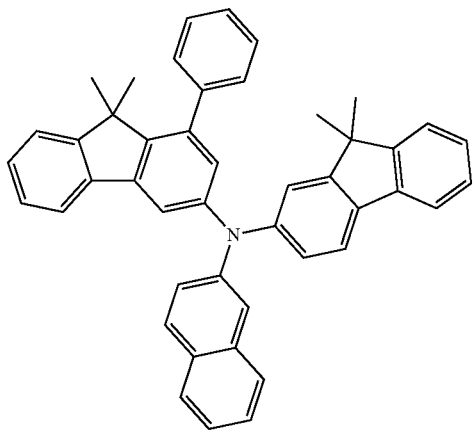

49
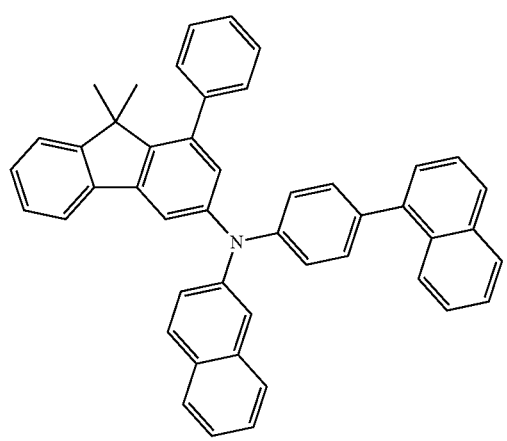
50
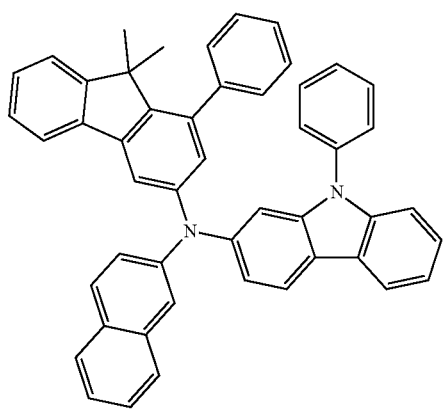
51
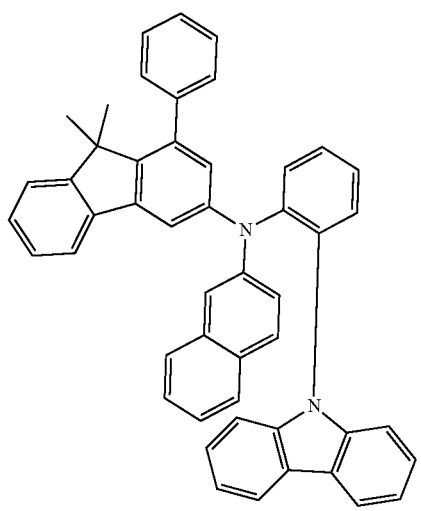
52
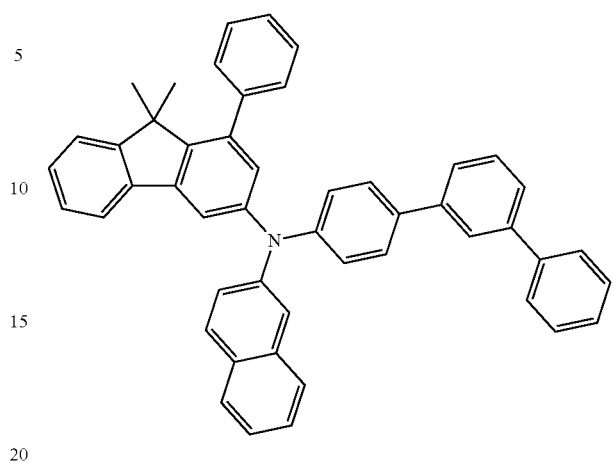
53
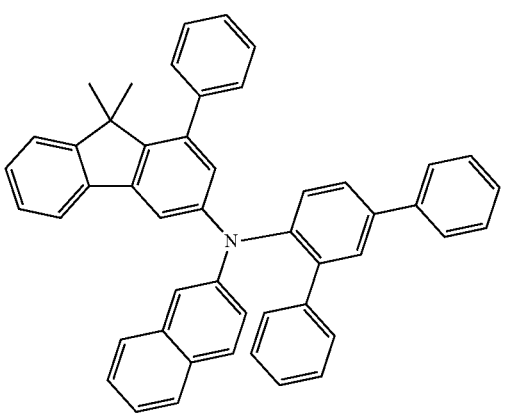
54
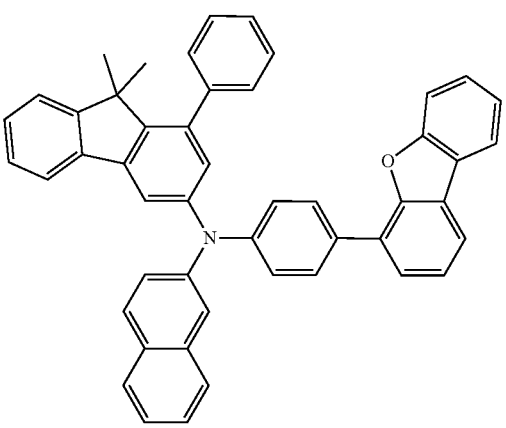

55
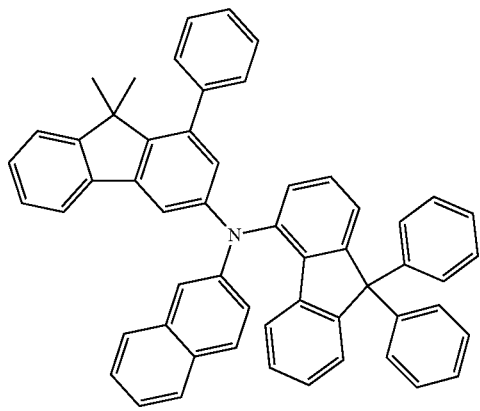
56
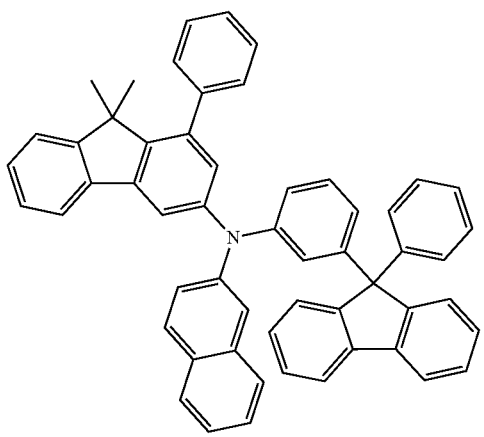
57
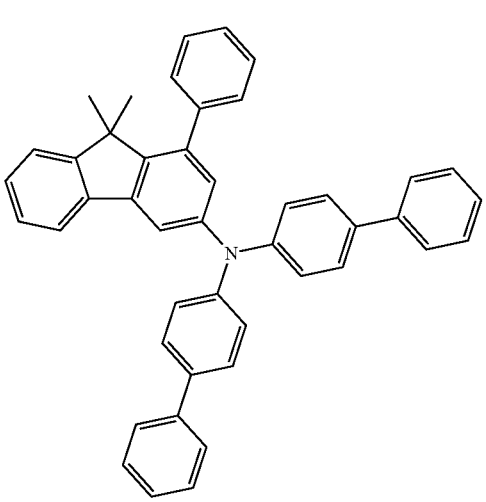
58
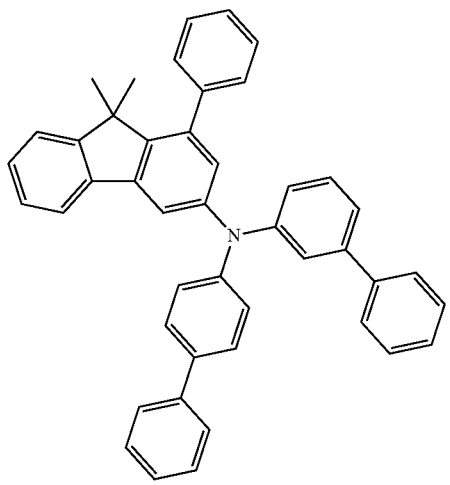
59
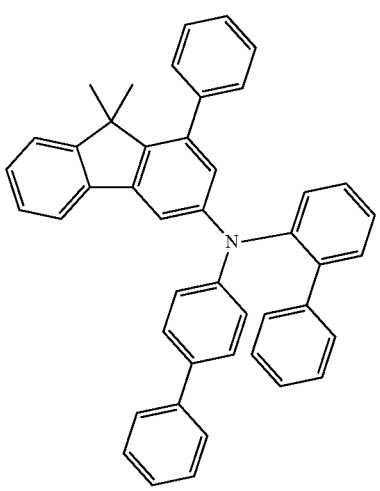
60
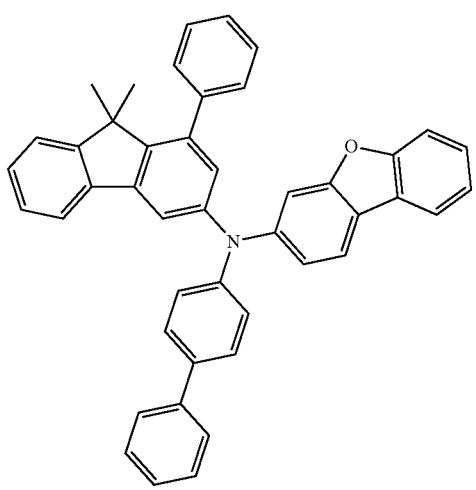

61
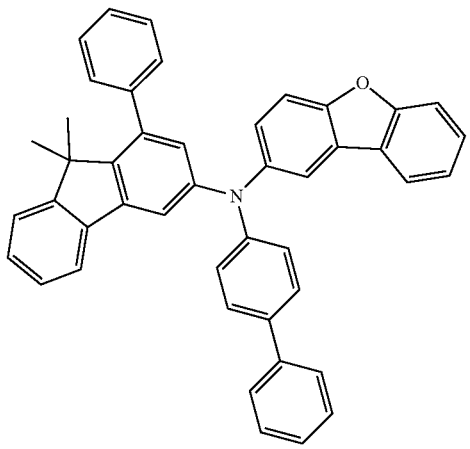
62
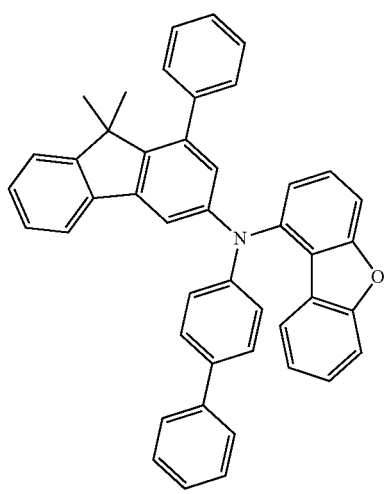
63
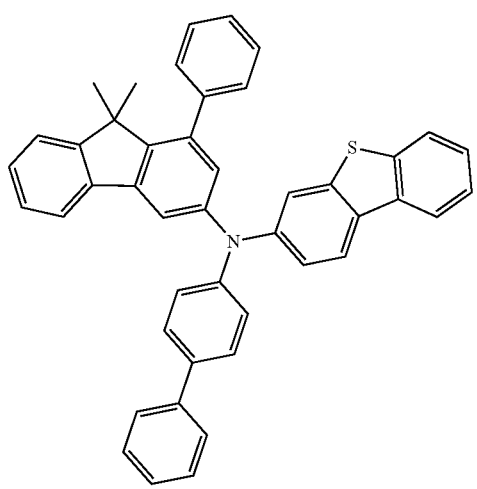
64
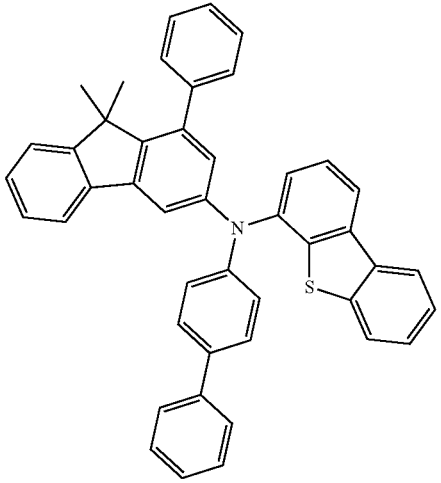
65
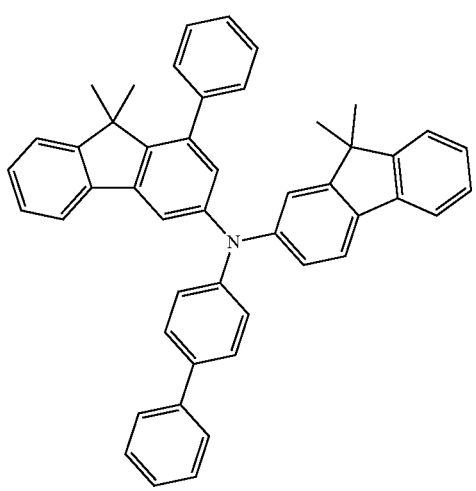
67
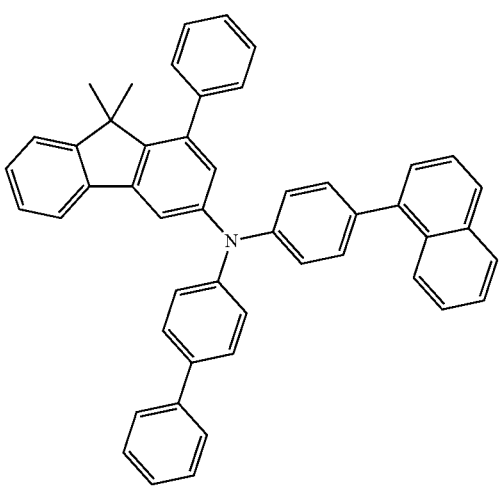

68
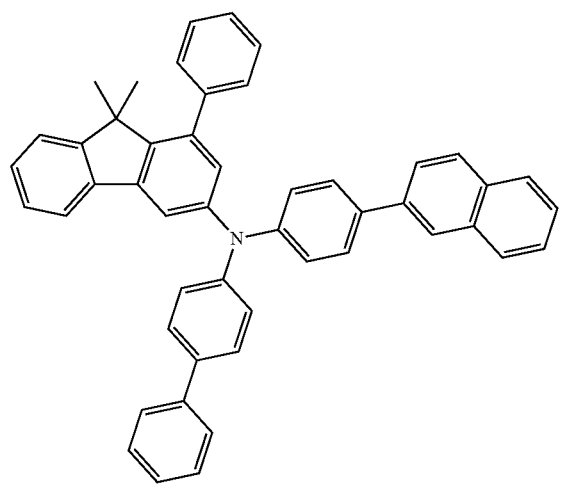
69
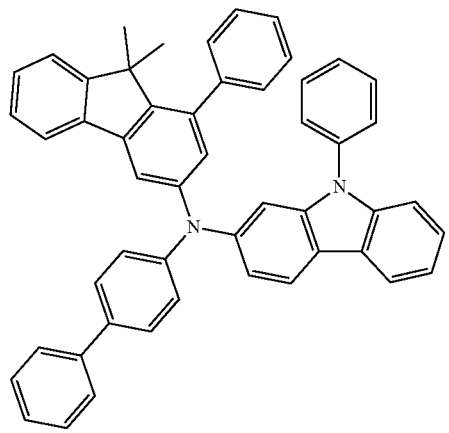
70
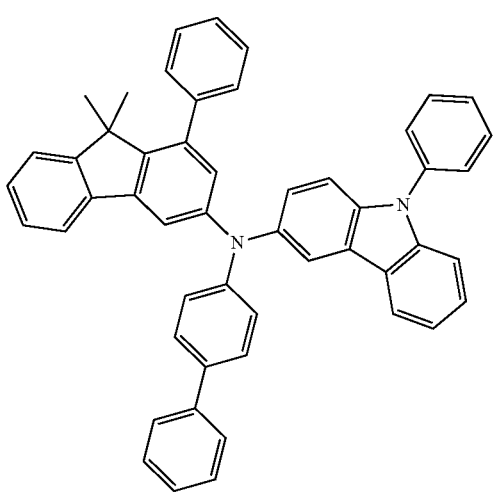
71
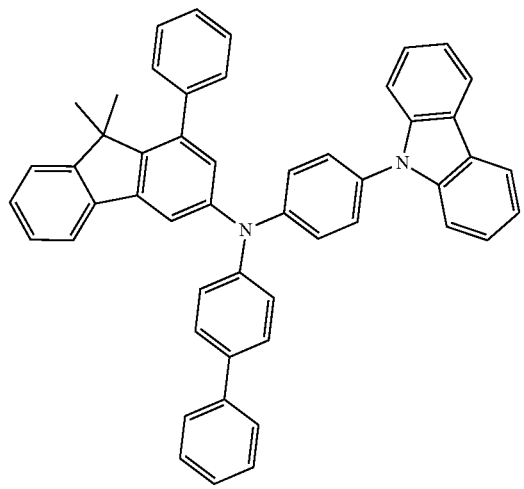
72
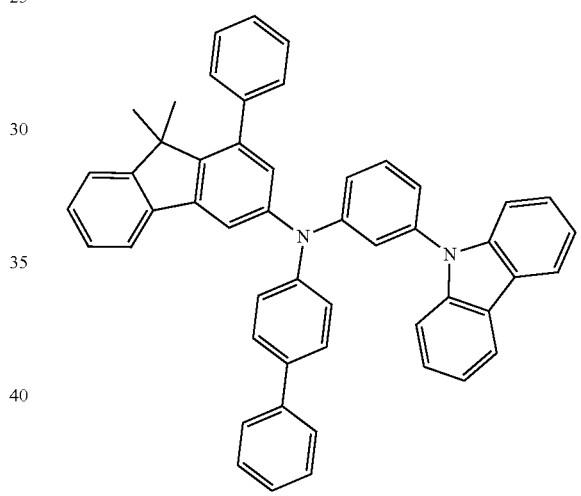
73
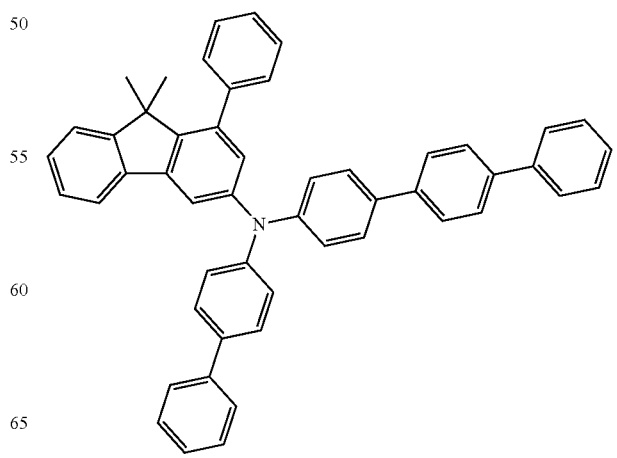

74
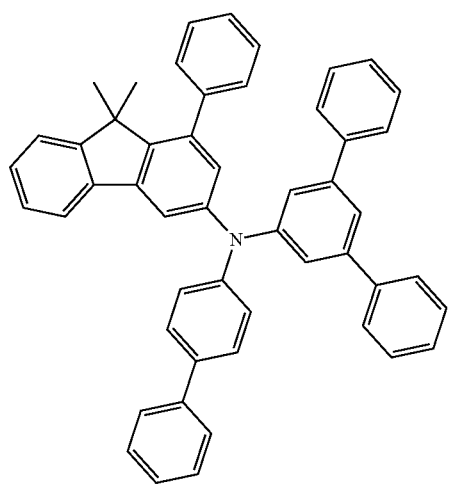
75
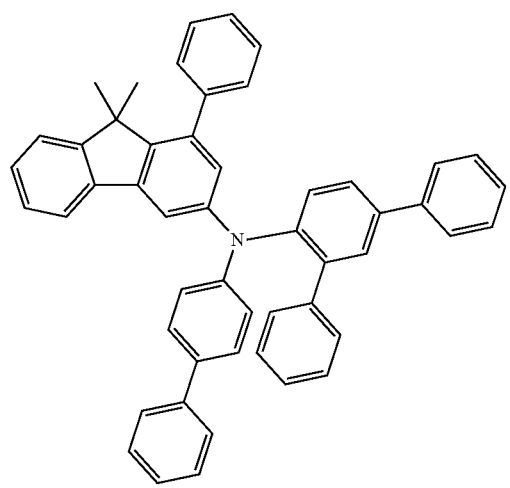
76
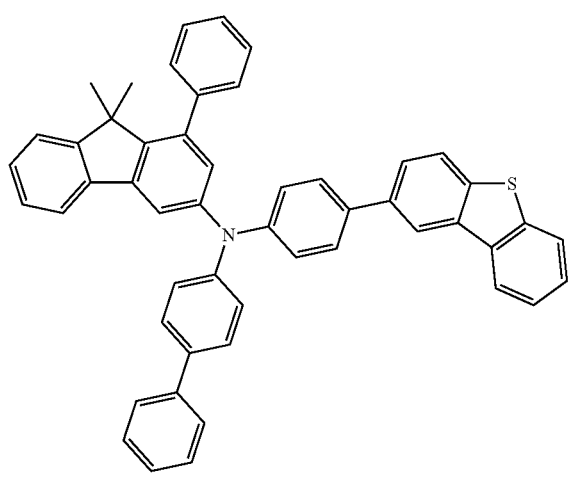
77
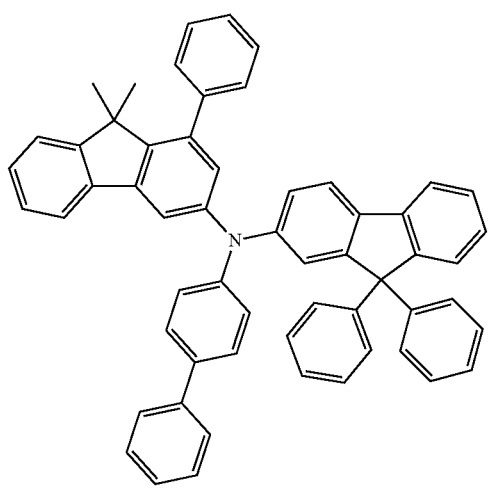
78
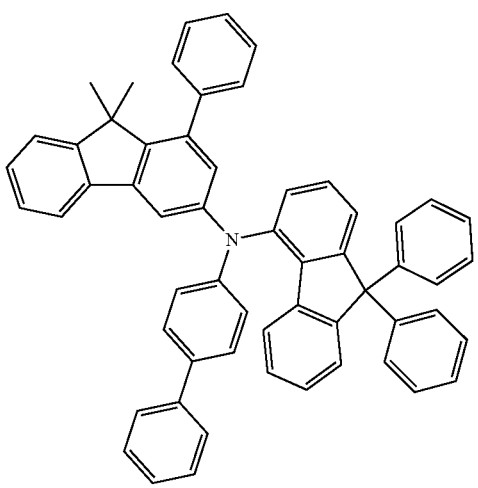
79
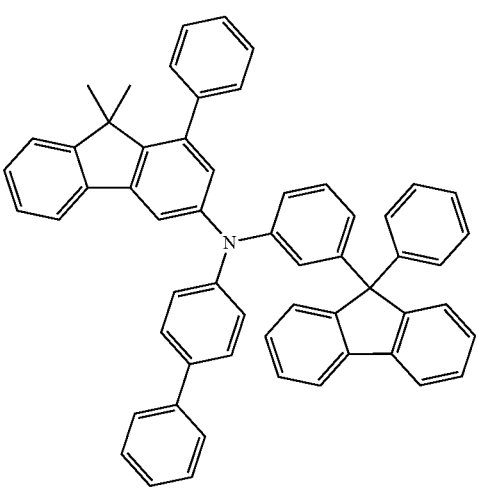

80
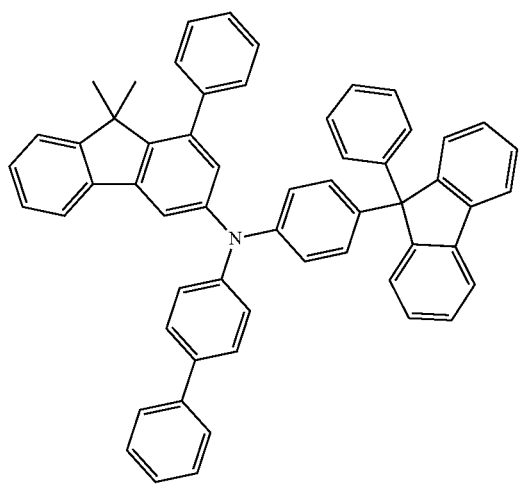
81
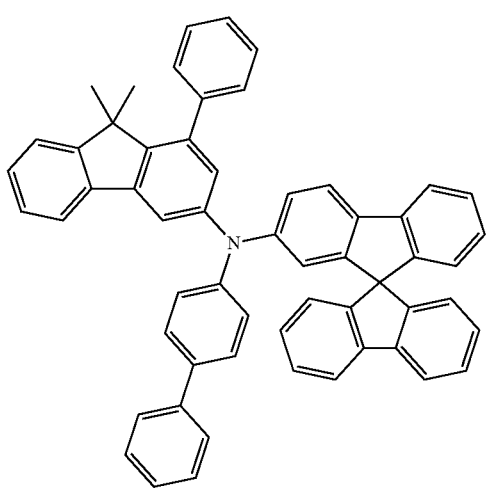
82
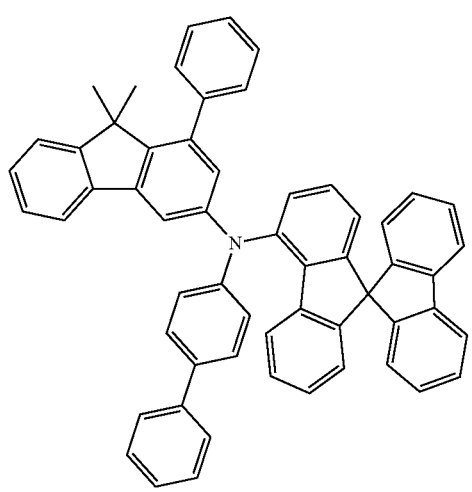
83
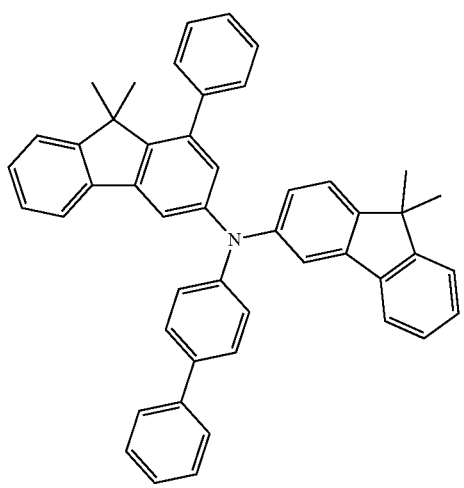
84
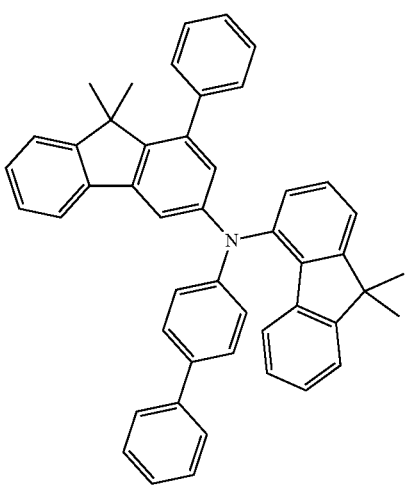
85
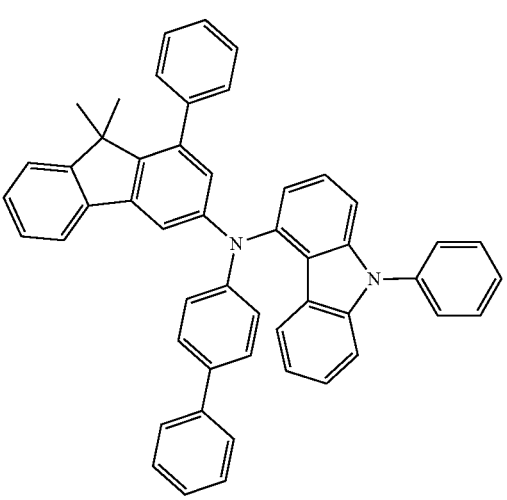

86
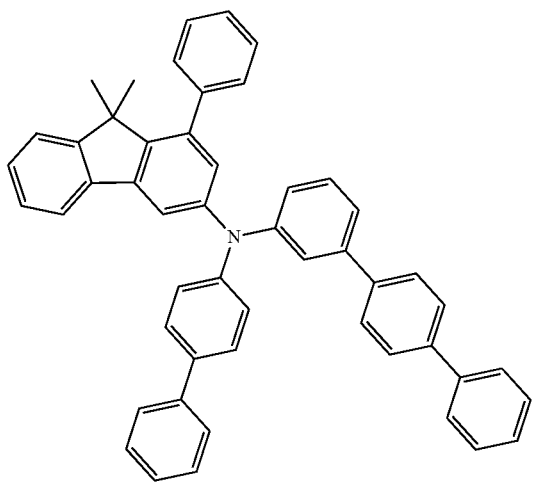
87
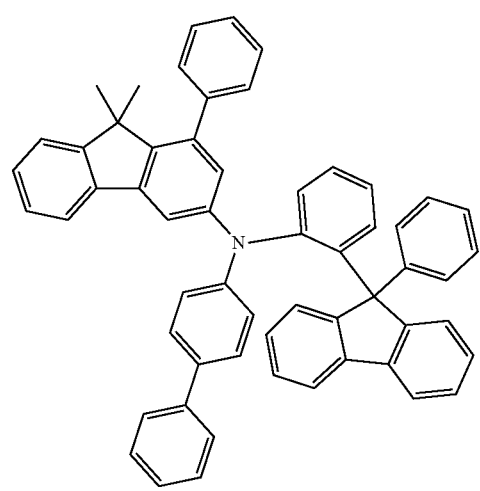
88
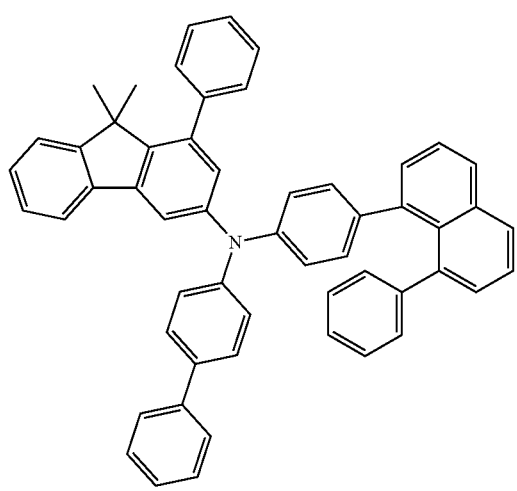
89
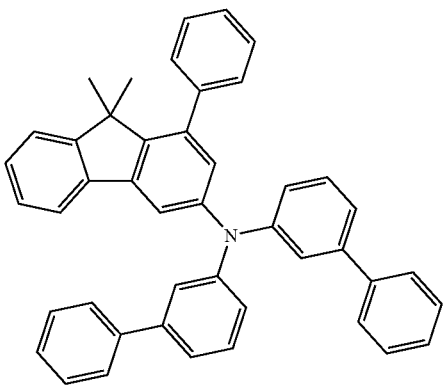
90
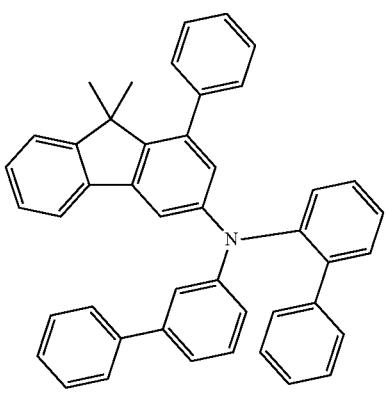
91
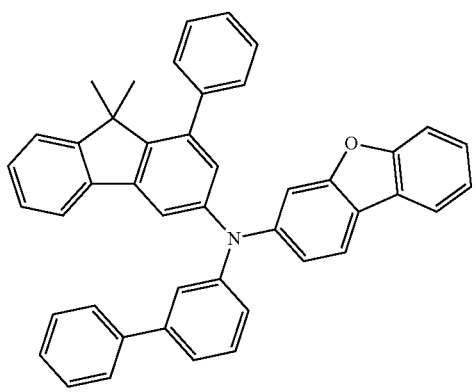
92
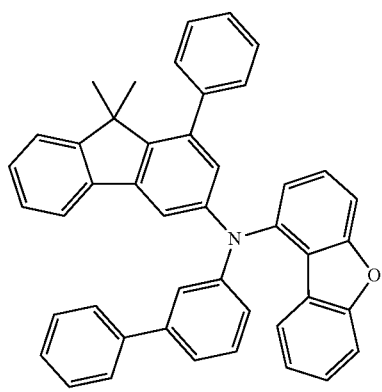

93
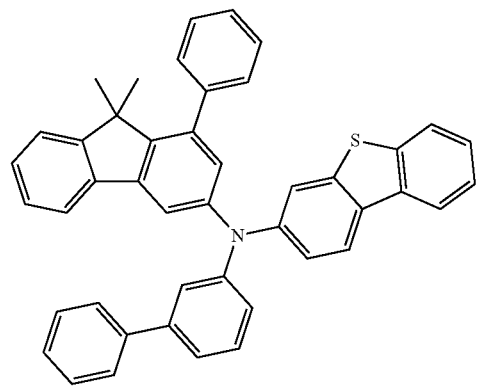
94
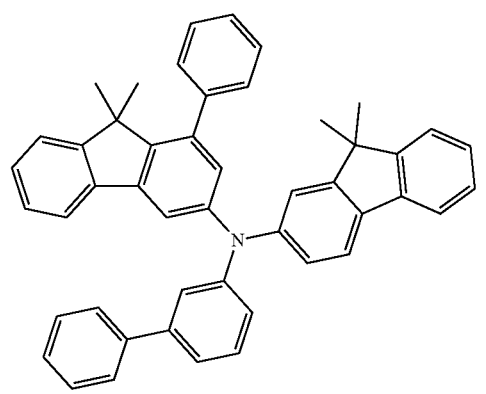
95
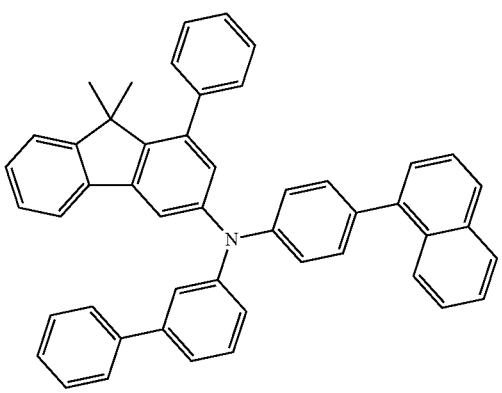
96
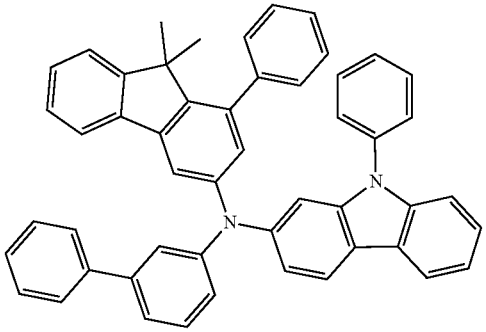
97
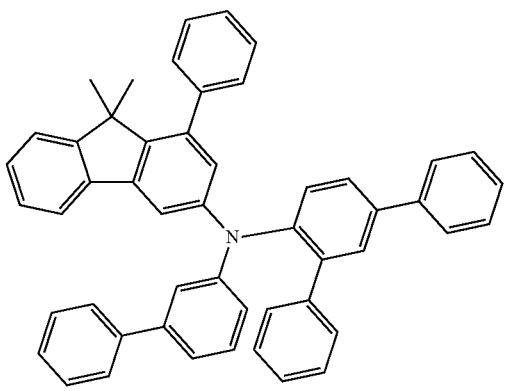
98
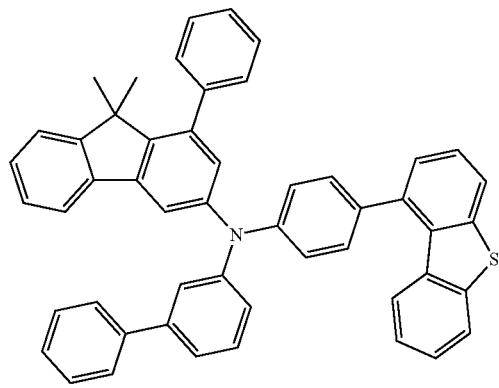
99
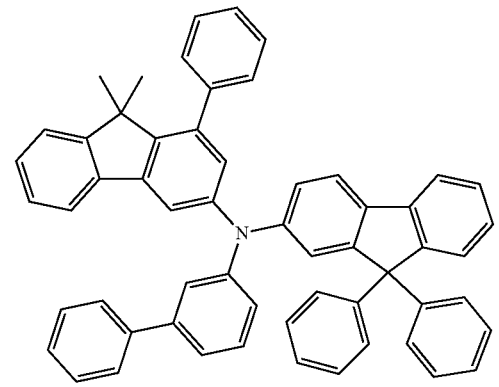
100
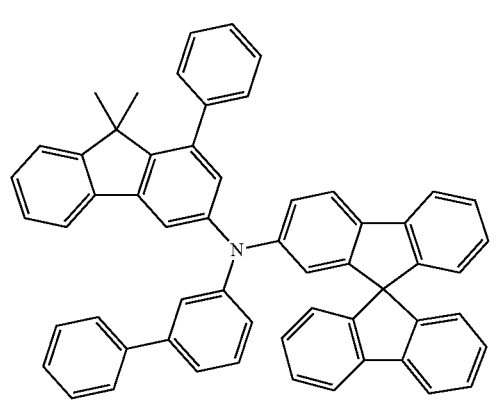

101
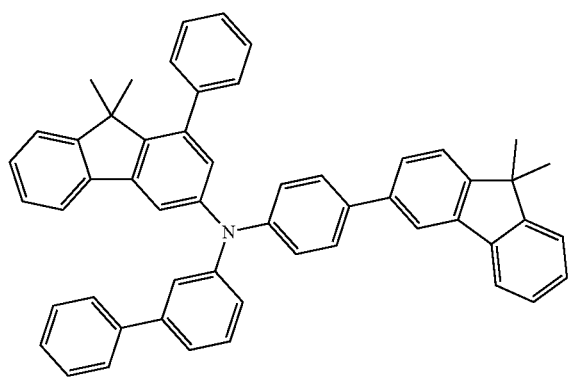
103
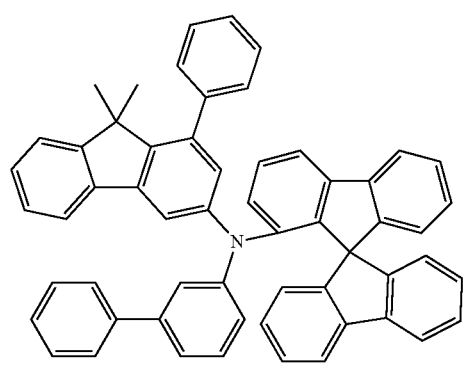
104
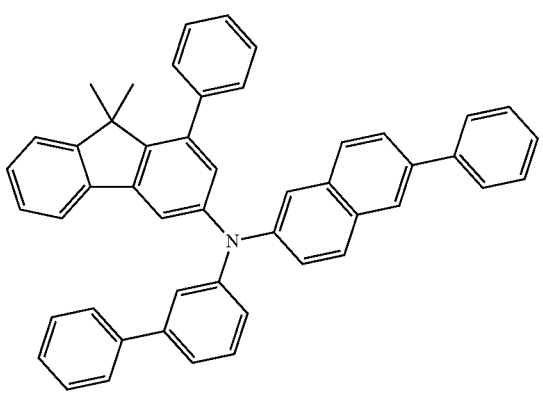
105
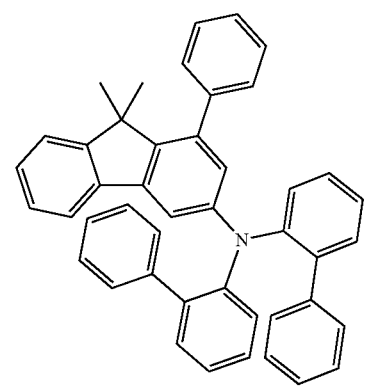
106
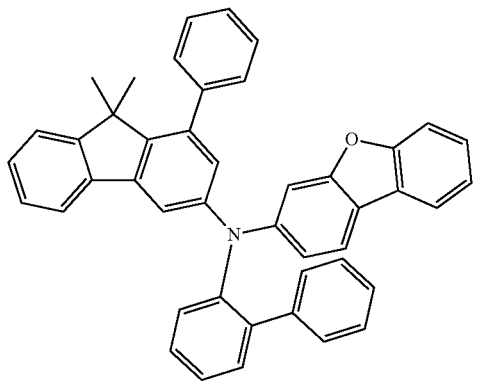
107
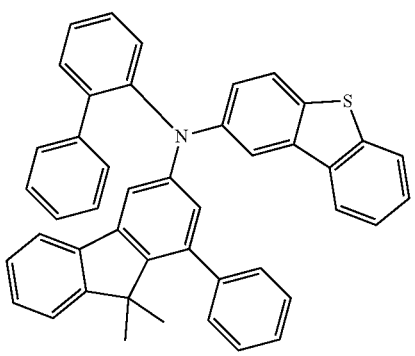
108
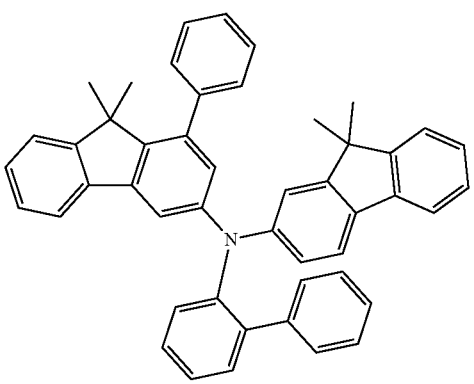
109
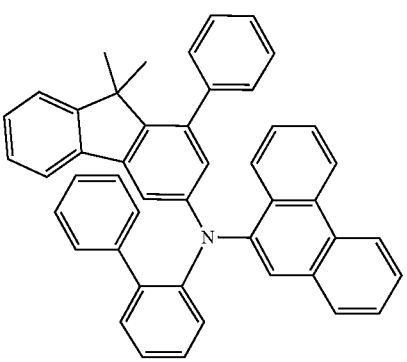

110
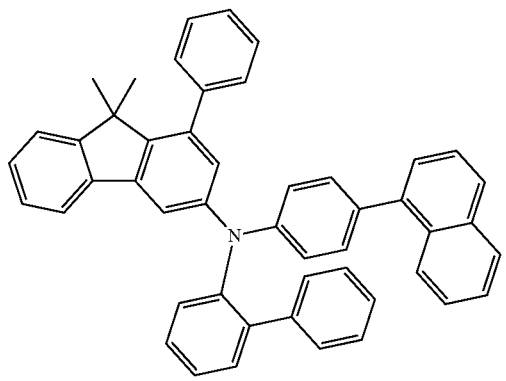
111
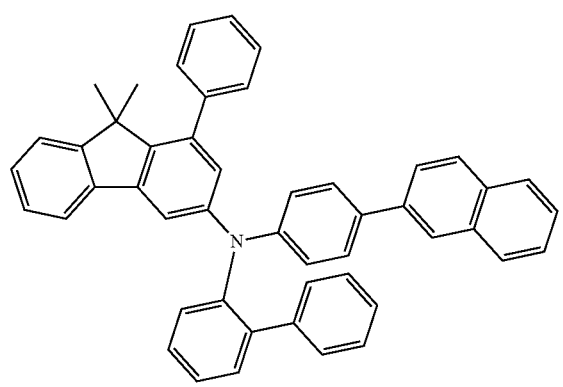
112
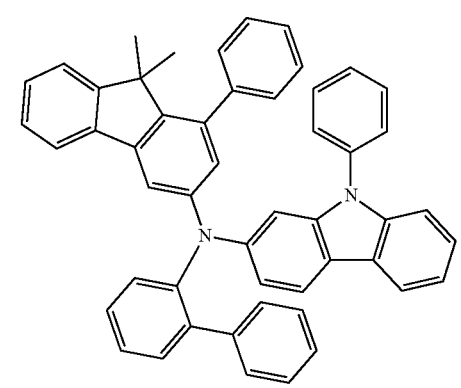
113
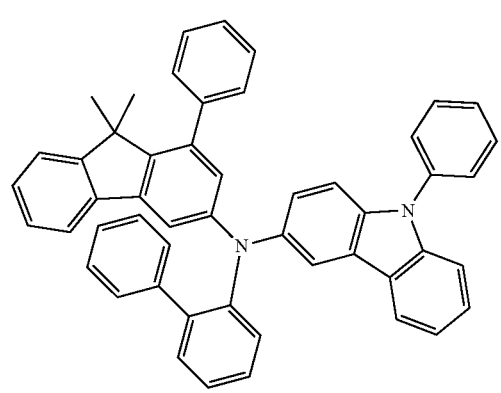
114
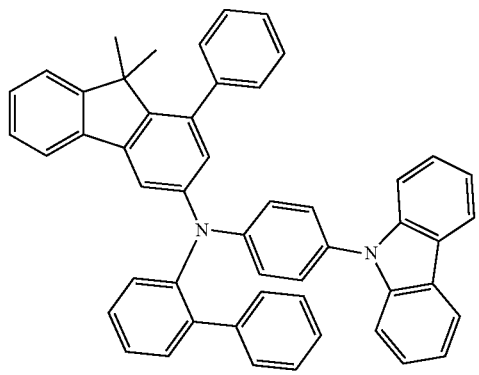
115
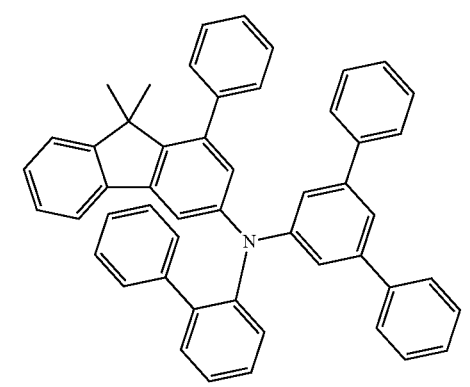
116
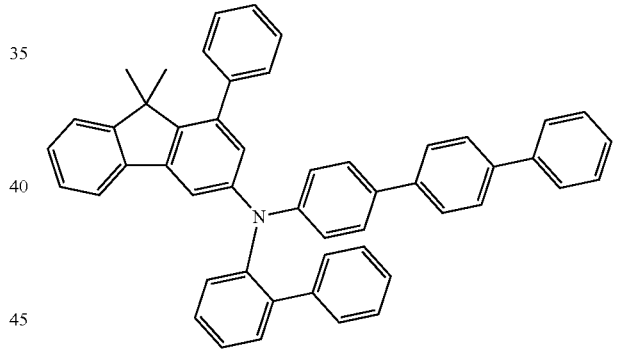
117
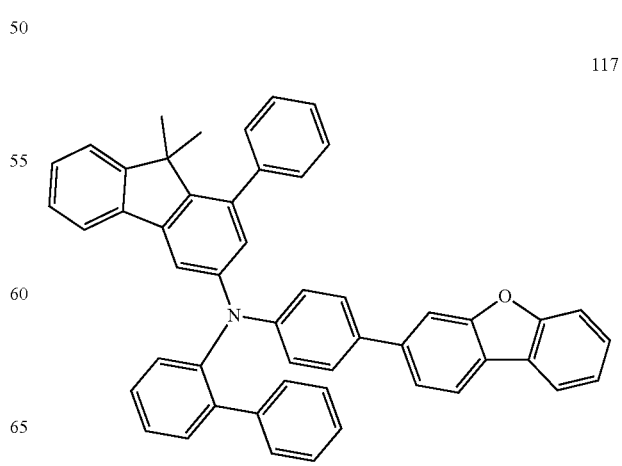

118
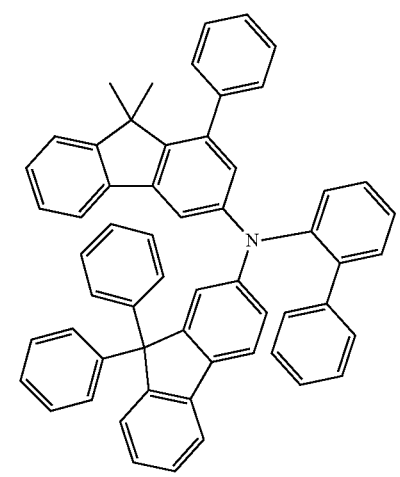
119
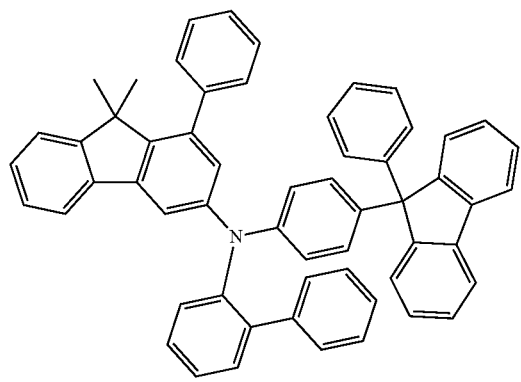
120
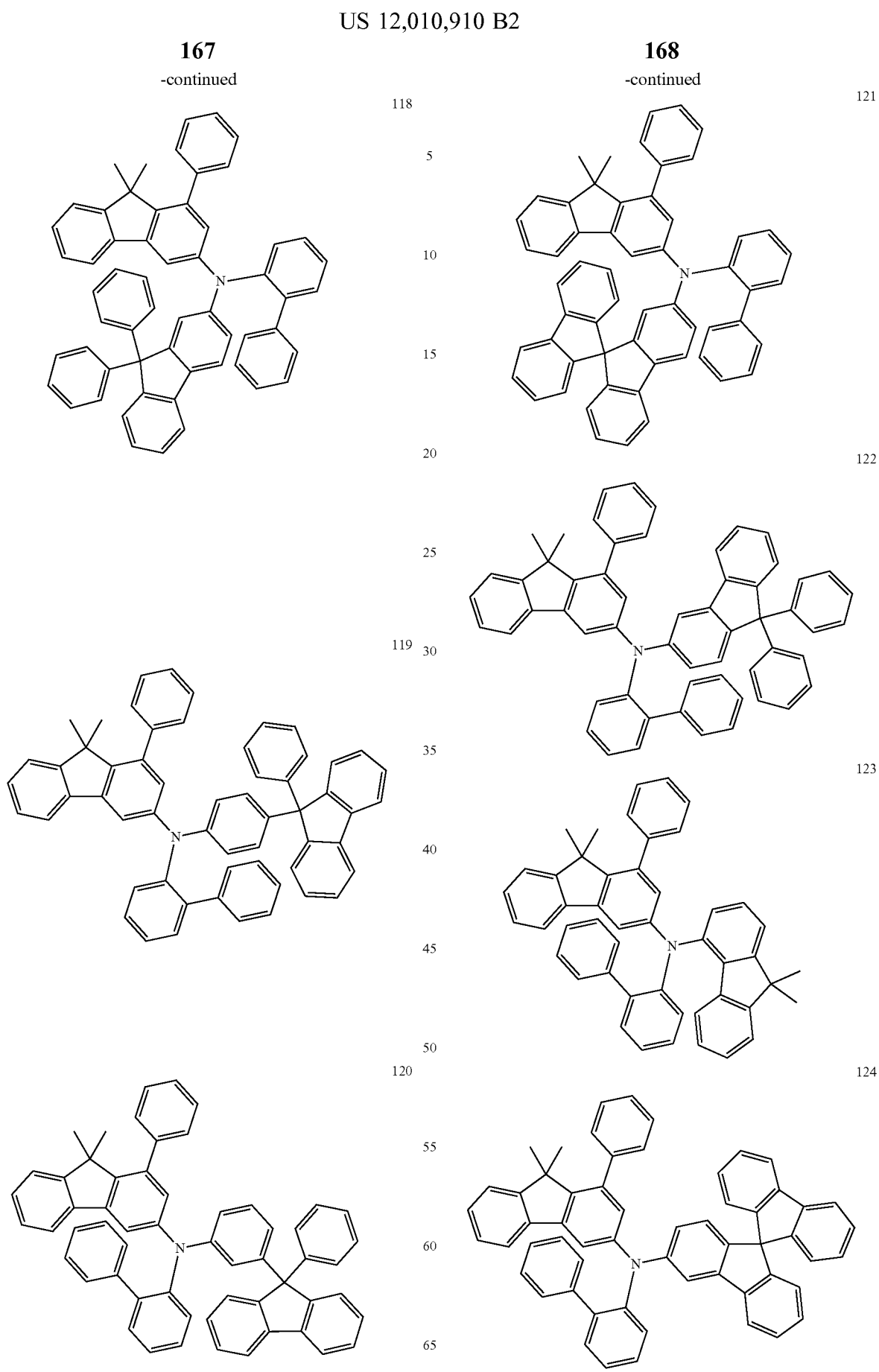
121
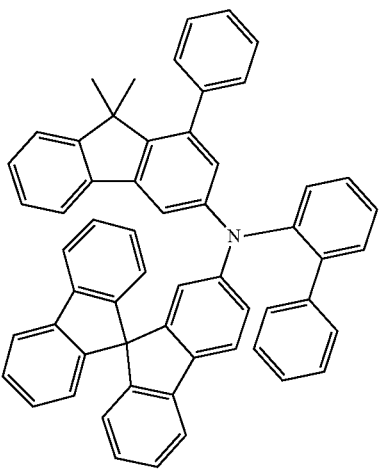
122
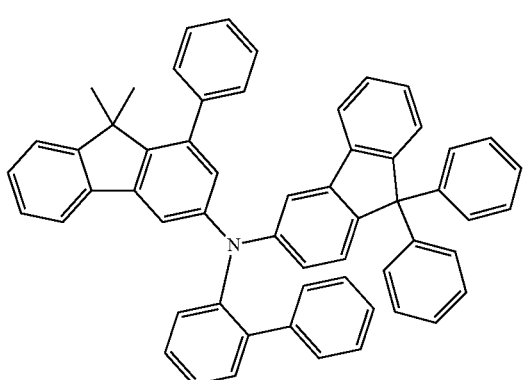
123
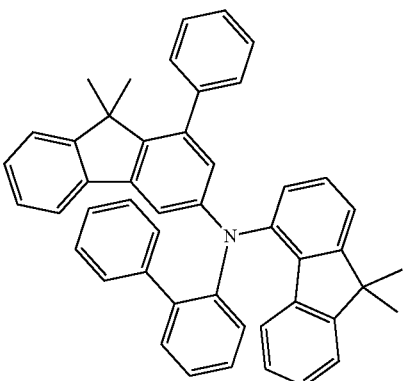
124
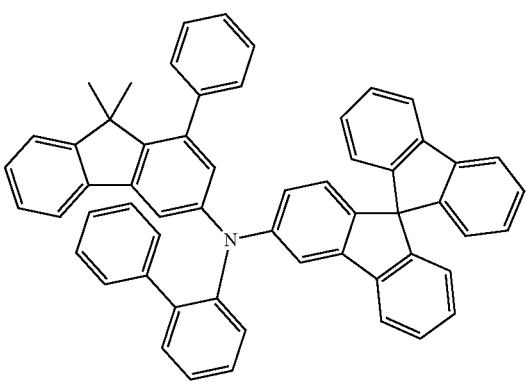

125
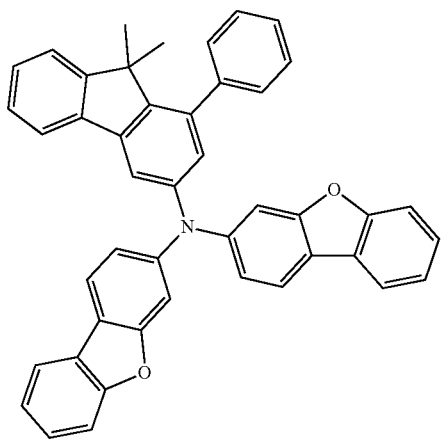
126
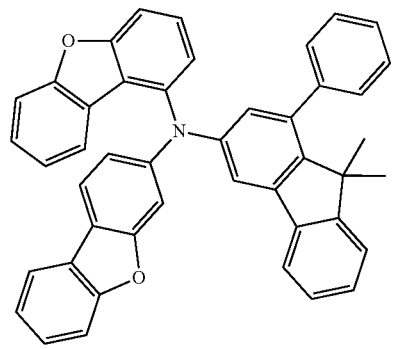
127
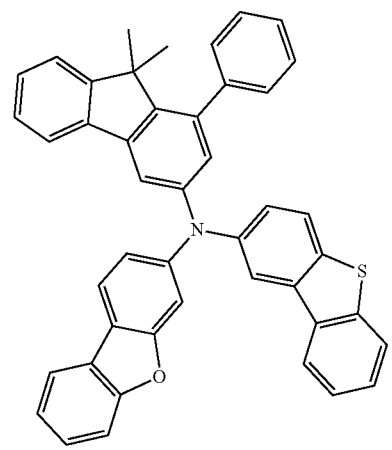
128
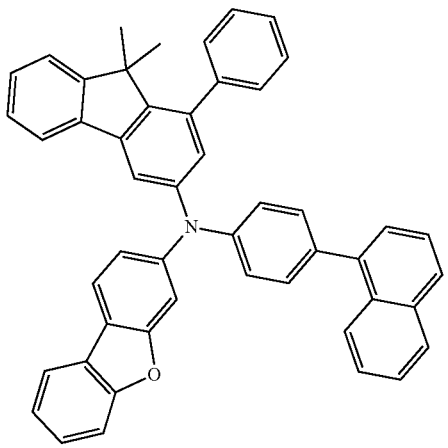
129
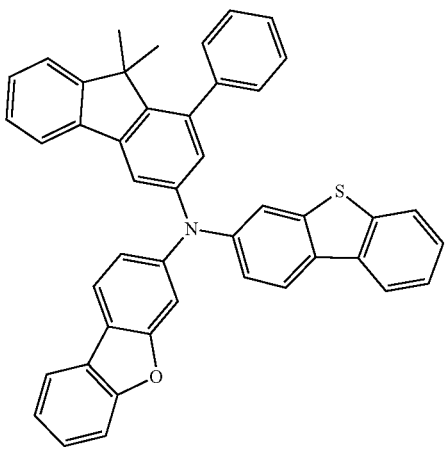
130
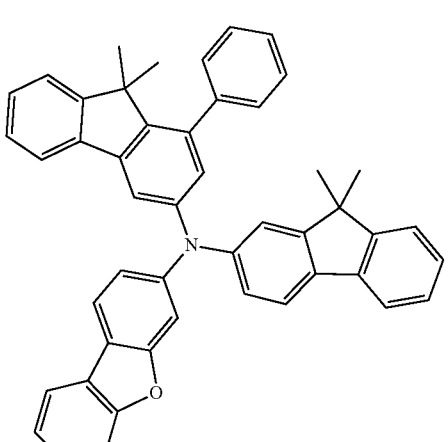

131
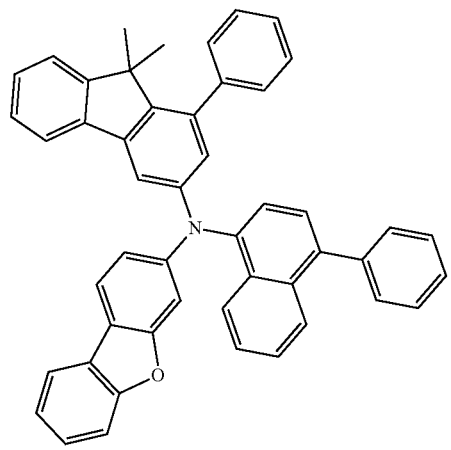
132
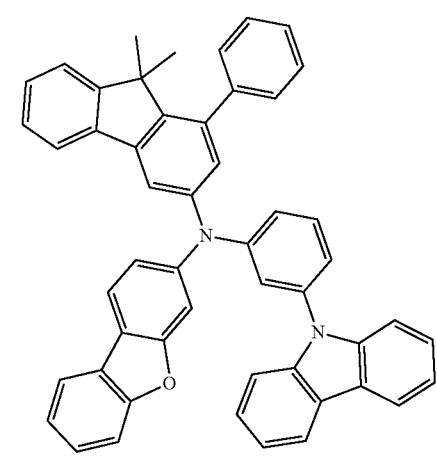
133
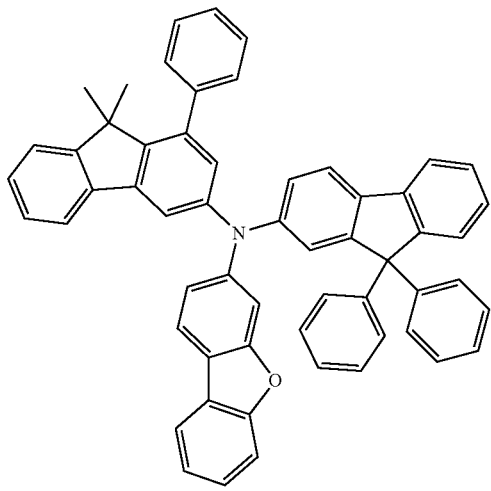
134
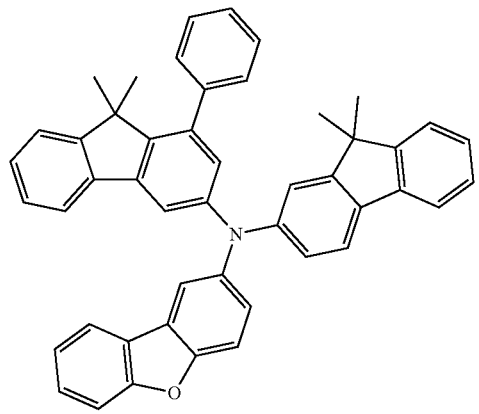
135
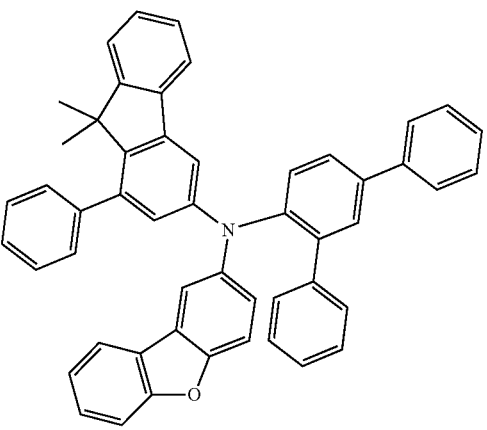
136
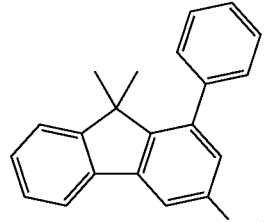
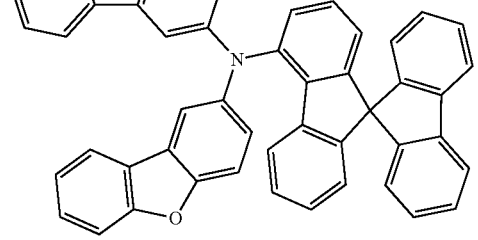
137
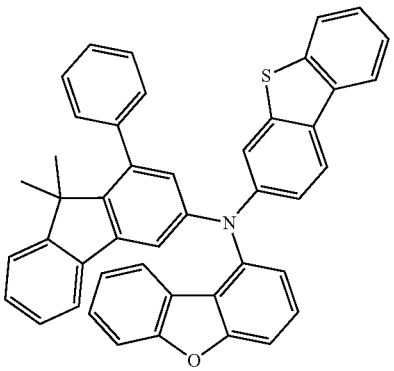

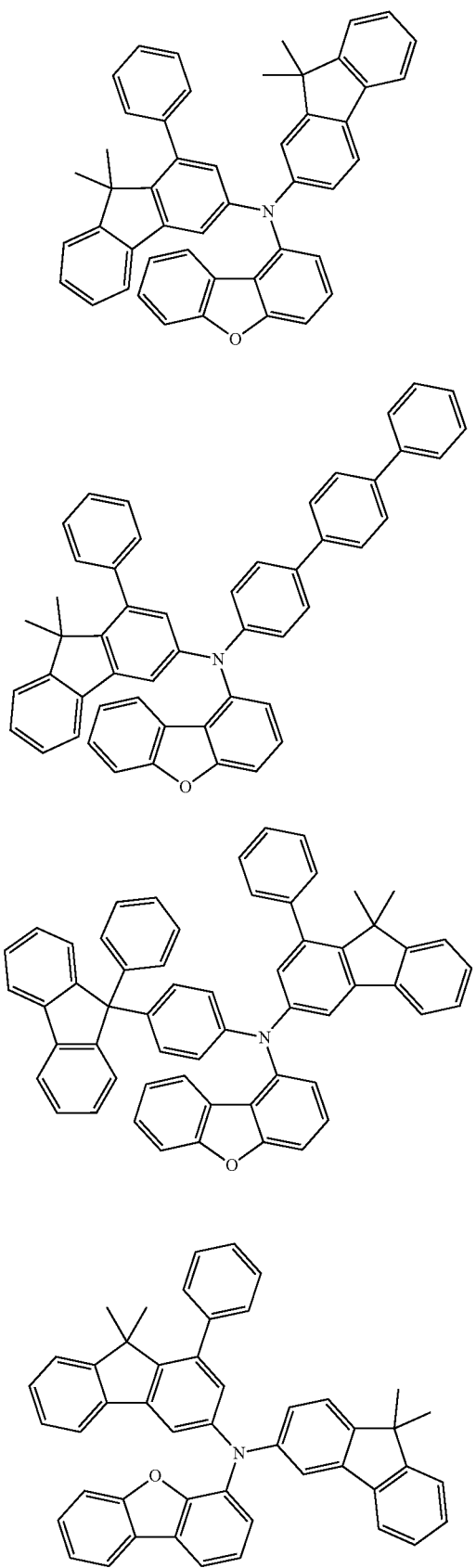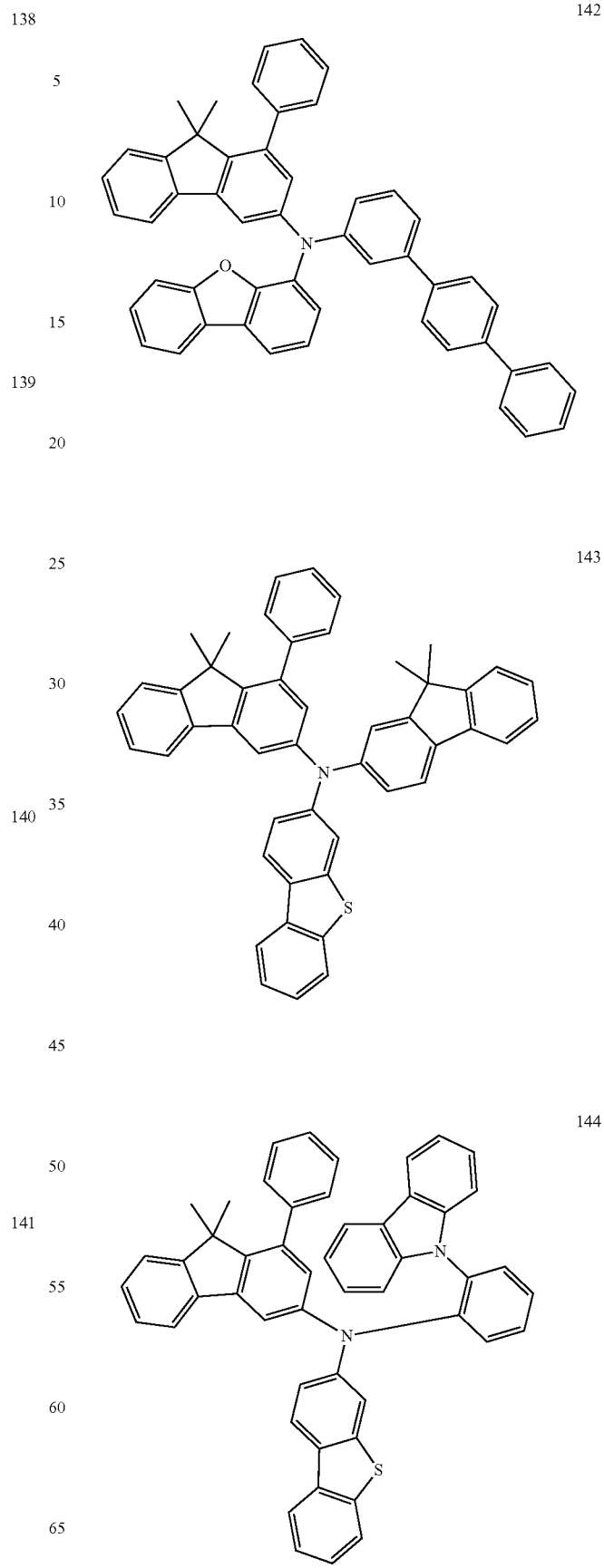

145
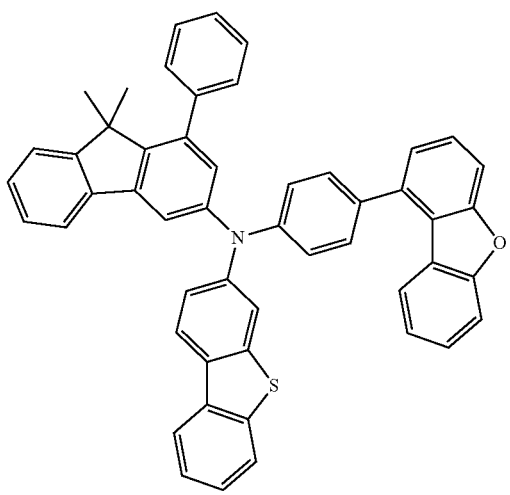
146
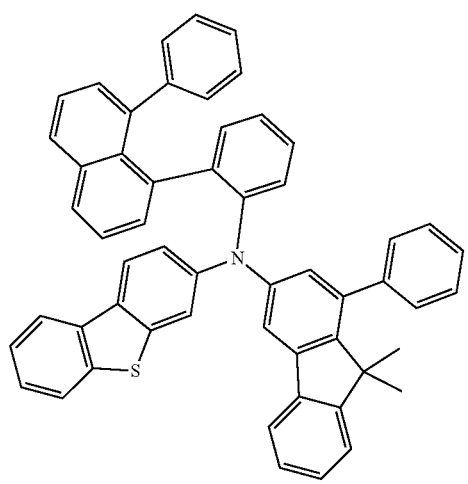
149
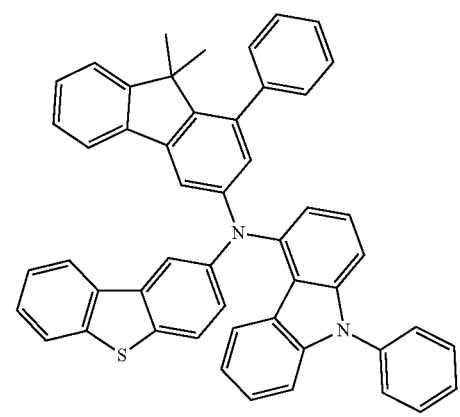
150
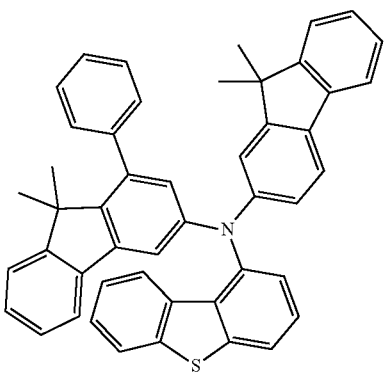
151
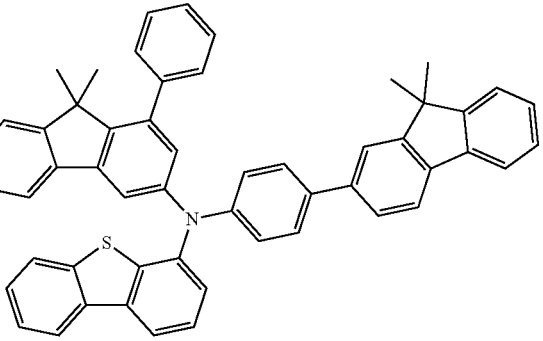
152
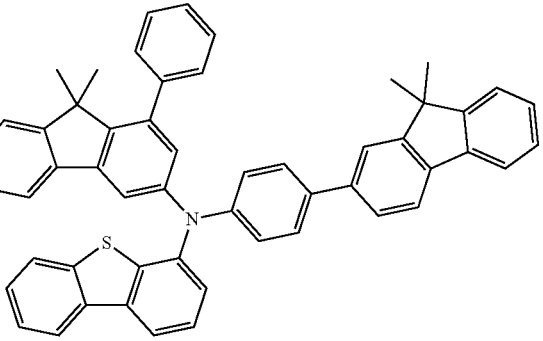
153
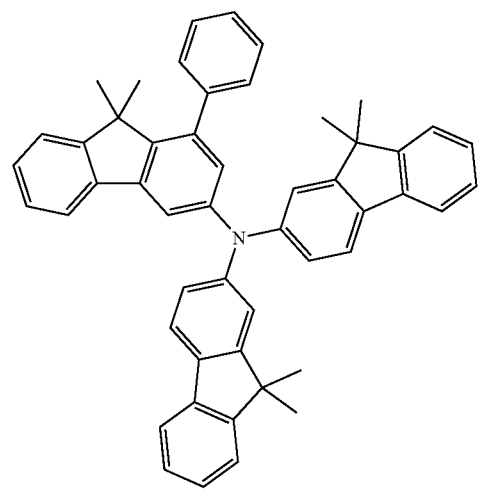

-continued
155
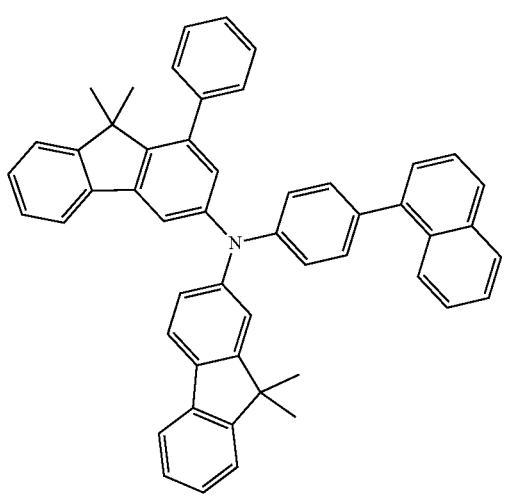
156
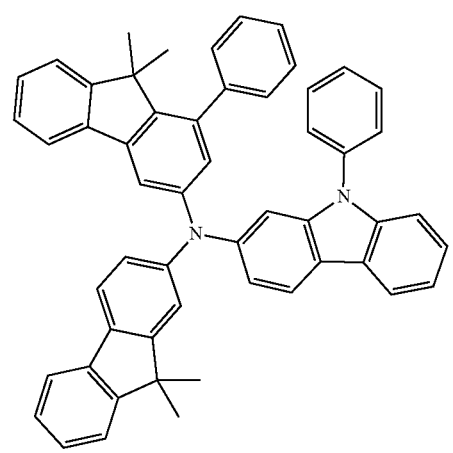
-continued
158
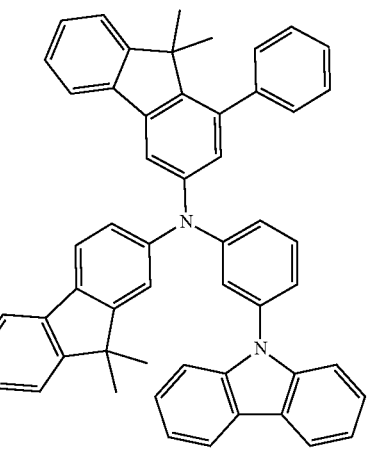
159
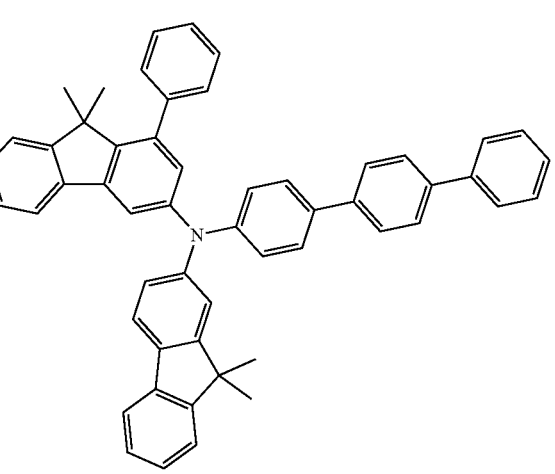
157
160
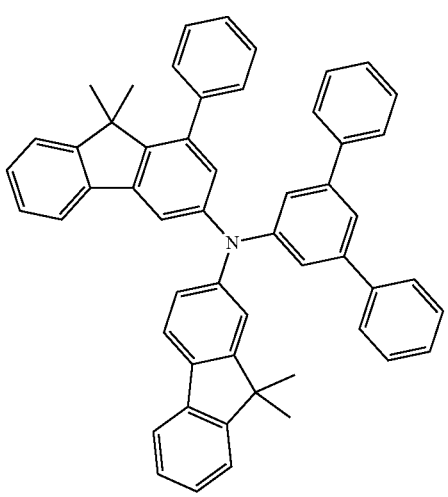

161
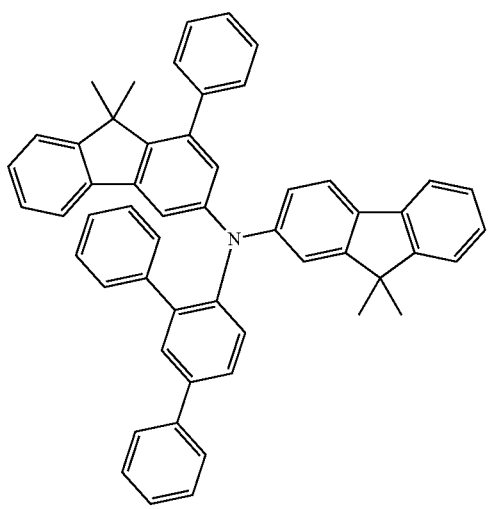
162
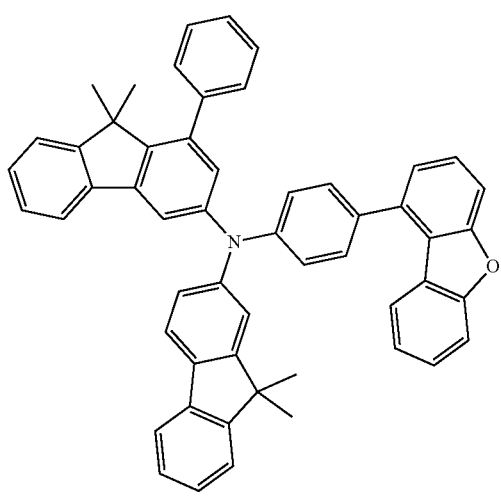
163
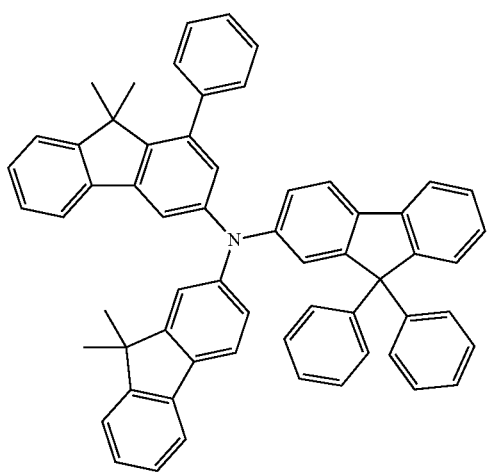
164
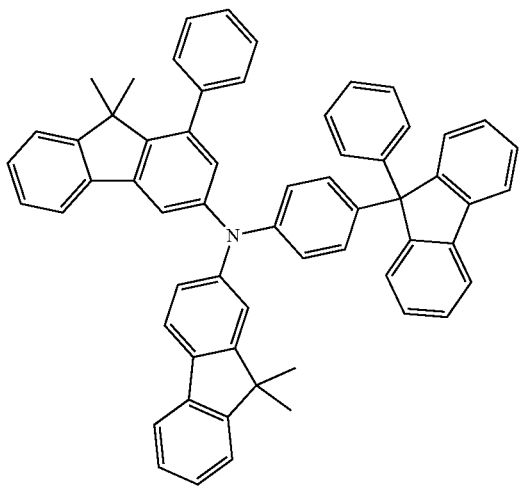
165
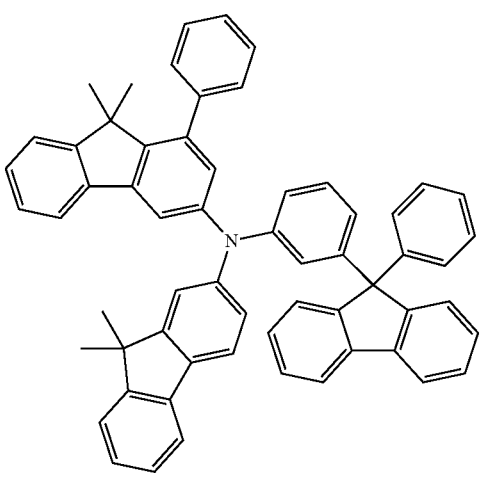
166
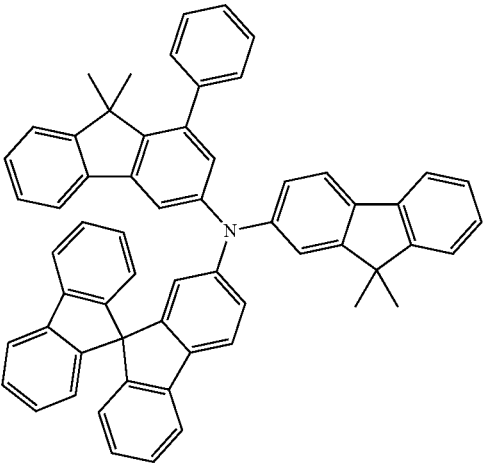

167
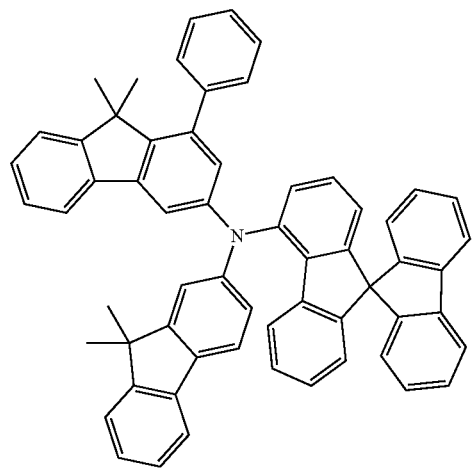
168
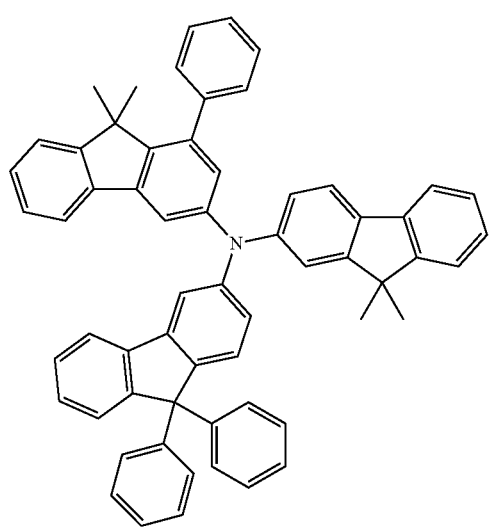
169
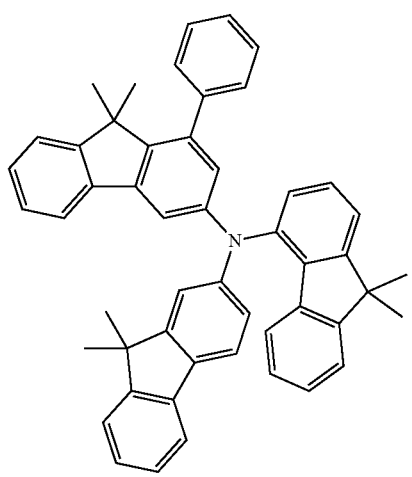
170
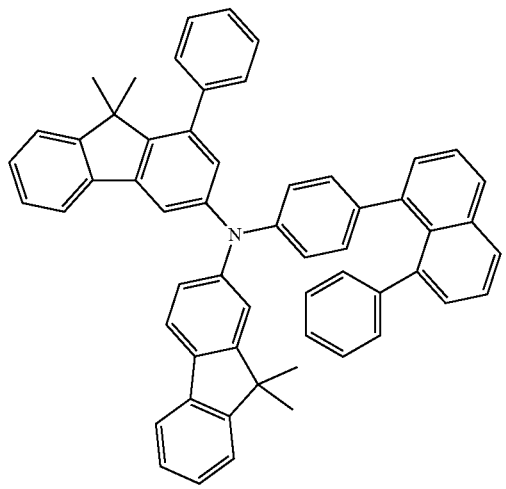
172
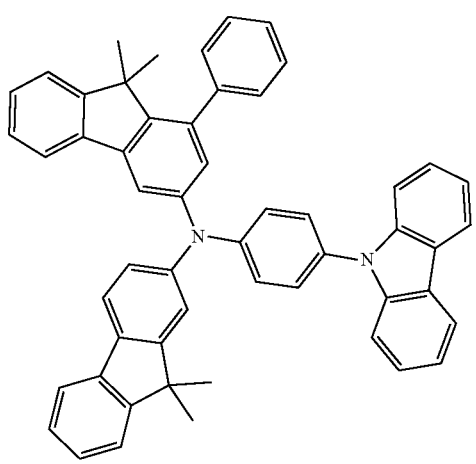
173
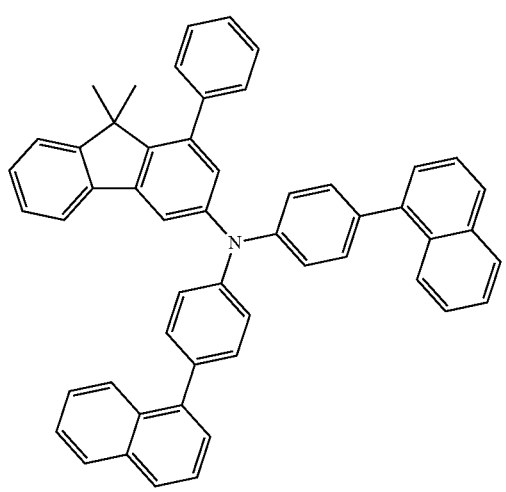

174
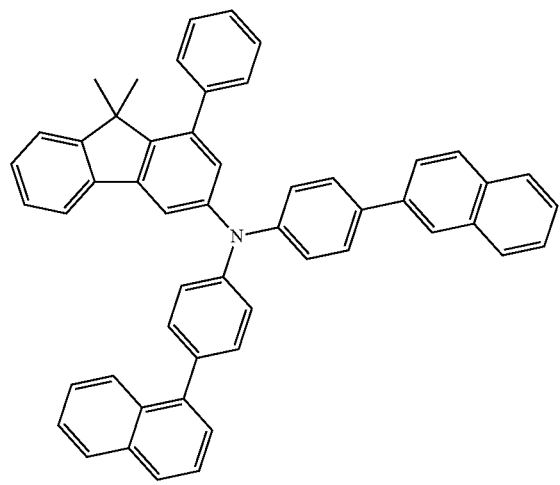
175
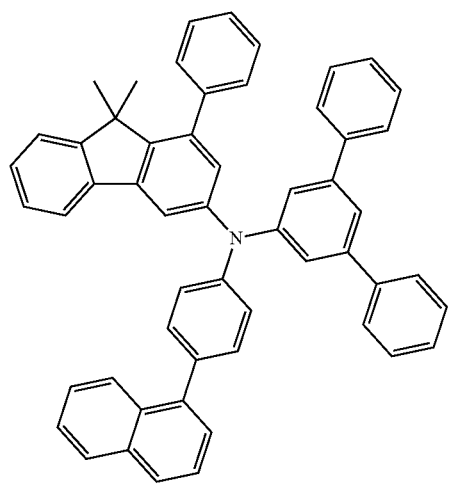
176
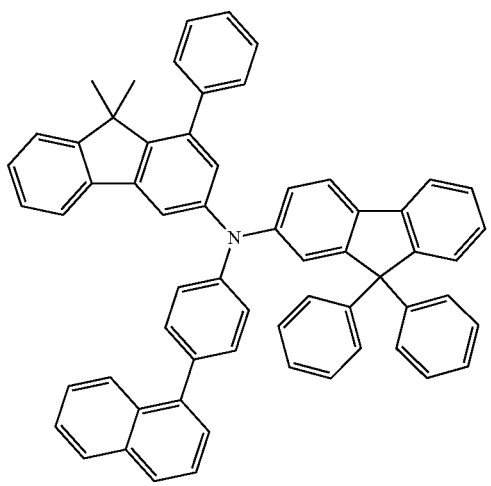
177
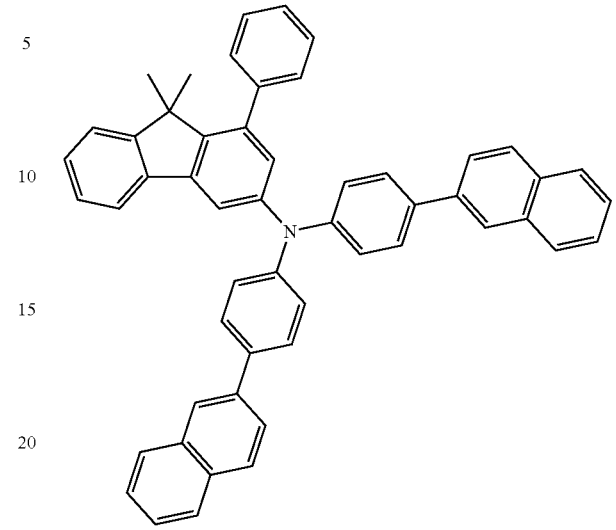
178
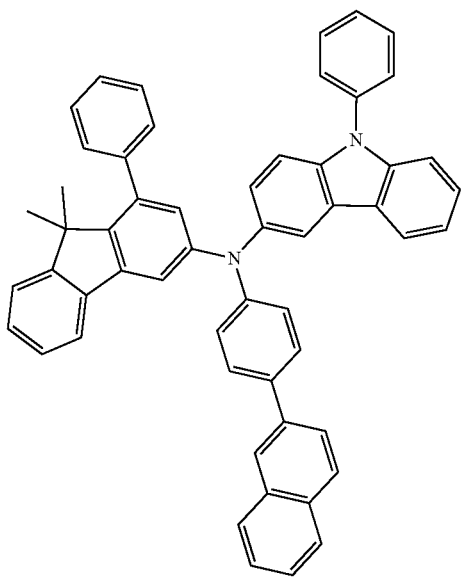
179
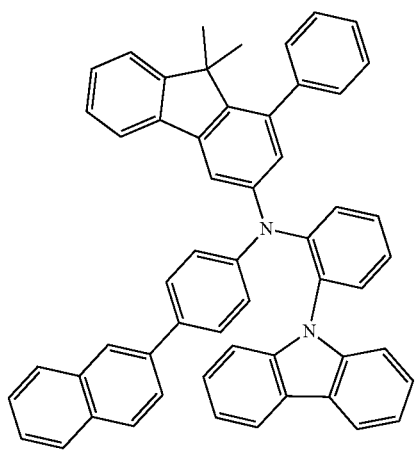

180
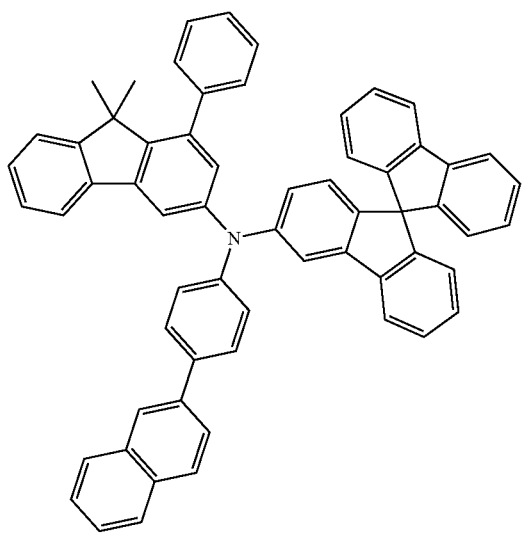
181
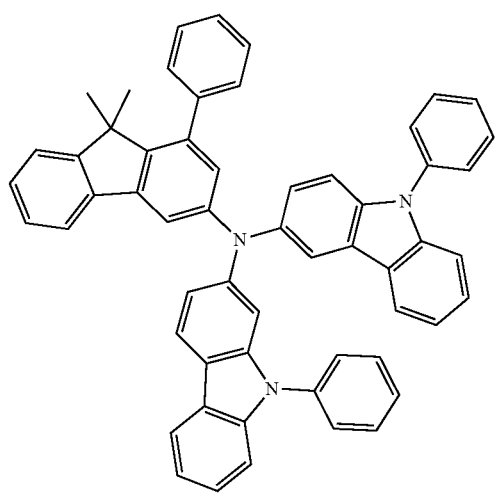
182
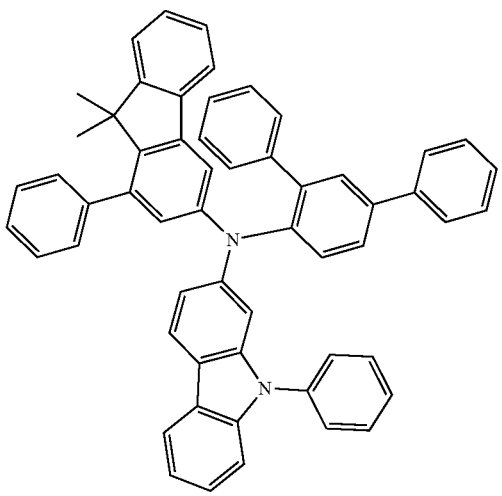
183
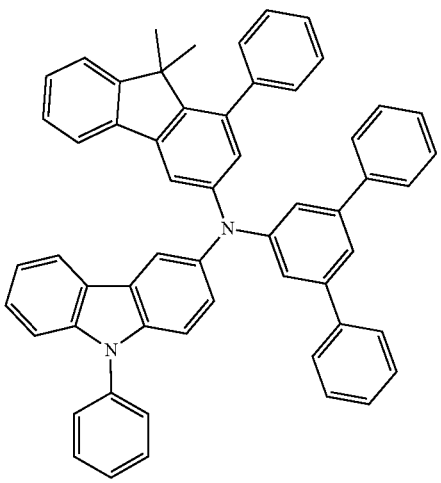
184
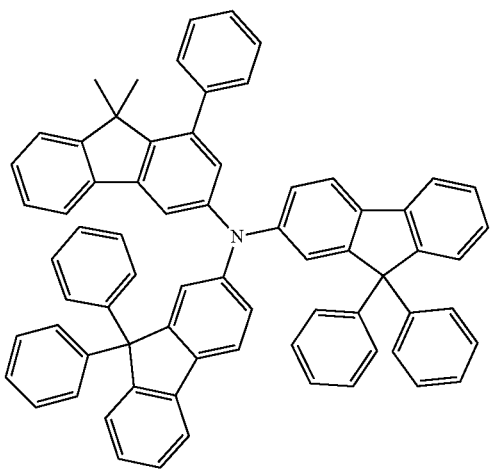
185
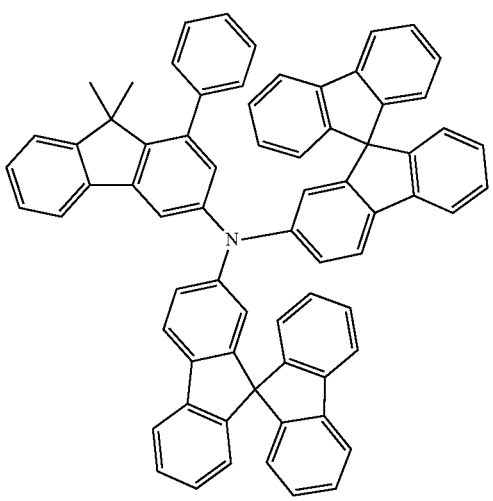

186
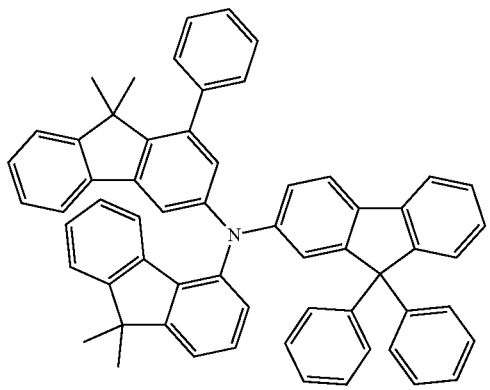
187
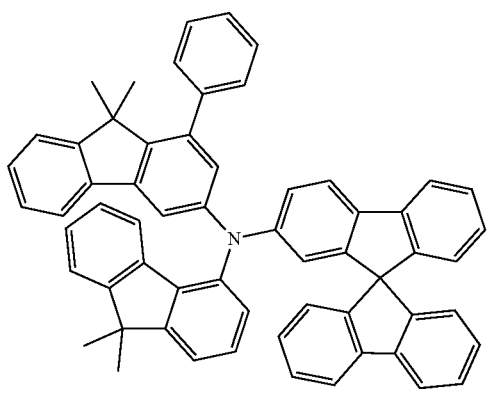
188
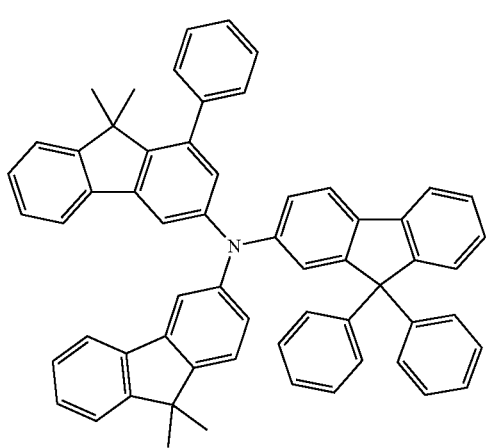
189
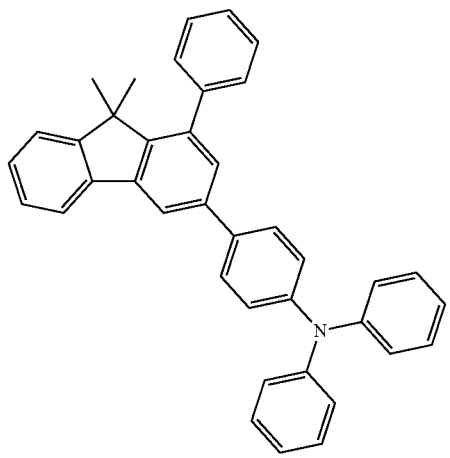
190
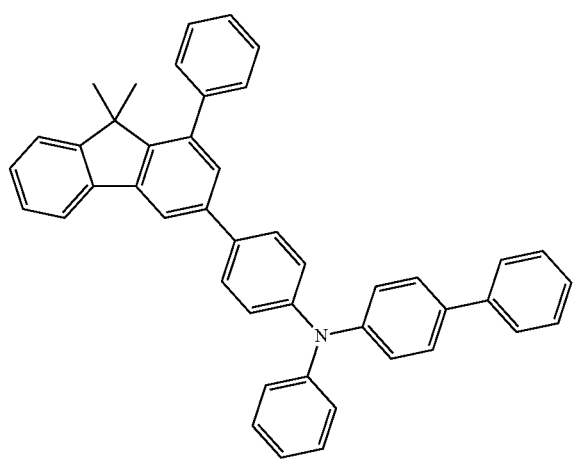
191
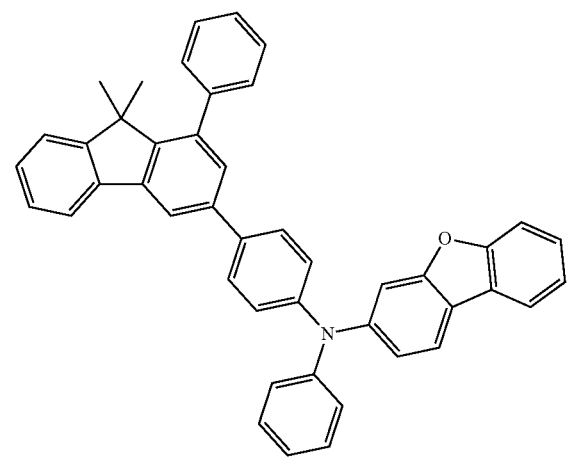

192
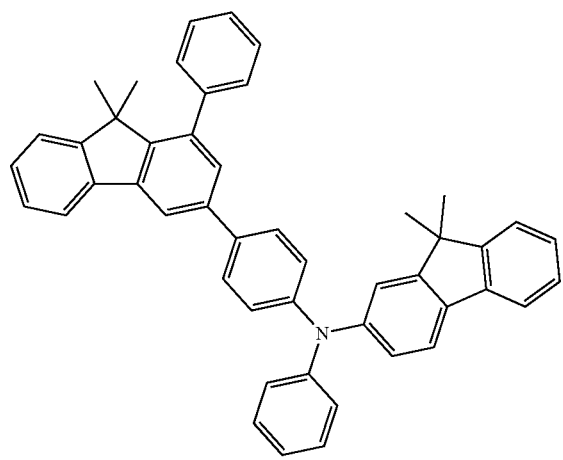
193
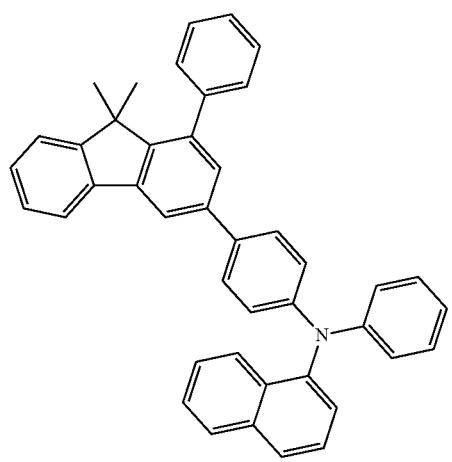
194
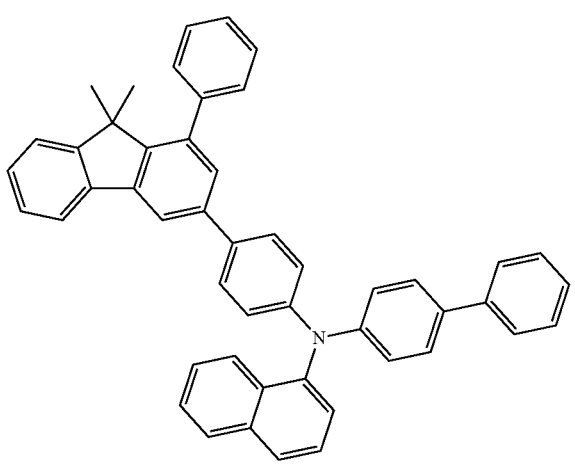
195
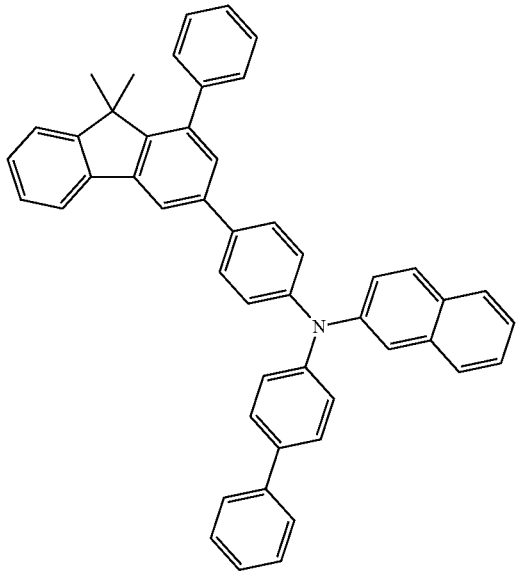
196
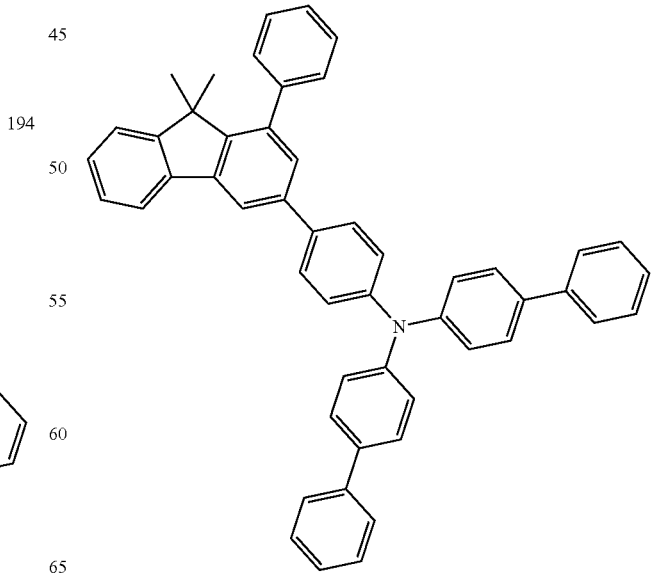

197
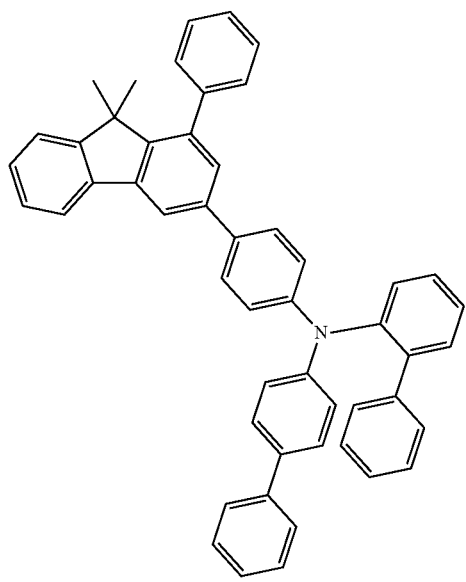
198
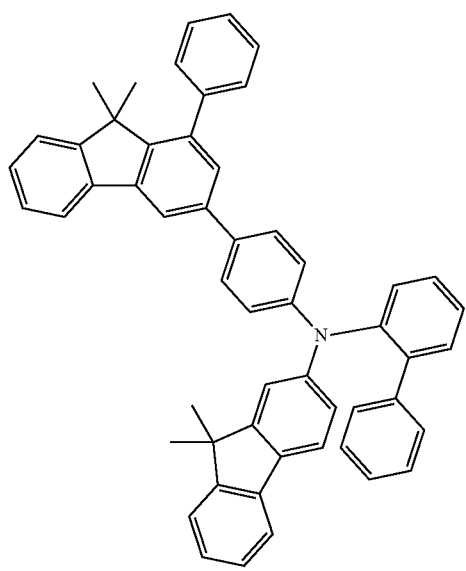
199
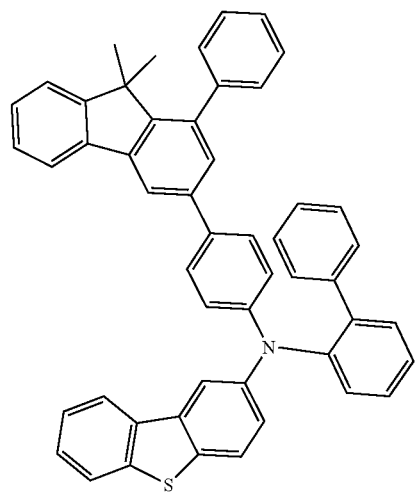
200
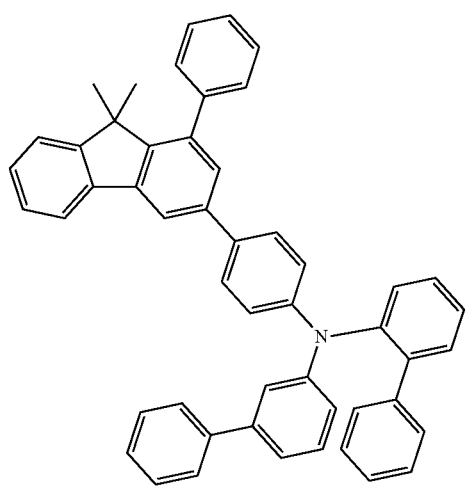
201
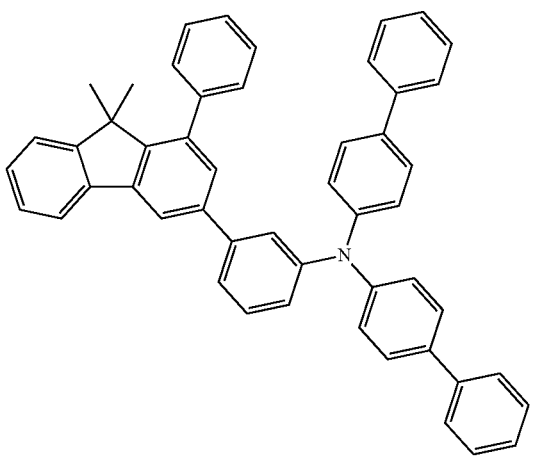
202
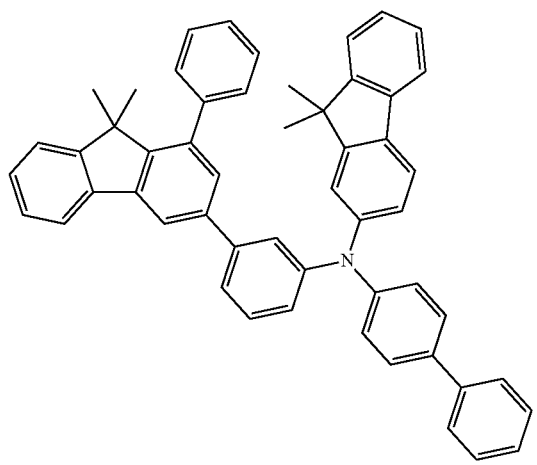

203
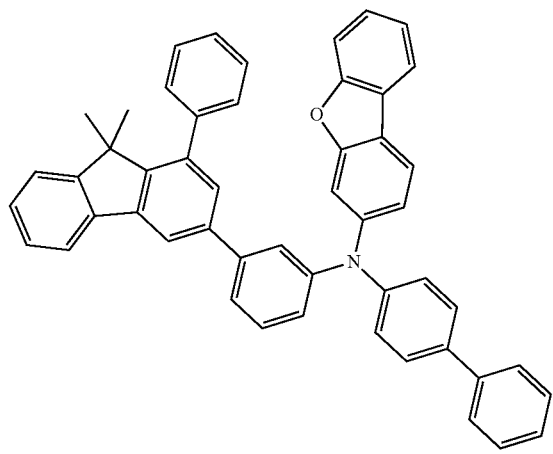
204
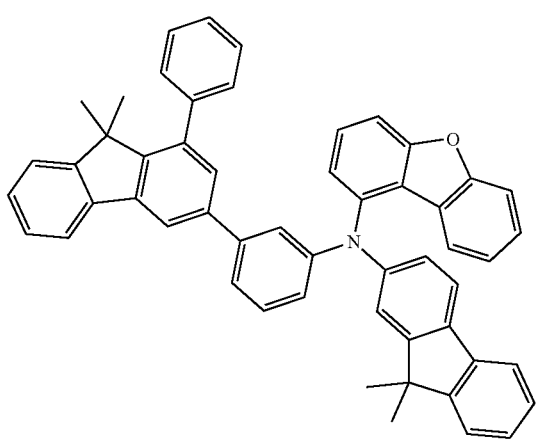
205
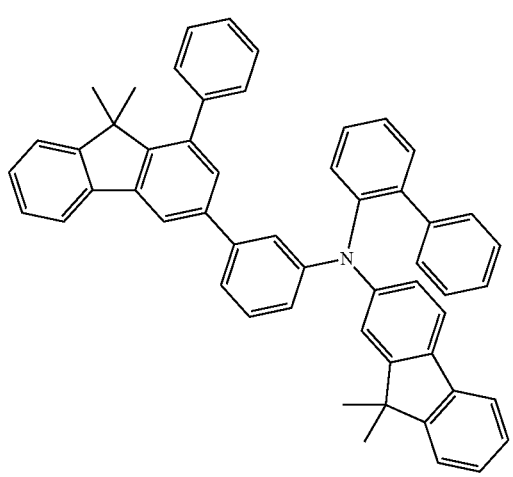
206
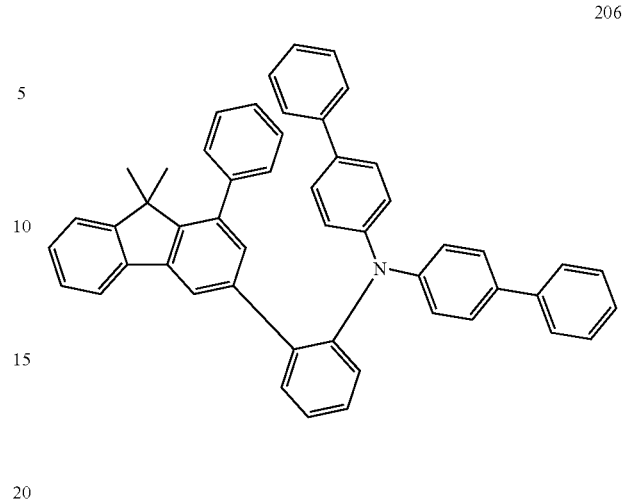
207
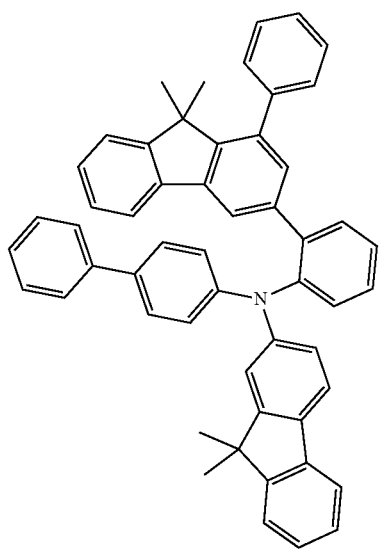
208
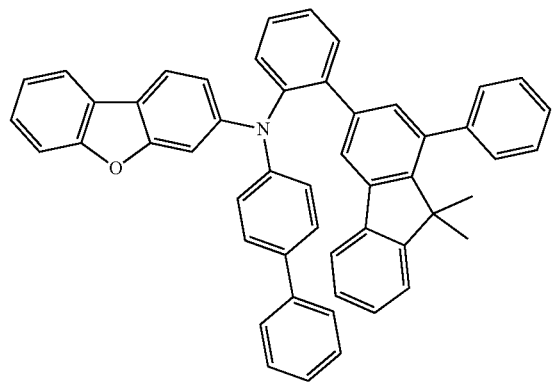

209
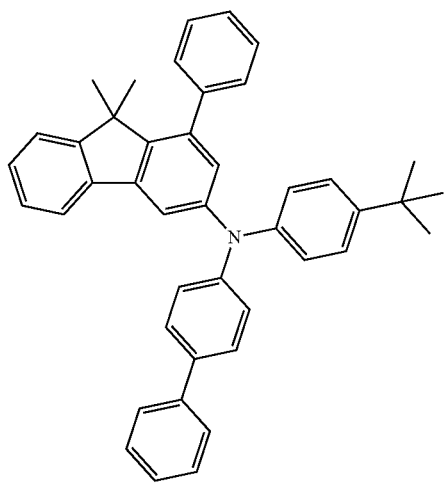
211
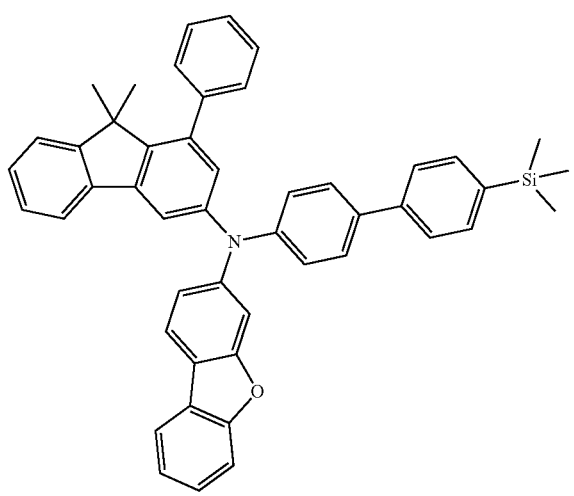
212
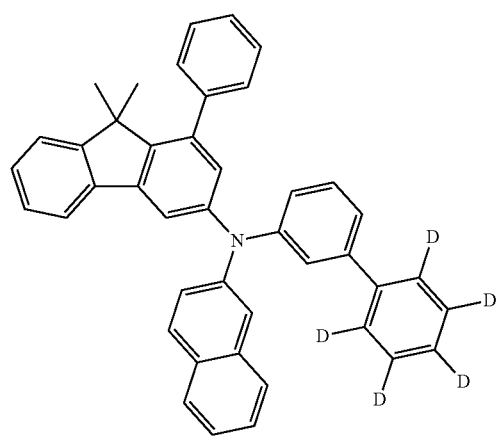
213
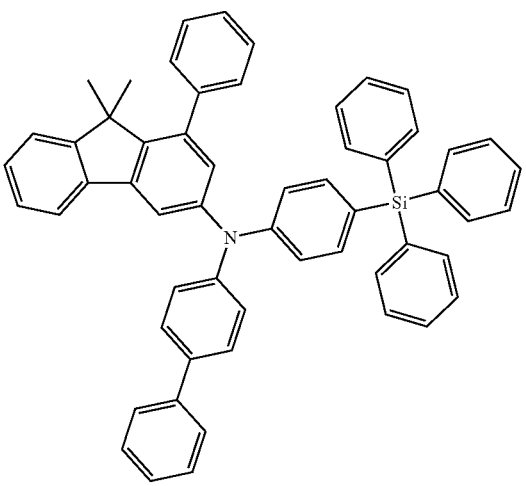
214
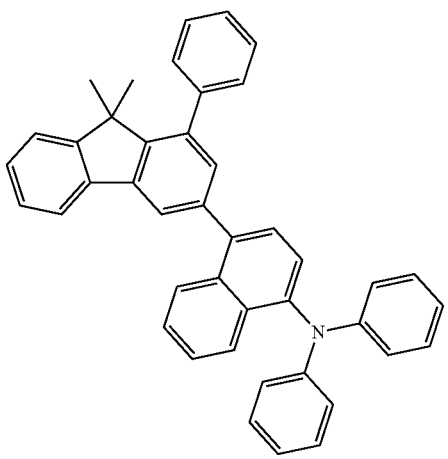
215
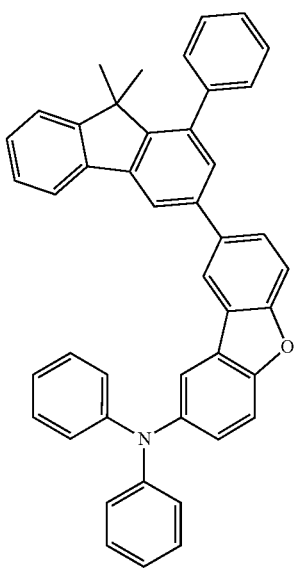

216

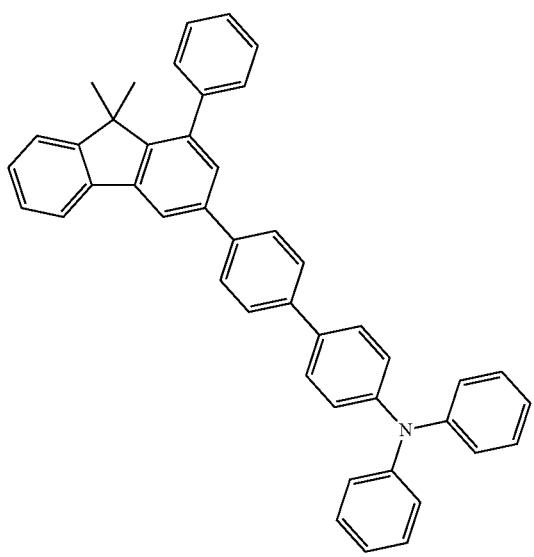

217

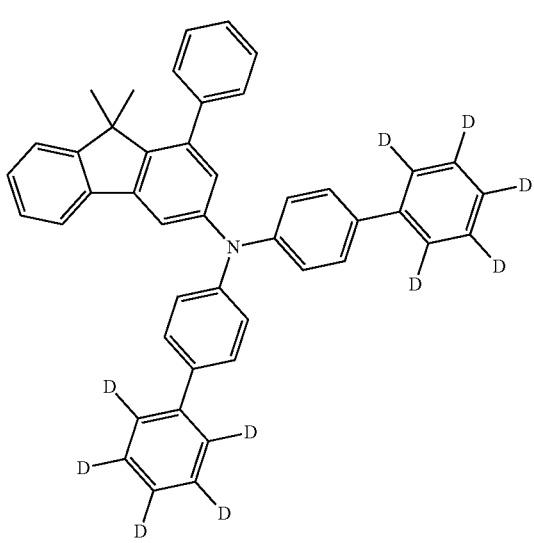

218

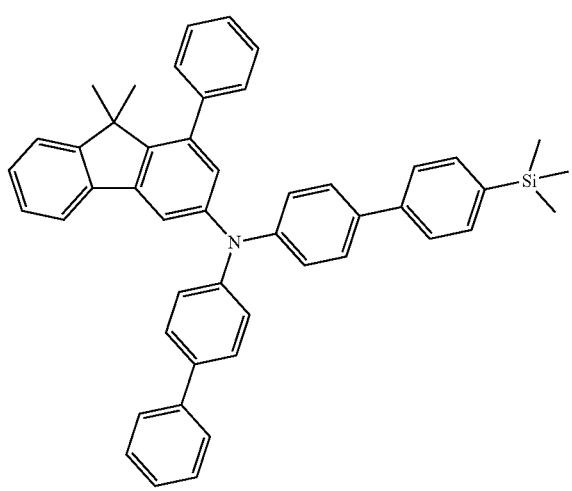

219

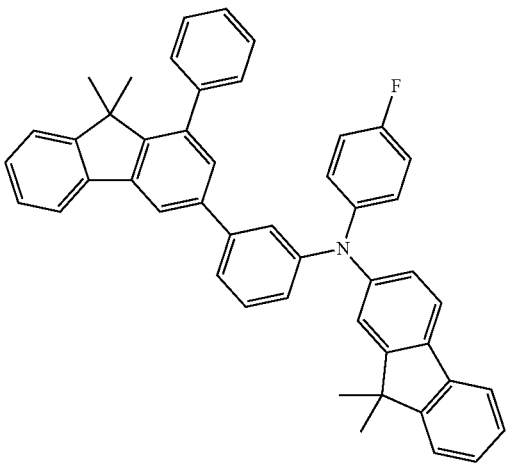

220

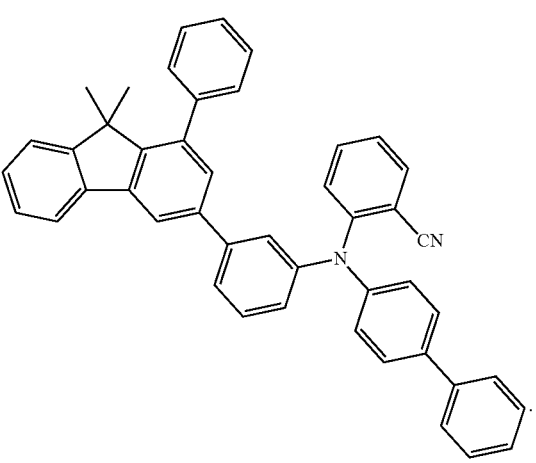

5. An electronic element, comprising an anode and a cathode disposed opposite to each other, and a functional layer disposed between the anode and the cathode, wherein the functional layer comprises the nitrogen-containing compound according to claim 1.

6. The electronic element according to claim 5, wherein the functional layer comprises an electron blocking layer, the electronic blocking layer comprising the nitrogen-containing compound.

7. The electronic element according to claim 5, wherein the electronic element is an organic electroluminescent device or a photoelectric conversion device.

8. An electronic device, comprising the electronic element according to claim 5.

* * * * *